US011779629B2

(12) United States Patent
Cashman

(10) Patent No.: US 11,779,629 B2
(45) Date of Patent: *Oct. 10, 2023

(54) COMPOSITIONS COMPRISING CYCLIC PEPTIDES DERIVED FROM AN A-BETA PEPTIDE

(71) Applicant: The University of British Columbia, Vancouver (CA)

(72) Inventor: Neil R. Cashman, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/999,849

(22) Filed: Aug. 21, 2020

(65) Prior Publication Data

US 2021/0038678 A1 Feb. 11, 2021

Related U.S. Application Data

(63) Continuation of application No. 16/148,601, filed on Oct. 1, 2018, now Pat. No. 10,751,382, which is a (Continued)

(51) Int. Cl.

*A61K 38/00* (2006.01)
*A61K 38/17* (2006.01)

(Continued)

(52) U.S. Cl.

CPC .............. *A61K 38/07* (2013.01); *A61K 38/12* (2013.01); *A61K 39/385* (2013.01); *A61K 47/643* (2017.08); *A61K 47/646* (2017.08); *A61P 25/28* (2018.01); *C07K 5/081* (2013.01); *C07K 5/0808* (2013.01); *C07K 5/0812* (2013.01); *C07K 5/0815* (2013.01); *C07K 5/0819* (2013.01); *C07K 5/0821* (2013.01); *C07K 5/1021* (2013.01); *C07K 5/1024* (2013.01); *C07K 7/06* (2013.01); *C07K 7/64* (2013.01); *C07K 14/4711* (2013.01); *C07K 16/18* (2013.01); *C12N 5/16* (2013.01); *G01N 33/6896* (2013.01); *A61K 38/00* (2013.01); *A61K 38/05* (2013.01); *A61K 38/08* (2013.01); *A61K 39/00* (2013.01); *A61K 39/39* (2013.01); *A61K 39/395* (2013.01); *A61K 39/3955* (2013.01); *A61K 39/39533* (2013.01); *A61K 45/05* (2013.01); *A61K 45/06* (2013.01); *A61K 47/6803* (2017.08); *A61K 47/6921* (2017.08); *A61K 49/1818* (2013.01); *A61K 49/1866* (2013.01); *A61K 51/088* (2013.01); *A61K 51/10* (2013.01); *A61K 51/1018* (2013.01); *A61K 2039/505* (2013.01); *A61K 2039/55505* (2013.01); *A61K 2039/6081* (2013.01); *A61K 2300/00* (2013.01); *A61L 27/227* (2013.01); *A61L 27/34* (2013.01); *A61L 29/085* (2013.01); *A61L 29/16* (2013.01); *A61L 31/10* (2013.01); *A61L 31/16* (2013.01); *C07K 5/101* (2013.01); *C07K 7/08* (2013.01); *C07K 14/435* (2013.01); *C07K 2317/20* (2013.01); *C07K 2317/24* (2013.01); *C07K 2317/30* (2013.01); *C07K 2317/33* (2013.01); *C07K 2317/34* (2013.01); *C07K 2317/524* (2013.01); *C07K 2317/526* (2013.01); *C07K 2317/54* (2013.01); *C07K 2317/55* (2013.01); *C07K 2317/56* (2013.01); *C07K 2317/565* (2013.01); *C07K 2317/569* (2013.01);

(Continued)

(58) Field of Classification Search

CPC ... C07K 5/00; C07K 5/10; C07K 5/12; C07K 7/06; C07K 7/08; C07K 14/4711; C07K 5/101; C07K 5/0821; C07K 5/1016; C07K 5/1019; C07K 5/1021; C07K 7/64; A61K 38/00; A61K 38/10; A61K 38/12; A61K 38/1716; A61K 38/02; A61K 38/08; A61K 38/1709; A61K 39/00; A61K 2039/6081; A61P 25/28; A61P 25/00; G01N 33/6896; G01N 2333/4709; G01N 2800/2821

See application file for complete search history.

(56) References Cited

U.S. PATENT DOCUMENTS 5,283,185 A 2/1994 Epand et al.
5,562,909 A * 10/1996 Allcock .............. C08G 79/025 424/193.1

(Continued)

FOREIGN PATENT DOCUMENTS

CN 101670105 A 3/2010
CN 101802007 A 8/2010

(Continued)

OTHER PUBLICATIONS

Rahimi et al. Chapter 6, Modulators of Amyloid-beta-protein (Abeta) Self-Assembly, 2016, Developing Therapeutics for Alzheimer's disease: dx.doi.org/10.1016/B978-0-12-802173-6.00006-X.*

(Continued)

*Primary Examiner* — Chang-Yu Wang

(74) *Attorney, Agent, or Firm* — Bereskin & Parr LLP; Carmela De Luca

(57) ABSTRACT

The disclosure pertains to methods of treating or preventing a disease or condition associated with and/or induced by soluble A-beta oligomer such as Alzheimer's disease by administering to a subject in need thereof conformation specific and/or selective antibodies or binding fragments thereof and related products.

9 Claims, 19 Drawing Sheets

Specification includes a Sequence Listing.

Related U.S. Application Data continuation of application No. 15/808,842, filed on Nov. 9, 2017, now abandoned, which is a continuation-in-part of application No. PCT/CA2017/050866, filed on Jul. 18, 2017, and a continuation-in-part of application No. PCT/CA2016/051300, filed on Nov. 9, 2016, and a continuation-in-part of application No. PCT/CA2016/051303, filed on Nov. 9, 2016, and a continuation-in-part of application No. PCT/CA2016/051305, filed on Nov. 9, 2016.

(60) Provisional application No. 62/507,587, filed on May 17, 2017, provisional application No. 62/507,633, filed on May 17, 2017, provisional application No. 62/443,766, filed on Jan. 8, 2017.

(51) Int. Cl.

| | |
|---|---|
| ***C07K 7/00*** | (2006.01) |
| ***C07K 5/12*** | (2006.01) |
| ***A61K 38/07*** | (2006.01) |
| ***A61K 38/12*** | (2006.01) |
| ***A61K 39/385*** | (2006.01) |
| ***A61K 47/64*** | (2017.01) |
| ***C07K 14/47*** | (2006.01) |
| ***C07K 5/117*** | (2006.01) |
| ***C07K 7/06*** | (2006.01) |
| ***C07K 7/64*** | (2006.01) |
| ***C12N 5/16*** | (2006.01) |
| ***G01N 33/68*** | (2006.01) |
| ***A61P 25/28*** | (2006.01) |
| ***C07K 16/18*** | (2006.01) |
| ***C07K 5/083*** | (2006.01) |
| ***C07K 5/087*** | (2006.01) |
| ***C07K 5/09*** | (2006.01) |
| ***C07K 5/093*** | (2006.01) |
| ***C07K 5/097*** | (2006.01) |
| ***C07K 5/113*** | (2006.01) |
| *A61K 39/00* | (2006.01) |
| *A61K 51/08* | (2006.01) |
| *A61K 49/18* | (2006.01) |
| *A61K 45/00* | (2006.01) |
| *A61K 39/395* | (2006.01) |
| *A61K 38/05* | (2006.01) |
| *A61K 51/10* | (2006.01) |
| *A61K 47/68* | (2017.01) |
| *A61K 38/08* | (2019.01) |
| *A61K 39/39* | (2006.01) |
| *A61K 45/06* | (2006.01) |
| *A61K 47/69* | (2017.01) |
| *A61L 31/10* | (2006.01) |
| *A61L 27/34* | (2006.01) |
| *A61L 29/16* | (2006.01) |
| *A61L 31/16* | (2006.01) |
| *A61L 29/08* | (2006.01) |
| *A61L 27/22* | (2006.01) |
| *G01N 33/50* | (2006.01) |
| *C07K 5/103* | (2006.01) |
| *C07K 14/435* | (2006.01) |
| *C12N 5/10* | (2006.01) |
| *C07K 7/08* | (2006.01) |

(52) U.S. Cl.

CPC .. *C07K 2317/624* (2013.01); *C07K 2317/626* (2013.01); *C07K 2317/70* (2013.01); *C07K 2317/76* (2013.01); *C07K 2317/92* (2013.01); *C07K 2317/94* (2013.01); *C07K 2319/00* (2013.01); *C12N 5/10* (2013.01); *G01N 33/5058* (2013.01); *G01N 2333/4709* (2013.01); *G01N 2800/28* (2013.01); *G01N 2800/2821* (2013.01); *G01N 2800/387* (2013.01)

(56) References Cited

U.S. PATENT DOCUMENTS

| | | | | |
|---|---|---|---|---|
| 5,593,846 | A | 1/1997 | Schenk et al. | |
| 5,770,429 | A | 6/1998 | Lonberg et al. | |
| 5,814,014 | A | 9/1998 | Elsberry et al. | |
| 6,043,283 | A | 3/2000 | Giulian | |
| 6,071,493 | A | 6/2000 | Giulian | |
| 6,114,598 | A | 9/2000 | Kucherlapati et al. | |
| 6,150,584 | A | 11/2000 | Kucherlapati et al. | |
| 6,319,498 | B1 | 11/2001 | Findeis et al. | |
| 6,451,544 | B2 | 9/2002 | Giulian | |
| 6,475,742 | B2 | 11/2002 | Giulian | |
| 6,475,745 | B1 | 11/2002 | Giulian | |
| 6,875,434 | B1 | 4/2005 | Schenk | |
| 6,890,535 | B1 | 5/2005 | Schenk | |
| 6,913,745 | B1 | 7/2005 | Schenk | |
| 6,923,964 | B1 | 8/2005 | Schenk | |
| 6,936,252 | B2 | 8/2005 | Gilbert et al. | |
| 7,012,061 | B1 | 3/2006 | Reiss et al. | |
| 7,179,892 | B2 | 2/2007 | Basi et al. | |
| 7,189,819 | B2 | 3/2007 | Basi et al. | |
| 7,256,273 | B2 | 8/2007 | Basi et al. | |
| 7,288,523 | B2 * | 10/2007 | Nordstedt | C07K 5/0808 514/17.8 |
| 7,314,974 | B2 | 1/2008 | Cao et al. | |
| 7,575,880 | B1 | 8/2009 | Schenk | |
| 7,582,733 | B2 | 9/2009 | Basi et al. | |
| 7,588,766 | B1 | 9/2009 | Schenk | |
| 7,625,560 | B2 | 12/2009 | Basi et al. | |
| 7,700,751 | B2 | 4/2010 | Basi et al. | |
| 7,790,856 | B2 | 9/2010 | Schenk | |
| 7,794,719 | B2 * | 9/2010 | Bardroff | A61P 25/14 530/388.1 |
| 7,871,615 | B2 | 1/2011 | Basi et al. | |
| 7,893,214 | B2 | 2/2011 | Schenk | |
| 7,932,048 | B2 | 4/2011 | Mendez | |
| 7,964,192 | B1 | 6/2011 | Schenk | |
| 7,977,316 | B2 | 7/2011 | Schenk | |
| 8,003,097 | B2 | 8/2011 | Schroeter et al. | |
| 8,034,339 | B2 | 10/2011 | Schenk | |
| 8,124,081 | B2 | 2/2012 | Schenk | |
| 8,128,928 | B2 | 3/2012 | Basi et al. | |
| 8,216,577 | B2 * | 7/2012 | Bardroff | A61K 39/0007 530/388.1 |
| 8,329,886 | B2 * | 12/2012 | Bardroff | A61P 25/00 536/23.53 |
| 8,613,920 | B2 | 12/2013 | Lieberburg et al. | |
| 8,613,931 | B2 | 12/2013 | Mandler et al. | |
| 8,623,365 | B2 | 1/2014 | Davies | |
| 8,784,810 | B2 | 7/2014 | Lieberburg et al. | |
| 8,916,165 | B2 | 12/2014 | Basi et al. | |
| 9,051,363 | B2 | 6/2015 | Basi et al. | |
| 9,067,981 | B1 | 6/2015 | Basi et al. | |
| 9,084,832 | B2 | 7/2015 | Nordström et al. | |
| 9,216,217 | B2 * | 12/2015 | Cashman | C07K 16/18 |
| 9,221,812 | B2 | 12/2015 | Kroth et al. | |
| 9,334,303 | B2 | 5/2016 | Mediannikov et al. | |
| 9,493,496 | B2 | 11/2016 | Geng et al. | |
| 9,535,076 | B2 | 1/2017 | Kayed et al. | |
| 9,644,025 | B2 | 5/2017 | Black et al. | |
| 9,849,165 | B2 * | 12/2017 | Cashman | A61K 39/0005 |
| 10,501,733 | B2 | 12/2019 | King et al. | |
| 2001/0016326 | A1 | 8/2001 | Giulian | |
| 2001/0016327 | A1 | 8/2001 | Giulian | |
| 2004/0116337 | A1 | 6/2004 | Kapurniotu et al. | |
| 2005/0169925 | A1 * | 8/2005 | Bardroff | A61P 25/00 530/388.26 |
| 2005/0267029 | A1 | 12/2005 | Ancsin et al. | |
| 2007/0110750 | A1 | 5/2007 | Glabe et al. | |
| 2008/0107649 | A1 | 5/2008 | Zurbriggen | |

(56) References Cited

U.S. PATENT DOCUMENTS

| | | | | |
|---|---|---|---|---|
| 2008/0299111 | A1 | 12/2008 | Delacourte et al. | |
| 2009/0246191 | A1 | 10/2009 | O'Nuallain et al. | |
| 2010/0104504 | A1 | 4/2010 | Echeverria Moran | |
| 2010/0172907 | A1* | 7/2010 | Bardroff | A61P 25/14<br>435/254.2 |
| 2011/0171243 | A1 | 7/2011 | Mandler et al. | |
| 2012/0047601 | A1 | 2/2012 | Scheller | |
| 2012/0225478 | A1* | 9/2012 | Bardroff | A61P 25/16<br>536/23.53 |
| 2012/0328605 | A1 | 12/2012 | Larocque et al. | |
| 2013/0084283 | A1* | 4/2013 | Cashman | A61P 25/28<br>424/133.1 |
| 2013/0136747 | A1* | 5/2013 | Bardroff | A61P 25/28<br>435/7.1 |
| 2013/0252901 | A1 | 9/2013 | Mediannikov et al. | |
| 2015/0105344 | A1 | 4/2015 | Geng et al. | |
| 2015/0322143 | A1 | 11/2015 | Kayed | |
| 2016/0195548 | A1 | 7/2016 | Sarasa Barrio | |
| 2016/0228522 | A1* | 8/2016 | Cashman | A61K 39/0005 |
| 2017/0021020 | A1 | 1/2017 | Bollyky et al. | |
| 2018/0030429 | A1* | 2/2018 | King | C12N 9/88 |
| 2018/0125920 | A1* | 5/2018 | Cashman | C12N 5/16 |
| 2018/0319856 | A1* | 11/2018 | Cashman | C07K 14/4711 |
| 2018/0330045 | A1* | 11/2018 | Plotkin | G16B 15/20 |
| 2018/0346534 | A1* | 12/2018 | Cashman | G01N 33/6896 |
| 2018/0346535 | A1* | 12/2018 | Cashman | C07K 5/1021 |
| 2019/0151401 | A1* | 5/2019 | Cashman | A61K 38/07 |

FOREIGN PATENT DOCUMENTS

| | | | |
|---|---|---|---|
| CN | 102112488 | A | 6/2011 |
| CN | 102209730 | A | 10/2011 |
| CN | 102858796 | A | 1/2013 |
| CN | 102869680 | A | 1/2013 |
| EP | 1676859 | A1 | 7/2006 |
| EP | 2377860 | A1 | 10/2011 |
| EP | 2511296 | A1 | 10/2012 |
| JP | 2003-503312 | A5 | 1/2003 |
| JP | 2004-526693 | A | 9/2004 |
| JP | 2006-513259 | A | 4/2006 |
| JP | 2010-505415 | A | 2/2010 |
| JP | 2011-504360 | A | 2/2011 |
| JP | 2011504360 | A | 2/2011 |
| JP | 2011-057582 | A | 3/2011 |
| JP | 2011-522841 | A | 8/2011 |
| JP | 2011-526885 | A | 10/2011 |
| JP | 2012-524023 | A | 10/2012 |
| JP | 2012524023 | A | 10/2012 |
| JP | 2013-500941 | A | 1/2013 |
| JP | 2013500941 | A | 1/2013 |
| JP | 2013-524774 | A | 6/2013 |
| JP | 2013-537424 | A | 10/2013 |
| JP | 2013537424 | A | 10/2013 |
| JP | 2014-516357 | A | 7/2014 |
| JP | 2016-501870 | A | 1/2016 |
| WO | 88/09336 | A1 | 5/1988 |
| WO | 90/14387 | A1 | 5/1990 |
| WO | 91/17271 | A1 | 5/1991 |
| WO | 92/01047 | A1 | 7/1991 |
| WO | 96/14831 | A1 | 11/1994 |
| WO | 95/17211 | A1 | 12/1994 |
| WO | 1995/006477 | A1 | 3/1995 |
| WO | 95/34323 | A2 | 6/1995 |
| WO | 96/06627 | A1 | 7/1995 |
| WO | 01/62801 | A2 | 2/2001 |
| WO | 2001/39796 | A2 | 6/2001 |
| WO | 2001062801 | A2 | 8/2001 |
| WO | 02/064734 | A2 | 8/2002 |
| WO | 2003/070760 | A2 | 2/2003 |
| WO | 2004/058239 | A1 | 7/2003 |
| WO | 2003/070760 | A2 | 8/2003 |
| WO | 2003070760 | A2 | 8/2003 |
| WO | 2004/013172 | A2 | 2/2004 |
| WO | 2004/029629 | A1 | 4/2004 |
| WO | 2004/071408 | A2 | 8/2004 |
| WO | 2006/066089 | A1 | 12/2005 |
| WO | 2006/069718 | A1 | 7/2006 |
| WO | 2006/095041 | A1 | 9/2006 |
| WO | 2006125324 | A1 | 11/2006 |
| WO | 2007/068429 | A1 | 12/2006 |
| WO | 2007/059000 | A2 | 5/2007 |
| WO | 2008/060364 | A2 | 5/2008 |
| WO | 2008/011348 | A2 | 7/2008 |
| WO | 2008/088983 | A1 | 7/2008 |
| WO | 2008088983 | A1 | 7/2008 |
| WO | 2008/156621 | A1 | 12/2008 |
| WO | 2008/156622 | A1 | 12/2008 |
| WO | 2009086539 | A2 | 12/2008 |
| WO | 2009/048537 | A2 | 4/2009 |
| WO | 2009/048538 | A2 | 4/2009 |
| WO | 2009/052439 | A2 | 4/2009 |
| WO | 2009/065054 | | 5/2009 |
| WO | 2009143489 | A2 | 11/2009 |
| WO | 2009/149486 | A2 | 12/2009 |
| WO | 2009/149487 | A2 | 12/2009 |
| WO | 2009149487 | A2 | 12/2009 |
| WO | 2010/002251 | A1 | 1/2010 |
| WO | 2010002251 | A1 | 1/2010 |
| WO | 2010/040209 | A1 | 4/2010 |
| WO | 2010119704 | A1 | 10/2010 |
| WO | 2010/128139 | A1 | 11/2010 |
| WO | 2011016238 | A1 | 2/2011 |
| WO | 2011/033046 | A1 | 3/2011 |
| WO | 2011/104696 | A1 | 9/2011 |
| WO | 2011/106885 | | 9/2011 |
| WO | 2012/104824 | A1 | 8/2012 |
| WO | 2002/096937 | A2 | 12/2012 |
| WO | 2013/020723 | | 2/2013 |
| WO | 2013/071267 | A1 | 5/2013 |
| WO | 2013071267 | A1 | 5/2013 |
| WO | 2013/164357 | A1 | 11/2013 |
| WO | 2014/031697 | A2 | 2/2014 |
| WO | 2014/161875 | A1 | 4/2014 |
| WO | 2016/082729 | A1 | 6/2014 |
| WO | 2015/017900 | A1 | 2/2015 |
| WO | 2015031698 | A1 | 3/2015 |
| WO | 2015/113169 | | 9/2015 |
| WO | 2017/079831 | A1 | 5/2017 |
| WO | 2017/079833 | A1 | 5/2017 |
| WO | 2017/079835 | A1 | 5/2017 |
| WO | 2017/079836 | A1 | 5/2017 |
| WO | 2018/014126 | A1 | 1/2018 |
| WO | 2019/014768 | A1 | 1/2019 |

OTHER PUBLICATIONS

Arai et al. Angew. Chem. Int. Ed., 2014; 53:8236-8239.*

Dhawan et al., Pharma. Sci. Encyc. Drug. Discov.Dev. Man. 2010, retrieved from the website: onlinelibrary.wiley.com/doi/epdf/10.1002/9780470571224.pse436 on Mar. 12, 2021.*

Alsalahat, PhD Dissertation, 2012, School of Pharmacy and Pharmaceutical Sciencies, University of Manchester.*

Tjernberg et al. J. Biol. Chem. 1996; 271:8545-8548.*

Simms, PhD Disseratation, Dalhousie University, Apr. 2015.*

Giulian et al..J. Biol. Chem., 1998; 273:29719-29726.*

Roy, PhD Dissertation, Department of Chemistry, University of Calgary, Calgary, 2010.*

Zola, Stuart M. et al. "A Behavioral Task Predicts Conversion to Mild Cognitive Impairment and Alzheimer's Disease." American Journal of Alzheimer's Disease & Other Dementias. 28(2) 179-184 (2012).

Lu, J.X. et al. "Molecular Structure of Beta-Amyloid Fibrils in Alzheimer's Disease Brain Tissue" Cell vol. 154(6) p. 1257 (2013).

Xiao, Y. et al. A Beta (1-42) Fibril Structure Illuminates Self-Recognition and Replication of Amyloid in Alzheimer's Disease. Nat.Struct.Mol.Biol. vol. 22(6) p. 499-505 (2015).

Petkova, A. et al. Experimental Constraints on Quaternary Structure in Alzheimer's Beta-Amyloid Fibrils Biochemistry. vol. 45 p. 498 (2006).

Giulian, D. "The HHQK domain of β-amyloid provides a structural basis for the immunopathology of Alzheimer's disease." J. Biol. Chem. 1998, 273(45), 29719-26.

(56) References Cited

OTHER PUBLICATIONS

Winkler, K. "Competition of Aβ amyloid peptide and apolipoprotein E for receptor-mediated endocytosis." J. Lipid Res. 1999, 40(3), 447-55.
Crespi, Gabriela A. N. et al. "Molecular basis for mid-region amyloid-b capture by leading Alzheimer's disease immunotherapies." Scientific Reports. 5 : 9649, 2015.
Hilser, Vincent J. et al. "Structure-based calculation of the equilibrium folding pathway of proteins. correlation with hydrogen exchange protection factors." J. Mol. Biol., 262:756-772, 1996.
Cohen, Samuel I. A. et al. Proliferation of amyloid-β42 aggregates occurs through a secondary nucleation mechanism. Proc. Natl.l Acad. Sci. USA, 110(24):9758-9763, 2013.
Sormanni, Pietro et al. The camsol method of rational design of protein mutants with enhanced solubility. Journal of Molecular Biology, 427(2):478-490, 2015.
Blacker, Deborah et al. Reliability and Validity of NINCDS-ADRDA Criteria for Alzheimer's Disease The National Institute of Mental Health Genetics Initiative. Arch Neurol. 51(12):1198-1204 (1994).
Hamley, I.W. "PEG-Peptide Conjugates" 2014; 15, 1543-1559; dx.doi.org/10.1021/bm500246w.
Roberts, MJ. et al. "Chemistry for peptide and protein PEGylation" (2014) 64: 116-127.
Karlin, Samuel et al. Methods for assessing the statistical significance of molecular sequence features by using general scoring schemes. Proc. Natl. Acad. Sci. U.S.A. 87:2264-2268.
Karlin, Samuel et al. Applications and statistics for multiple high-scoring segments in molecular sequences. 1993, Proc. Natl. Acad. Sci. U.S.A. 90:5873-5877.
Altschul et al. Basic Local Alignment Search Tool. 1990, J. Mol. Biol. 215:403.
Altschul et al. Gapped BLAST and PSI-BLAST: a new generation of protein database search programs. 1997, Nucleic Acids Res. 25:3389-3402.
Myers et al. Optimal alignments in linear space. 1988, Cabios 4:11-17.
Kohler G. et al. Continuous cultures of fused cells secreting antibody of predefined specificity. Nature 256:495-497, 1975.
Ward et al. Binding activities of a repertoire of single immunoglobulin variable domains secreted from *Escherichia coli*. Nature 41:544-546 1989.
Riechmann et al. Reshaping human antibodies for therapy. Nature, 332:323-327, 1988.
Wang, J. et al. Effects of an amyloid-beta 1-42 oligomers antibody screened from a phage display library in APP/PS1 transgenic mice. Brain Res. Mar. 15, 2016, vol. 1635, pp. 169-179.
Yu YZ, et al. Strikingly reduced amyloid burden and improved behavioral performance in Alzheimer's disease mice immunized with recombinant chimeric vaccines by hexavalent foldable A_1-15 fused to toxin-derived carrier proteins. J Alzheimers Dis 2014;41:243-60.
Wang, HC, et al. Peripherally administered sera antibodies recognizing amyloid-beta oligomers mitigate Alzheimer's disease-like pathology and cognitive decline in aged 3xTg-AD mice, Vaccine 2016.
Langer, Franziska et al. Soluble A{beta} Seeds are Potent Inducers of Cerebral {beta}-Amyloid Deposition. J Neurosci 31: 41. 14488-14495 Oct. 2011.
Fritschi, Sarah K. et al. Highly potent soluble amyloid-β seeds in human Alzheimer brain but not cerebrospinal fluid. Brain: a journal of neurology 137: Pt 11. 2909-2915 Nov. 2014.
Paganetti PA et al. Amyloid precursor protein truncated at any of the γ-secretase sites is not cleaved to β-amyloid, J.Neurosci. Res. 46 (1996) 283-293.
Kahlert H. et al. Characterization of major allergens of Parietaria officinalis. Int Arch Allergy Immunol Feb. 1996; 109 (2):141-9.
Kaplan Johanne. Harnessing the Power of Precision Medicine to Conquer Neurodegenerative Diseases. Presented Sep. 14, 2016.

Goni, Fernando et al. Production of Monoclonal Antibodies to Pathologic β-sheet Oligomeric Conformers in Neurodegenerative Diseases. Scientific Reports. Aug. 2017. 7:9881.
Wilcock, Donna M. et al. Passive immunotherapy against Aβ in aged APP-transgenic mice reverses cognitive deficits and depletes parenchymal amyloid deposits in spite of increased vascular amyloid and microhemorrhage. Journal of Neuroinflammation, 2004, 1:24.
Racke, Margaret M. et al. Exacerbation of Cerebral Amyloid Angiopathy-Associated Microhemorrhage in Amyloid Precursor Protein Transgenic Mice by Immunotherapy is Dependent on Antibody Recognition of Deposited Forms of Amyloid β. The Journal of Neuroscience, Jan. 19, 2005. 25(3):629-636.
Pfeifer M. et al. Cerebral Hemorrhage After Passive Anti-Aβ Immunotherapy. Science. vol. 298 Nov. 15, 2002.
Wilcock, Donna M. et al. Deglycosylated Anti-Amyloid-β Antibodies Eliminate Cognitive Deficits and Reduce Parenchymal Amyloid with Minimal Vascular Consequences in Aged Amyloid Precursor Protein Transgenic Mice. Journal of Neuroscience. May 17, 2006. 26(20):5340-5346.
Kaplan, Johanne. Targeting of Toxic Amyloid-Beta Oligomer Species by Monoclonal Antibody PMN310: Precision Drug Design for Alzheimer's Disease. Abstract and slides presented at the Alzheimer's Association International Conference Jul. 17, 2017 in London, England.
Aprile_Francesco A. Selective targeting of primary and secondary nucleation pathways in Aβ42 aggregation using a rational antibody scanning method. Science Advances. Jun. 21, 2017. 2017;3: E1700488.
NCBI Blast: Protein Sequence (8 letters). CDR-H1 GYSFTSYW. Retrieved on Feb. 8, 2017 from blast.ncbi.nlm.nih.gov/Blast.cgi>>.
NCBI Blast: Protein Sequence (9 letters). CDR-H2 VHPGRGVST. Retrieved on Feb. 8, 2017 from blast.ncbi.nlm.nih.gov/Blast.cgi>>.
NCBI Blast: Protein Sequence (13 letters). CDR-H3 SRSHGNTYWFFDV. Retrieved on Feb. 8, 2017 from //blast.ncbi.nlm.nih.gov/Blast.cgi>>.
NCBI Blast: Protein Sequence (11 letters). CDR-L1 QSIVHSNGNTY. Retrieved on Feb. 8, 2017 from blast.ncbi.nlm.nih.gov/Blast.cgi>>.
NCBI Blast: Protein Sequence (3 letters). CDR-L2 KVS. Retrieved on Feb. 8, 2017 from blast.ncbi.nlm.nih.gov/Blast.cgi>>.
NCBI Blast: Protein Sequence (9 letters). CDR-L3 FQGSHVPFT. Retrieved on Feb. 8, 2017 from blast.ncbi.nlm.nih.gov/Blast.cgi>>.
Sardar Sinha, Maitrayee et al. Alzheimer's disease pathology propagetion by exosomes containing toxic amyloid-beta oligomers. Acta Neuropathologica. Jun. 2018.
Giulian, D. et al. The HHQK Domain of b-Amyloid Provides a Structural Basis for the Immunopathology of Alzheimer's Disease. The Journal of Biological Chemistry. vol. 273, No. 45, issue of Nov. 6, pp. 29719-29726, 1998.
Windler K. et al. Competition of Aβ amyloid peptide and apolipoprotein E for receptor-mediated endocytosis. Journal of Lipid Research, vol. 40, 1999.
Kaplan, Johanne. Pre-Clinical: Basic Therapeutics—Targeting Amyloid or TAU. Presented at the Alzheimer's International Conference Jul. 2007.
Aprile, Francesco A. et al. Selective targeting of primary and secondary nucleation pathways in Aβ42 aggregation using a rational antibody scanning method. Molecular Neuroscience, Science Advances; 2017, 3. Jun. 21, 2017.
Silverman, Judith et al. Novel Amyloid-β Oligomer-Specific Epitopes: A Hypothesis Drivin Aproach to Alzheimer's Immunotherapeutics. Abstract presented at the Alzheimer's Association International Conference Jul. 2016.
Gibbs, Ebrima et al. Rational generation of Aβ oligomer-specific antibodies through computational identification of conformational epitopes. Abstract presented at the Alzheimer's Association International Conference on Jul. 2017.
Plotkin, Steven et al. A computational Method to Predict Disease-Specific Epitopes in Aβ, and its Application to Oligomer-Selective Antibodies for Alzheimer's Immunotherapy. Presented Jul. 27, 2016.
Tjernberg L.O., et al. Arrest of Amyloid Fibril Formation by a Pentapeptide Ligand. The Journal of Biological Chemistry. vol. 271, No. 15, Issue of Apr. 12, pp. 8545-8548, 1996.

(56) References Cited

OTHER PUBLICATIONS

Hollta, Mikko et al. Evaluating Amyloid-β Oligomers in Cerebrospinal Fluid as a Biomarker for Alzheimer's Disease. Plos One. Jun. 2013, vol. 8, Issue 6.
Plotkin, Steven et al. Achieving the optimal profile for Alzheimer's immunotherapy: Rational generation of antibodies specific for toxic Aβ oligomers. Abstract presented at the American Academy of Neurology conference on Apr. 2017.
Lesne, S. E. et al. Brain amyloid-beta oligomers in ageing and Alzheimer's disease. Brain 136, 1383-1398, 2013.
Ferreira, S. T., et al. Soluble amyloid-b oligomers as synaptotoxins leading to cognitive impairment in Alzheimer's disease. Frontiers in Cellular Neuroscience 9, (2015).
Figueiredo, C. P. et al. Memantine rescues transient cognitive impairment caused by high-molecular-weight abeta oligomers but not the persistent impairment induced by low-molecular-weight oligomers. J Neurosci 33, 9626-9634, 2013.
Cashman, Neil et al. Epitope Identification of Toxic Propagating Strains of Aβ Oligomers. presented at PRION 2017, the International Conference Deciphering Neurodegenerative Disorders in Edinburgh, Scottland on May 25, 2017.
Krafft, Grant et al. ACU-193: A candidate therapeutic antibody that selectively targets soluble beta-amyloid oligomers, Alzheimer's & Dementia: The Journal of the Alzheimer's Association, Jan. 1, 2013, pp. P326-P326.
Hoogerhout, Peter et al. A Cyclic Undecamer Peptide Mimics a Turn in Folded Alzheimer Amyloid β and Elicits Antibodies against Oligomeric and Fibrillar Amyloid and Plaques, Plos One, vol. 6, No. 4, Jan. 1, 2011, pp. e19110-e19110.
Arai, Tadamasa et al. A Cyclic KLVFF-Derived Peptide Aggregation Inhibitor Induces the Formation of Less-Toxic Off-Pathway Amyloid-β Oligomers, Chembiochem, vol. 15, No. 17, Sep. 26, 2014, pp. 2577-2583.
Cho, Patricia Y. et al. A Cyclic Peptide Mimic of the β-Amyloid Binding Domain on Transthyretin, ACS Chemical Neuroscience, vol. 6, No. 5, Mar. 9, 2015, pp. 778-789.
Liu, Cong et al. Characteristics of Amyloid-Related Oligomers Revealed by Crystal Structures of Macrocyclic β-Sheet Mimics, Journal of the American Chemical Society, vol. 133, No. 17, May 4, 2011, pp. 6736-6744.
Perez De La Lastra, J. M. et al. Epitope mapping of 10 monoclonal antibodies against the pig analogue of human membrane cofactor protein (MCP), Immunology, vol. 96, No. 4, Apr. 1, 1999, pp. 663-670.
Huse, William D. et al. Generation of a Large Combinatorial Library of the Immunoglobulin Repertoire on Phage Lambda. Science, vol. 246, 1275-1291 (1989).
Roder. J.C. et al. The EBV-Hybridoma Technique. Methods in Enzymology. vol. 21 (1986) (Abstract provided).
Foote, Jefferson et al. Antibody Framework Residues Affecting the Confirmation of the Hypervariable Loops. J. Mol Biol, 224:487-499 (1992).
McCafferty, John et al. Phage antibodies: filamentous phage displaying antibody variable domains. Nature, 348:552-554 (1990).
Carter, Paul et al. Engineering antibodies for imaging and therapy. Current Opinion in Biotechnology, 8:449-454 (1997).
Kozbor, Danuta et al. The production of monoclonal antibodies from human lymphocytes. Immunnology Today, vol. 4, No. 3, pp. 72-79 (1983).
Tapiola, Tero et al. Cerebrospinal Fluid B-Amyloid 42 and Tau Proteins as Biomarkers of Alzheimer-Type Pathologic Changes in the Brain. 66(3), 382-389 (2009).
Bard, Frederique et al. Epitope and isotype specificities of antibodies to β-amyloid peptide for protection against Alzheimer's disease-like neuropathology. Proc. Natl. Acad. Sci. USA, 100(4):2023-2028 (2003).
Fukumoto, H. et al. High-molecular-weight beta-amyloid oligomers are elevated in cerebrospinal fluid of Alzheimer patients. The FASED Journal 24, 2716-2726 (2010).
Rudikoff et al., Single amino acid substitution altering antigen-binding specificity. Proc Natl Acad Sci USA 1982; 79:1979-1983.
MacCallum et al., Antibody-antigen Interactions: Contact Analysis and Binding Site Topography. J. Mol. Biol., 1996;262:732-745.
Pascalis et al., Grafting of "Abbreviated" Complementarity-Determining Regions Containing Specificity-Determining Regions Containing Specificity-Determining Residues Essential for Ligand Contact to Engineer a Less Immunogenic Humanized Monoclonal Antibody. The Journal of Immunology, 2002; 169: 3076-3084.
Casset et al., A peptide mimetic of an anti-CD4 monoclonal antibody by rational design. BBRC, 2003; 307:198-205.
Vajdos et al., Comprehensive Functional Maps of the Antigen-binding Site of an Anti-ErbB2 Antibody Obtained with Shotgun Scanning Mutagenesis. J. Mol. Med., 2002; 320: 415-428.
Holm et al., Functional mapping and single chain construction of the anti-cytokeratin 8 monoclonal antibody TS1. Mol. Immunol., 2007; 44: 1075-1084.
Chen et al., Selection and Analysis of an Optimized Anti-VEGF Antibody: Crystal Structure of an Affinity-matured Fab in Complex with Antigen. J. Mol. Bio., 1999; 293: 865-881.
Wu et al., Humanization of a Murine Monoclonal Antibody by Simultaneousl Optimization of Framework and CDR Residues. J. Mol. Biol., 1999; 294: 151-162.
Burgess et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue. J of Cell Bio. 1990, 111:2129-2138.
Bowie et al., Deciphering the Message in Protein Sequences: Tikerance to Amino Acid Substitutions. Science, 1990, 247:1306-1310.
Pawson et al., Assembly of Cell Regulatory Systems Through Protein Interaction Domains. Science, 2003, 300:445-452.
Alaoui-Ismaili et al., Design of second generation therapeutic recombinant bone morphogenetic proteins. Cytokine Growth Factor Rev. 2009; 20:501-507.
Guo et al., Protein tolerance to random amino acid change. PNAS 2004; 101:9205-9210.
Hillen, Heinz et al. Generation and Therapeutic Efficacy of Highly Oligomer-Specific beta-Amyloid Antibodies, The Journal of Neuroscience, Society for Neuroscience, US, vol. 30, No. 31, Aug. 4, 2010, pp. 10369-10379.
Hoogerhout, Peter et al. A Cyclic Undecamer Peptide Mimics a Turn in Folded Alzheimer Amyloid 13 and Elicits Antibodies against Oligomeric and Fibrillar Amyloid and Plaques, Plos One, vol. 6, No. 4, Jan. 1, 2011, pp. e19110-e19110.
Krafft, Grant et al. ACU-193: A candidate therapeutic antibody that selectively targets soluble beta-amyloid bligomers Alzheimer's & Dementia: The Journal of the Alzheimer's Association, Jan. 1, 2013, pp. 326-326.
Gibbs, E. et al. Rational Generation of Aβ oligomer-specific antibodies through computational identification of conformational epitopes, Mar. 2017, Abstract from Neurodegenerative Diseases, vol. 17, Supplement 1.
Gibbs, E. et al. Rational Generation of Aβ oligomer-specific antibodies through computational identification of conformational epitopes, Apr. 22-28, 2017, Poster Presentation AAN 2017 Annual Meeting in Boston Massachusetts.
Plotkin, S. et al. Achieving the optimal profile for Alzheimer's immunotherapy: Rational generation of antibodies specific for toxic Aβ oligomers (P6.084), Apr. 17, 2017, Poster from Neurology, vol. 88, 16 Supplement; P6.084.
Kaplan, J. et al. Targeting of Toxic Amyloid-Beta Oligomer Species by Monoclonal Antibody PMN310: Precision Drug Design for Alzheimer's Disease, 2017, Abstract from Alzheimer's & Dementia. 13. P592. 10.1016/j.jalz.2017.07.225.
Cashman, N. Translating the Disruptive Science of Protein Misfolding to Neurodegenerative Disease, Sep. 28, 2017, Neurosciences, Oral Presentation.
Pham J.D. et al. "A Fibril-Like Assembly of Oligomers of a Peptide Derived from B-Amyloid" Journal of the American Chemical Society (2014) 136(6): 12682-12690.

(56) References Cited

OTHER PUBLICATIONS

Tjernberg L.O. et al. "Assembling amyloid fibrils from designed structures containing a significant amyloid B-peptide fragment" Biochemical Journal (2002) 366(1): 343-351.
CAS RN 1347591-03-0, STN Entry Date Dec. 2, 2011.
CAS RN 176390-22-0 (1996), STN Entry Date May 17, 1996.
CAS RN 176390-11-7, STN Entry Date May 17, 1996.
Manea et al. "Antibody Recognition and Conformational Flexibility of a Plaque-Specific B-Amyloid Epitope Modulated by Non-native Peptide Flanking Regions" Journal of Medicinal Chemistry (2008) 51(5): 1150-1161.
Ghosh, A. K. and Osswald, H. L., "BACE1 (B-Secretase) Inhibitors for the Treatment of Alzheimer's Disease", Chem Soc Rev. Oct. 7, 2014; 43(19): 6765-6813.
Hefti, F. et al. "The case for soluble AB oligomers as a drug target in Alzheimer's disease", Trends in Pharmacological Sciences, May 2013, vol. 34, No. 5, 261-266.
Neves V. et al. "Antibody approaches to treat brain illnesses", Trends in Biotechnology, 2015, 1-31.
Birks, J. "Cholinesterase inhibitors for Alzheimer's disease", Cochrane Database Syst Rev. Jan. 25, 2006; (1): CD005593.
Walsh D. M. and Selkoe D. J., "AB Oligomers—a decade of discovery", Journal of Neurochemistry, 2007, 101, 1172-1184.
Brown S. D. et al., "Twenty-one Genome Sequences from *Pseudomonas* Species and 19 Genome Sequences from Diverse Bacteria Isolated from the Rhizosphere and Endosphere of Populus deltoides"; J. Banteriol, 2012, 194: 5991-5993.
Lai et al. (ECO:00003131EMBL:KCZ50447.1), mentioned at p. 17 of the Office Action dated Dec. 21, 2021, in U.S. Appl. No. 17/006,219.

* cited by examiner

Formula (I)

Cyclo(CGHHQKG) (SEQ ID NO: 2)

Chemical Formula: $C_{30}H_{45}N_{13}O_8S$
Molecular Weight: 747.83

Formula (II)

Cyclo(C-PEG2-HHQKG) (SEQ ID NO: 3)

Chemical Formula: $C_{34}H_{53}N_{13}O_{10}S$
Molecular Weight: 835.93

Formula (III) Cyclo(CGHHQK-PEG2) (SEQ ID NO: 4)

Chemical Formula: $C_{34}H_{53}N_{13}O_{10}S$
Molecular Weight: 835.93

Formula (IV)

Cyclo(CGQKLVG) (SEQ ID NO: 6)

Chemical Formula: $C_{29}H_{51}N_9O_8S$
Molecular Weight: 685.84

Formula (V)

Cyclo(C-PEG2-QKLVG) (SEQ ID NO: 7)

Chemical Formula: $C_{33}H_{59}N_9O_{10}S$
Molecular Weight: 773.94

Formula (VI) Cyclo(CGQKLV-PEG2) (SEQ ID NO: 8)

Chemical Formula: $C_{33}H_{59}N_9O_{10}S$
Molecular Weight: 773.94

Formula (VII)

Cyclo(CGHDSGG) (SEQ ID NO: 10)

Chemical Formula: $C_{22}H_{31}N_9O_{10}S$
Molecular Weight: 613.60

Formula (VIII)

Cyclo(C-PEG2-HDSGG) (SEQ ID NO: 11)

Chemical Formula: $C_{26}H_{39}N_9O_{12}S$
Molecular Weight: 701.71

Formula (IX)

Cyclo(CGHDSG-PEG2) (SEQ ID NO: 12)

Chemical Formula: $C_{26}H_{39}N_9O_{12}S$
Molecular Weight: 701.71

FIG. 2A Positive control (6E10 antibody) — Aβ Plaque — Cadaveric AD brain

FIG. 2B Cell nuclei — 303-25-1B4

FIG. 2C Cell nuclei — Clone 301-17 (12G11)

FIG. 2D Cell nuclei — Clone 305-62 (8H10)

Recombinant Antibody 301-17 (IgG1)

#, different from Vehicle (p < 0.05)
*, different from AβO (p < 0.05)

*, different from Vehicle (p < 0.0001)
#, different from AβO (p < 0.0001)

Recombinant Antibody 301-17 (IgG1)

*Different from vehicle control ($p < 0.05$)
Different from AbO ($p < 0.05$)

*, different from Vehicle (p<0,05)
#, different from AbO (p<0,05)
AbO = Abeta oligomers

*, different from Vehicle (p<0,05)
#, different from AbO (p<0,05)
AbO = Abeta oligomers Recombinant antibody 301-17 (IgG1)

*Different from vehicle control ($p < 0.05$)
Different from AbO ($p < 0.05$)

*Different from vehicle control ($p < 0.05$)
Different from AbO ($p < 0.05$)

COMPOSITIONS COMPRISING CYCLIC PEPTIDES DERIVED FROM AN A-BETA PEPTIDE

RELATED APPLICATIONS

This application is a continuation of U.S. patent application Ser. No. 16/148,601 (now issued as U.S. Pat. No. 10,751,382B2), filed Oct. 1, 2018, which is a continuation of U.S. patent application Ser. No. 15/808,842 (now abandoned), filed Nov. 9, 2017; which is a continuation in part of PCT/CA2016/051300, filed Nov. 9, 2016; PCT/CA2016/051305, filed Nov. 9, 2016; PCT/CA2016/051303, filed Nov. 9, 2016; and PCT/CA2017/050866, filed Jul. 18, 2017; and which also claims priority to U.S. provisional applications Ser. No. 62/443,766, filed Jan. 8, 2017; 62/507,633, filed May 17, 2017; and 62/507,587, filed May 17, 2017. All of these applications are incorporated herein by reference in their entirety.

INCORPORATION OF SEQUENCE LISTING

A computer readable form of the Sequence Listing "7685-P53259US04_RevisedSequenceListing.txt" (111,429 bytes), submitted via EFS-WEB and created on Mar. 4, 2021, is herein incorporated by reference.

FIELD

The present disclosure relates to methods for treating or inhibiting amyloid-beta oligomer related diseases and particularly to methods exploiting the use of conformational A-beta epitopes that were predicted and shown to be selectively accessible in A-beta oligomers.

BACKGROUND

Amyloid-beta (A-beta), which exists as a 36-43 amino acid peptide, is a product released from amyloid precursor protein (APP) by the enzymes β and γ secretase. In AD patients, A-beta can be present in soluble monomers, insoluble fibrils and soluble oligomers. In monomer form, A-beta exists as a predominantly unstructured polypeptide chain. In fibril form, A-beta can aggregate into distinct morphologies, often referred to as strains. Several of these structures have been determined by solid-state NMR.

For, example, structures for several strains of fibrils are available in the Protein Data Bank (PDB), a crystallographic database of atomic resolution three dimensional structural data, including a 3-fold symmetric Aβ structure (PDB entry, 2M4J); a two-fold symmetric structure of Aβ-40 monomers (PDB entry 2LMN), and a single-chain, parallel in-register structure of Aβ-42 monomers (PDB entry 2MXU).

The structure of 2M4J is reported in Lu et al [8], and the structure of 2MXU is reported in Xiao et al [9]. The structure of 2LMN is reported in Petkova et al [10].

A-beta oligomers have been shown to kill cell lines and neurons in culture and block a critical synaptic activity that subserves memory, referred to as long term potentiation (LTP), in slice cultures and living animals.

The structure of the oligomer has not been determined to date. Moreover, NMR and other evidence indicates that the oligomer exists not in a single well-defined structure, but in a conformationally-plastic, malleable structural ensemble with limited regularity. Moreover, the concentration of toxic oligomer species is far below either that of the monomer or fibril (estimates vary but are on the order of 1000-fold below or more), making this target elusive.

Antibodies that bind A-beta have been described.

WO2009048538A2 titled USE OF ANTI-AMYLOID ANTIBODY IN OCULAR DISEASES discloses chimeric antibodies that recognize one or more binding sites on A-beta and are useful for the treatment for ocular diseases.

U.S. Pat. No. 9,221,812B2 titled COMPOUNDS FOR THE TREATMENT OF DISEASES ASSOCIATED WITH AMYLOID OR AMYLOID-LIKE PROTEINS describes pharmaceutical compositions and discontinuous antibodies that bind A-beta including an epitope between amino acid residues 12 to 24 for the treatment of amyloid-related diseases.

WO2003070760A2 titled ANTI-AMYLOID BETA ANTIBODIES AND THEIR USE discloses antibodies that recognize an A-beta discontinuous epitope, wherein the first region comprises the amino acid sequence AEFRHDSGY (SEQ ID NO: 203) or a fragment thereof and wherein the second region comprises the amino acid sequence VHHQKLVFFAEDVG (SEQ ID NO: 204) or a fragment thereof.

US20110171243A1 titled COMPOUNDS TREATING AMYLOIDOSES discloses a peptide mimotope capable of inducing the in vivo formation of antibodies that bind HQKLVF (SEQ ID NO: 17) and/or HQKLVFFAED (SEQ ID NO: 13), and its use.

WO2008088983A1 and WO2001062801A2 disclose a pegylated antibody fragment that binds A-beta amino acids 13-28 (HHQKLVFFAEDVGSNK) (SEQ ID NO: 14) and its use in treating A-beta related diseases.

WO2009149487A2 titled COMPOUNDS FOR TREATING SYMPTOMS ASSOCIATED WITH PARKINSON'S DISEASE describes compounds comprising a peptide having binding capacity for an antibody specific for an A-beta epitope such as EVHHQKL (SEQ ID NO: 205), HQKLVF (SEQ ID NO: 17) and HQKLVFFAED (SEQ ID NO: 13).

The HHQK (SEQ ID NO: 1) domain is described as involved in plaque induction of neurotoxicity in human microglia, as described in Giulian D et al. [11] and Winkler et al. [12]. Non-antibody therapeutic agents that bind HHQK (SEQ ID NO: 1) have been disclosed for the treatment of protein folding diseases (US20150105344A1, WO2006125324A1).

WO2010128139A1 titled BIOMARKERS AND METHODS FOR DIAGNOSING ALZHEIMER'S DISEASE AND/OR MILD COGNITIVE IMPAIRMENT discloses a diagnostic method for Alzheimer's disease through assessing levels of antibodies capable of binding pGlu A-Beta in a given subject's body fluid.

WO2011033046A1 titled NOVEL ASSAY FOR THE DETECTION OF AMYLOID BETA PEPTIDES discloses a method for detection of A-beta (1-40).

WO2014161875A1 titled METHOD FOR DETECTING Aβ-SPECIFIC ANTIBODIES IN A BIOLOGICAL SAMPLE discloses a method for detecting A-beta-specific antibodies using A-beta variants for the diagnosis of Alzheimer's disease.

U.S. Pat. Nos. 5,766,846; 5,837,672; and 5,593,846 (which are incorporated herein by reference) describe the production of murine monoclonal antibodies to the central domain of the Aβ peptide. WO 01/62801 describes antibodies that bind A-beta between amino acids 13-28. WO2004071408 discloses humanized antibodies. WO2008088983A1 describes an antibody fragment that binds amyloid beta (A-beta) peptide and is covalently attached to one or more molecules of polyethylene glycol (PEG), the antibody fragment specifically binding human A-beta peptide between amino acid positions 13-28. Solanezumab and Crenezumab bind amino acids 16-26 on A-beta. Crenezumab interacts with the monomer, oligomer and fibril. Midregion antibodies, including solanezumab (picomolar affinity) and crenezumab (nanomolar affinity), appear to preferentially bind monomeric A-beta [16].

Antibodies that preferentially or selectively bind A-beta oligomers and inhibit A-beta oligomerization are desirable for therapeutic intervention.

SUMMARY

Described herein and in International Application WO2017/079833 filed Nov. 9, 2016 and International Application PCT/CA2017/050866 filed Jul. 18, 2017 each of which are incorporated herein by reference are conformational epitopes in A-beta comprising and/or consisting of residues HHQK (SEQ ID NO: 1) or a part thereof, and antibodies thereto. Also described herein and in International application WO2017/079835 filed Nov. 9, 2016, incorporated herein by reference, are conformational epitopes in A-beta comprising and/or consisting of residues QKLV (SEQ ID NO: 5) or a part thereof, and antibodies thereto. Further described herein and in International application WO2017/079831 filed Nov. 9, 2016 incorporated herein by reference, are conformational epitopes in A-beta comprising and/or consisting of residues HDSG (SEQ ID NO: 9) or a part thereof, and antibodies thereto.

Unlike some other A-beta antibodies, antibodies raised to immunogenic cyclic conformations of the epitopes HHQK (SEQ ID NO: 1), QKLV (SEQ ID NO: 5) or HDSG (SEQ ID NO: 9) specifically bound oligomeric A-beta in preference to monomeric or fibril forms (see for example FIG. 8). As demonstrated herein, antibodies that specifically and/or selectively bind said conformational epitopes inhibit and/or prevent neurotoxicity and memory deficits induced by soluble A-beta oligomers in a mouse model.

Injection of oligomer forms of A-beta into the brains of mice causes a neurological deficit that can be assessed in a memory-behavior test called novel object recognition as described further below. Normal mice exposed to an object remember the familiar object when re-exposed to it and spend more time exploring a newly introduced object. In contrast, A-beta oligomer-injected mice lose the ability to discriminate between known and novel objects and spend equivalent amounts of time exploring both. Results obtained in this assay showed that administration to mice of an antibody that selectively binds cyclo(CGHHQKG) (SEQ ID NO: 2), cyclo(CGQKLVG) (SEQ ID NO: 6) or cyclo (CGHDSGG) (SEQ ID NO:10) inhibited the loss of short-term memory formation caused by injection of soluble A-beta oligomers.

Accordingly, provided herein are methods for treating or preventing a disease or condition associated with and/or induced by soluble A-beta oligomer comprising administering to a subject in need thereof a compound, immunogen, composition, antibody, nucleic acid or cell described herein.

In an embodiment, the method of treating or preventing a disease or condition associated with and/or induced by soluble A-beta oligomer comprises administering to a subject in need thereof: an isolated conformation specific and/or selective antibody or binding fragment thereof that specifically and/or selectively binds to a cyclic compound comprising an A-beta peptide having a sequence of QKL, HQK, KLV, HHQK (SEQ ID NO: 1), QKLV (SEQ ID NO: 5) or HDSG (SEQ ID NO: 9), they cyclic compound optionally having a sequence of SEQ ID NO: 2, 3, 4, 6, 7, 8, 10, 11 or 12; an immunogen comprising a cyclic compound comprising an A-beta peptide having a sequence of QKL, HQK, KLV, HHQK (SEQ ID NO: 1), QKLV (SEQ ID NO: 5) or HDSG (SEQ ID NO: 9); a cell expressing said antibody or binding fragment thereof; or a nucleic acid encoding said antibody or binding fragment thereof.

In an embodiment, the disease or condition associated with and/or induced by soluble A-beta oligomer is cognitive deficits, optionally loss of short term memory formation.

In an embodiment, the disease or condition associated with and/or induced by soluble soluble A-beta oligomer A-beta is Alzheimer's disease (AD).

In an embodiment, the treatment is prophylactic treatment. For example in an embodiment, the antibody is administered to a subject with a predisposition to developing a disease or condition associated with and/or induced by soluble A-beta oligomer or showing an early sign of AD pathology. For example, AD pathology develops first in the perirhinal and enthorinal cortex before the hippocampus.

In an embodiment, the disease or condition is perirhinal cortex dysfunction or pathology. In another embodiment, the disease or condition is enthorinal cortex dysfunction or pathology.

In an embodiment, the disease or condition is associated with and/or induced by soluble A-beta 1-42 oligomer.

In an aspect, an immunogen described herein is administered for treating or preventing a disease or condition associated with and/or induced by soluble A-beta oligomer.

In an aspect the immunogen comprises a cyclic compound which comprises: an A-beta peptide the peptide comprising HQK and up to 6 A-beta contiguous residues, and a linker, wherein the linker is covalently coupled to the A-beta peptide N-terminus residue and the A-beta C-terminus residue.

In another aspect, the cyclic compound comprises: an A-beta peptide, the A-beta peptide comprising QKL and up to 8, 7 or 6 A-beta residues, and a linker, wherein the linker is covalently coupled to the A-beta peptide N-terminus residue and the A-beta C-terminus residue.

In yet another aspect, the cyclic compound comprises: an A-beta peptide, the A-beta peptide comprising HDSG (SEQ ID NO: 9) and up to 8, 7 or 6 A-beta residues, and a linker, wherein the linker is covalently coupled to the A-beta peptide N-terminus residue and the A-beta C-terminus residue.

In an embodiment, the A-beta peptide is selected from a peptide having a sequence of any one of SEQ ID NOS: 1, 5, 10, 202 or a part thereof.

In another embodiment, the cyclic compound is cyclic peptide.

In another embodiment, the linker comprises or consists of 1-8 amino acids, optionally, 3, 4 or 5, and/or equivalently functioning molecules and/or one or more functionalizable moieties.

In another embodiment, the linker amino acids are selected from A and G, and/or wherein the functionalizable moiety is C. In another embodiment, the linker comprises or consists of amino acids GCG or CGC.

In another embodiment, the linker comprises a PEG molecule.

In another embodiment, the cyclic compound is selected from the structures in FIG. 1A-FIG. 1C.

An aspect includes an immunogen comprising the cyclic compound optionally for treating or preventing a disease or condition associated with and/or induced by soluble A-beta oligomer. In an embodiment, the compound is coupled to a carrier protein or immunogenicity enhancing agent.

In another embodiment, the carrier protein is bovine serum albumin (BSA) or the immunogenicity-enhancing agent is keyhole Keyhole Limpet Haemocyanin (KLH).

In another aspect a composition comprising the immunogen described herein is administered.

In an embodiment, the composition described herein, further comprises an adjuvant.

In another embodiment, the adjuvant is aluminum phosphate or aluminum hydroxide.

In another aspect an isolated conformation specific and/or selective antibody that specifically and/or selectively binds to an A-beta peptide having a sequence of HQK, HHQK (SEQ ID NO: 1), HQKL (SEQ ID NO: 202), QKL, QKLV (SEQ ID NO: 5), HDSG (SEQ ID NO: 9) or a related epitope sequence presented in a cyclic compound described herein, is provided. In embodiments said antibody is administered in a method described herein.

In another embodiment, the antibody selectively binds to a cyclic compound comprising HHQK (SEQ ID NO: 1), QKLV (SEQ ID NO: 5), HDSG (SEQ ID NO: 9) over a corresponding linear peptide, optionally wherein the antibody is at least 2 fold, 3 fold, at least 5 fold, at least 10 fold, at least 20 fold, at least 30 fold, at least 40 fold, at least 50 fold, at least 100 fold, at least 500 fold, at least 1000 fold more selective for the cyclic compound over the corresponding linear compound.

In another embodiment, the antibody selectively binds A-beta oligomer over A-beta monomer and/or A-beta fibril.

In another embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold, at least 1000 fold more selective for A-beta oligomer over A-beta monomer and/or A-beta fibril.

In another embodiment, the antibody does not specifically and/or selectively bind a linear peptide comprising sequence HHQK (SEQ ID NO: 1) or a related epitope, optionally wherein the sequence of the linear peptide is a linear version of a cyclic compound used to raise the antibody, optionally a linear peptide having a sequence as set forth in SEQ ID NO: 2.

In another embodiment, the antibody does not specifically and/or selectively bind a linear peptide comprising sequence QKLV (SEQ ID NO: 5) or a related epitope, optionally wherein the sequence of the linear peptide is a linear version of a cyclic compound used to raise the antibody, optionally a linear peptide having a sequence CGQKLVG (SEQ ID NO: 6).

In another embodiment, the antibody does not specifically and/or selectively bind a linear peptide comprising sequence HDSG (SEQ ID NO: 9) or a related epitope, optionally wherein the sequence of the linear peptide is a linear version of a cyclic compound used to raise the antibody, optionally a linear peptide having a sequence SEQ ID NO: 10.

In another embodiment, the antibody lacks or has negligible binding to A-beta monomer and/or A-beta fibril plaques in situ.

In another embodiment, the antibody is a monoclonal antibody or a polyclonal antibody.

In another embodiment, the antibody is a humanized antibody, optionally comprising a variable domain described in Table 12 or 13.

In another embodiment, the antibody is an antibody binding fragment selected from Fab, Fab', F(ab')2, scFv, dsFv, ds-scFv, dimers, nanobodies, minibodies, diabodies, and multimers thereof.

In an embodiment, the antibody comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences in Table 9 A to I or Table 15.

For example, in an embodiment, the antibody comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences: SEQ ID NOs: 20-25, SEQ ID NOs: 26-31, SEQ ID NOs:32-37, SEQ ID NOs: 32-34 and 38-40; SEQ ID NOs:41-46; SEQ ID NOs:47-52, SEQ ID NOs:53-58, SEQ ID NOs:59-64, SEQ ID NOs:59-61 and 65-67; SEQ ID NOs:59-61 and 68-70; SEQ ID NOs:71-76, SEQ ID NOs:71-73 and 77-79; SEQ ID NOs: 71-73 and 80-82 and SEQ ID NOs: 185-190.

In an embodiment, the antibody or binding fragment comprises a heavy chain variable region comprising: i) an amino acid sequence of a heavy chain variable sequence as set forth in Table 10; ii) an amino acid sequence with at least 50%, at least 60%, at least 70%, at least 80% or at least 90% sequence identity to said heavy chain variable sequence set out in Table 10, 12 or 13, wherein the CDR sequences are the corresponding CDRs as set forth in Table 9, or iii) a conservatively substituted amino acid sequence i) wherein the CDR sequences are the corresponding CDRs as set forth in Table 9; and a light chain variable region comprising i) an amino acid sequence of a light chain variable sequence as set forth in Table 10, ii) an amino acid sequence with at least 50%, at least 60%, at least 70%, at least 80%, at least 90% sequence identity to said light chain variable sequence as set out in Table 10, 12 or 13, wherein the CDR sequences are the corresponding CDRs as set forth in Table 9, or iii) a conservatively substituted amino acid sequence i) wherein the CDR sequences a are the corresponding CDRs as set forth in Table 9.

In an embodiment a combination of antibodies and/or binding fragments thereof described herein are administered.

In another embodiment, the antibody of binding fragment competes for binding to human A-beta with an antibody comprising the CDR sequence set (e.g. CDR H1-3 and CDR L1-3) as recited herein, for example in Table 9, the variable sequence set (e.g. Heavy chain and light chain variable regions, for example in Table 10, 12 or 13) and/or antibody produced by the hybridoma cell line deposited under the provisions of the Budapest Treaty with the American Type Culture Collection (ATCC®) 10801 University Blvd., Manassas, Va., 20110-2209, USA on Jul. 19, 2017 and given the Accession number PTA-124318.

In yet another aspect an immunoconjugate comprising the antibody or binding fragment described herein and a detectable label or cytotoxic agent. In embodiments, said immunoconjugate is administered in methods provided herein.

An aspect includes a composition comprising the antibody or binding fragment described herein, or the immunoconjugate described herein as well as combinations of two or more antibodies or binding fragments thereof described herein, optionally with a diluent. In embodiments, the composition is administered in methods provided herein In yet a further aspect a nucleic acid molecule encoding a proteinaceous portion of the compound or immunogen described herein, the antibody described herein or proteinaceous immunoconjugates described herein. In some embodiments the nucleic acid molecule is administered in methods provided herein.

In another aspect a vector comprising the nucleic acid described herein is provided and optionally administered in methods provided herein.

In another aspect a cell expressing an antibody or binding fragment described herein is provided. In embodiments, said cell is administered in methods provided herein.

Also provided is a hybridoma cell line deposited under the provisions of the Budapest Treaty with the American Type Culture Collection (ATCC®) 10801 University Blvd., Manassas, Va., 20110-2209, USA on Jul. 19, 2017 and given the Accession number PTA-124318.

An aspect includes a kit comprising the compound described herein, the immunogen described herein, an antibody described herein, the immunoconjugate described herein, the composition described herein, the nucleic acid molecule described herein, the vector described herein or the cell described herein optionally for use in treating or preventing a disease or condition associated with and/or induced by soluble A-beta oligomer.

An aspect includes a method of making the antibody described herein, comprising administering the compound or immunogen described herein or a composition comprising said compound or immunogen to a subject and isolating antibody and/or cells expressing antibody specific or selective for the compound or immunogen administered and/or A-beta oligomers, optionally lacking or having negligible binding to a linear peptide comprising the A-beta peptide and/or lacking or having negligible plaque binding for use in treating or preventing a disease or condition associated with and/or induced by soluble A-beta oligomer.

An aspect includes a method of determining if a biological sample comprises A-beta, the method comprising:

a. contacting the biological sample with an antibody described herein or the immunoconjugate described herein; and
b. detecting the presence of any antibody complex.

In another embodiment, the method comprises:

a. contacting the sample with the antibody described herein or the immunoconjugate described herein that is specific and/or selective for A-beta oligomers under conditions permissive for forming an antibody: A-beta oligomer complex; and
b. detecting the presence of any complex;

the presence of detectable complex is indicative that the sample may contain A-beta oligomer; and c. optionally treating the subject.

In another embodiment, the amount of complex is measured.

In another embodiment, the sample comprises brain tissue or an extract thereof, whole blood, plasma, serum and/or CSF.

In another embodiment, the sample is a human sample.

In another embodiment, the sample is compared to a control, optionally a previous sample.

In another embodiment, the level of A-beta is detected by SPR.

An aspect includes a method of measuring a level of A-beta oligomers in a subject, the method comprising administering to a subject at risk or suspected of having or having AD, an immunoconjugate comprising an antibody described herein wherein the antibody is conjugated to a detectable label; and detecting the label, optionally quantitatively detecting the label.

In an embodiment, the label is a positron emitting radionuclide.

An aspect includes a method of inducing an immune response for treating or preventing a disease or condition related with and/or induced by soluble A-beta oligomer in a subject, comprising administering to the subject a compound or combination of compounds described herein, optionally a cyclic compound comprising HQK or HHQK (SEQ ID NO: 1), QKL, QKLV (SEQ ID NO: 5) or HDSG (SEQ ID NO: 9) or a related epitope peptide sequence, an immunogen and/or composition comprising said compound or said immunogen; and optionally isolating cells and/or antibodies that specifically or selectively bind the A-beta peptide in the compound or immunogen administered.

An aspect includes a method of inhibiting A-beta oligomer propagation for treating or preventing a disease or condition associated with and/or induced by soluble A-beta oligomer, the method comprising contacting a cell or tissue expressing A-beta with or administering to a subject in need thereof an effective amount of an A-beta oligomer specific or selective antibody, binding fragment or immunoconjugate described herein.

Another aspect includes a method of treating AD and/or other A-beta amyloid associated and/or induced diseases and conditions, the method comprising administering to a subject in need thereof i) an effective amount of an antibody or immunoconjugate described herein, optionally an A-beta oligomer specific or selective antibody, or a pharmaceutical composition comprising said antibody; 2) administering an isolated cyclic compound comprising HQK, HHQK (SEQ ID NO: 1), QKL, QKLV (SEQ ID NO: 5) or HDSG (SE ID NO: 9) or a related epitope sequence or immunogen or pharmaceutical composition comprising said cyclic compound, or 3) a nucleic acid or vector comprising a nucleic acid encoding the antibody of 1 or the immunogen of 2, to a subject in need thereof.

In an embodiment, a biological sample from the subject to be treated is assessed for the presence or levels of A-beta using an antibody described herein.

In another embodiment, more than one antibody or immunogen is administered.

In another embodiment, the antibody, immunoconjugate, immunogen, composition or nucleic acid or vector is administered directly to the brain or other portion of the CNS.

In another embodiment, the composition is a pharmaceutical composition comprising the compound or immunogen in admixture with a pharmaceutically acceptable, diluent or carrier.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

DETAILED DESCRIPTION OF THE DISCLOSURE

Figure 1A:
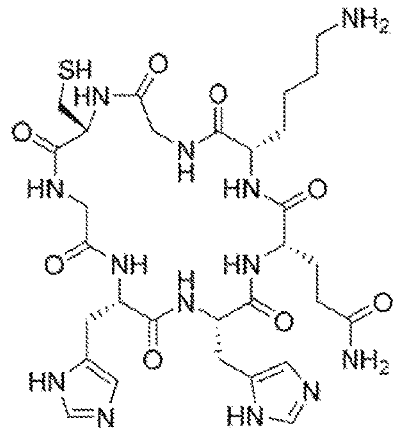
FIG. 1A: Schematic representations of cyclic peptides containing the epitope residues HHQK (SEQ ID NO: 1), including the cyclic peptide CGHHQKG (SEQ ID NO: 2) with circular peptide bond, the cyclic peptide C-PEG2-HHQKG (SEQ ID NO: 3) with PEG2 linker between the C and H residues, and the cyclic peptide CGHHQK-PEG2 (SEQ ID NO: 4) with PEG2 linker between the K and C residues.
Figure 1A:
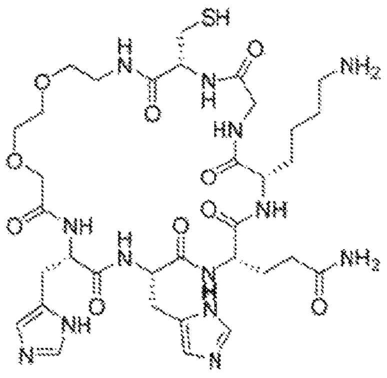
Figure 1A:
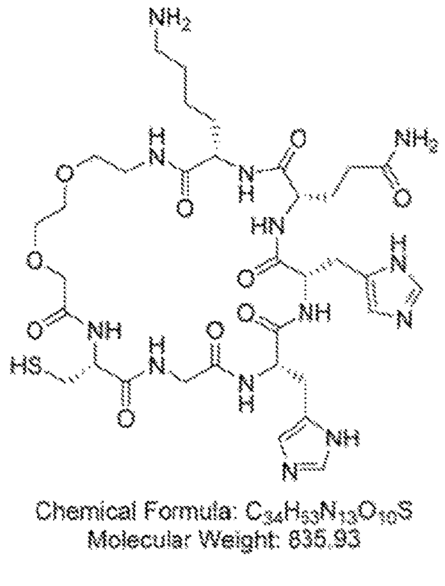
Figure 1B:
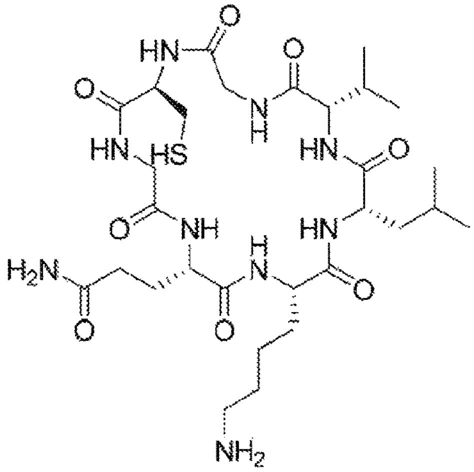
FIG. 1B: is a schematic showing a series of cyclic compounds comprising QKLV (SEQ ID NO: 5).
Figure 1B:
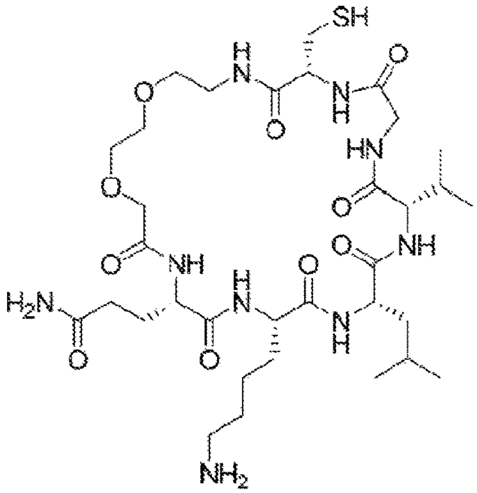
Figure 1B:
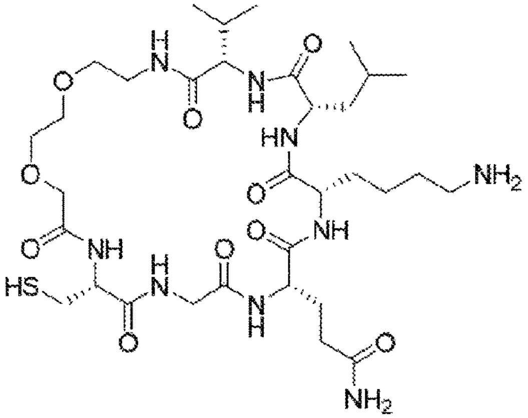
Figure 1C:
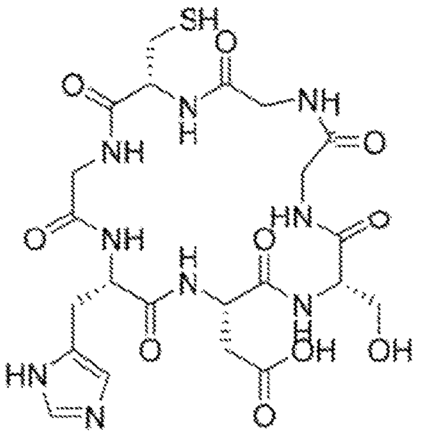
FIG. 1C: Schematic representations of cyclic peptides comprising HDSG (SEQ ID NO: 9), including the cyclic peptide with circular peptide bond, the cyclic peptide with PEG2 linker between the G and C residues, and the cyclic peptide with PEG2 linker between the C and H residues.
Figure 1C:
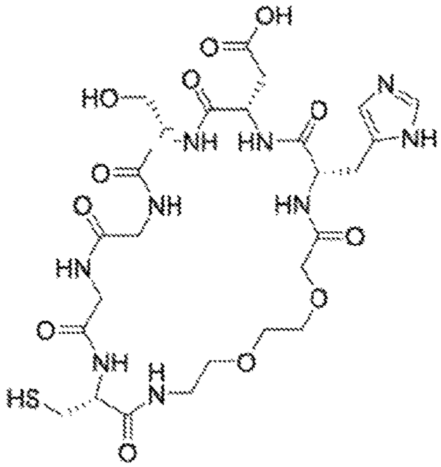
Figure 1C:
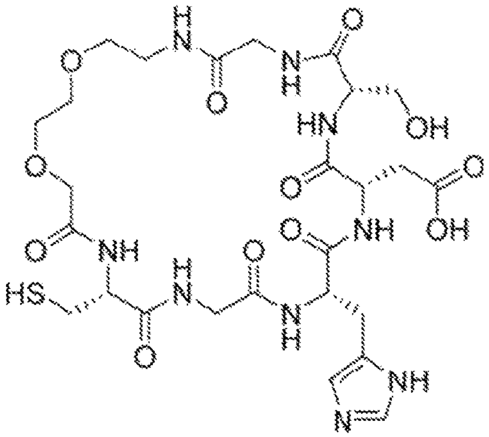
Figure 2A:
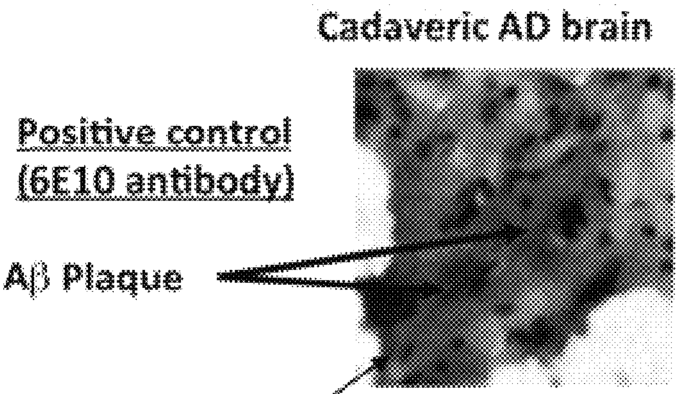
FIG. 2A: Immunohistochemical staining of plaque from cadaveric AD brain using 6E10 positive control antibody.
Figure 2B:
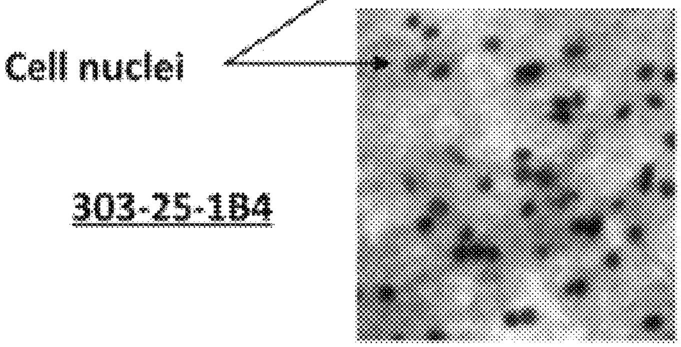
FIG. 2B: Immunohistochemical staining of plaque from cadaveric AD brain using an antibody (303-25-1B4) raised against cyclo(CGHDSGG) (SEQ ID NO:10).
Figure 2C:
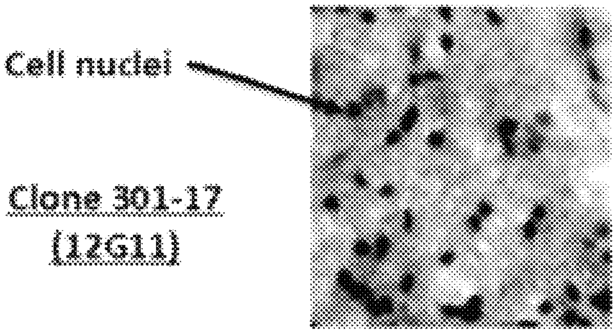
FIG. 2C: Immunohistochemical staining of plaque from cadaveric AD brain using purified monoclonal antibody (301-17, 12G11) raised against cyclo(CGHHQKG) (SEQ ID NO: 2).
Figure 2D:
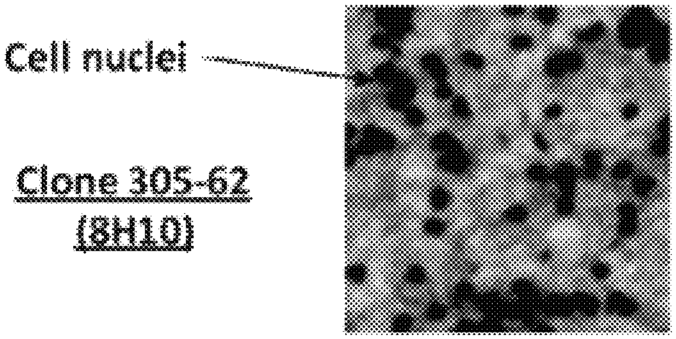
FIG. 2D: Immunohistochemical staining of plaque from cadaveric AD brain using purified antibody (305-62, 8H10) raised against cyclo(CGQKLVG) (SEQ ID NO: 6).

Provided herein are methods for using antibodies, immunotherapeutic compositions and methods which target epitopes preferentially accessible in toxic oligomeric species of A-beta, including oligomeric species associated with Alzheimer's disease. A region in A-beta has been identified that may be specifically and/or selectively accessible to antibody binding in oligomeric species of A-beta.

Generation of oligomer-specific or oligomer selective antibodies was accomplished through the identification of targets on A-beta peptide that are not present, or present to a lesser degree, on either the monomer and/or fibril. Oligomer-specific epitopes need not differ in primary sequence from the corresponding segment in the monomer or fibril, however they would be conformationally distinct in the context of the oligomer. That is, they would present a distinct conformation in terms of backbone and/or side-chain orientation in the oligomer that would not be present (or would be unfavourable) in the monomer and/or fibril.

Antibodies raised to linear peptide regions tend not to be selective for oligomer, and thus bind to monomer as well.

As described herein, to develop antibodies that may be selective for oligomeric forms of A-beta, the inventors sought to identify regions of A-beta sequence that are prone to disruption in the context of the fibril, and that may be exposed as well on the surface of the oligomer.

The inventors have identified region predicted to be prone to disruption in the context of the fibril. The inventors designed cyclic compounds comprising the identified target region to satisfy criteria of an alternate conformation such as a different curvature profile vs residue index, higher exposed surface area, and/or did not readily align by root mean squared deviation (RMSD) to either the linear or fibril ensembles. HQK, HHQK (SEQ ID NO: 1), HQKL (SEQ ID NO: 202), QKLV (SEQ ID NO: 5) and HDSG (SEQ ID NO: 9) were identified as regions prone to disruption and cyclic compounds were designed comprising the identified target regions.

As shown in the Examples, an immunogen comprising the cyclic compounds SEQ ID Nos: 2, 6 and 10 were used to produce monoclonal antibodies. Antibodies could be raised using a cyclic peptide comprising the target region, that selectively bound the cyclic peptide compared to a linear peptide of the same sequence (e.g. corresponding linear sequence). Experimental results are described and identify epitope-specific and conformationally selective antibodies that bind synthetic oligomer selectively compared to synthetic monomers. Further staining of AD brain tissue identified antibodies that show no or negligible plaque binding and in vitro studies found that the antibodies inhibited Aβ oligomer propagation and aggregation. Furthermore, antibody that selectively binds SEQ ID Nos: 2, 6 or 10 inhibits and/or prevents neurotoxicity and loss of memory formation induced by soluble A-beta oligomers in a mouse model.

I. Definitions

As used herein, the term ‘A-beta’ may alternately be referred to as ‘amyloid beta’, ‘amyloid D’, A-beta, A-beta or ‘Aβ’. Amyloid beta is a peptide of 36-43 amino acids and includes all wild-type and mutant forms of all species, particularly human A-beta. A-beta40 refers to the 40 amino acid form; A-beta42 refers to the 42 amino acid form, etc. The amino acid sequence of human wildtype A-beta42 is shown in SEQ ID NO: 19.

As used herein, the term “A-beta monomer” herein refers to any of the individual subunit forms of the A-beta (e.g. 1-40, 1-42, 1-43) peptide.

As used herein, the term “A-beta oligomer” herein refers to a plurality of any of the A-beta subunits wherein several (e.g. at least two) A-beta monomers are non-covalently aggregated in a conformationally-flexible, partially-ordered, three-dimensional globule of less than about 100, or more typically less than about 50 monomers. For example, an oligomer may contain 3 or 4 or 5 or more monomers. The term “A-beta oligomer” as used herein includes both synthetic A-beta oligomer and/or native A-beta oligomer. “Native A-beta oligomer” refers to A-beta oligomer formed in vivo, for example in the brain and CSF of a subject with AD.

As used herein, the term “A-beta fibril” refers to a molecular structure that comprises assemblies of non-covalently associated, individual A-beta peptides which show fibrillary structure under an electron microscope. The fibrillary structure is typically a “cross beta” structure; there is no theoretical upper limit on the size of multimers, and fibrils may comprise thousands or many thousands of monomers. Fibrils can aggregate by the thousands to form senile plaques, one of the primary pathological morphologies diagnostic of AD.

The term “HHQK (SEQ ID NO: 1)” means the amino acid sequence histidine, histidine, glutamine, lysine, as shown in SEQ ID NO: 1. Similarly HQK, HHQ, HHQKLV (SEQ ID NO: 8) HQKL (SEQ ID NO: 202) refers to the amino acid sequence identified by the 1-letter amino acid code. The term “QKLV (SEQ ID NO: 5)” means the amino acid sequence glutamine, lysine, leucine, and valine, as shown in SEQ ID NO: 5 and “HDSG (SEQ ID NO: 9)” means the amino acid sequence of histidine, aspartic acid, serine and glycine as shown in SEQ ID NO: 9. Depending on the context, the reference of the amino acid sequence can refer to a sequence in A-beta or an isolated peptide, such as the amino acid sequence of a cyclic compound.

The term “amino acid” includes all of the naturally occurring amino acids as well as modified L-amino acids. The atoms of the amino acid can include different isotopes. For example, the amino acids can comprise deuterium substituted for hydrogen nitrogen-15 substituted for nitrogen-14, and carbon-13 substituted for carbon-12 and other similar changes.

The term “antibody” as used herein is intended to include, monoclonal antibodies, polyclonal antibodies, single chain, veneered, humanized and other chimeric antibodies and binding fragments thereof, including for example a single chain Fab fragment, Fab'2 fragment or single chain Fv fragment. The antibody may be from recombinant sources and/or produced in animals such as rabbits, llamas, sharks etc. Also included are human antibodies that can be produced in transgenic animals or using biochemical techniques or can be isolated from a library such as a phage library. Humanized or other chimeric antibodies may include sequences from one or more than one isotype or class or species.

The phrase “isolated antibody” refers to antibody produced in vivo or in vitro that has been removed from the source that produced the antibody, for example, an animal, hybridoma or other cell line (such as recombinant insect, yeast or bacteria cells that produce antibody). The isolated antibody is optionally “purified”, which means at least: 80%, 85%, 90%, 95%, 98% or 99% purity.

The term “binding fragment” as used herein to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, dimers, nanobodies, minibodies, diabodies, and multimers thereof. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

The terms “IMGT numbering” or “ImMunoGeneTics database numbering”, which are recognized in the art, refer to a system of numbering amino acid residues which are more variable (i.e. hypervariable) than other amino acid residues in the heavy and light chain variable regions of an antibody, or antigen binding portion thereof.

When an antibody is said to bind to an epitope within specified residues, such as HHQK (SEQ ID NO: 1), what is meant is that the antibody specifically binds to a peptide or polypeptide containing the specified residues or a part thereof for example at least 1 residue or at least 2 residues, with a minimum affinity, and does not bind an unrelated sequence or unrelated sequence spatial orientation greater than for example an isotype control antibody. Such an antibody does not necessarily contact each residue of HHQK (SEQ ID NO: 1) (or a related epitope), and every single amino acid substitution or deletion within said epitope does not necessarily significantly affect and/or equally affect binding affinity.

When an antibody is said to selectively bind an epitope such as a conformational epitope, such as HHQK (SEQ ID NO: 1), what is meant is that the antibody preferentially binds one or more particular conformations containing the specified residues or a part thereof with greater affinity than it binds said residues in another conformation. For example, when an antibody is said to selectively bind a cyclopeptide comprising SEQ ID NO: 1, 5 or 9 or related epitope relative to a corresponding linear peptide, the antibody binds the cyclopeptide with at least a 2 fold greater affinity than it binds the linear peptide.

As used herein, the term "conformational epitope" refers to an epitope where the epitope amino acid sequence has a particular three-dimensional structure wherein at least an aspect of the three-dimensional structure not present or less likely to be present in a corresponding linear peptide is specifically and/or selectively recognized by the cognate antibody. The epitope e.g. HHQK (SEQ ID NO: 1), QKLV (SEQ ID NO: 5) or HDSG (SEQ ID NO: 9) may be partially or completely exposed on the molecular surface of oligomeric A-beta and partially or completely obscured from antibody recognition in monomeric or fibrillar plaque A-beta. Antibodies which specifically bind a conformation-specific epitope recognize the spatial arrangement of one or more of the amino acids of that conformation-specific epitope. For example, an HHQK (SEQ ID NO: 1) conformational epitope refers to an epitope of HHQK (SEQ ID NO: 1) that is recognized by antibodies selectively, for example at least 2 fold, 3 fold, 5 fold, 10 fold, 50 fold, 100 fold, 250 fold, 500 fold or 1000 fold or greater more selectivity as compared to antibodies raised using linear HHQK (SEQ ID NO: 1).

The term "related epitope" as used herein means at least two residues of HHQK (SEQ ID NO: 1), QKLV (SEQ ID NO: 5) or HDSG (SEQ ID NO: 9) that are antigenic when for example conjugated to KLH, optionally with respect to HHQK (SEQ ID NO: 1) sequences comprising HQK, and/or sequences comprising 1 2 or 3 amino acid residues in a A-beta N-terminal and/or 1 residue C-terminal to at least two residues of HHQK (SEQ ID NO: 1), for HDSG (SEQ ID NO: 9) 1 2 or 3 amino acid residues in a A-beta N-terminal and/or 1 2 or 3 amino acid residues in a A-beta C-terminal to HDSG (SEQ ID NO: 9) or for QKLV (SEQ ID NO: 5), comprising 1 2 or 3 amino acid residues in a A-beta C-terminal and/or 1 residue N-terminal to QKLV (SEQ ID NO: 5). For example HHQK (SEQ ID NO: 1) and HQKL (SEQ ID NO: 202) which share the subregion HQK were identified as regions prone to disorder in an A-beta fibril. HQK and HQKL (SEQ ID NO: 202) are accordingly related epitopes. Exemplary related epitopes can include epitopes whose sequences are shown in Table 8 (1). The related epitope is for example up to 6 A-beta residues.

The term "no or negligible plaque binding" or "lacks or has negligible plaque binding" as used herein with respect to an antibody means that the antibody does not show typical plaque morphology staining on immunohistochemistry (e.g. in situ) and the level of staining is comparable to or no more than 2 fold the level seen with an IgG negative (e.g. irrelevant) isotype control.

The term "Isolated peptide" refers to peptide that has been produced, for example, by recombinant or synthetic techniques, and removed from the source that produced the peptide, such as recombinant cells or residual peptide synthesis reactants. The isolated peptide is optionally "purified", which means at least: 80%, 85%, 90%, 95%, 98% or 99% purity and optionally pharmaceutical grade purity.

The term "detectable label" as used herein refers to moieties such as peptide sequences (such a myc tag, HA-tag, V5-tag or NE-tag), fluorescent proteins that can be appended or introduced into a peptide or compound described herein and which is capable of producing, either directly or indirectly, a detectable signal. For example, the label may be radio-opaque, positron-emitting radionuclide (for example for use in PET imaging), or a radioisotope, such as $^{3}H$, $^{13}N$, $^{14}C$, $^{18}F$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. The detectable label may be also detectable indirectly for example using secondary antibody.

The term "epitope" as commonly used means an antibody binding site, typically a polypeptide segment, in an antigen that is specifically recognized by the antibody. As used herein "epitope" can also refer to the amino acid sequences or part thereof identified on A-beta using the collective coordinates method described. For example an antibody generated against an isolated peptide corresponding to a cyclic compound comprising the identified target region HHQK SEQ ID NO: 1), recognizes part or all of said epitope sequence. An epitope is "accessible" in the context of the present specification when it is accessible to binding by an antibody.

The term "greater affinity" as used herein refers to a relative degree of antibody binding where an antibody X binds to target Y more strongly ($K_{on}$) and/or with a smaller dissociation constant ($K_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as $K_A$ equal to $1/K_D$ where $K_D$ is equal to $k_{on}/k_{off}$. The $ko_n$ and $k_{off}$ values can be measured using surface plasmon resonance technology, for example using a Molecular Affinity Screening System (MASS-1) (Sierra Sensors GmbH, Hamburg, Germany). An antibody that is selective for a conformation presented in a cyclic compound optional a cyclic peptide for example has a greater affinity for the cyclic compound (e.g. cyclic peptide) compared to a corresponding sequence in linear form (e.g. the sequence non-cyclized).

Also as used herein, the term "immunogenic" refers to substances that elicit the production of antibodies, activate T-cells and other reactive immune cells directed against an antigenic portion of the immunogen.

The term "corresponding linear compound" with regard to a cyclic compound refers to a compound, optionally a peptide, comprising or consisting of the same sequence or chemical moieties as the cyclic compound but in linear (i.e. non-cyclized) form, for example having properties as would be present in solution of a linear peptide. For example, the corresponding linear compound can be the synthesized peptide that is not cyclized.

As used herein "specifically binds" in reference to an antibody means that the antibody recognizes an epitope sequence and binds to its target antigen with a minimum affinity. For example a multivalent antibody binds its target with a $K_D$ of at least 1e-6, at least 1e-7, at least 1e-8, at least 1e-9, or at least 1e-10. Affinities greater than at least 1e-8 may be preferred. An antigen binding fragment such as Fab fragment comprising one variable domain, may bind its target with a 10 fold or 100 fold less affinity than a multivalent interaction with a non-fragmented antibody.

The term "selectively binds" as used herein with respect to an antibody that selectively binds a form of A-beta (e.g. fibril, monomer or oligomer) or a cyclic compound means that the antibody binds the form with at least 2 fold, at least 3 fold, or at least 5 fold, at least 10 fold, at least 100 fold, at least 250 fold, at least 500 fold or at least 1000 fold or more greater affinity. Accordingly an antibody that is more selective for a particular conformation (e.g. oligomer) preferentially binds the particular form of A-beta with at least 2 fold etc. greater affinity compared to another form and/or a linear peptide.

The term "linker" as used herein means a chemical moiety that can be covalently linked to the peptide comprising HHQK (SEQ ID NO: 1), optionally linked to HHQK (SEQ ID NO: 1) peptide N- and C-termini to produce a cyclic compound. The linker can comprise a spacer and/or one or more functionalizable moieties. The linker can be linked via the functionalizable moieties to a carrier protein or an immunogen enhancing agent such as keyhole limpet hemocyanin (KLH).

The term "spacer" as used herein means any preferably non-immunogenic or poorly immunogenic chemical moiety that can be covalently-linked directly or indirectly to a peptide N- and C-termini to produce a cyclic compound of longer length than the peptide itself, for example the spacer can be linked to the N- and C-termini of a peptide consisting of HHQK (SEQ ID NO: 1) to produce a cyclic compound of longer backbone length than the HHQK (SEQ ID NO: 1) sequence itself. That is, when cyclized the peptide with a spacer (for example of 3 amino acid residues) makes a larger closed circle than the peptide without a spacer. The spacer may include, but is not limited to, non-immunogenic moieties such as G, A, or PEG repeats. The spacer may comprise or be coupled to one or more functionalizing moieties, such as one or more cysteine (C) residues, which can be interspersed within the spacer or covalently linked to one or both ends of the spacer. Where a functionalizable moiety such as a C residue is covalently linked to one or more termini of the spacer, the spacer is indirectly covalently linked to the peptide. The spacer can also comprise the functionalizable moiety in a spacer residue as in the case where a biotin molecule is introduced into an amino acid residue.

The term "functionalizable moiety" as used herein refers to a chemical entity with a "functional group" which as used herein refers to a group of atoms or a single atom that will react with another group of atoms or a single atom (so called "complementary functional group") to form a chemical interaction between the two groups or atoms. In the case of cysteine, the functional group can be —SH which can be reacted to form a disulfide bond. Accordingly the linker can for example be CCC. The reaction with another group of atoms can be covalent or a strong non-covalent bond, for example as in the case as biotin-streptavidin bonds, which can have Kd~1e-14. A strong non-covalent bond as used herein means an interaction with a Kd of at least 1e-9, at least 1e-10, at least 1e-11, at least 1e-12, at least 1e-13 or at least 1e-14.

Proteins and/or other agents may be functionalized (e.g. coupled) to the cyclic compound, either to aid in immunogenicity, or to act as a probe in in vitro studies. For this purpose, any functionalizable moiety capable of reacting (e.g. making a covalent or non-covalent but strong bond) may be used. In one specific embodiment, the functionalizable moiety is a cysteine residue which is reacted to form a disulfide bond with an unpaired cysteine on a protein of interest, which can be, for example, an immunogenicity enhancing agent such as Keyhole limpet hemocyanin (KLH), or a carrier protein such as Bovine serum albumin (BSA) used for in vitro immunoblots or immunohistochemical assays.

The term "reacts with" as used herein generally means that there is a flow of electrons or a transfer of electrostatic charge resulting in the formation of a chemical interaction.

The term "animal" or "subject" as used herein includes all members of the animal kingdom including mammals, optionally including or excluding humans.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitution include:

Conservative Substitutions

| Type of Amino Acid | Substitutable Amino Acids |
|---|---|
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions·times·100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, word length=12 to obtain nucleotide sequences homologous to a nucleic acid molecules of the present application. BLAST protein searches can be performed with the XBLAST program parameters set, e.g., to score-50, word length=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

For antibodies, percentage sequence identities can be determined when antibody sequences maximally aligned by IMGT or other (e.g. Kabat numbering convention). After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

"Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/1), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage AD can be treated to prevent progression can be treated with a compound, antibody, immunogen, nucleic acid or composition described herein to prevent progression.

The term "administered" as used herein means administration of a therapeutically effective dose of a compound or composition of the disclosure to a cell or subject.

As used herein, the phrase "effective amount" means an amount effective, at dosages and for periods of time necessary to achieve a desired result. Effective amounts when administered to a subject may vary according to factors such as the disease state, age, sex, weight of the subject. Dosage regime may be adjusted to provide the optimum therapeutic response.

The term "pharmaceutically acceptable" means that the carrier, diluent, or excipient is compatible with the other components of the formulation and not substantially deleterious to the recipient thereof.

Compositions or methods "comprising" or "including" one or more recited elements may include other elements not specifically recited. For example, a composition that "comprises" or "includes" an antibody may contain the antibody alone or in combination with other ingredients.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The singular forms of the articles "a," "an," and "the" include plural references unless the context clearly dictates otherwise. For example, the term "a compound" or "at least one compound" can include a plurality of compounds, including mixtures thereof.

II. Methods

Conformation selective antibodies were raised to A-beta epitope sequences presented in a cyclic format as described herein. Said antibodies selectively bound synthetic and/or native oligomeric A-beta species compared to monomeric A-beta and A-beta fibril plaques. Further said antibodies were able to inhibit in vitro propagation of A-beta aggregation. In addition, as demonstrated in toxicity assays, said antibodies inhibited A-beta oligomer in vitro neural cell toxicity and prevented neurotoxicity and loss of memory formation induced by soluble A-beta oligomers in an in vivo mouse model. Several of the specific antibody sequences are described in PCT/CA2016/051300, filed Nov. 9, 2016; PCT/CA2016/051305, filed Nov. 9, 2016; PCT/CA2016/051303, filed Nov. 9, 2016; and PCT/CA2017/050866, filed Jul. 18, 2017. Additional antibodies are described herein. Uses of said antibodies are also provided.

III. Methods Using "Epitope" Compounds

Accordingly, the present disclosure provides for treating or preventing a disease or condition associated with and/or induced by soluble A-beta oligomer comprising administering to a subject in need thereof a compound, immunogen, composition, antibody, nucleic acid or cell described herein described herein.

In an embodiment, the compound, immunogen or antibody is directed to a conformational epitope in A-beta consisting of amino acids HHQK (SEQ ID NO: 1), HQKL (SEQ ID NO: 202) or a part thereof such as HQK, HHQK (SEQ ID NO: 1) corresponding to amino acids residues 13-16 on A-beta and HQKL (SEQ ID NO: 202) corresponding to amino acids 14-17. HHQK (SEQ ID NO: 1) and HQKL (SEQ ID NO: 202) were identified as regions prone to disorder in an A-beta fibril. The residues HHQK (SEQ ID NO: 1) and HQKL (SEQ ID NO: 202) emerged in predictions.

The residues QKLV (SEQ ID NO: 5) were identified as a region prone to disorder in an A-beta fibril. In an embodiment, the compound, immunogen or antibody is directed to a conformational epitope in A-beta consisting of amino acids QKLV (SEQ ID NO: 5), a part thereof such as QKL or a related epitope.

Also, the residues HDSG (SEQ ID NO: 9) were identified as a region prone to disorder in an A-beta fibril. In another embodiment, the compound, immunogen or antibody is directed to a conformational epitope in A-beta consisting of amino acids HDSG (SEQ ID NO: 9), a part thereof such as HDS or a related epitope.

In another aspect the subject is administered a compound comprising an A-beta peptide comprising or consisting of QKLV (SEQ ID NO: 5), HDSG (SEQ ID NO:9), a part thereof or a related epitope sequence and or combinations thereof.

In an aspect the subject is administered a compound comprising an A-beta peptide comprising or consisting of HHQK (SEQ ID NO: 1), a related epitope sequence including a part of any of the foregoing, wherein if the peptide is HHQK (SEQ ID NO: 1), the peptide is in a conformation that is distinct in at least one feature from linear HHQK (SEQ ID NO: 1). In an embodiment, the A-beta peptide is selected from HHQK (SEQ ID NO: 1). HQKL (SEQ ID NO: 202) and is comprised in a cyclic compound. The epitopes are included in the epitopes collectively referred to herein as HHQK (SEQ ID NO: 1) and related epitopes (and their sequences are collectively referred to as related epitope sequences). In an embodiment, the related epitope comprises or consists of HQKL (SEQ ID NO: 202), HQK and epitopes that comprise 1, 2 or 3 amino acids in A-beta either N-terminal and/or 1 amino acid C-terminal to HQK.

In an embodiment, the A-beta peptide comprises HQK or HHQK (SEQ ID NO: 1) or a related epitope, can include 1, 2 or 3 additional residues in A-beta N terminus of and/or 1, 2 or 3 amino acid C-terminus of HHQK (SEQ ID NO: 1). For example, the 3 amino acids N-terminal to HHQK (SEQ ID NO: 1) in A-beta are YEV and the 3 amino acids C-terminal to HHQK (SEQ ID NO: 1) are LVF. In an embodiment, the A-beta peptide is a maximum of 7 or 6 A-beta residues. In an embodiment, the A-beta peptide is a maximum of 5 A-beta residues. In yet another embodiment A-beta peptide (e.g. in the compound such as a cyclic compound) is 4 A-beta residues, optionally HHQK (SEQ ID NO: 1).

In an embodiment, the A-beta peptide comprising QKLV (SEQ ID NO: 5) can include 1, 2 or 3 additional residues in A-beta C-terminus and/or 1, 2 or 3 additional residue in A-beta N-terminus of QKLV (SEQ ID NO: 5). The 3 amino acids N-terminal to QKLV (SEQ ID NO: 5) in A-beta are VHH and the 3 amino acids C-terminal to QKLV (SEQ ID NO: 5) are FFA. In an embodiment the A-beta peptide is a maximum of 7 amino acids, 6 amino acids or 5 amino acids.

In an embodiment, the A-beta peptide comprising HDSG (SEQ ID NO: 9) can include 1, 2 or 3 additional residues in A-beta C-terminus and/or 1, 2 or 3 additional residue in A-beta N-terminus of HDSG (SEQ ID NO: 9). The 3 amino acids N-terminal to HDSG (SEQ ID NO: 9) in A-beta are EFR and the 3 amino acids C-terminal to HDSG (SEQ ID NO: 9) are YEV. In an embodiment the A-beta peptide is a maximum of 7 amino acids, 6 amino acids or 5 amino acids.

In an embodiment, the compound further includes a linker. The linker comprises a spacer and/or one or more functionalizable moieties. The linker can for example comprise 1, 2, 3, 4, 5, 6, 7 or 8 amino acids and/or equivalently functioning molecules such as polyethylene glycol (PEG) moieties, and/or a combination thereof. In an embodiment, the spacer amino acids are selected from non-immunogenic or poorly immunogenic amino acid residues such as G and A, for example the spacer can be GGG, GAG, G(PEG)G, PEG-PEG (also referred to as PEG2)-GG and the like. One or more functionalizable moieties e.g. amino acids with a functional group may be included for example for coupling the compound to an agent or detectable tag or a carrier such as BSA or an immunogenicity enhancing agent such as KLH.

In an embodiment the linker comprises GC-PEG, PEG-GC, GCG or PEG2-CG.

In an embodiment, the linker comprises 1, 2, 3, 4, 5, 6, 7 or 8 amino acids.

In certain embodiments, the cyclic compound has a maximum of 12, 11, 10, 9, 8, or 7 residues, optionally amino acids and/or equivalent units such as PEG units or other similar sized chemical moieties.

In embodiments wherein the A-beta peptide comprising for example HQK or HHQK (SEQ ID NO: 1), HDSG (SEQ ID NOL9) or QKLV (SEQ ID NO: 5), includes 1, 2 or 3 additional residues found in A-beta that are N- and/or C-terminal to the epitope sequence the linker in the cyclized compound is covalently linked to the N- and/or C-termini of the A-beta residues. Where the A-beta peptide is HHQK (SEQ ID NO: 1), the linker is covalently linked to residues H and K.

In an embodiment, the compound is a cyclic compound, such as a cyclopeptide, optionally a cyclopeptide described herein.

Proteinaceous portions of compounds (or the compound wherein the linker is also proteinaceous) may be prepared by chemical synthesis using techniques well known in the chemistry of proteins such as solid phase synthesis or synthesis in homogenous solution.

Reference to the "cyclic peptide" or "cyclopeptide" herein can refer to a fully proteinaceous compound (e.g. wherein the linker is for example 1, 2, 3, 4, 5, 6, 7 or 8 amino acids). It is understood that properties described for the cyclic peptide determined in the examples can be incorporated in other compounds (e.g. other cyclic compounds) comprising non-amino acid linker molecules.

The linear peptide comprising the A-beta sequence can be comprised in a linear compound. The linear compound or the linear peptide comprising HHQK (SEQ ID NO: 1), QKLV (SEQ ID NO: 5) or HDSG (SEQ ID NO: 9) is in an embodiment, a corresponding linear peptide. In another embodiment, the linear peptide is any length of A-beta peptide comprising the epitope sequence), including for example a linear peptide comprising A-beta residues 1-35, or smaller portions thereof such as A-beta residues 10-20, 11-20, 12-20, 13-20, 10-19, 10-18 and the like etc. The linear peptide can in some embodiments also be a full length A-beta peptide.

The cyclic compound can be synthesized as a linear molecule with the linker covalently attached to the N-terminus or C-terminus of the peptide comprising the A-beta peptide, prior to cyclization. Alternatively part of the linker is covalently attached to the N-terminus and part is covalently attached to the C-terminus prior to cyclization. In either case, the linear compound is cyclized for example in a head to tail cyclization (e.g. amide bond cyclization).

In some embodiments, the linker is indirectly coupled to the N- and C-terminus residues of the A-beta peptide.

In an embodiment, the cyclic compound is a compound in FIG. 1.

Methods for making cyclized peptides are known in the art and include SS-cyclization or amide cyclization (head-to-tail, or backbone cyclization). Methods are further described in the Examples. For example, a peptide with "C" residues at its N- and C-termini, can be reacted by SS-cyclization to produce a cyclic peptide.

In an embodiment an immunogen comprising a compound, optionally a cyclic compound described herein is administered for treating or preventing an oligomeric A-beta disease. In an embodiment, the immunogen is prepared with sterile reagents and/or distilled water.

In an embodiment, the immunogen is a cyclic peptide comprising A-beta peptide described herein.

In an embodiment, the immunogen comprises immunogenicity enhancing agent such as Keyhole Limpet Hemocyanin (KLH). The immunogenicity enhancing agent can be coupled to the compound either directly, such as through an amide bound, or indirectly through a chemical linker.

The immunogen can be produced by conjugating the cyclic compound containing the A-beta peptide to an immunogenicity enhancing agent such as Keyhole Limpet Hemocyanin (KLH) or a carrier such bovine serum albumin (BSA) using for example the method described in Lateef et al 2007, herein incorporated by reference. In an embodiment, the method described in Example 1 is used.

An immunogen is suitably prepared or formulated for administration to a subject, for example, the immunogen may be sterile, or purified.

A further aspect is administration of an isolated nucleic acid encoding the proteinaceous portion of a compound or immunogen described herein.

In embodiment, the nucleic acid molecule encodes any one of the amino acid sequences sent forth herein, such as antibody or fragment thereof, optionally a binding fragment.

A further aspect is administration of a vector comprising said nucleic acid. Suitable vectors are described elsewhere herein.

IV. Antibodies, Immunoconjugates, Cells and Nucleic Acids and Uses Thereof

Also provided is an antibody or binding fragment described herein, cells expressing such antibody or binding fragment, such as hybridoma cell lines as well as nucleic acids encoding said antibodies. Also provided are uses thereof for inhibiting A-beta propagation, and treating or preventing A-beta oligomer associated and/or induced conditions and diseases including memory loss, and Alzheimer's disease.

Accordingly, in an aspect, antibodies raised using the compounds and immunogens, including compounds and immunogens comprising the cyclic peptides described above can be used for treating AD and/or other A-beta amyloid associated and/or induced diseases and conditions.

Accordingly, an aspect includes an antibody or binding fragment thereof described herein. In an embodiment the antibody or binding fragment thereof comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences in Table 9, optionally Table 9B, 9C, 9G, 9H or 91.

Also provided in another aspect is an immunoconjugate comprising an antibody or binding fragment described herein, optionally with the amino acid sequences of said CDRs comprising the sequences in Table 9B, 9C, 9G, 9H or 91 and a detectable label or cytotoxic agent, optionally, wherein the detectable label comprises a positron emitting radionuclide, optionally for use in subject imaging such as PET imaging.

A further aspect includes a hybrdioma cell line deposited under the provisions of the Budapest Treaty with the American Type Culture Collection (ATCC®) 10801 University Blvd., Manassas, Va., 20110-2209, USA on Jul. 19, 2017 and given the Accession number PTA-124318.

Also provided in another aspect is an antibody produced by the hybrdioma cell line deposited under the provisions of the Budapest Treaty with the American Type Culture Collection (ATCC®) 10801 University Blvd., Manassas, Va., 20110-2209, USA on Jul. 19, 2017 and given the Accession number PTA-124318.

Antibodies described herein and immunoconjugates comprising a cytotoxic agent can be used to inhibit A-beta oligomer associated and/or induced conditions and diseases and/or to inhibit A-beta oligomer propagation.

Accordingly, an aspect includes a method of treating or preventing a disease or condition associated with and/or induced by soluble A-beta oligomer comprising administering to a subject in need thereof: an isolated conformation specific and/or selective antibody or binding fragment thereof that specifically and/or selectively binds to a cyclic compound comprising an A-beta peptide having a sequence of QKL, HQK, KLV, HHQK (SEQ ID NO: 1), QKLV (SEQ ID NO: 5) or HDSG (SEQ ID NO: 9), they cyclic compound optionally having a sequence of SEQ ID NO: 2, 3, 4, 6, 7, 8, 10, 11 or 12; an immunogen comprising a cyclic compound comprising an A-beta peptide having a sequence of QKL, HQK, KLV, HHQK (SEQ ID NO: 1), QKLV (SEQ ID NO: 5) or HDSG (SEQ ID NO: 9); a cell expressing said antibody or binding fragment thereof; or a nucleic acid encoding said antibody or binding fragment thereof.

Also provided in an embodiment, is a method of inhibiting A-beta oligomer propagation, the method comprising contacting a cell or tissue expressing A-beta with or administering to a subject in need thereof an effective amount of an isolated A-beta oligomer specific or selective antibody or binding fragment thereof that specifically and/or selectively binds to a cyclic compound comprising an A-beta peptide having a sequence of QKL, HQK, KLV, HHQK (SEQ ID NO: 1), QKLV (SEQ ID NO: 5) or HDSG (SEQ ID NO: 9), they cyclic compound optionally having a sequence of SEQ ID NO: 2, 3, 4, 6, 7, 8, 10, 11 or 12; an immunogen comprising a cyclic compound comprising an A-beta peptide having a sequence of QKL, HQK, KLV, HHQK (SEQ ID NO: 1), QKLV (SEQ ID NO: 5) or HDSG (SEQ ID NO: 9); a cell expressing said antibody or binding fragment thereof; or a nucleic acid encoding said antibody or binding fragment therefore immunoconjugate thereof, to inhibit A-beta aggregation and/or oligomer propagation.

In an embodiment, the method includes administration of an antibody (including a binding fragment thereof) that specifically binds to an A-beta peptide having a sequence HQK, HHQK (SEQ ID NO: 1), QKLV (SEQ ID NO: 5), HDSG (SEQ ID NO: 9) or a related epitope sequence described herein.

In an embodiment the antibody is specific and/or selective for A-beta peptide presented in the cyclic compound.

In an embodiment, the cyclic compound is a cyclic peptide optionally one described herein. The terms cyclopeptide and cyclic peptide are used interchangeably herein.

In an embodiment, the antibody specifically and/or selectively binds the A-beta peptide presented in the cyclic compound relative to a corresponding linear compound comprising the A-beta peptide.

In an embodiment, the antibody does not bind a linear peptide comprising the sequence HHQK (SEQ ID NO: 1), QKLV (SEQ ID NO: 5), or HDSG (SEQ ID NO: 9) optionally wherein the sequence of the linear peptide is a linear version of a cyclic sequence used to raise the antibody, optionally as set forth in SEQ ID NOs: 2, 6 or 10.

In an embodiment the antibody is isolated. In an embodiment, the antibody is an exogenous antibody.

In an embodiment, the antibody does not specifically bind and/or is not selective for linear HQKLVF (SEQ ID NO: 17), linear HQKLVFF (SEQ ID NO: 18), linear HQKLVFFAED (SEQ ID NO: 13), or linear HHQKLVFFAEDVGSNK (SEQ ID NO: 14) relative to cyclic compound comprising an A-beta peptide consisting of HHQK (SEQ ID NO: 1), HQK or HQKL (SEQ ID NO: 202). In an embodiment, the antibody does not specifically bind and/or is not selective for linear peptides consisting of HHQK (SEQ ID NO: 1). Selective binding can be measured using an ELISA or surface plasmon resonance measurement, as described herein.

In an embodiment, the antibody does not bind a linear peptide comprising the sequence QKLV (SEQ ID NO: 5) or HDSG (SEQ ID NO: 9), optionally wherein the sequence of the linear peptide is a linear version of a cyclic sequence used to raise the antibody as described herein.

In an embodiment, the antibody does not specifically or appreciably bind monomeric A-beta. In an embodiment, the antibody does not specifically or appreciably bind A-beta senile plaques, for example, in situ in AD brain tissue.

In another embodiment, the antibody does not selectively bind monomeric A-beta compared to native- or synthetic oligomeric A-beta.

In an embodiment, the antibody selectively binds a cyclic compound comprising SEQ ID NO: 1 or a part thereof, SEQ ID NO: 5 or a part thereof, or SEQ ID NO: 9 or a part thereof or a related epitope optionally in the context of cyclo (CGHHQKG) (SEQ ID NO: 2), cyclo(CGQKLVG) (SEQ ID NO: 6) or cyclo (CGHDSGG) (SEQ ID NO: 10), respectively relative to the corresponding linear peptide. For example, in an embodiment the antibody selectively binds HHQK (SEQ ID NO: 1) QKLV (SEQ ID NO: 5), HDSG (SEQ ID NO: 9) or a related epitope sequence in a cyclic conformation and has at least 2 fold, at least 5 fold, at least 10 fold at least 20 fold, at least 30 fold, at least 40 fold, at least 50 fold, at least 100 fold, at least 500 fold, at least 1000 fold more selectivity for the epitope in the cyclic conformation compared to a linear compound such as a corresponding linear compound, for example as measured by ELISA or surface plasmon resonance, optionally using a method described herein.

In an embodiment, the antibody selectively binds a cyclic compound comprising the epitope sequence relative to linear peptide or a species of A-beta such as A-beta oligomer relative to monomer. In an embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold, at least 1000 fold more selective for the cyclic compound and/or A-beta oligomer over a species of A-beta selected from A-beta monomer and/or A-beta fibril In an embodiment, the A-beta oligomer comprises A-beta 1-42 subunits.

In an embodiment, the antibody lacks A-beta fibril plaque (also referred to as senile plaque) staining. Absence of plaque staining can be assessed by comparing to a positive control such as A-beta-specific antibodies 6E10 and 4G8 (Biolegend, San Diego, CA), or 2C8 (Enzo Life Sciences Inc., Farmingdale, NY) and an isotype control. An antibody described herein lacks or has negligible A-beta fibril plaque staining if the antibody does not show typical plaque morphology staining and the level of staining is comparable to or no more than 2 fold the level seen with an IgG negative isotype control. The scale can for example set the level of staining with isotype control at 1 and with 6E10 at 10. An antibody lacks A-beta fibril plaque staining if the level of staining on such a scale is 2 or less. In embodiment, the antibody shows minimal A-beta fibril plaque staining, for example on the foregoing scale, levels scored at less about or less than 3.

In an embodiment, the antibody is produced using a cyclic compound or immunogen described herein, optionally using a method described herein.

In an embodiment, the antibody is a monoclonal antibody. In an embodiment, the antibody is a chimeric antibody such as a humanized antibody comprising the CDR sequences as recited in Table 9.

To produce monoclonal antibodies, antibody producing cells (lymphocytes) can be harvested from a subject immunized with an immunogen described herein, and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with the desired epitopes and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 41:544-546 (1989); Huse et al., Science 246:1275-1281 (1989); and McCafferty et al., Nature 348: 552-554 (1990).

In an embodiment, the antibody is a humanized antibody.

The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (e.g. Scotgen Limited, 2 Holly Road, Twickenham, Middlesex, Great Britain.).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

Humanized antibodies can be produced as antigen binding fragments such as Fab, Fab' F(ab')2, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

In an embodiment, the humanized antibody comprises a heavy chain variable domain and/or light chain variable domain listed in Table 12 or 13 or a sequence with at least 50% or more sequence identity thereto wherein the CDR sequences are maintained.

Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced where members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region (JH) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Antibodies including humanized or human antibodies are selected from any class of immunoglobulins including: IgM, IgG, IgD, IgA or IgE; and any isotype, including: IgG1, IgG2, IgG3 and IgG4. The humanized or human antibody may include sequences from one or more than one isotype or class.

Additionally, antibodies specific for the epitopes described herein are readily isolated by screening antibody phage display libraries. For example, an antibody phage library is optionally screened by using a disease specific epitope of the current invention to identify antibody fragments specific for the disease specific epitope. Antibody fragments identified are optionally used to produce a variety of recombinant antibodies that are useful with different embodiments of the present invention. Antibody phage display libraries are commercially available, for example, through Xoma (Berkeley, California) Methods for screening antibody phage libraries are well known in the art.

A further aspect is administration of an antibody and/or binding fragment thereof comprising a light chain variable region and a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences set forth in Table 9.

In an embodiment, the antibody is a humanized antibody comprising the CDR sequences as recited in Table 9.

Also provided in another embodiment, is an antibody or binding fragment thereof or administration of an antibody or binding fragment thereof comprising the CDRs in Table 9 or Table 15 and a light chain variable region and a heavy chain variable region, optionally in the context of a single chain antibody.

For example, the antibody and/or binding fragment thereof administered comprises a light chain variable region and a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences set forth in Table 9.

In an embodiment, the antibody or binding fragment comprises a heavy chain variable region comprising: i) an amino acid sequence of a heavy chain variable sequence as set forth in Table 10; ii) an amino acid sequence with at least 50%, at least 60%, at least 70%, at least 80% or at least 90% sequence identity to said heavy chain variable sequence set out in Table 10, 12 or 13, wherein the CDR sequences are the corresponding CDRs as set forth in Table 9, or iii) a conservatively substituted amino acid sequence i) wherein the CDR sequences are the corresponding CDRs as set forth in Table 9; and wherein the antibody or binding fragment thereof comprises a light chain variable region comprising i) an amino acid sequence of a light chain variable sequence as set forth in Table 10, 12 or 13, ii) an amino acid sequence with at least 50%, at least 60%, at least 70%, at least 80%, at least 90% sequence identity to said light chain variable sequence as set out in Table 10, 12 or 13, wherein the CDR sequences are the corresponding CDRs as set forth in Table 9, or iii) a conservatively substituted amino acid sequence i) wherein the CDR sequences a are the corresponding CDRs as set forth in Table 9.

For example, in an embodiment the antibody administered comprises a heavy chain variable region comprises: i) an amino acid sequence as set forth in SEQ ID NO: 84; ii) an amino acid sequence with at least 50%, at least 60%, at least 70%, at least 80% or at least 90% sequence identity to SEQ ID NO: 84, wherein the CDR sequences are as set forth in SEQ ID NO: 20, 21 and 22, or iii) a conservatively substituted amino acid sequence i). In another aspect the antibody administered comprises a light chain variable region comprising i) an amino acid sequence as set forth in SEQ ID NO: 86, ii) an amino acid sequence with at least 50%, at least 60%, at least 70%, at least 80% or at least 90% sequence identity to SEQ ID NO: 86, wherein the CDR sequences are as set forth in SEQ ID NO: 23, 24 and 25 or iii) a conservatively substituted amino acid sequence of i), wherein the CDR sequences are as set forth in SEQ ID NO: 23, 24 and 25. In another embodiment, the heavy chain variable region amino acid sequence is encoded by a nucleotide sequence as set out in SEQ ID NO: 83 or a codon degenerate optimized version thereof. In another embodiment, the antibody comprises a light chain variable region amino acid sequence encoded by a nucleotide sequence as set out in SEQ ID NO: 85 or a codon degenerate or optimized version thereof. In an embodiment, the heavy chain variable region comprises an amino acid sequence as set forth in SEQ ID NO: 84. In an embodiment, the light chain variable region comprises an amino acid sequence as set forth in SEQ ID NO: 86.

As another example, the antibody comprises a heavy chain variable region comprises: i) an amino acid sequence as set forth in SEQ ID NO: 98 or 102; ii) an amino acid sequence with at least 50%, at least 60%, at least 70%, at least 80% sequence identity to SEQ ID NO: 98 or 102, wherein the CDR sequences are as set forth in SEQ ID NO: 41, 42, 43, 47, 48, and/or 49, or iii) a conservatively substituted amino acid sequence i) wherein the CDR sequences are as set forth in SEQ ID NO:41, 42, 43, 47, 48, and/or 49. In another aspect the antibody comprises a light chain variable region comprising i) an amino acid sequence as set forth in SEQ ID NO: 100 or 104, ii) an amino acid sequence with at least 50%, at least 60%, at least 70%, at least 80% 70% sequence identity to SEQ ID NO:100 or 104, wherein the CDR sequences are as set forth in SEQ ID NO: 44, 45, 46, 50, 51, and/or 52, or iii) a conservatively substituted amino acid sequence of i) wherein the CDR sequences are as set forth in SEQ ID NO: 41, 42, 43, 47, 48, and/or 49. In another embodiment, the heavy chain variable region amino acid sequence is encoded by a nucleotide sequence as set out in SEQ ID NO: 97 or 101 or a codon degenerate optimized version thereof. In another embodiment, the antibody comprises a light chain variable region amino acid sequence encoded by a nucleotide sequence as set out in SEQ ID NO: 99 or 103 or a codon degenerate or optimized version thereof. In an embodiment, the heavy chain variable region comprises an amino acid sequence as set forth in SEQ ID NO: 98 or 102. In an embodiment, the light chain variable region comprises an amino acid sequence as set forth in SEQ ID NO: 100 or 104.

Other similar examples there the variable region of the heavy and/or light chain have at least 50%, at least 60%, at least 70%, at least 80% 70% sequence identity and where the CDRs are maintained can be determined on the basis of the Tables 9 and 10, 12 and 14.

In another aspect the antibody that is administered is an antibody that specifically binds a same epitope as the antibody with CDR sequences as recited in Table 9, with variable regions as recited in Table 10, 12 or 13 or produced by the hybrdioma cell line deposited under the provisions of the Budapest Treaty with the American Type Culture Collection (ATCC®) 10801 University Blvd., Manassas, Va., 20110-2209, USA on Jul. 19, 2017 and given the Accession number PTA-124318.

Another aspect is an antibody that specifically binds A-beta or SEQ ID NO: 2, 6 or 10 (e.g. the same epitope as the antibody with CDR sequences as recited in Table 9).

Another aspect includes an antibody or binding fragment or administration of an antibody that competes for binding to human A-beta with an antibody comprising the CDR sequences as recited in Table 9 or 15, or the variable domain sequences in Tables 10, 12 or 13.

In an embodiment, the antibody or binding fragment thereof competes for binding with an antibody comprising a light chain variable region and a heavy chain variable region the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences in Tables 9B, 9C, 9G, 9H or 91.

Competition between antibodies can be determined for example using an assay in which an antibody under test is assessed for its ability to inhibit specific binding of a reference antibody to the common antigen. A test antibody competes with a reference antibody if an excess of a test antibody (e.g., at least a 2 fold, 5, fold, 10 fold or 20 fold) inhibits binding of the reference antibody by at least 50%, at least 75%, at least 80%, at least 90% or at least 95% as measured in a competitive binding assay.

In a further aspect the antibody administered is an antibody conjugated to a therapeutic, detectable label or cytotoxic agent.

A further aspect relates to an antibody complex comprising an antibody described herein and/or a binding fragment thereof and oligomeric A-beta.

In a further aspect an isolated nucleic acid encoding an antibody or part thereof described herein is administered.

Nucleic acids encoding a heavy chain or a light chain can also be administered, for example encoding a heavy chain comprising CDR-H1, CDR-H2 and/or CDR-H3 regions described herein or encoding a light chain comprising CDR-L1, CDR-L2 and/or CDR-L3 regions described herein.

The present disclosure also includes administration of variants of the nucleic acid sequences that encode for the antibody and/or binding fragment thereof disclosed herein. For example, the variants include nucleotide sequences that hybridize to the nucleic acid sequences encoding the antibody and/or binding fragment thereof disclosed herein under at least moderately stringent hybridization conditions or codon degenerate or optimized sequences. In another embodiment, the variant nucleic acid sequences have at least 50%, at least 60%, at least 70%, most preferably at least 80%, even more preferably at least 90% and even most preferably at least 95% sequence identity to nucleic acid sequences encoding in Table 10, 12 or 13.

A further aspect is an isolated nucleic acid encoding an antibody described herein. In embodiments said isolated nucleic acid is administered to a subject in need thereof.

Another aspect is an expression cassette or vector comprising the nucleic acid herein disclosed. In an embodiment, the vector is an isolated vector, optionally for administration to a subject in need thereof.

The vector can be any vector, including vectors suitable for producing an antibody and/or binding fragment thereof or expressing a peptide sequence described herein.

The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes or antibodies described herein.

In an embodiment, the vector is suitable for expressing for example single chain antibodies by gene therapy. The vector can be adapted for specific expression in neural tissue, for example using neural specific promoters and the like. In an embodiment, the vector comprises an IRES and allows for expression of a light chain variable region and a heavy chain variable region. Such vectors can be used to deliver antibody in vivo.

Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, the regulatory sequences direct or increase expression in neural tissue and/or cells.

In an embodiment, the vector is a viral vector.

The recombinant expression vectors may also contain a marker gene which facilitates the selection of host cells transformed, infected or transfected with a vector for expressing an antibody or epitope peptide described herein.

The recombinant expression vectors may also contain expression cassettes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, MA) and pRIT5 (Pharmacia, Piscataway, NJ) which fuse glutathione S-transferase (GST), maltose E binding protein, or protein A, respectively, to the recombinant protein.

Systems for the transfer of genes for example into neurons and neural tissue both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome-DNA complexes. Another approach is the use of AAV plasmids in which the DNA is polycation-condensed and lipid entrapped and introduced into the brain by intracerebral gene delivery (Leone et al. US Application No. 2002076394).

Accordingly, in another aspect, the compounds, immunogens, nucleic acids, vectors and antibodies described herein for administration may be formulated in vesicles such as liposomes, nanoparticles, and viral protein particles, for example for delivery of antibodies, compounds, immunogens and nucleic acids described herein. In particular synthetic polymer vesicles, including polymersomes, can be used to administer antibodies.

Also provided in another aspect is administration of a cell, optionally an isolated and/or recombinant cell, expressing an antibody described herein or comprising a vector herein disclosed.

The recombinant cell can be generated using any cell suitable for producing a polypeptide, for example suitable for producing an antibody and/or binding fragment thereof. For example to introduce a nucleic acid (e.g. a vector) into a cell, the cell may be transfected, transformed or infected, depending upon the vector employed.

Suitable host cells include a wide variety of prokaryotic and eukaryotic host cells. For example, the proteins described herein may be expressed in bacterial cells such as *E. coli*, insect cells (using baculovirus), yeast cells or mammalian cells.

In an embodiment, the cell is a eukaryotic cell selected from a yeast, plant, worm, insect, avian, fish, reptile and mammalian cell.

In an embodiment, the cell is a neural cell.

Yeast and fungi host cells suitable for expressing an antibody or peptide include, but are not limited to *Saccharomyces cerevisiae, Schizosaccharomyces pombe*, the genera *Pichia* or *Kluyveromyces* and various species of the genus *Aspergillus*. Examples of vectors for expression in yeast S. cerivisiae include pYepSec1, pMFa, pJRY88, and pYES2 (Invitrogen Corporation, San Diego, CA). Protocols for the transformation of yeast and fungi are well known to those of ordinary skill in the art.

Mammalian cells that may be suitable include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

In an embodiment, the cell is a fused cell producing an antibody specific and/or selective for an epitope or epitope sequence described herein, including for example that selectively binds A-beta oligomers over A-beta monomers, selectively binds an epitope sequence presented in a cyclic compound relative to a linear compound or lacks or has negligible plaque binding.

V. Compositions and Methods for Using

A further aspect is a composition comprising a compound, immunogen, nucleic acid, vector or antibody or binding fragment described herein. In embodiments, said composition is administered in a method described herein.

The composition can for example include 1, 2, 3 or more antibodies or binding fragments thereof, immunoconjugates, compounds, cells or nucleic acids described herein.

In an embodiment, the composition comprises a diluent.

Suitable diluents for nucleic acids include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

In an embodiment, the composition is a pharmaceutical composition comprising any of the peptides, immunogens, antibodies, nucleic acids or vectors disclosed herein, and optionally comprising a pharmaceutically acceptable carrier.

The compositions described herein can be prepared by per se known methods for the preparation of pharmaceutically acceptable compositions that can be administered to subjects, optionally as a vaccine, such that an effective quantity of the active substance is combined in a mixture with a pharmaceutically acceptable vehicle.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N, N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In an embodiment comprising a compound or immunogen described herein, the composition comprises an adjuvant.

Adjuvants that can be used for example, include Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Aluminum hydroxide, aluminum sulfate and aluminum phosphate (collectively commonly referred to as alum) are routinely used as adjuvants. A wide range of extrinsic adjuvants can provoke potent immune responses to immunogens. These include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In an embodiment, the adjuvant is aluminum hydroxide. In another embodiment, the adjuvant is aluminum phosphate. Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-AI-D-isoglu-L-Ala-dipalmitoxy propylamide (DTP-DPP) theramide (TM)), or other bacterial cell wall components.

The adjuvant may be administered with an immunogen as a single composition. Alternatively, an adjuvant may be administered before, concurrent and/or after administration of the immunogen.

Commonly, adjuvants are used as a 0.05 to 1.0 percent solution in phosphate–buffered saline. Adjuvants enhance the immunogenicity of an immunogen but are not necessarily immunogenic themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune responses. As such, embodiments may encompass compositions further comprising adjuvants.

Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, MT) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium*, or *Shigella flexneri*, saponins, or polylactide glycolide (PLGA) microspheres) can also be used in mucosal administration.

Other adjuvants include cytokines such as interleukins for example IL-1, IL-2 and IL-12, chemokines, for example CXCL10 and CCL5, macrophage stimulating factor, and/or tumor necrosis factor. Other adjuvants that may be used include CpG oligonucleotides (Davis. Curr Top Microbiol Immunol., 247:171-183, 2000).

Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-AI-D-isoglu-L-Ala-dipalmitoxy propylamide (DTP-DPP) theramide (TM), or other bacterial cell wall components.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

An adjuvant may be coupled to an immunogen for administration. For example, a lipid such as palmitic acid, may be coupled directly to one or more peptides such that the change in conformation of the peptides comprising the immunogen does not affect the nature of the immune response to the immunogen.

In an embodiment, the composition comprises an antibody described herein. In another embodiment, the composition comprises an antibody described herein and a diluent. In an embodiment, the composition is a sterile composition.

A further aspect provides prior to administering the compound, immunogen, composition, antibody, nucleic acid or cell described herein detecting whether a biological sample comprises A-beta oligomers the method comprising contacting the biological sample with an antibody described herein and/or detecting the presence of any antibody complex. In an embodiment the method is for detecting whether the biologic sample comprises oligomeric A-beta.

In an embodiment, if A-beta oligomer is detected the subject is administered a compound, immunogen, antibody or compositions described herein.

In an embodiment, the method comprises:

a. contacting the biologic sample with an antibody described herein that is specific and/or selective for A-beta oligomer herein under conditions permissive to produce an antibody: A-beta oligomer complex;

b. detecting the presence of any complex;

wherein the presence of detectable complex is indicative that the sample may contain A-beta oligomer; and c. treating the subject with a compound, immunogen, antibody or composition described herein.

In an embodiment, the level of complex formed is compared to a test antibody such as a suitable Ig control or irrelevant antibody.

In an embodiment, the detection is quantitated and the amount of complex produced is measured. The measurement can for example be relative to a standard.

In an embodiment, the measured amount is compared to a control.

In another embodiment, the method comprises:

(a) contacting a test sample of said subject with an antibody described herein, under conditions permissive to produce an antibody-antigen complex;

(b) measuring the amount of the antibody-antigen complex in the test sample; and (c) comparing the amount of antibody-antigen complex in the test sample to a control;

wherein detecting antibody-antigen complex in the test sample as compared to the control indicates that the sample comprises oligomeric A-beta and treating the subject with an antibody described herein if sample comprises oligomeric A-beta above a threshold.

The control can be a sample control (e.g. from a subject without AD, or from a subject with a particular form of AD, mild, moderate or advanced), or be a previous sample from the same subject for monitoring changes in A-beta oligomer levels in the subject.

In an embodiment, an antibody described herein is used.

In an embodiment, the sample is a biological sample. In an embodiment, the sample comprises brain tissue or an extract thereof and/or CSF. In an embodiment, the sample comprises whole blood, plasma or serum. In an embodiment, the sample is obtained from a human subject. In an embodiment, the subject is suspected of, at a risk of or has AD.

A number of methods can be used to detect an A-beta: antibody complex and thereby determine if the sample comprises A-beta oligomers are present in a sample using the antibodies described herein, including immunoassays such as flow cytometry, Western blots, ELISA, and immunoprecipitation followed by SDS-PAGE immunocytochemistry.

As described in the Examples surface plasmon resonance technology can be used to assess conformation specific binding. If the antibody is labeled or a detectably labeled secondary antibody specific for the complex antibody is used, the label can be detected. Commonly used reagents include fluorescent emitting and HRP labeled antibodies. In quantitative methods, the amount of signal produced can be measured by comparison to a standard or control. The measurement can also be relative.

A further aspect includes a method of measuring a level of or imaging A-beta in a subject or tissue, optionally where the A-beta to be measured or imaged is oligomeric A-beta prior to administering, a compound, immunogen, composition, antibody, nucleic acid or cell described herein. In an embodiment, the method comprises administering to a subject at risk or suspected of having or having AD, an antibody conjugated to a detectable label; and detecting the label, optionally quantitatively detecting the label. The label in an embodiment is a positron emitting radionuclide which can for example be used in PET imaging.

A further aspect includes a method of inducing an immune response in a subject to treat or prevent a disease associated with and/or induced by soluble A-beta, comprising administering to the subject a compound, immunogen and/or composition comprising a compound described herein.

In an embodiment, the immunogen administered comprises a compound of FIG. 1.

In an embodiment, the subject is a non-human subject such as a rodent. Antibody producing cells generated can also be used in an embodiment to produce a hybridoma cell line.

It is demonstrated herein that the antibodies raised against immunogens comprising SEQ ID NO: 2, 6 and 10, can specifically and/or selectively bind A-beta oligomers and lack A-beta plaque staining. Oligomeric A-beta species are believed to be the toxic propagating species in AD. Further as shown herein, said antibodies inhibited A-beta aggregation and A-beta oligomer propagation. Accordingly, also provided are methods of inhibiting A-beta oligomer propagation, the method comprising contacting a cell or tissue expressing A-beta with or administering to a subject in need thereof an effective amount of an A-beta oligomer specific or selective antibody described herein to inhibit A-beta aggregation and/or oligomer propagation. In vitro the assay can be monitored as described in the Examples.

The antibodies can be used for example for treating AD and/or other A-beta amyloid associated and/or induced diseases and conditions. For example, variants of Lewy body dementia and in inclusion body myositis (a muscle disease) exhibit similar plaques as AD and A-beta can also form aggregates implicated in cerebral amyloid angiopathy.

In an embodiment the method is for treating or preventing AD and/or other A-beta amyloid associated and/or induced diseases or conditions, the method comprising administering to a subject in need thereof i) an effective amount of an antibody described herein, optionally an A-beta oligomer specific or selective or a pharmaceutical composition comprising said antibody; or 2) administering an isolated cyclic compound comprising SEQ ID NO: 1 5 or 9 or a related epitope sequence or immunogen or pharmaceutical composition comprising said cyclic compound, to a subject in need thereof. In other embodiments, nucleic acids encoding the antibodies or immunogens described herein can also be administered to the subject, optionally using vectors suitable for delivering nucleic acids in a subject.

In an embodiment, a biological sample from the subject to be treated is assessed for the presence or levels of A-beta using an antibody described herein. In an embodiment, a subject with detectable A-beta levels (e.g. A-beta antibody complexes measured in vitro or measured by imaging) is treated with the antibody.

The antibody and immunogens can for example be comprised in a pharmaceutical composition as described herein, and formulated for example in vesicles for improving delivery.

One or more antibodies targeting HHQK (SEQ ID NO: 1), HDSG (SEQ ID NO: 9) or QKLV (SEQ ID NO: 5) and/or related antibodies can be administered in combination. In addition the antibodies disclosed herein can be administered with one or more other treatments such as a beta-secretase inhibitor or a cholinesterase inhibitor.

In an embodiment, the antibody is a conformation specific/selective antibody, optionally that specifically or selectively binds A-beta oligomer.

Also provided are uses of the compositions, antibodies, isolated peptides, immunogens and nucleic acids for treating or preventing AD and/or other A-beta associated and/or induced diseases or conditions.

In an embodiment, the disease or condition associated with and/or induced by soluble A-beta oligomer is cognitive deficits, optionally loss of short term memory formation.

In an embodiment, the disease or condition associated with and/or induced by soluble soluble A-beta oligomer A-beta is Alzheimer's disease (AD).

In an embodiment, the treatment is prophylactic treatment. For example in an embodiment, the antibody is administered to a subject with a predisposition to developing a disease or condition associated with and/or induced by soluble A-beta oligomer.

In an embodiment, the disease or condition is perirhinal cortex dysfunction or pathology. In another embodiment, the disease or condition is enthorinal cortex dysfunction or pathology.

In an embodiment, the disease or condition is associated with and/or induced by soluble A-beta 1-42 oligomer.

The compositions, compounds, antibodies, isolated peptides, immunogens and nucleic acids, vectors etc. described herein can be administered for example, by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

In certain embodiments, the pharmaceutical composition is administered systemically.

In other embodiments, the pharmaceutical composition is administered directly to the brain or other portion of the CNS. For example such methods include the use of an implantable catheter and a pump, which would serve to discharge a pre-determined dose through the catheter to the infusion site. A person skilled in the art would further recognize that the catheter may be implanted by surgical techniques that permit visualization of the catheter so as to position the catheter adjacent to the desired site of administration or infusion in the brain. Such techniques are described in Elsberry et al. U.S. Pat. No. 5,814,014 "Techniques of Treating Neurodegenerative Disorders by Brain Infusion", which is herein incorporated by reference. Also contemplated are methods such as those described in US patent application 20060129126 (Kaplitt and During "Infusion device and method for infusing material into the brain of a patient". Devices for delivering drugs to the brain and other parts of the CNS are commercially available (e.g. SynchroMed© EL Infusion System; Medtronic, Minneapolis, Minnesota)

In another embodiment, the pharmaceutical composition is administered to the brain using methods such as modifying the compounds to be administered to allow receptor-mediated transport across the blood brain barrier.

Other embodiments contemplate the co-administration of the compositions, compounds, antibodies, isolated peptides, immunogens and nucleic acids described herein with biologically active molecules known to facilitate the transport across the blood brain barrier.

Also contemplated in certain embodiments, are methods for administering the compositions, compounds, antibodies, isolated peptides, immunogens and nucleic acids described herein across the blood brain barrier such as those directed at transiently increasing the permeability of the blood brain barrier as described in U.S. Pat. No. 7,012,061 "Method for increasing the permeability of the blood brain barrier", herein incorporated by reference.

VI. Kits for Use in Methods

A further aspect relates to a kit comprising i) an antibody and/or binding fragment thereof, ii) a nucleic acid, iii) peptide or immunogen, iv) composition or v) recombinant cell described herein, comprised in a vial such as a sterile vial or other housing and optionally a reference agent and/or instructions for use thereof for use in treating or preventing a disease or condition associated with and/or induced by soluble A-beta oligomer.

In an embodiment, the kit further comprises one or more of a collection vial, standard buffer and detection reagent.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Immunogens

Cyclic peptides cyclo(CGHHQKG) (SEQ ID NO: 2) cyclo(CGQKLVG) (SEQ ID NO: 6), and cyclo (CGHDSGG) (SEQ ID NO: 10) and corresponding linear peptides were prepared (CPC Scientific, Sunnyvale, CA, USA)

Peptides were generated at CPC Scientific, Sunnyvale, CA, USA (both cyclic and linear). Peptides were conjugated to KLH (for immunizing) and BSA (for screening) using a trifluoroacetate counter ion protocol. Peptides were desalted and checked by MS and HPLC and deemed 95% pure. Peptides were shipped to IPA for use in production of monoclonal antibodies in mouse.

Antibody Generation

Hybridomas and monoclonal antibodies were generated to cyclo(CGHHQKG) (SEQ ID NO: 2), cyclo(CGQKLVG) (SEQ ID NO: 6) and cyclo (CGHDSGG) (SEQ ID NO: 10) each linked to Keyhole Limpet Hemocyanin (KLH).

The cyclopeptides linked to KLH were sent for mouse monoclonal antibody production (ImmunoPrecise Antibodies LTD (Victoria BC, Canada), following protocols approved by the Canadian Council on Animal Care. Mouse sera were screened using the conformational peptide used for producing the antibodies linked to BSA and the linear peptides.

Fifty day old female BALB/c mice (Charles River Laboratories, Quebec) were immunized. A series of subcutaneous aqueous injections containing antigen but no adjuvant were given over a period of 19 days. Mice were immunized with 100 µg per mouse per injection of a 0.5 mg/mL cyclic peptide-KLH solution in sterile saline. All 4 mice were euthanized on Day 19 and lymphocytes were harvested for hybridoma cell line generation.

Fusion/Hybridoma Development

Lymphocytes were isolated and fused with murine SP2/0 myeloma cells in the presence of poly-ethylene glycol (PEG 1500). Fused cells were cultured using HAT selection. This method uses a semi-solid methylcellulose-based HAT selective medium to combine the hybridoma selection and cloning into one step. Single cell-derived hybridomas grow to form monoclonal colonies on the semi-solid media. 10 days after the fusion event, resulting hybridoma clones were transferred to 96-well tissue culture plates and grown in HT containing medium until mid-log growth was reached (5 days).

Example 2

Hybridoma Analysis

Tissue culture supernatants from the hybridomas were tested by indirect ELISA on screening antigen (cyclic peptide-BSA) and probed for both IgG and IgM antibodies using a Goat anti-IgG/IgM(H&L)-HRP secondary and developed with TMB substrate. Clones >0.2 OD in this assay were taken to the next round of testing. Positive cultures were retested on screening antigen to confirm secretion and on an irrelevant antigen (Human Transferrin) to eliminate non-specific mAbs and rule out false positives. Selected clones were isotyped by antibody trapping ELISA to determine if they are IgG or IgM isotype. Selected clones were also tested by indirect ELISA on other cyclic peptide-BSA conjugates as well as linear peptide-BSA conjugates to evaluate cross-reactivity and linker reactivity. Antibodies were also screened by SPR analysis.

ELISA Antibody Screening

ELISA plates were coated with 1) 0.1 ug/well cyclopeptide-conjugated-BSA at 100 uL/well in carbonate coating buffer (pH 9.6) O/N at 4 C; 2) 0.1 ug/well linear-peptide-conjugated-BSA at 100 uL/well in carbonate coating buffer (pH 9.6) O/N at 4 C; or 3) 0.1 ug/well Negative-Peptide at 100 uL/well in carbonate coating buffer (pH 9.6) O/N at 4 C. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate TMB was added at 50 uL/well, developed in the dark and stopped with equal volume 1 M HCl.

SPR Binding Assays

SPR Analysis of Antibody Binding to Cyclic Peptides, A-Beta Monomers and Oligomers A-beta Monomer and Oligomer Preparation: Recombinant A-beta40 and 42 peptides (California Peptide, Salt Lake City UT, USA) were dissolved in ice-cold hexafluoroisopropanol (HFIP). The HFIP was removed by evaporation overnight and dried in a SpeedVac centrifuge. To prepare monomers, the peptide film was reconstituted in DMSO to 5 mM, diluted further to 100 μM in dH2O and used immediately. Oligomers were prepared by diluting the 5 mM DMSO peptide solution in phenol red-free F12 medium (Life Technologies Inc., Burlington ON, Canada) to a final concentration of 100 μM and incubated for 24 hours to 7 days at 4° C.

SPR Analysis of Cyclic Peptide, A-beta Monomer and Oligomer binding: All SPR measurements were performed using a Molecular Affinity Screening System (MASS-1) (Sierra Sensors GmbH, Hamburg, Germany), an analytical biosensor that employs high intensity laser light and high speed optical scanning to monitor binding interactions in real time. The primary screening of tissue culture supernatants was performed using an SPR direct binding assay, whereby BSA-conjugated peptides, A-beta42 Monomer and A-beta42 Oligomer are covalently immobilized on individual flow cells of a High Amine Capacity (HAC) sensorchip (Sierra Sensors GmbH, Hamburg, Germany) and antibodies flowed over the surface. Each sample was diluted and injected in duplicate over the immobilized peptide and BSA reference surfaces, followed by injection of running buffer only for the dissociation phase. After every analytical cycle, the sensor chip surfaces were regenerated. Sensorgrams were double-referenced by subtracting out binding from the BSA reference surfaces and blank running buffer injections, and binding response report points collected in the dissociation phase.

Protein G purified mAbs were analyzed in a secondary screen using an SPR indirect (capture) binding assay, whereby the antibodies were immobilized on a protein A-derivatized sensorchip (XanTec Bioanalytics GmbH, Duesseldorf, Germany) and A-beta40 Monomer, A-beta42 Oligomer, pooled soluble brain extracts flowed over the surface. The specificity of the antibodies was verified in an SPR direct binding assay by covalently immobilizing A-beta42 Monomer and A-beta42 Oligomer on individual flow cells of a HAC sensorchip and flowing purified mAbs over the surface.

To further verify and validate A-beta42 Oligomer binding, antibodies were covalently immobilized, followed by the injection over the surface of commercially-prepared stable A-beta42 Oligomers (SynAging SAS, Vandœuvre-lès-Nancy, France), Isotyping The hybridoma antibodies were isotyped using antibody trap experiments. Trap plates were coated with 1:10,000 Goat anti-mouse IgG/IgM(H&L) antibody at 100 uL/well carbonate coating buffer pH9.6 overnight at 4 C. No blocking step was used. Primary antibody (hybridoma supernatants) was added (100 ug/mL). Secondary Antibody 1:5,000 Goat anti-mouse IgGγ-HRP or 1:10,000 Goat anti-mouse IgMμ-HRP at 100 uL/well in PBS-Tween for 1 hour at 37 C with shaking. All washing steps were performed for 30 mins with PBS-Tween. The substrate TMB was added at 50 uL/well, developed in the dark and stopped with equal volume 1 M HCl.

Antibody Sequencing

The CDR and variable regions of the heavy and light chains were sequenced. Immunoglobulin gene transcripts expressed by the hybridomas were amplified from cDNA generated from the hybridoma cells using standard RT-PCR and sequenced using a standard dye-terminator capillary sequencing method.

Biological Deposit

The 301-17 hybridoma was deposited under the provisions of the Budapest Treaty with the American Type Culture Collection (ATCC®) 10801 University Blvd., Manassas, Va., 20110-2209, USA on Jul. 19, 2017 and given the Accession number PTA-124318.

Example 3

HHQK (SEQ ID NO: 1)

Antibodies to Cyclo(CGHHQKG) (SEQ ID NO: 2)

The Antibodies were Tested as Described in Example 2.

ELISA and SPR testing found that hybridoma clones bound the cyclopeptide preferentially over the linear peptide.

Clones 301-3, 301-11 and 301-17 raised against cyclo (CGHHQKG) (SEQ ID NO: 2) were selected for further analysis.

Isotyping revealed 301-3, 301-11 and 301-17 were IgG3 subtypes.

Antibodies were tested in one or more assays for their ability to bind cyclic peptide, linear peptide, A-beta 1-42 monomer and A-beta 1-42 oligomers prepared as described above.

ELISA and SPR assays confirmed that the antibodies preferentially bound the cylopeptide relative to the linear peptide (and were not cross reactive to unrelated cyclic peptides) and/or preferentially bound Ab oligomers relative to monomers.

Antibody Sequence

Clones 301-3, 301-11 and 301-17 antibodies were sequenced as further provided below. The CDR sequences of 301-3 and 301-11 are provided in Table 9(C and B). The CDRs for 301-17 are provided in SEQ ID NOs: 20-25. The consensus DNA sequence and polypeptide sequences of the variable portion of the heavy and light chain of the antibodies are provided in Table 10A.

As shown, the heavy chain CDRs for 301-3 and 301-11 were identical for CDRs 1 and 2 and CDR3 varied at one position. Two light chains were sequenced for 301-3. One light chain was near identical to the light chain for 301-11.

Example 4

Antibodies to cyclo(CGQKLVG) (SEQ ID NO: 6)

The antibodies were tested as described in Example 2.

ELISA and SPR testing found that hybridoma clones bound the cyclopeptide preferentially over the linear peptide.

Clones 305-59, 305-61, 350-62 raised against cyclo (CGQKLVG) (SEQ ID NO: 6) were selected for further analysis.

Isotyping revealed 305-59, 305-61, 350-62 were IgG1, IgG3 and IgG1 subtypes respectively.

Antibodies were tested in one or more assays for their ability to bind cyclic peptide, linear peptide, A-beta 1-42 monomer and A-beta 1-42 oligomers prepared as described above.

ELISA and SPR assays confirmed that the antibodies preferentially bound the cylopeptide relative to the linear peptide (and were not cross reactive to unrelated cyclic peptides) and/or preferentially bound Ab oligomers relative to monomers.

Antibody Sequence

Clones 305-59, 305-61, 350-62 antibodies were sequenced as further provided below. The CDR sequences of 305-61, 301-62 and 305-59, are provided in Table 9 (D, E and I). The consensus DNA sequence and polypeptide sequences of the variable portion of the heavy and light chain of the antibodies are provided in Table 10B.

Example 5

Antibodies to cyclo(CGHDSGG) (SEQ ID NO: 10)

The antibodies were tested as described in Example 2.

ELISA and SPR testing found that hybridoma clones bound the cyclopeptide preferentially over the linear peptide.

Clones 303-25, 303-26 and 303-30 raised against cyclo (CGHDSGG) (SEQ ID NO: 10) were selected for further analysis.

Isotyping revealed 303-25, 303-26 and 303-30 were IgG2a, IgG1 and IgG1 subtypes respectively. Threes clones of antibody 303-26 and three clones of 303-30 which differed in their kappa chain were identified.

Antibodies were tested in one or more assays for their ability to bind cyclic peptide, linear peptide, A-beta 1-42 monomer and A-beta 1-42 oligomers prepared as described above.

ELISA and SPR assays confirmed that the antibodies preferentially bound the cylopeptide relative to the linear peptide (and were not cross reactive to unrelated cyclic peptides) and/or preferentially bound Ab oligomers relative to monomers.

Antibody Sequence

Clones 303-25, 303-26 and 303-30 antibodies were sequenced as further provided below. The CDR sequences are provided in Table 9 (F, G and H). The consensus DNA sequence and polypeptide sequences of the variable portion of the heavy and light chain of the antibodies are provided in Table 10C.

Example 6

Methods:

Immunohistochemistry

Immunohistochemistry was performed on frozen human brain sections, with no fixation or antigen retrieval. In a humidified chamber, non-specific staining was blocked by incubation with serum-free protein blocking reagent (Dako Canada Inc., Mississauga, ON, Canada) for 1 h. The following primary antibodies were used for immunostaining: mouse monoclonal isotype controls IgG1, IgG2a, and IgG2b, and anti-amyloid β 6E10, all purchased from Biolegend, and purified antibodies 301-11, 301-17, 305-59, 305-61, 305-62, 303-25, 303-26 and 303-30 reactive to the corresponding cyclopeptide. All antibodies were used at 1 μg/mL. Sections were incubated at room temperature for 1 h, and washed 3×5 min in TBS-T. Anti-Mouse IgG Horseradish Peroxidase conjugated (1:1000, ECL) was applied to sections and incubated 45 min, then washed 3×5 min in TBS-T. DAB chromogen reagent (Vector Laboratories, Burlington ON, Canada) was applied and sections rinsed with distilled water when the desired level of target to background staining was achieved. Sections were counterstained with Mayer's haematoxylin, dehydrated and cover slips were applied. Slides were examined under a light microscope (Zeiss Axiovert 200M, Carl Zeiss Canada, Toronto ON, Canada) and representative images captured at 20 and 40× magnification using a Leica DC300 digital camera and software (Leica Microsystems Canada Inc., Richmond Hill, ON). Images were optimized in Adobe Photoshop using Levels Auto Correction.

CSF and Brain Extracts

Brain Extracts

Human brain tissues were obtained from the University of Maryland Brain and Tissue Bank upon approval from the UBC Clinical Research Ethics Board (C04-05 95). CSFs were obtained from patients assessed at the UBC Hospital Clinic for Alzheimer's and Related Disorders. The study was approved by the UBC Clinical Research Ethics Board, and written consent from the participant or legal next of kin was obtained prior to collection of CSF samples. Clinical diagnosis of probable AD was based on NINCDS-ADRDA criteria. CSFs were collected in polypropylene tubes, processed, aliquoted into 100 μL polypropylene vials, and stored at −80° C. within 1 hour after lumbar puncture.

Homogenization: Human brain tissue samples were weighed and subsequently submersed in a volume of fresh, ice cold TBS and EDTA-free protease inhibitor cocktail from Roche Diagnostics (Laval QC, Canada) such that the final concentration of brain tissue was 20% (w/v). Tissue was homogenized in this buffer using a mechanical probe homogenizer (3×30 sec pulses with 30 sec pauses in between, all performed on ice). TBS homogenized samples were then subjected to ultracentrifugation (70,000×g for 90 min). Supernatants were collected, aliquoted and stored at −80° C. The protein concentration of TBS homogenates was determined using a BCA protein assay (Pierce Biotechnology Inc, Rockford IL, USA).

CSF

CSF was pooled from 9 donors with AD and 9 donors without AD. Samples were analyzed by SPR using purified IgG at a concentration of 30 micrograms/ml for all antibodies. Mouse IgG was used as an antibody control, and all experiments were repeated at least 2 times.

Positive binding in CSF and brain extracts was confirmed using antibody 6E10.

SPR Analysis of Brain Extracts 4 brain extracts from AD patients and 4 brain extracts from age-matched controls were pooled and analyzed. Brain samples, homogenized in TBS, included frontal cortex Brodmann area 9. All experiments were performed using a Molecular Affinity Screening System (MASS-1) (Sierra Sensors GmbH, Hamburg, Germany), an analytical biosensor that employs high intensity laser light and high speed optical scanning to monitor binding interactions in real time as described in Example 6. Purified antibodies generated for cyclopeptides described herein were captured on separate flow cells of a protein A-derivatized sensor chip and diluted samples injected over the surfaces for 180 seconds, followed by 120 seconds of dissociation in buffer and surface regeneration. Binding responses were double-referenced by subtraction of mouse control IgG reference surface binding and assay buffer, and the different groups of samples compared.

SPR Analysis of Synthetic Oligomer Binding

Serial 2-fold dilutions (7.8 nM to 2000 nM) of commercially-prepared synthetic amyloid beta oligomers (SynAging SAS, Vandœuvre-lès-Nancy, were tested for binding to covalently immobilized antibodies by SPR. Antibody mAb6E10 and mouse control IgG were used as positive and negative controls respectively. Monomer binding was assessed in a separate assay as described in Example 2.

Results

CSF, Brain Extracts and Immunohistochemistry

Antibodies were tested for their ability to bind A-beta in CSF, soluble brain extracts and tissue samples of cavaderic AD brains. Strength of relative positivity in the tables is shown by the number plus signs.

IHC results are also summarized in Table 1, 3 and 5 where "+/−" denotes staining similar to or distinct from isotype control but without clear plaque morphology.

FIG. 2A-FIG. 2D shows an example of the lack of plaque staining on fresh frozen sections with antibody 303-25, 301-17 and 305-62 compared to the positive plaque staining seen with 6E10 antibody.

As shown in Tables 1-6 and FIG. 2A-FIG. 2D, antibodies raised to the cyclopeptides bound to A-beta in brain extracts and/or CSF, but did not appreciably bind to monomers on SPR, and did not appreciably bind to plaque fibrils by IHC. They did bind commercially prepared oligomers of A-beta preferentially.

Each of the antibodies tested (301-17, 301-3, 301-11, 303-25, 303-26, 303-30 305-59, 305-61. 305-62) as well as the positive control antibody but not the control IgG antibody bound the commercial preparation of oligomeric A-beta.

TABLE 1

Summary of binding characteristics

| | Clone # | Oligomers/ Monomers | CSF AD/ Non-AD | Brain Extract AD/ Non-AD | IHC— Plaque Staining |
|---|---|---|---|---|---|
| cyclo(CGHHQKG) (SEQ ID NO: 2) | 301-03 | ++ | + | ++ | +/− |
| | 301-11 | ++ | ++ | ++ | +/− |
| | 301-17 | ++ | + | ++ | − |

*Scoring is relative to other clones in the same sample category.

TABLE 2

A-beta Oligomer and Monomer binding

| Clone tested | 301-1D6 (03) | 301-11 | 301-17 |
|---|---|---|---|
| oligomer | 15.07, 13.78* RU | 19.27 RU | 24.01, 34.08 RU* |
| monomer | −0.6 RU** | −0.1 RU** | 0.3 RU** |

*the results of two assays using synthetic commercially prepared oligomers

**monomer preparations were made and assayed as described in Example 2

Formalin fixed brain tissue of a confirmed AD patient was also tested. The results are shown in Table 7. The brain tissues were fixed in 10% buffered formalin for several days and paraffin processed in the Sakura VIP tissue processors. Tissue sections were probed with 1 µg/ml of antibody with and without microwave antigen retrieval (AR). The pan-amyloid beta reactive antibody 6E10 was included along with selected antibody clones as a positive control. Antibodies were diluted in Antibody Diluent (Ventana), color was developed with OptiView DAB (Ventana). The staining was performed on the Ventana Benchmark XT IHC stainer. Images were obtained with an Olympus BX45 microscope. Images were analyzed blind by a professional pathologist with expertise in neuropathology.

TABLE 3

Summary of binding characteristics

| | Clone # | Oligomers/ Monomers | CSF AD/ Non-AD | Brain Extract AD/ Non-AD | IHC— Plaque Staining |
|---|---|---|---|---|---|
| cyclo(CGQKLVG) (SEQ ID NO: 6) | 305-59 (5G1) | ++ | − | ++ | +/− |
| | 305-61 (7E9) | ++ | ++ | − | − |
| | 305-62 (8H10) | ++ | − | + | − |

* Scoring is relative to other clones in the same sample category

TABLE 4

A-beta Oligomer and Monomer binding

| Clone tested | 305-59 | 305-61 | 305-62 |
|---|---|---|---|
| oligomer | 11.73 RU | 12.23, 17.53* | 8.76, 12.34 RU* |
| monomer | −0.2 RU** | 0.2 RU** | −0.1** |

*the results of two assays using synthetic commercially prepared oligomers

**monomer preparations were made and assayed as described in Example 2

TABLE 5

Binding properties

| | Clone # | Oligomers/ Monomers | CSF AD/ Non-AD | Brain Extract AD/ Non-AD | IHC— Plaque Staining |
|---|---|---|---|---|---|
| cyclo(CGHDSGG) (SEQ ID NO: 10) | 303-25 | ++ | +++ | + | − |
| | 303-26 | + | − | ++ | − |
| | 303-30 | ++ | − | ++ | +/− |

TABLE 6

| A-beta Oligomer binding RU values subtracted for monomer binding | | | |
|---|---|---|---|
| Clone tested | 303-26 | 303-25 | 303-30 |
| oligomer | 2.97 | 18.29, 9.43** | 13.64 |
| Monomer | −1.0* | −0.2* | −0.2* |

*the results of two assays using synthetic commercially prepared oligomers
**monomer preparations were made and assayed as described in Example 2

TABLE 7

| Plaque staining in formalin fixed brain tissues | | |
|---|---|---|
| Epitope | Antibodies to test | Staining of senile plaque amyloid |
| 301 | 11 | Neg |
| | 17 | Neg |
| 303 | 25 | Neg |
| 305 | 59 (5G1) | possible weak staining |
| | 61 (7E9) | Neg |
| | 62 (8H10) | Neg |
| Positive Control | 6E10 | strongly positive |

Example 7

Inhibition of Oligomer Propagation

The biological functionality of antibodies was tested in vitro by examining their effects on Amyloid Beta (Aβ) aggregation using the Thioflavin T (ThT) binding assay. Aβ aggregation is induced by and propagated through nuclei of preformed small Aβ oligomers, and the complete process from monomeric Aβ to soluble oligomers to insoluble fibrils is accompanied by concomitantly increasing beta sheet formation. This can be monitored by ThT, a benzothiazole salt, whose excitation and emission maxima shifts from 385 to 450 nm and from 445 to 482 nm respectively when bound to beta sheet-rich structures and resulting in increased fluorescence. Briefly, Aβ 1-42 (Bachem Americas Inc., Torrance, CA) was solubilized, sonicated, diluted in Tris-EDTA buffer (pH7.4) and added to wells of a black 96-well microtitre plate (Greiner Bio-One, Monroe, NC) to which equal volumes of cyclopeptide raised antibody or irrelevant mouse IgG antibody isotype controls were added, resulting in a 1:5 molar ratio of Aβ31-42 peptide to antibody. ThT was added and plates incubated at room temperature for 24 hours, with ThT fluorescence measurements (excitation at 440 nm, emission at 486 nm) recorded every hour using a Wallac Victor3v 1420 Multilabel Counter (PerkinElmer, Waltham, MA). Fluorescent readings from background buffer were subtracted from all wells, and readings from antibody only wells were further subtracted from the corresponding wells.

As shown in FIG. 3A-FIG. 3F, Aβ42 aggregation, as monitored by ThT fluorescence, demonstrated a sigmoidal shape characterized by an initial lag phase with minimal fluorescence, an exponential phase with a rapid increase in fluorescence and finally a plateau phase during which the Aβ molecular species are at equilibrium and during which there is no increase in fluorescence. Co-incubation of Aβ42 with an irrelevant mouse antibody did not have any significant effect on the aggregation process. In contrast, co-incubation of Aβ42 with the test antibodies completely inhibited all phases of the aggregation process. In contrast, co-incubation of Aβ42 with the test antibodies completely inhibited all phases of the aggregation process.

Figure 3A:
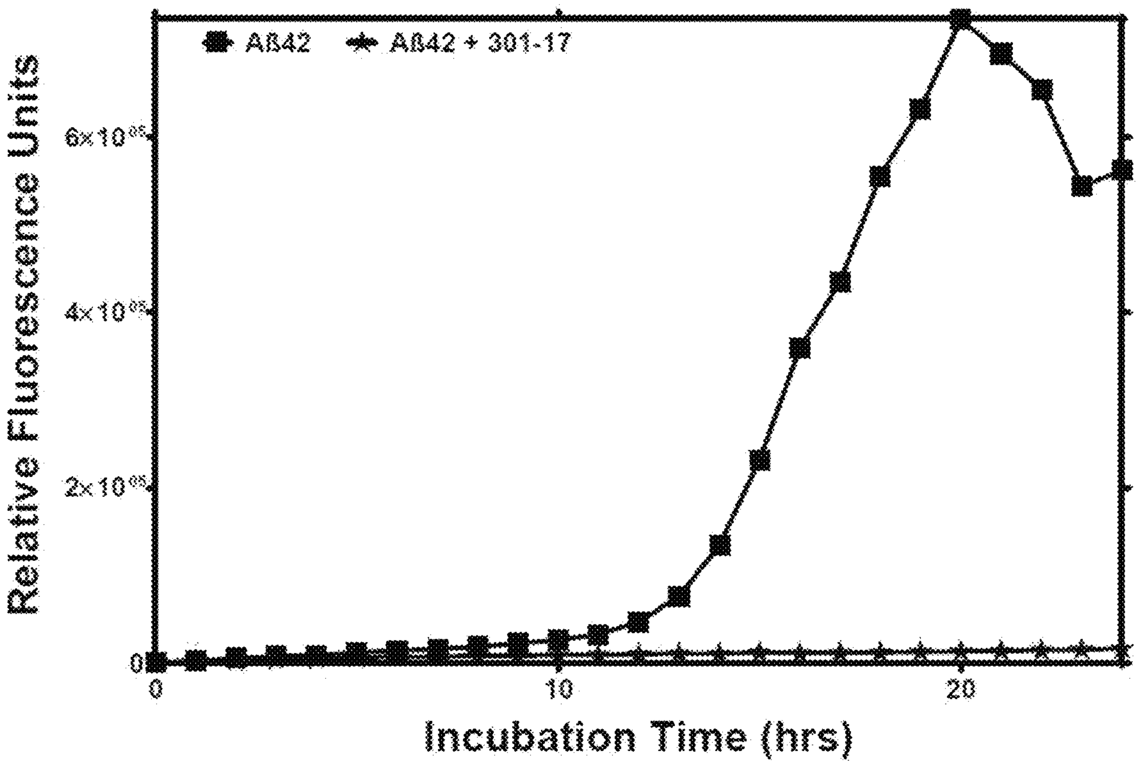
FIG. 3A-FIG. 3D: Are a series of plots showing propagation of A-beta aggregation in vitro in the presence or absence of representative antibody raised using a cyclic peptide comprising HHQK (SEQ ID NO: 1) or QKLV (SEQ ID NO: 5). Plots showing propagation of A-beta aggregation in vitro in the presence (stars) or absence (squares) of representative antibodies
Figure 3B:
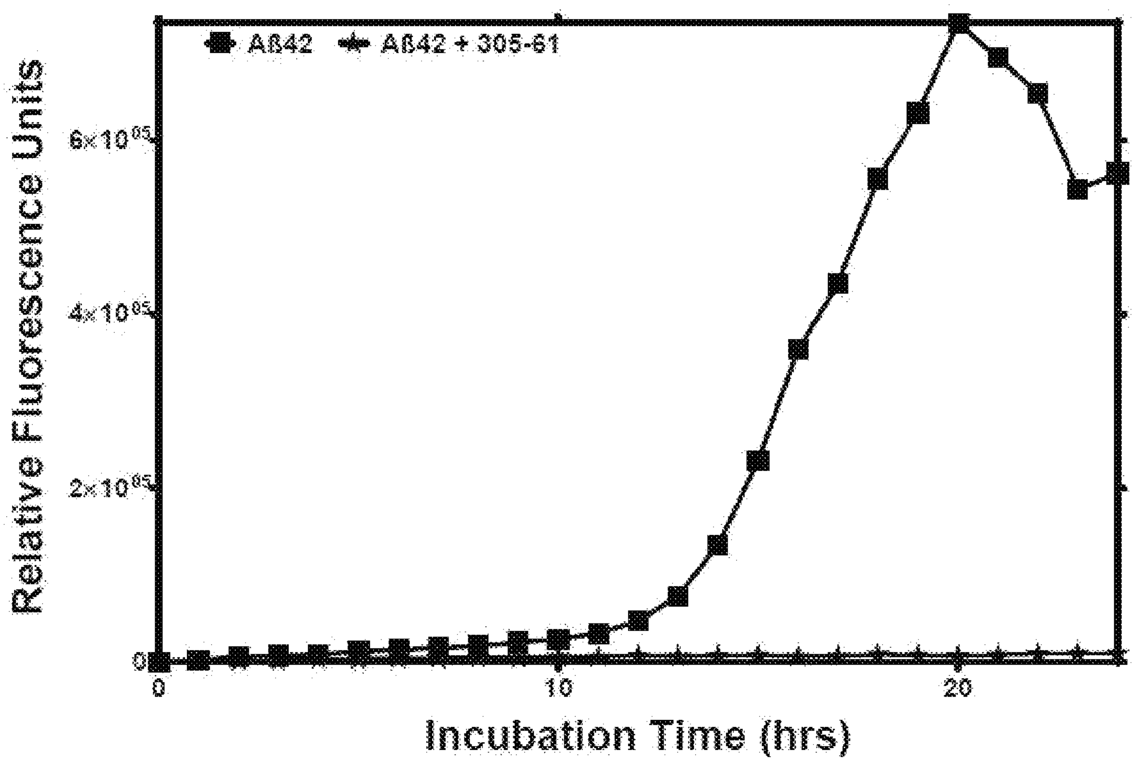
Figure 3C:
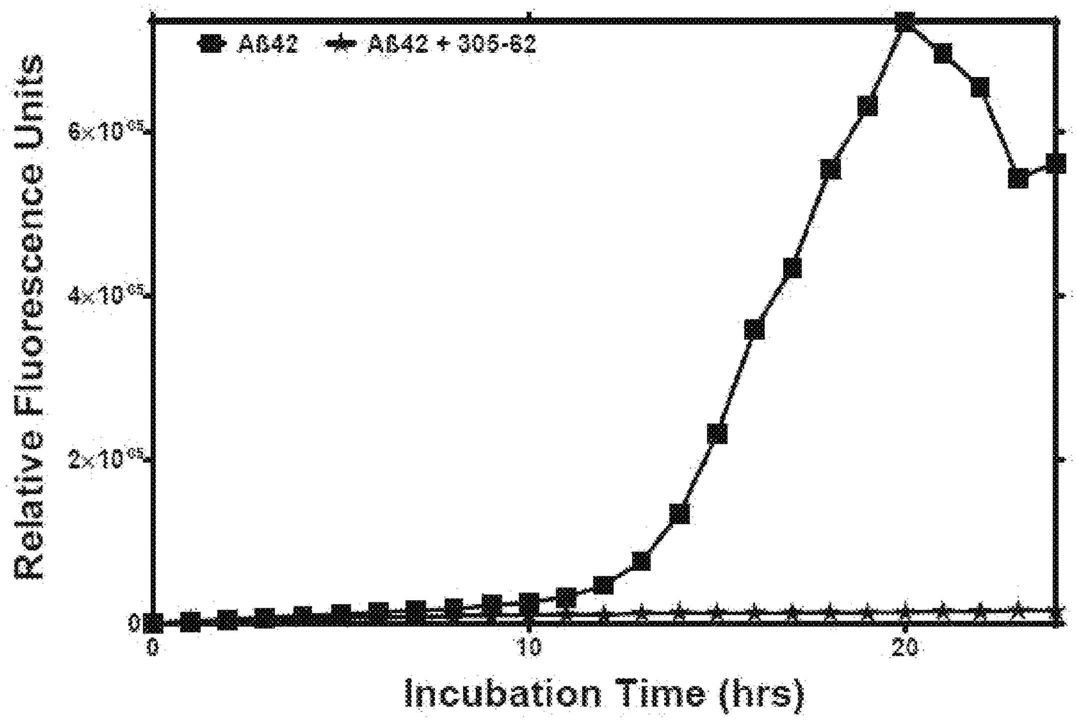
Figure 3D:
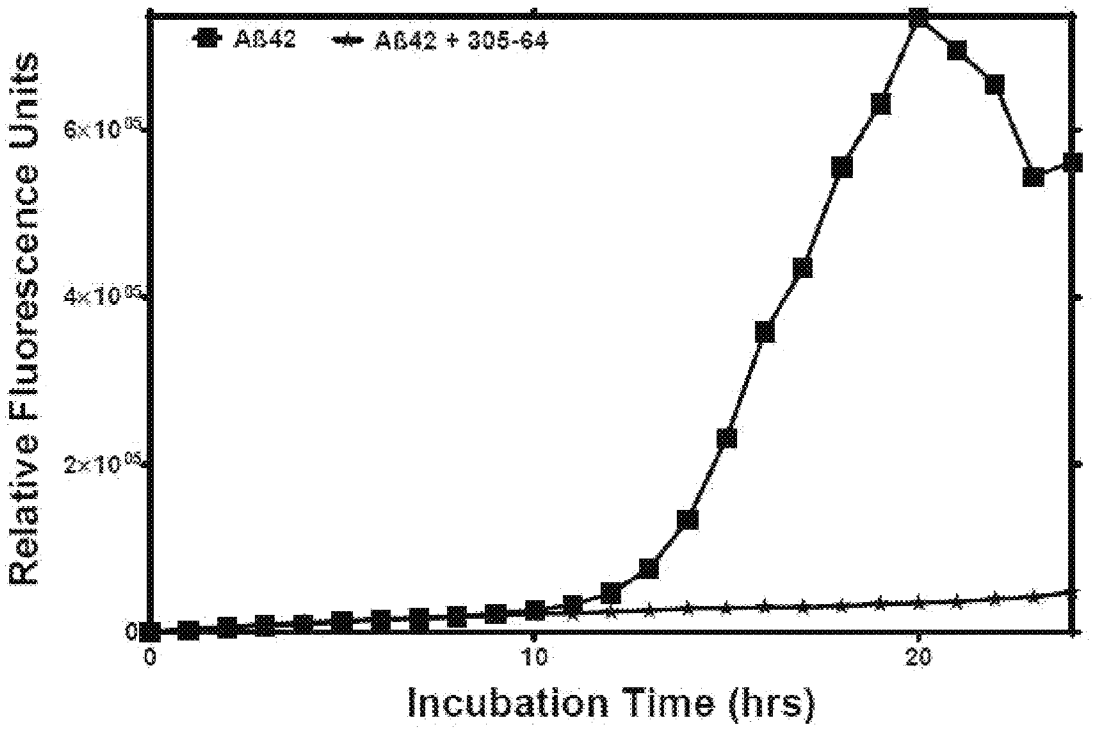

Results obtained with antibody 301-17 (IgG3 isotype) are shown in FIG. 3A. Results obtained with antibodies 305-61, 305-62 and 305-64 are shown in FIG. 3B, FIG. 3C and FIG. 3D. 305-59 was also tested and showed similar results (FIG. 3F).

Figure 3E:
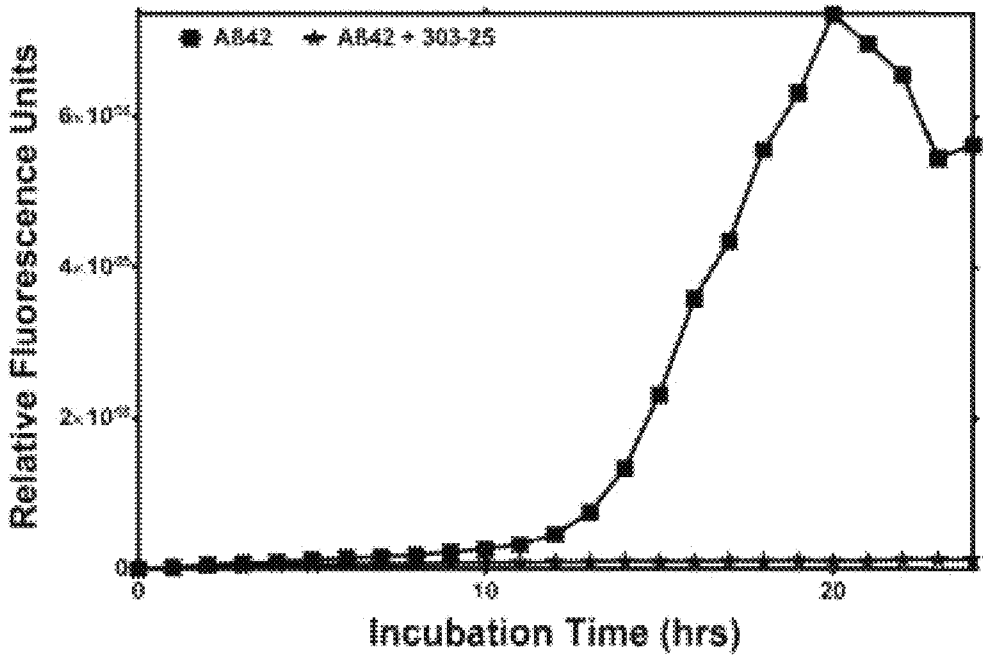
FIG. 3E and FIG. 3F are plots showing propagation of A-beta aggregation in vitro in the presence or absence of a representative antibody raised using a cyclic peptide comprising HDSG (SEQ ID NO:9) or QKLV (SEQ ID NO: 5), respectively.
Figure 3F:
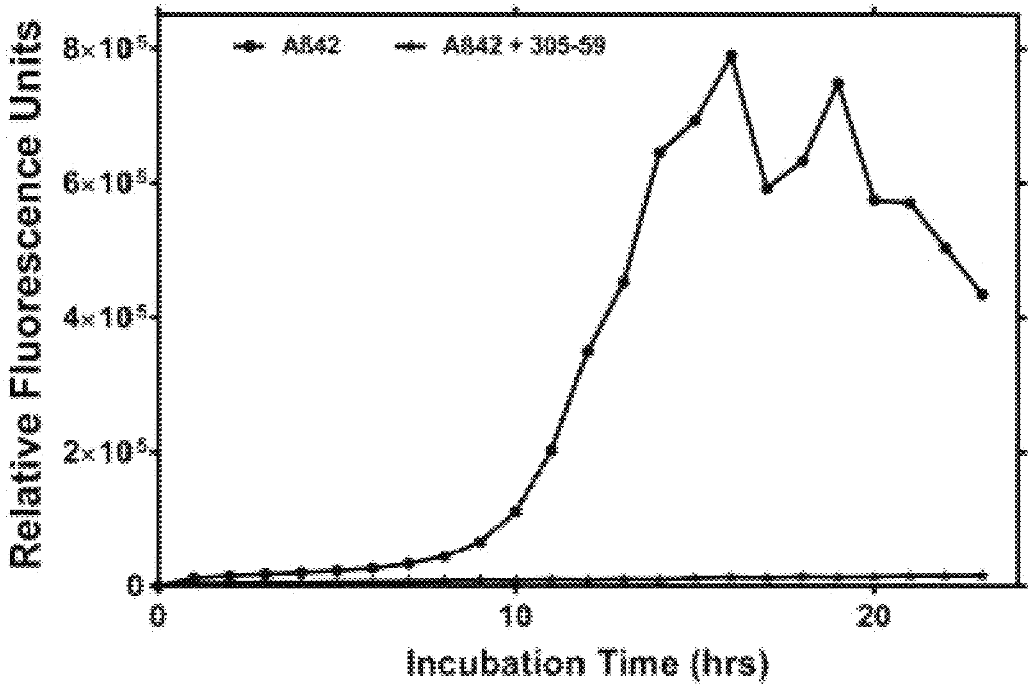

Results were also obtained with antibody 303-25 which is shown in FIG. 3E. 303-30 was also tested and showed similar results.

As the ThT aggregation assay mimics the in vivo biophysical/biochemical stages of Aβ propagation and aggregation from monomers, oligomers, protofibrils and fibrils that is pivotal in AD pathogenesis, the antibodies raised to cyclo(CGHHQKG) (SEQ ID NO: 2), cyclo CGQKLVG (SEQ ID NO: 6) or cyclo(CGHDSGG) (SEQ ID NO: 10), demonstrate the potential to completely abrogate this process. Isotype control performed using mouse IgG control showed no inhibition.

Example 8

Toxicity Inhibition Assay

The inhibition of toxicity of A-beta42 oligomers by antibodies raised to the cyclopeptides were tested in a rat primary cortical neuron assay.

Antibody and control IgG are each adjusted to a concentration such as 2 mg/mL. Various molar ratios of A-beta oligomer and antibody are tested along with a vehicle control, A-beta oligomer alone and a positive control such as the neuroprotective peptide humanin HNG.

An exemplary set up is shown in Table 8.

Following preincubation for 10 minutes at room temperature, the volume is adjusted to 840 microlitres with culture medium. The solution is incubated for 5 min at 37 C. The solution is then added directly to the primary cortical neurons and cells are incubated for 24 h. Cell viability can be determined using the MTT assay.

TABLE 8

| AβO/AB molar ratio | Aβo (μL) | AβO (μM) | AB (μM) | AB (μL) | Medium (μL) | Final volume (μL) |
|---|---|---|---|---|---|---|
| 5/1 | 1.68 | 4.2 | 0.84 | 12.73 | 185.6 | 200 |
| 1/1 | 1.68 | 4.2 | 4.20 | 63.64 | 134.7 | 200 |
| 1/2 | 1.68 | 4.2 | 8.4 | 127.27 | 71.1 | 200 |

AβO working solution: 2.2 mg/mL-500 μM

| | |
|---|---|
| CTRL vehicle: | 1.68 μL of oligomer buffer + 127.3 μL PBS + 711 μL culture medium |
| CTRL AβO: | 1.68 μL of AβO + 127.3 μL PBS + 711 μL culture medium |
| CTRL HNG: | 1.68 μL of AβO + 8.4 μL HNG (100 nM final) + 127.3 μL PBS + 702.6 μL culture medium |

Figure 4A:
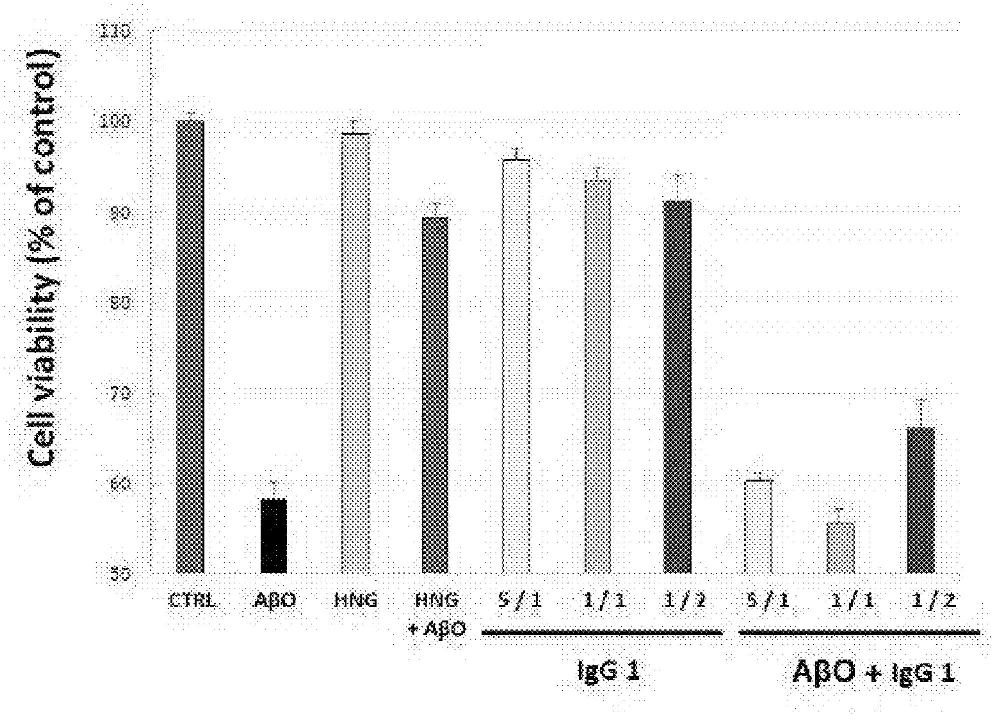
FIG. 4A-FIG. 4F: A series of plots showing the viability of rat primary cortical neurons exposed to toxic A-beta oligomers (AβO) in the presence or absence of different molar ratios of a negative isotype control (A) or an antibody raised against cyclo(CGHHQKG) (SEQ ID NO: 2) (B), raised against cyclo(CGQKLV) (SEQ ID NO: 6) (C) and (D), raised against cyclo(CGHHQKG) (SEQ ID NO: 2)(E), raised against cyclo(CGHDSGG) (SEQ ID NO: 10) F. Controls include neurons cultured alone (CTRL), neurons incubated with antibody without oligomers and neurons cultured with the neuroprotective humanin peptide (HNG) with or without oligomers.
Figure 4B:
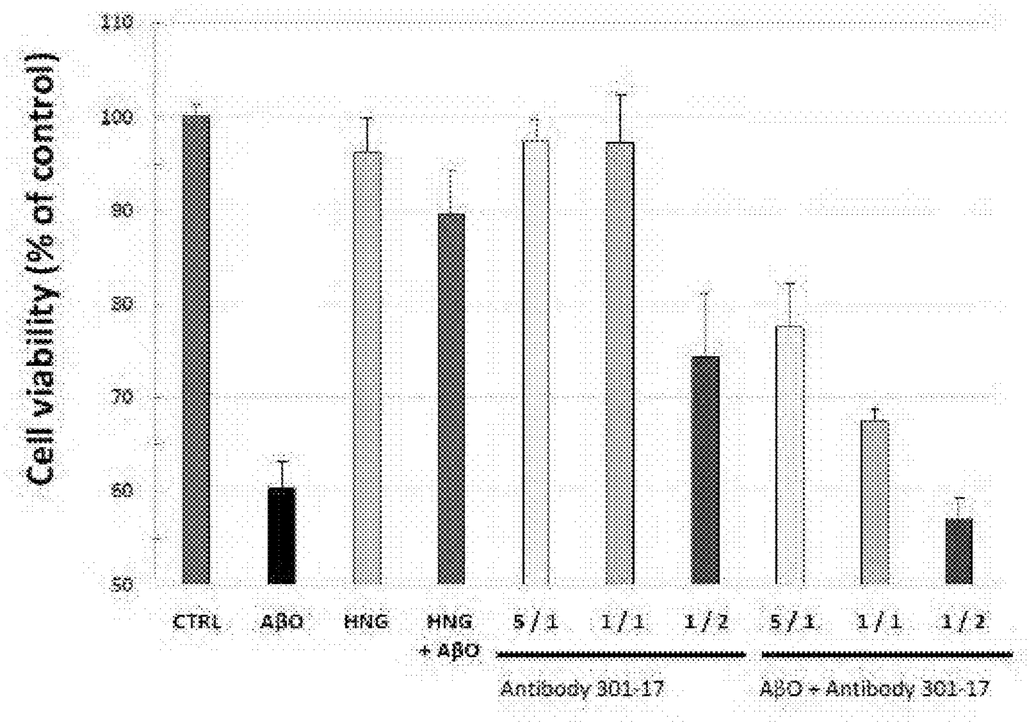

In a first assay, the antibody 301-17 alone showed some toxicity at the highest concentration (½ oligomer/antibody ratio), likely due to endotoxin contamination of the antibody preparation, but demonstrated inhibition of A-beta oligomer toxicity when added at lower concentrations (1/1 and 5/1 oligomer/antibody ratios) (FIG. 4B).

Figure 5A:
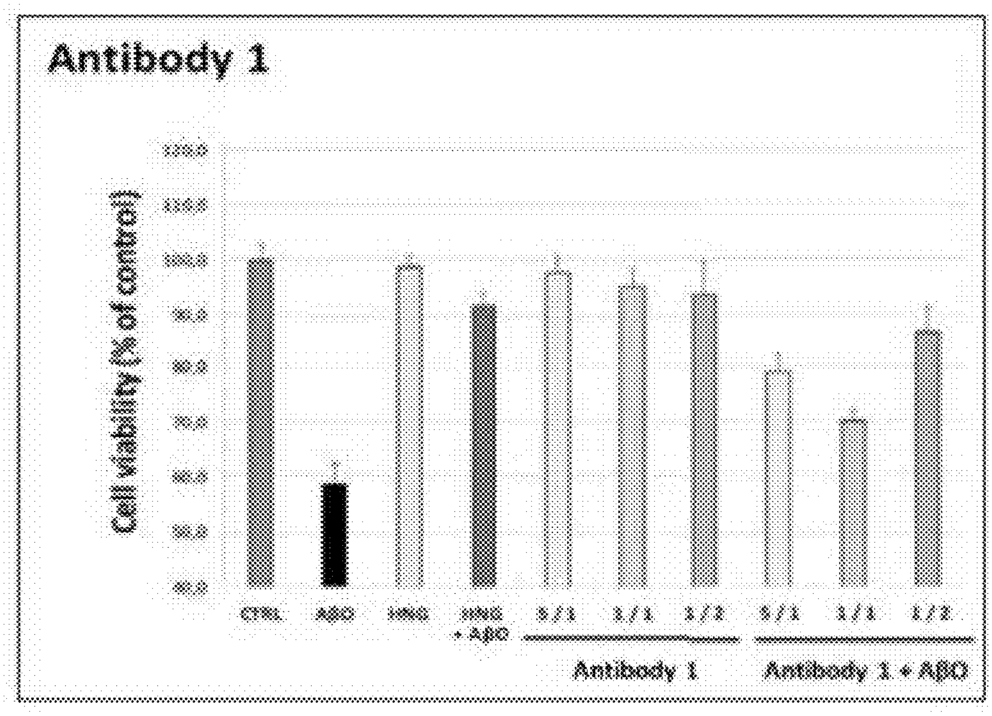
FIG. 5A: A plot showing the viability of rat primary cortical neurons exposed to toxic A-beta oligomers (AβO) in the presence or absence of different molar ratios of an antibody raised using a cyclic peptide comprising HHQK (SEQ ID NO: 1) (A) and prepared under low endotoxin conditions. Controls include neurons cultured alone (CTRL), neurons incubated with antibody without oligomers and neurons cultured with the neuroprotective humanin peptide (HNG) with or without oligomers.
Figure 5B:
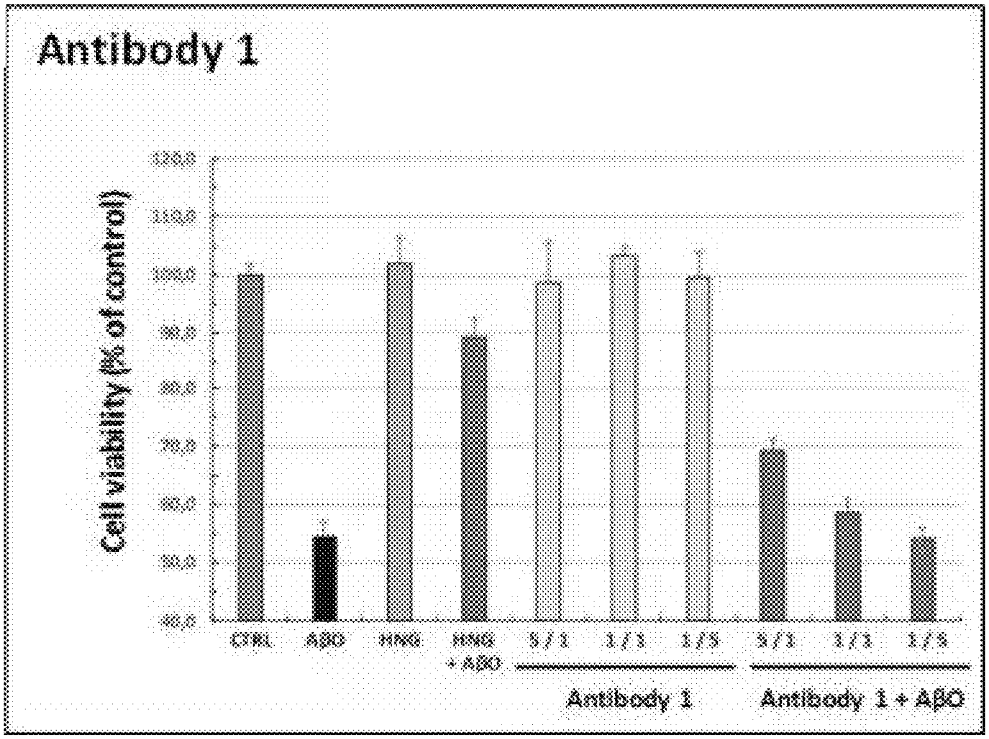
FIG. 5B: A plot showing the viability of rat primary cortical neurons exposed to toxic A-beta oligomers in the presence or absence of different molar ratios of recombinant 301-17 antibody (IgG1).

The assay was repeated using an antibody preparation generated under low endotoxin conditions. This time, in the absence of A-beta oligomers, the antibody alone had no effect on neuronal cell viability. When incubated in the presence of A-beta oligomers, the antibody inhibited A-beta oligomer-induced neuronal death at all molar ratios tested (FIG. 5A). The assay was repeated using recombinant 301-17 antibody grafted to a mouse IgG1 backbone. Again, in the absence of A-beta oligomers, the antibody alone had no effect on neuronal cell viability. When incubated in the presence of A-beta oligomers, the antibody inhibited A-beta oligomer-induced neuronal death at all molar ratios tested (FIG. 5B).

Figure 4C:
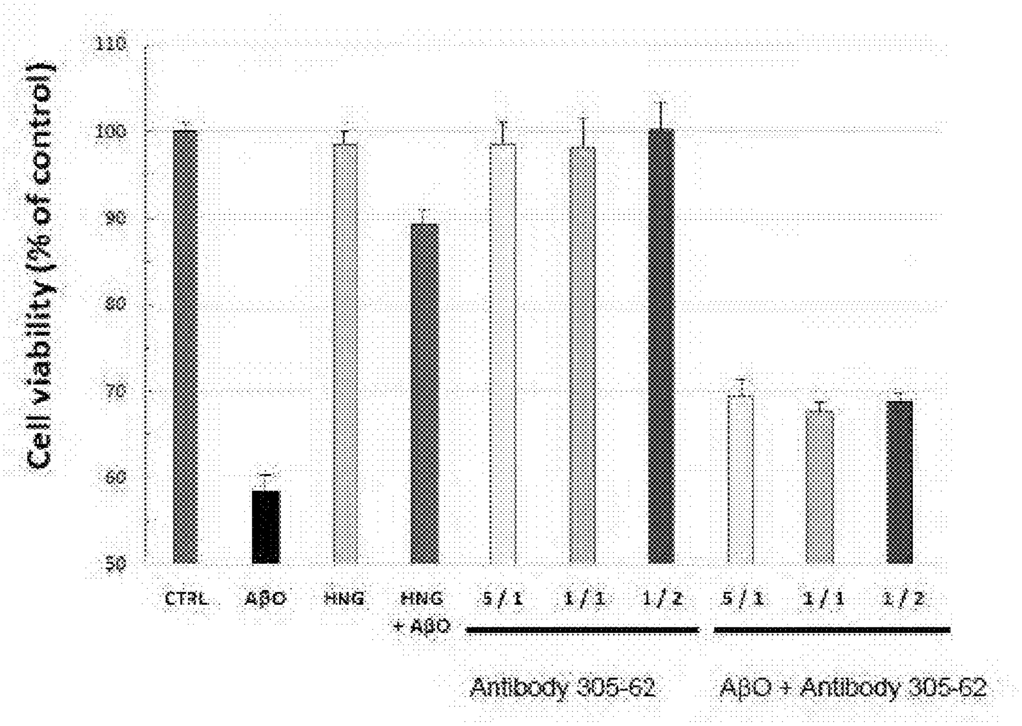
Figure 4D:
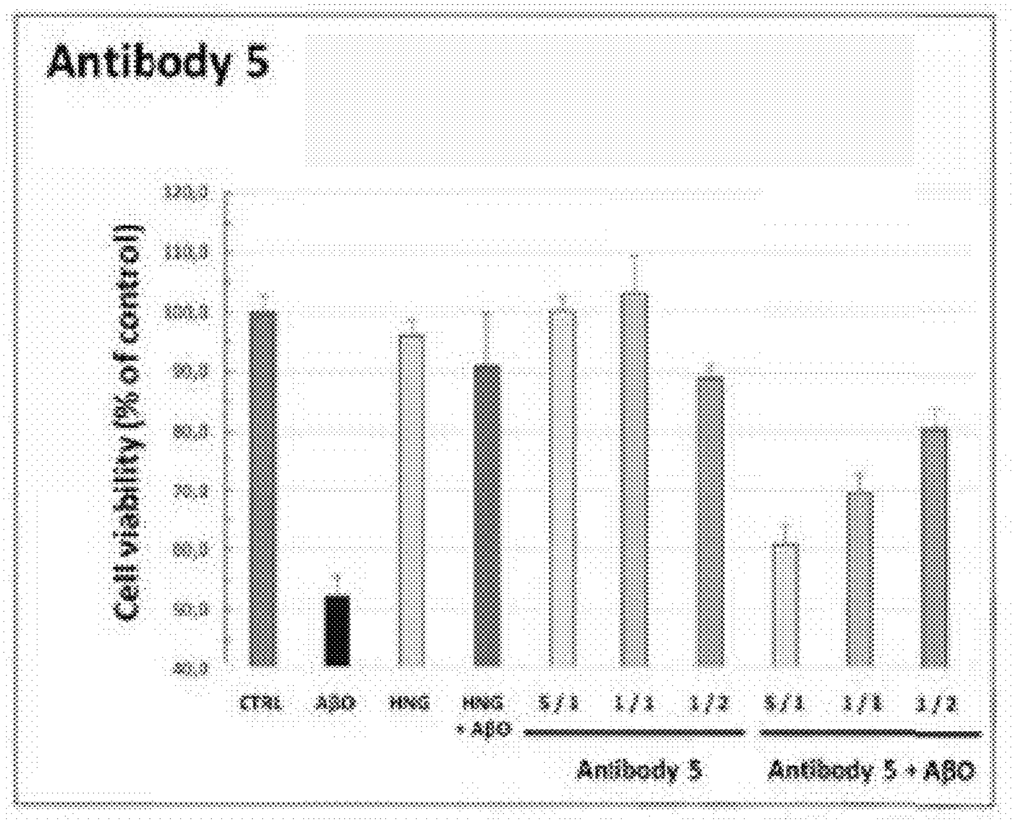
Figure 4E:
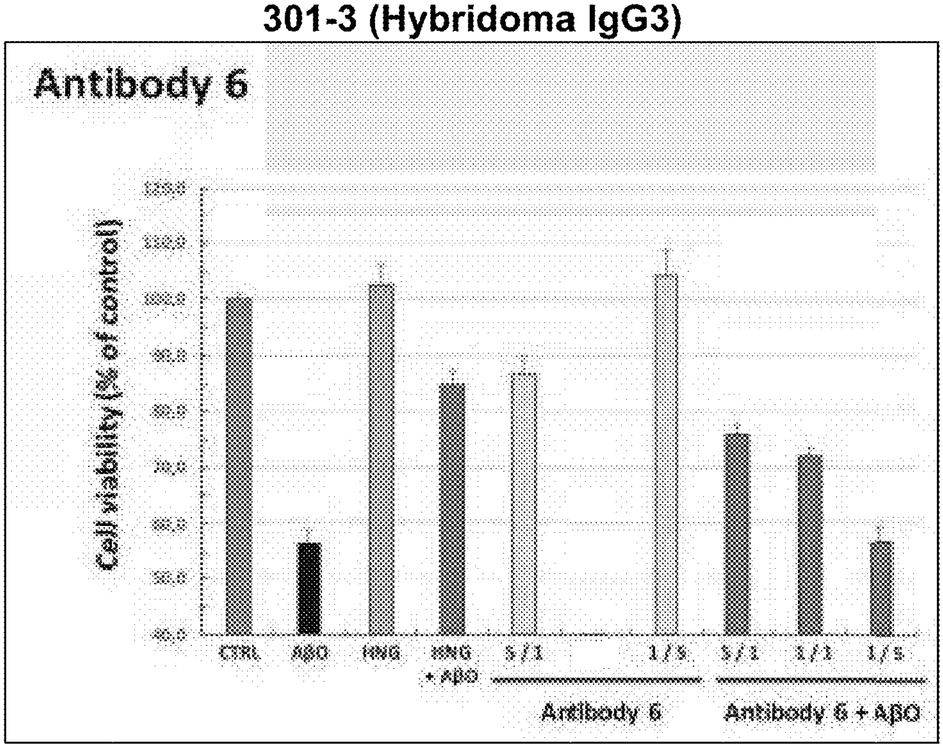

Antibody 301-3 was also tested in the assay. Like 301-17, antibody alone showed no toxicity to neuronal cell viability whereas when antibody when incubated in the presence of A-beta oligomers, the antibody inhibited A-beta oligomer-induced neuronal death at all molar ratios tested (FIG. 4E).

This test was also conducted using antibody 305-62. The antibody alone showed no toxicity (FIG. 4C) and inhibition of A-beta oligomer toxicity was observed for all concentrations of antibody to oligomer: 1:5, 1:1 and 2:1 (FIG. 4C). This test was also conducted using antibody 305-61. The antibody alone showed no toxicity (FIG. 4D) and inhibition of A-beta oligomer toxicity was observed for all concentrations of antibody to oligomer: 1:5, 1:1 and 2:1 (FIG. 4D). The presence of antibody 301-61 resulted in a dose-dependent protection toward AβO-induced cell death (FIG. 4D). The maximal neuroprotection was reached at a molar ratio of 1:2 (AβO:AB1) resulting in a remaining cell viability of 80.1±3.8% of control.

Figure 4F:
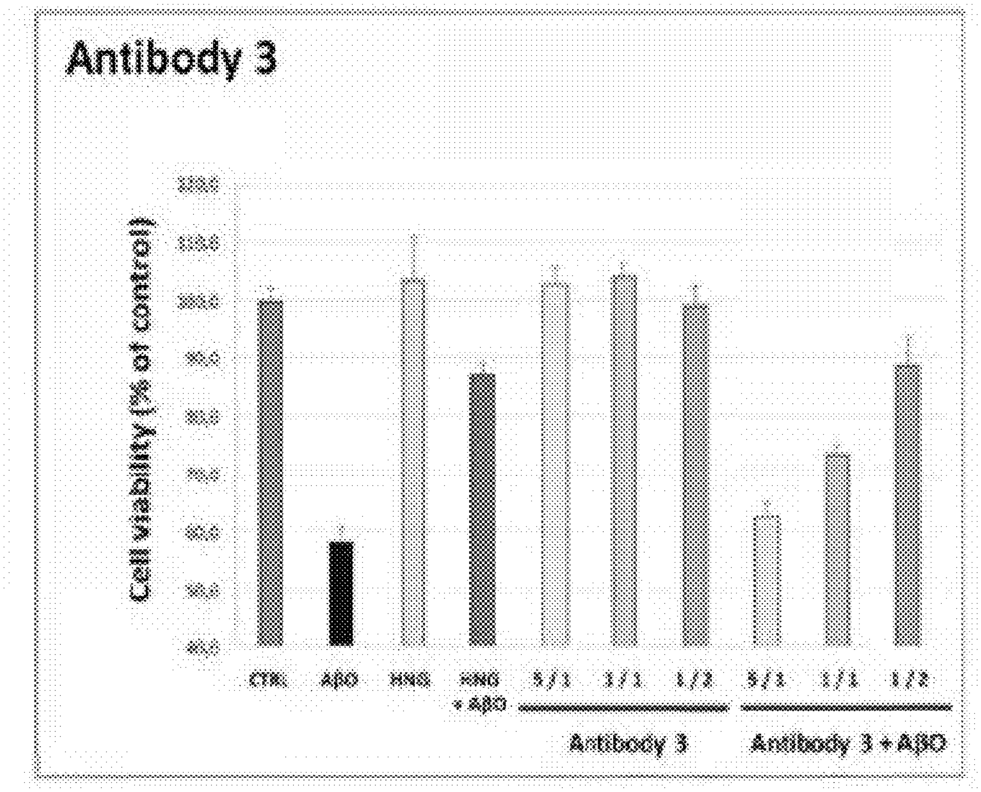

The test was also conducted using antibody 303-25. The antibody alone showed no toxicity (FIG. 4F) and inhibition of A-beta oligomer toxicity was observed for all concentrations of antibody to oligomer: 1:5, 1:1 and 2:1 (FIG. 4F). In the absence of AβO, antibody 303-25 had no effect on cell viability (FIG. 4F). The presence of antibody 3 resulted in a dose-dependent protection toward AβO-induced cell death. The maximal neuroprotection was reached at a molar ratio of 1:2 (AβO:AB1) resulting in a remaining cell viability of 88.8±4.8% of control.

Controls are shown in FIG. 4A. (NB: FIG. 4B, FIG. 4C and FIG. 4E show decreasing ratio of test antibody:oligomer whereas FIG. 4D and FIG. 4F show an increasing ratio of test antibody:oligomer).

Example 9

RT-PCR was carried out using 5' RACE and gene specific reverse primers which amplify the appropriate mouse immunoglobulin heavy chain (IgG1/IgG3/IgG2A) and light chain (kappa) variable region sequences.

The specific bands were excised and cloned into pCR-Blunt II-TOPO vector for sequencing, and the constructs were transformed into *E. coli*

At least 8 colonies of each chain were picked & PCR screened for the presence of amplified regions prior to sequencing. Selected PCR positive clones were sequenced. The complementarity determining regions (CDRs) are identified according to IMGT/LIGM-DB.

CDR Sequencing-cyclo(CGHHQKG) (SEQ ID NO: 2) Antibodies

The CDR sequences of 301-17 which was determined to have an IgG3 heavy chain and a kappa light chain are in Table 9A. The consensus DNA sequence and protein sequences of the variable portion of the heavy and light chain are provided in Table 10A.

The CDR sequences of 301-11 are in Table 9B. The consensus DNA sequence and protein sequences of the variable portion of the heavy and light chain are provided in Table 10A.

The CDR sequences of antibody 301-03 (1 and 2) raised against cyclo(CGHHQKG) are provided in Table 9C. The consensus DNA sequence and protein sequences of the variable portion of the heavy and light chain are provided in Table 10A.

CDR Sequencing-cyclo(CGQKLVG) (SEQ ID NO: 6) Antibodies

The CDR sequences of 305-61 (7E9.1) which was determined to have an IgG3 heavy chain and a kappa light chain are in Table 9D. The consensus DNA sequence and protein sequences of the variable portion of the heavy and light chain are provided in Table 10B.

The CDR sequences of 305-62 (8H10) which was determined to have an IgG1 heavy chain and a kappa light chain are in Table 9E. The consensus DNA sequence and protein sequences of the variable portion of the heavy and light chain are provided in Table 10B.

The CDR sequences of 305-59 which was determined to have an IgG1 heavy chain and a kappa light chain are in Table 91. The consensus DNA sequence and protein sequences of the variable portion of the heavy and light chain are provided in Table 10B.

CDR Sequencing-cyclo(CGHDSGG) (SEQ ID NO: 10) Antibodies

The CDR sequences of 303-25 which was determined to have an IgG heavy chain and a kappa light chain are in Table 9F. The consensus DNA sequence and protein sequences of the variable portion of the heavy and light chain are provided in Table 10C.

The CDR sequences of 303-26 (3 kappa chains) and 303-30 are in Table 9G and 9H respectively. The consensus DNA sequence and protein sequences of the variable portion of the heavy and light chain are provided in Table 10C.

TABLE 9A

CDR sequences of antibody 301-17 raised against cyclo(CGHHQKG) (SEQ ID NO: 2)

| Chain | CDR | Sequence | SEQ ID NO. |
|---|---|---|---|
| Heavy | CDR-H1 | GYSFTSYW | 20 |
| | CDR-H2 | VHPGRGVST | 21 |
| | CDR-H3 | SRSHGNTYWFFDV | 22 |
| Light | CDR-L1 | QSIVHSNGNTY | 23 |
| | CDR-L2 | KVS | 24 |
| | CDR-L3 | FQGSHVPFT | 25 |

TABLE 9B

CDR sequences of antibody 301-11 raised against cyclo(CGHHQKG) (SEQ ID NO: 2)

| Chain | CDR | Sequence | SEQ ID NO. |
|---|---|---|---|
| Heavy | CDR-H1 | GFTFSDYY | 26 |
| | CDR-H2 | ISDGGSYT | 27 |
| | CDR-H3 | ARDYYGSSSYTSGFAY | 28 |
| Light | CDR-L1 | QSLLNSRTRKNY | 29 |
| | CDR-L2 | WAS | 30 |
| | CDR-L3 | KQSYNLYT | 31 |

TABLE 9C

CDR sequences of antibody 301-03 (1 and 2) raised against cyclo (CGHHQKG) (SEQ ID NO: 2)

| Chain | CDR | Sequence | SEQ ID NO. |
|---|---|---|---|
| Heavy | CDR-H1 | GFTFSDYY | 32 |
| | CDR-H2 | ISDGGSYT | 33 |
| | CDR-H3 | ARDYYGSNSYTSGFAY | 34 |
| Light | CDR-L1 | QSLLNSRTRKNY | 35 |
| | CDR-L2 | WAS | 36 |
| | CDR-L3 | KQSYNLYT | 37 |
| Light | CDR-L1 | QSIVHSNGNTY | 38 |
| | CDR-L2 | KVS | 39 |
| | CDR-L3 | FQGSHVPLT | 40 |

TABLE 9D

CDR sequences of antibody 305-61 (7E9) raised against cyclo (CGQKLVG) (SEQ ID NO: 6)

| Chain | CDR | Sequence | SEQ ID NO. |
|---|---|---|---|
| Heavy | CDR-H1 | GYTFTDYE | 41 |
| | CDR-H2 | IDPETGDT | 42 |
| | CDR-H3 | TSPIYYDYDWFAY | 43 |
| Light | CDR-L1 | QSLLNNRTRKNY | 44 |
| | CDR-L2 | WAS | 45 |
| | CDR-L3 | KQSYNLRT | 46 |

TABLE 9E

CDR sequences of antibody 305-62 (8H10) raised against cyclo (CGQKLVG) (SEQ ID NO: 6)

| Chain | CDR | Sequence | SEQ ID NO |
|---|---|---|---|
| Heavy | CDR-H1 | GFSLSTSGMG | 47 |
| | CDR-H2 | IWWDDDK | 48 |
| | CDR-H3 | ARSITTVVATPFDY | 49 |
| Light | CDR-L1 | QNVRSA | 50 |
| | CDR-L2 | LAS | 51 |
| | CDR-L3 | LQHWNSPFT | 52 |

TABLE 9F

CDR sequences of antibody 303-25 raised against cyclo (CGHDSGG) (SEQ ID NO: 10)

| Chain | CDR | Sequence | SEQ ID NO |
|---|---|---|---|
| Heavy | CDR-H1 | GYTFTSYW | 53 |
| | CDR-H2 | IDPSDSQT | 54 |
| | CDR-H3 | SRGGY | 55 |
| Light | CDR-L1 | QDINNY | 56 |
| | CDR-L2 | YTS | 57 |
| | CDR-L3 | LQYDNLWT | 58 |

TABLE 9G

CDR sequences of antibody 303-26 raised against cyclo (CGHDSGG) (SEQ ID NO: 10)

| Chain | CDR | Sequence | SEQ ID NO |
|---|---|---|---|
| Heavy | CDR-H1 | GYTFTSYW | 59 |
| | CDR-H2 | IDPSDSET | 60 |
| | CDR-H3 | TRGTY | 61 |
| Light 1 | CDR-L1 | QSVSTSSYSY | 62 |
| | CDR-L2 | YAS | 63 |
| | CDR-L3 | QHSLEIPWT | 64 |
| Light 2 | CDR-L1 | SSVSSAY | 65 |
| | CDR-L2 | STS | 66 |
| | CDR-L3 | HQYHRSPFT | 67 |
| Light 3 | CDR-L1 | SQDINKYIAWY | 68 |
| | CDR-L2 | NTS | 69 |
| | CDR-L3 | LQHDNLWT | 70 |

TABLE 9H

CDR sequences of antibody 303-30 raised against cyclo (CGHDSGG) (SEQ ID NO: 10)

| Chain | CDR | Sequence | SEQ ID NO |
|---|---|---|---|
| Heavy | CDR-H1 | GYTFTSYW | 71 |
| | CDR-H2 | IDPSDSET | 72 |
| | CDR-H3 | TRGTY | 73 |
| Light 1 | CDR-L1 | QSVSTSSYSY | 74 |
| | CDR-L2 | YAS | 75 |
| | CDR-L3 | QHSLEIPWT | 76 |

TABLE 9H-continued

| CDR sequences of antibody 303-30 raised against cyclo (CGHDSGG) (SEQ ID NO: 10) | | | |
|---|---|---|---|
| Chain | CDR | Sequence | SEQ ID NO |
| Light 2 | CDR-L1 | SSVSSAY | 77 |
| | CDR-L2 | STS | 78 |
| | CDR-L3 | HQYHRSPFT | 79 |
| Light 3 | CDR-L1 | SQDINKYIAWY | 80 |
| | CDR-L2 | NTS | 81 |
| | CDR-L3 | LQHDNLWT | 82 |

TABLE 9I

| CDR sequences of antibody 305-59 raised against cyclo (CGQKLVG) (SEQ ID NO: 6) | | | |
|---|---|---|---|
| Chain | CDR | Sequence | SEQ ID NO |
| Heavy | CDR-H1 | GFNIKDTY | 185 |
| | CDR-H2 | IAPASGNT | 186 |
| | CDR-H3 | ARHVY | 187 |
| Light | CDR-L1 | QSVSND | 188 |
| | CDR-L2 | YAS | 189 |
| | CDR-L3 | QQDYISPYT | 190 |

TABLE 10A

Heavy chain and light chain variable sequences of antibodies raised against cyclo (CGHHQKG) (SEQ ID NO: 2) Consensus DNA sequence and translated protein sequences of the variable region. The complementarity determining regions (CDRs) are underlined according to IMGT/LIGM-DB

| Isotype | Consensus DNA Sequence | Protein sequence |
|---|---|---|
| 301-17<br>IgG3<br>SEQ ID NO: 83,<br>84 | ATGGGATGGAGCTGTATCATCCTCTTTTTGGTAGCAACAGCTACAGGTGTCCACTC<br>CCAGGTCCAACTGCAGCAGCCTGGGGCTGAGCTTGTGAAGCCTGGGGCTTCAGTGA<br>AAATGTCCTGCAAGGCTTCT**GGCTACAGCTTCACCAGCTACTGG**ATAAACTGGGTG<br>AAGCAGAGGCCTGGACAAGGCCTTGAGTGGATTGGAGAT**GTTCATCCTGGTAGAGG**<br>**TGTTTCTACC**TACAATGCGAAGTTCAAGAGCAAGGCCACACTGACTCTAGACACGT<br>CCTCCAGCACAGCCTACATGCAGCTCAGCAGCCTGACATCTGAGGACTCTGCGGTC<br>TATTATTGT**TCAAGATCCCACGGTAATACCTACTGGTTCTTCGATGTC**TGGGGCGC<br>AGGGACCACGGTCACCGTCTCCTCAGCTACAACAACAGCCCCATCT | MGWSCIILFLVATATGVHSQ<br>VQLQQPGAELVKPGASVKMS<br>CKAS**GYSFTSYW**INWVKQRP<br>GQGLEWIGD**VHPGRGVST**YN<br>AKFKSKATLTLDTSSSTAYM<br>QLSSLTSEDSAVYYC**SRSHG**<br>**NTYWFFDV**WGAGTTVTVSSA<br>TTTAPS |
| 301-17<br>Kappa<br>SEQ ID NO: 85,<br>86 | ATGAAGTTGCCTGTTAGGCTGTTGGTGCTGATGTTCTGGATTCCTGCTTCCAGCAG<br>TGATGTTTTGATGACCCAAACTCCACTCTCCCTGCCTGTCAGTCTTGGAGATCAAG<br>CCTCCATCTCTTGCAGATCTAGT**CAGAGCATTGTACATAGTAATGGAAACACCTAT**<br>TTAGAATGGTACCTGCAGAAACCAGGCCAGTCTCCAAAGCTCCTGATCTACAA**AGT**<br>**TTCC**AACCGATTTTCTGGGGTCCCAGACAGGTTCAGTGGCAGTGGATCAGGGACAG<br>ATTTCACACTCAAGATCAGCAGAGTGGAGGCTGAGGATCTGGGAGTTTATTACTGC<br>**TTTCAAGGTTCACATGTTCCATTCACG**TTCGGCTCGGGGACAAAGTTGGAAATAAA<br>ACGGGCTGATGCT | MKLPVRLLVLMFWIPASSSD<br>VLMTQTPLSLPVSLGDQASI<br>SCRSS**QSIVHSNGNTY**LEWY<br>LQKPGQSPKLLIY**KVS**NRFS<br>GVPDRFSGSGSGTDFTLKIS<br>RVEAEDLGVYYC**FQGSHVPF**<br>**T**FGSGTKLEIKRADA |
| 301-11<br>IgG3<br>SEQ ID NO: 87,<br>88 | ATGAACTTTGGGCTCAGCTTGATTTTCCTTGTCCTTGTTTTAAAAGGTGTCCAGTG<br>TGAAGTGCAGCTGGTGGAGTCTGGGGGAGGCTTAGTGAAGCCTGGAGGGTCCCTGA<br>AACTCTCCTGTGCAGCCTCT**GGATTCACTTTCAGTGACTATTAC**ATGTATTGGGTT<br>CGCCAGACTCCGGAAAAGAGGCTGGAGTGGGTCGCAACC**ATTAGTGATGGTGGTAG**<br>**TTACACC**TCCTATCCAGACAGTGTGAAGGGACGATTCACCATCTCCAGAGACAATG<br>CCAAGAACAACCTGTACCTGCAAATGAGCAGTCTGAGGTCTGAGGACACAGCCATG<br>TATTACTGT**GCAAGAGATTACTACGGTAGTAGTAGCTACACCTCGGGCTTTGCTTA**<br>**C**TGGGGCCAAGGGACTCTGGTCACTGTCTCTGCA | MNFGLSLIFLVLVLKGVQCE<br>VQLVESGGGLVKPGGSLKLS<br>CAAS**GFTFSDYY**MYWVRQTP<br>EKRLEWVAT**ISDGGSYT**SYP<br>DSVKGRFTISRDNAKNNLYL<br>QMSSLRSEDTAMYYC**ARDYY**<br>**GSSSYTSGFAY**WGQGTLVTV<br>SA |
| 301-11<br>Kappa<br>SEQ ID NO: 89,<br>90 | ATGGATTCACAGGCCCAGGTTCTTATATTGCTGCTGCTATGGGTATCTGGTACCTG<br>TGGGGACATTGTGATGTCACAGTCTCCATCCTCCCTGGCTGTGTCAACAGGAGAGA<br>AGGTCACTATGAGCTGCAAATCCAGT**CAGAGTCTGCTCAACAGTAGAACCCGAAAG**<br>**AACTAC**TTGGCTTGGTACCAGCAGAAACCAGGGCAGTCTCCTAAACTGCTGATCTA<br>C**TGGGCATCC**ACTAGGGAATCTGGGGTCCCTGATCGCTTCACAGGCAGTGGATCTG<br>GGACAGATTTCACTCTCACCATCAGCAGTGTGCAGGCTGAAGACCTGGCAGTTTAT<br>TACTGC**AAGCAATCTTATAATCTGTACACG**TTCGGAGGGGGGACCAAGCTGGAAAT<br>AAAA | MDSQAQVLILLLLWVSGTCG<br>DIVMSQSPSSLAVSTGEKVT<br>MSCKSS**QSLLNSRTRKNY**LA<br>WYQQKPGQSPKLLII**WAS**TR<br>ESGVPDRFTGSGSGTDFTLT<br>ISSVQAEDLAVYYC**KQSYNL**<br>**YT**EGGGTKLEIK |
| 301-03<br>IgG3<br>SEQ ID NO: 91,<br>92 | ATGAACTTCGGGCTCAGCTTGATTTTCCTTGTCCTTGTTTTAAAAGGTGTCCAGTG<br>TGAAGTGCAGCTGGTGGAGTCTGGGGGAGGCTTAGTGAAGCCTGGAGGGTCCCTGA<br>AACTCTCCTGTGCAGCCTCT**GGATTCACTTTCAGTGACTATTAC**ATGTATTGGGTT<br>CGCCAGACTCCGGAAAAGAGGCTGGAGTGGGTCGCAACC**ATTAGTGATGGTGGTAG**<br>**TTACACC**TCCTATCCAGACAGTGTGAAGGGGCGATTCACCATCTCCAGAGACAGTG<br>CCAAGAACAACCTGTACCTGCAAATGAGCAGTCTGAAGTCTGAGGACACAGCCATG<br>TATTACTGT**GCAAGAGATTACTACGGTAGTAATAGTTACACCTCGGGCTTTGCTTA**<br>**C**TGGGGCCAAGGGACTCTGGTCACTGTCTCTGCA | MNFGLSLIFLVLVLKGVQCE<br>VQLVESGGGLVKPGGSLKLS<br>CAAS**GFTFSDYY**MYWVRQTP<br>EKRLEWVAT**ISDGGSYT**SYP<br>DSVKGRFTISRDSAKNNLYL<br>QMSSLKSEDTAMYYC**ARDYY**<br>**GSNSYTSGFAY**WGQGTLVTV<br>SA |

TABLE 10A-continued

Heavy chain and light chain variable sequences of antibodies raised against cyclo (CGHHQKG) (SEQ ID NO: 2) Consensus DNA sequence and translated protein sequences of the variable region. The complementarity determining regions (CDRs) are underlined according to IMGT/LIGM-DB

| Isotype | Consensus DNA Sequence | Protein sequence |
|---|---|---|
| 301-03<br>Kappa 1<br>SEQ ID NO: 93,<br>94 | ATGGATTCACAGGCCCAGGTTCTTATATTGCTGCTGCTATGGGTATCTGGTACCTG<br>TGGGGACATTGTGATGTCACAGTCTCCATCCTCCCTGGCTGTGTCAGCAGGAGAGA<br>AGGTCACTATGAGCTGCAAATCCAGT**CAGAGTCTGCTCAATAGTAGAACCCGAAAG**<br>**AACTAC**TTGGCTTGGTACCAGCAGAAACCAGGGCAGTCTCCTAAACTGCTGATCTA<br>C**TGGGCATCC**ACTAGGGAATCTGGGGTCCCTGATCGCTTCACAGGCAGTGGATCTG<br>GGACAGATTTCACTCTCACCATCAGCAGTGTGCAGGCTGAAGACCTGGCAGTTTAT<br>TACTGC**AAGCAATCTTATAATCTGTACACG**TTCGGAGGGGGGACCAAGCTGGAAAT<br>AAAA | MDSQAQVLILLLLWVSGTCG<br>DIVMSQSPSSLAVSAGEKVT<br>MSCKSS**QSLLNSRTRKNY**LA<br>WYQQKPGQSPKLLIY**WAS**TR<br>ESGVPDRFTGSGSGTDFTLT<br>ISSVQAEDLAVYYC**KQSYNL**<br>**YT**FGGGTKLEIK |
| 301-03<br>Kappa 2<br>SEQ ID NO: 95,<br>96 | ATGAAGTTGCCTGTTAGGCTGTTGGTGCTGATGTTCTGGATTCCTGCTTCCAGCAG<br>TGATGTTTTGATGACCCAAACTCCACTCTCCCTGCCTGTCAGTCTTGGAGATCAAG<br>CCTCCATCTCTTGCAGATCTAGT**CAGAGCATTGTACATAGTAATGGAAACACCTAT**<br>TTAGAATGGTACCTGCAGAAACCAGGCCAGTCTCCAAAGCTCCTGATCTAC**AAAGT**<br>**TTCC**AACCGATTTTCTGGGGTCCCAGACAGGTTCAGTGGCAGTGGATCAGGGACAG<br>ATTTCACACTCAAGATCAGCAGAGTGGAGGCTGAGGATCTGGGAGTTTATTTCTGC<br>**TTTCAAGGTTCACATGTTCCTCTCACG**TTCGGTGCTGGGACCAAGCTGGAGCTGAA<br>A | MKLPVRLLVLMFWIPASSSD<br>VLMTQTPLSLPVSLGDQASI<br>SCRSS**QSIVHSNGNTY**LEWY<br>LQKPGQSPKLLIY**KVS**NRFS<br>GVPDRFSGSGSGTDFTLKIS<br>RVEAEDLGVYFC**FQGSHVPL**<br>**T**FGAGTKLELK |

TABLE 10B

Heavy chain and light chain variable sequences of an antibody raised against cyclo (CGQKLVG) (SEQ ID NO: 6) Consensus DNA sequence and translated protein sequences of the variable region. The complementarity determining regions (CDRs) are underlined according to IMGT/LIGM-DB.

| Isotype | Consensus DNA Sequence | Protein sequence |
|---|---|---|
| 305-61<br>IgG<br>SEQ ID NO:<br>97, 98 | ATGGAATGGAGCTGGGTCTTTCTCTTCCTCCTGTCAGTAATTGCA<br>GGTGTCCAATCCCAGGTTCAACTGCAGCAGTCTGGGGCTGAGCTG<br>GTGAGGCCTGGGGCTTCAGTGACGCTGTCCTGCAAGGCTTCG**GGC**<br>**TACACATTTACTGACTAT**GAAATGCACTGGGTGAAGCAGACACCT<br>GTGCATGGCCTGGAATGGATTGGAGCT**ATTGATCCTGAAACTGGT**<br>**GATACT**GCCTACAATCAGGAGTTCAAGGGCAAGGCCACACTGACT<br>GCAGACAAATCCTCCAGCACAGCCTACATGGAGCTCCGCAGCCTG<br>ACATCTGAGGACTCTGCCGTCTATTACTGT**ACAAGCCCCATCTAC**<br>**TATGATTACGACTGGTTTGCTTAC**TGGGGCCACGGGACTCTGGTC<br>ACTGTCTCTGCAGCTACAACAACAGCCCCATCT | MEWSWVFLFLLSVIAG<br>VQSQVQLQQSGAELVR<br>PGASVTLSCKAS**GYTF**<br>**TDYE**MHWVKQTPVHGL<br>EWIGA**IDPETGDT**AYN<br>QEFKGKATLTADKSSS<br>TAYMELRSLTSEDSAV<br>YYC**TSPIYYDYDWFAY**<br>WGHGTLVTVSAATTTA<br>PS |
| 305-61<br>Kappa<br>SEQ ID NO:<br>99, 100 | ATGGATTCACAGGCCCAGGTTCTTATATTGCTGCTGCTATGGGTA<br>TCTGGTACCTGTGGGGACATTGTGATGTCACAGTCTCCATCCTCC<br>CTGGCTGTGTCAGCAGGAGAGAAGGTCACTATGAGCTGCAAATCC<br>AGT**CAGAGTCTGCTCAACAATAGAACCCGAAAGAACTAC**TTGGCT<br>TGGTACCAGCAGAAACCAGGGCAGTCTCCTAAACTGCTGATCTAC<br>**TGGGCATCC**ACTAGGGAATCTGGGGTCCCTGATCGCTTCACAGGC<br>AGTGGATCTGGGACAGATTTCACTCTCACCATCAGCAGTGTGCAG<br>GCTGAAGACCTGGCAGTTTATTACTGC**AAGCAATCTTATAATCTT**<br>**CGGACG**TTCGGTGGAGGCACCAAGCTGGAAATCAAACGGGCTGAT<br>GCT | MDSQAQVLILLLLWVS<br>GTCGDIVMSQSPSSLA<br>VSAGEKVTMSCKSS**QS**<br>**LLNNRTRKNY**LAWYQQ<br>KPGQSPKLLIY**WAS**TR<br>ESGVPDRFTGSGSGTD<br>FTLTISSVQAEDLAVY<br>YC**KQSYNLRT**FGGGTK<br>LEIKRADA |
| 305-62<br>IgG1<br>SEQ ID NO:<br>101, 102 | ATGGACAGGCTTACTTCTTCATTCCTGCTGCTGATTGTCCCTGCA<br>TATGTCTTGTCCCAAGTTACTCTAAAAGAGTCTGGCCCTGGGATA<br>TTGAAGCCCTCACAGACCCTCAGTCTGACTTGTTCTTTCTCT**GGG**<br>**TTTTCACTGAGCACTTCTG**GTATGGGTGTAGGCTGGATTCGTCAG<br>CCTTCAGGGAAGGGTCTGGAGTGGCTGGCACAC**ATTTGGTGGGAT**<br>**GATGATAAG**TACTATAACCCATCCCTGAAGAGCCAGCTCACAATC<br>TCCAAGGATACCTCCAGAAACCAGGTATTCCTCAAGATCACCAGT<br>GTGGACACTGCAGATACTGCCACTTACTACTGT**GCTCGAAGTATT**<br>**ACTACGGTAGTAGCTACGCCCTTTGACTAC**TGGGGCCAAGGCACC<br>ACTCTCACAGTCTCCTCAGCCAAAACGACAC | MDRLTSSFLLLIVPAY<br>VLSQVTLKESGPGILK<br>PSQTLSLTCSFS**GFSL**<br>**STSGMG**VGWIRQPSGK<br>GLEWLAH**IWWDDDK**YY<br>NPSLKSQLTISKDTSR<br>NQVFLKITSVDTADTA<br>TYYC**ARSITTVVATPF**<br>**DY**WGQGTTLTVSSAKT<br>T |
| <br>305-62<br>Kappa<br>SEQ ID NO:<br>103, 104 | ATGGGCATCAAGATGGAGTTTCAGACCCAGGTCTTTGTATTCGTG<br>TTGCTCTGGTTGTCTGGTGTTGATGGAGACATTGTGATGACCCAG<br>TCTCAAAAATTCATGTCCACATCAGTAGGAGACAGGGTCAGCATC<br>ACCTGCAAGGCCAGT**CAGAATGTTCGTTCTGCT**GTAGCCTGGTAT<br>CAACAGAAACCAGGGCAGTCTCCTAAAGCACTGATTTAC**CTGGCA**<br>**TCC**AACCGGCACACTGGAGTCCCTGATCGCTTCACAGGCAGTGGA<br>TCTGGGACAGATTTCACTCTCACCATTAGCAATGTGCATTCTGAA | MGIKMEFQTQVFVFVL<br>LWLSGVDGDIVMTQSQ<br>KFMSTSVGDRVSITCK<br>AS**QNVRSA**VAWYQQKP<br>GQSPKALIY**LAS**NRHT<br>GVPDRFTGSGSGTDFT<br>LTISNVHSEDLTDYFC |

TABLE 10B-continued

Heavy chain and light chain variable sequences of an antibody raised against cyclo (CGQKLVG) (SEQ ID NO: 6) Consensus DNA sequence and translated protein sequences of the variable region. The complementarity determining regions (CDRs) are underlined according to IMGT/LIGM-DB.

| Isotype | Consensus DNA Sequence | Protein sequence |
|---|---|---|
| | GACCTGACAGATTATTTCTGT**CTGCAACATTGGAATTCTCCGTTC** | **LQHWNSPFT**FGGGTKL |
| | **ACG**TTCGGAGGGGGGACCAAGCTGGAAATAAAACGGGCTGATGCT | EIKRADA |
| 305-59 | ATGAAATTCAGCTGGGTCATCTTCTTCCTGATGGCAGTGGTTACA | MKFSWVIFFLMAVVTG |
| IgG1 | GGGGTCAATTCAGAGGTTCAGCTGCAGCAGTCTGGGGCAGAGCTT | VNSEVQLQQSGAELVK |
| SEQ ID NO: | GTGAAGCCAGGGGCCTCAGTCAAGTTGTCCTGCACAGTTTCT**GGC** | PGASVKLSCTVS**GFNI** |
| 191, 192 | **TTCAACATTAAAGACACCTAT**GTGCACTGGGTGAAGCAGAGGCCT | **KDTY**VHWVKQRPEQGL |
| | GAACAGGGCCTGGAGTGGATTGGAAGG**ATTGCTCCTGCGAGTGGT** | EWIGR**IAPASGNT**KYA |
| | **AATACT**AAATATGCCCCGAATTTCCAGGACAAGGCCACTATAACA | PNFQDKATITADTSSN |
| | GCGGACACATCCTCCAACACAGCCTACCTGCAGCTCAACAGCCTG | TAYLQLNSLTSEDTAV |
| | ACATCTGAGGACACTGCCGTCTATTACTGT**GCGCGTCACGTCTAC** | YYC**ARHVY**WGQGTLVT |
| | TGGGGCCAAGGGACTCTGGTCACTGTCTCTGCA | VSA |
| 305-59 | ATGAAGTCACAGACCCAGGTCTTCGTATTTCTACTGCTCTGTGTG | MKSQTQVFVFLLLCVS |
| kappa | TCTGGTGCTCATGGGAGTATTGTGATGACCCAGACTCCCAAATTC | GAHGSIVMTQTPKFLL |
| SEQ ID NO: | CTGCTTGTATCAGCAGGAGACAGGGTTACCATAACCTGCAAGGCC | VSAGDRVTITCKAS**QS** |
| 193 , 194 | AGT**CAGAGTGTGAGTAATGAT**GTAGTTTGGTACCAACAGAAGCCA | **VSND**VVWYQQKPGQSP |
| | GGGCAGTCTCCTAAACTGCTGATATAC**TATGCATCC**AATCGCTAC | KLLIY**YAS**NRYTGVPD |
| | ACTGGAGTCCCTGATCGCTTTACTGGcAGTGGATATGGGACGGAT | RFTGSGYGTDFTFTIS |
| | TTCACTTTCACCATCAGCACTGTGcAGGcTGAAGAccTGGCAGTT | TVQAEDLAVYFC**QQDY** |
| | TATTTCTGT**CAGCAGGATTATATCTCTCCGTACACG**TTCGGAGGG | **ISPYT**FGGGTKLEIK |
| | GGGACCAAGCTGGAAATAAAA | |

TABLE 10C

Heavy chain and light chain variable sequences of an antibody raised against cyclo(CGHDSGG) (SEQ ID NO: 10) Consensus DNA sequence and translated protein sequences of the variable region. The complementarity determining regions (CDRs) are underlined according to IMGT/LIGM-DB.

| Isotype | Consensus DNA Sequence | Protein sequence |
|---|---|---|
| 303-25 | ATGGGATGGAGCTGTATCATCCTCTTCTTGGTAGCAACAGCTACA | MGWSCIILFLVATATG |
| IgG2a | GGTGTCCACTCCCAGGTCCAACTGCAGCAGCCTGGGGCTGAGCTG | VHSQVQLQQPGAELVR |
| SEQ ID NO: | GTGAGGCCTGGGGCTTCAGTGAAGCTGTCCTGCAAGGCTTCT**GGC** | PGASVKLSCKAS**GYTF** |
| 105, 106 | **TACACCTTCACCAGCTACTGG**ATGAACTGGGTGAAGCAGAGGCCT | **TSYW**MNWVKQRPGQGL |
| | GGACAAGGCCTTGAATGGATTGGTATG**ATTGATCCTTCAGACAGT** | EWIGMI**DPSDSQT**HYN |
| | **CAAACT**CACTACAATCAAATGTTCAAGGACAAGGCCACATTGACT | QMFKDKATLTVDKSSS |
| | GTAGACAAATCCTCCAGCACAGCCTACCTGCAGCTCAGCAGCCTG | TAYLQLSSLTSEDSAV |
| | ACATCTGAGGACTCTGCGGTCTATTACTGT**TCAAGAGGGGGCTAC** | YYC**SRGGY**WGQGTTLT |
| | TGGGGCCAAGGCACCACTCTCACAGTCTCCTCA | VSS |
| Kappa | ATGAGACCGTCTATTCAGTTCCTGGGGCTCTTGTTGTTCTGGCTT | MRPSIQFLGLLLFWLH |
| SEQ ID NO: | CATGGTGCTCAGTGTGACATCCAGATGACACAGTCTCCATCCTCA | GAQCDIQMTQSPSSLS |
| 107, 108 | CTGTCTGCATCTCTGGGAGGCAAAGTCACCATCACTTGCAAGGCA | ASLGGKVTITCKAS**QD** |
| | AGC**CAAGACATTAACAACTAT**ATAGCTTGGTACCAACACAAGCCT | **INNY**IAWYQHKPGKGP |
| | GGAAAAGGTCCTAGGCAGCTCATATAT**TACACATCT**ACATTGCAG | RQLIY**YTS**TLQPGIPS |
| | CCAGGCATCCCATCAAGGTTCAGTGGAAGTGGGTCTGGGAGAGAT | RFSGSGSGRDYSFTIS |
| | TATTCCTTCACCATCAGCGACCTGGAGCCTGAAGATATTGCAACT | DLEPEDIATYYC**LQYD** |
| | TATTATTGT**CTACAGTATGATAATCTGTGGACG**TTCGGTGGAGGC | **NLWT**FGGGTKLEIK |
| | ACCAAGCTGGAAATCAAA | |
| 303-26 | ATGGGATGGAGCTGTATCATCCTCTTTTTGGTAGCAACAGCTACA | MGWSCIILFLVATATG |
| IgG1 | GGTGTCCACTCCCAGGTCCAACTGCAGCAGCCTGGGGCTGAGCTG | VHSQVQLQQPGAELVR |
| SEQ ID NO: | GTGAGGCCTGGGTCTTCAGTGAAGCTGTCCTGCAAGGCTTCT**ggc** | PGSSVKLSCKAS**GYTF** |
| 109, 110 | **tacaccttcaccagctactgg**ATGAACTGGGTGAAGCAGAGGCCT | **TSYW**MNWVKQRPGQGL |
| | GGACAAGGCCTTGAATGGATTGGTATG**attgatccttcagacagt** | EWIGM**IDPSDSET**HYN |
| | **gaaact**CACTACAATCAAATGTTCAAGGACAAGGCCACATTGACT | QMFKDKATLTVDKSSS |
| | GTAGACAAATCCTCCAGCACAGCCTACATGCAGCTCAGCAGCCTG | TAYMQLSSLTSEDSAV |
| | ACATCTGAGGACTCTGCGGTCTATTACTGT**acaagagggacttac** | YYC**TRGTY**WGQGTQVT |
| | TGGGGCCAAGGGACTCAGGTCACTGTCTCTGCA | VSA |
| Kappa 1 | ATGGAGACAGACACACTCCTGCTATGGGTGCTGCTGCTCTGGGTT | METDTLLLWVLLLWVP |
| SEQ ID NO: | CCAGGTTCCACTGGTGACATTGTGCTGACACAGTCTCCTGCTTCC | GSTGDIVLTQSPASLA |
| 111, 112 | TTAGCTGTATCTCTGGGGCAGAGGGCCACCATCTCATGCAGGGCC | VSLGQRATISCRAS**QS** |
| | AGC**caaagtgtcagtacatctagctatagttat**ATGCACTGGTAC | **VSTSSYSY**MHWYQQKP |
| | CAACAGAAACCAGGACAGCCACCCAAACTCCTCATCAAG**tatgca** | GQPPKLLIK**YAS**NLES |

TABLE 10C-continued

Heavy chain and light chain variable sequences of an antibody raised against cyclo(CGHDSGG) (SEQ ID NO: 10) Consensus DNA sequence and translated protein sequences of the variable region. The complementarity determining regions (CDRs) are underlined according to IMGT/LIGM-DB.

| Isotype | Consensus DNA Sequence | Protein sequence |
|---|---|---|
| | **tcc**AACCTAGAATCTGGGGTCCCTGCCAGGTTCAGTGGCAGTGGG | GVPARFSGSGSGTDFT |
| | TCTGGGACAGACTTCACCCTCAACATCCATCCTGTGGAGGAGGAG | LNIHPVEEEDTATYYC |
| | GATACTGCAACATATTACTGT**cagcacagtttggagattccgtgg** | **QHSLEIPWT**FGGGTKL |
| | **acg**TTCGGTGGAGGCACCAAGCTGGAAATCAAA | EIK |
| Kappa 2 | ATGGATTTTCAGGTGCAGATTTTCAGCTTCATGCTAATCAGTGCC | MDFQVQIFSFMLISAS |
| SEQ ID NO: | TCAGTCATAATGTCCAGAGGACAAATTGTTCTCACCCAGTCTCCA | VIMSRGQIVLTQSPAI |
| 113, 114 | GCAATCATGTCTGCATCTCTAGGGGAACGGGTCACCATGACCTGC | MSASLGERVTMTCTAS |
| | ACTGCCAGC**tcaagtgttagttccgcttac**TTGCACTGGTACCAG | **SSVSSAY**LHWYQQKPG |
| | CAGAAGCCAGGATCCTCCCCCAAACTCTGGATTTAT**agcacatcc** | SSPKLWIY**STS**NLASG |
| | AACCTGGCTTCTGGAGTCCCAACTCGCTTCAGTGGCAGTGGATCT | VPTRFSGSGSGTSYSL |
| | GGGACCTCTTACTCTCTCACAATCAGCAGCATGGAGGCTGAAGAT | TISSMEAEDAATYYC**H** |
| | GCTGCCACTTATTACTGC**caccagtatcatcgttccccgttcacg** | **QYHRSPFT**FGAGTKLE |
| | TTCGGTGCTGGGACCAAGCTGGAGCTGAAA | LK |
| Kappa 3 | ATGAGACCGTCTATTCAGTTCCTGGGGCTCTTGTTGTTCTGGCTT | MRPSIQFLGLLLFWLH |
| SEQ ID NO: | CATGGTGCTCAGTGTGACATCCAGATGACACAGTCTCCATACTCA | GAQCDIQMTQSPYSLS |
| 115, 116 | CTGTCTGCATCTCTGGGAGGCAAAGTCACCATCACTTGCAAGGCA | ASLGGKVTITCKA**SQD** |
| | **agccaagacattaacaagtatatagcttggtac**CAACACAAGCCT | **INKYIAWY**QHKPGKGP |
| | GGAAAAGGTCCTAGGCTGCTCATACAT**aacacatct**ACATTACAG | RLLIH**NTS**TLQPGIPS |
| | CCAGGCATCCCATCAAGGTTCAGTGGAAGTGGGTCTGGGAGAGAT | RFSGSGSGRDYSFSIS |
| | TATTCCTTCAGCATCAGCAACCTGGAGCCTGAAGATATTGCAACT | NLEPEDIATYYC**LQHD** |
| | TATTATTGT**ctacagcatgataatctgtggacg**TTCGGTGGAGGC | **NLWT**FGGGTKLEIK |
| | ACCAAGCTGGAAATCAAA | |
| 303-30 | ATGGGATGGAGCTGTATCATCCTCTTTTTGGTAGCAACAGCTACA | MGWSCIILFLVATATG |
| IgG1 | GGTGTCCACTCCCAGGTCCAACTGCAGCAGCCTGGGGCTGAGCTG | VHSQVQLQQPGAELVR |
| SEQ ID NO: | GTGAGGCCTGGGTCTTCAGTGAAGCTGTCCTGCAAGGCTTCT**ggc** | PGSSVKLSCKAS**GYTF** |
| 117, 118 | **tacaccttcaccagctactgg**ATGAACTGGGTGAAGCAGAGGCCT | **TSYW**MNWVKQRPGQGL |
| | GGACAAGGCCTTGAATGGATTGGTATG**attgatccttcagacagt** | EWIGM**IDPSDSET**HYN |
| | **gaaact**CACTACAATCAAATGTTCAAGGACAAGGCCACATTGACT | QMFKDKATLTVDKSSS |
| | GTAGACAAATCCTCCAGCACAGCCTACATGCAGCTCAGCAGCCTG | TAYMQLSSLTSEDSAV |
| | ACATCTGAGGACTCTGCGGTCTATTACTGT**acaagagggacttac** | YYC**TRGTY**WGQGTQVT |
| | TGGGGCCAAGGGACTCAGGTCACTGTCTCTGCA | VSA |
| Kappa 1 | ATGGAGACAGACACACTCCTGCTATGGGTGCTGCTGCTCTGGGTT | METDTLLLWVLLLWVP |
| SEQ ID NO: | CCAGGTTCCACTGGTGACATTGTGCTGACACAGTCTCCTGCTTCC | GSTGDIVLTQSPASLA |
| 119, 120 | TTAGCTGTATCTCTGGGGCAGAGGGCCACCATCTCATGCAGGGCC | VSLGQRATISCRAS**QS** |
| | AGC**caaagtgtcagtacatctagctatagttat**ATGCACTGGTAC | **VSTSSYSY**MHWYQQKP |
| | CAACAGAAACCAGGACAGCCACCCAAACTCCTCATCAAG**tatgca** | GQPPKLLIK**YAS**NLES |
| | **tcc**AACCTAGAATCTGGGGTCCCTGCCAGGTTCAGTGGCAGTGGG | GVPARFSGSGSGTDFT |
| | TCTGGGACAGACTTCACCCTCAACATCCATCCTGTGGAGGAGGAG | LNIHPVEEEDTATYYC |
| | GATACTGCAACATATTACTGT**cagcacagtttggagattccgtgg** | **QHSLEIPWT**FGGGTKL |
| | **acg**TTCGGTGGAGGCACCAAGCTGGAAATCAAA | EIK |
| Kappa 2 | ATGGATTTTCAGGTGCAGATTTTCAGCTTCATGCTAATCAGTGCC | MDFQVQIFSFMLISAS |
| SEQ ID NO: | TCAGTCATAATGTCCAGAGGACAAATTGTTCTCACCCAGTCTCCA | VIMSRGQIVLTQSPAI |
| 121, 122 | GCAATCATGTCTGCATCTCTAGGGGAACGGGTCACCATGACCTGC | MSASLGERVTMTCTAS |
| | ACTGCCAGC**tcaagtgttagttccgcttac**TTGCACTGGTACCAG | **SSVSSAY**LHWYQQKPG |
| | CAGAAGCCAGGATCCTCCCCCAAACTCTGGATTTAT**agcacatcc** | SSPKLWIY**STS**NLASG |
| | AACCTGGCTTCTGGAGTCCCAACTCGCTTCAGTGGCAGTGGATCT | VPTRFSGSGSGTSYSL |
| | GGGACCTCTTACTCTCTCACAATCAGCAGCATGGAGGCTGAAGAT | TISSMEAEDAATYYC**H** |
| | GCTGCCACTTATTACTGC**caccagtatcatcgttccccgttcacg** | **QYHRSPFT**FGAGTKLE |
| | TTCGGTGCTGGGACCAAGCTGGAGCTGAAA | LK |
| Kappa 3 | ATGAGACCGTCTATTCAGTTCCTGGGGCTCTTGTTGTTCTGGCTT | MRPSIQFLGLLLFWLH |
| SEQ ID NO: | CATGGTGCTCAGTGTGACATCCAGATGACACAGTCTCCATACTCA | GAQCDIQMTQSPYSLS |
| 123, 124 | CTGTCTGCATCTCTGGGAGGCAAAGTCACCATCACTTGCAAGGCA | ASLGGKVTITCKA**SQD** |
| | **agccaagacattaacaagtatatagcttggtac**CAACACAAGCCT | **INKYIAWY**QHKPGKGP |
| | GGAAAAGGTCCTAGGCTGCTCATACAT**aacacatct**ACATTACAG | RLLIH**NTS**TLQPGIPS |
| | CCAGGCATCCCATCAAGGTTCAGTGGAAGTGGGTCTGGGAGAGAT | RFSGSGSGRDYSFSIS |
| | TATTCCTTCAGCATCAGCAACCTGGAGCCTGAAGATATTGCAACT | NLEPEDIATYYC**LQHD** |
| | TATTATTGT**ctacagcatgataatctgtggacg**TTCGGTGGAGGC | **NLWT**FGGGTKLEIK |
| | ACCAAGCTGGAAATCAAA | |

TABLE 11

| A-beta Sequences and compounds comprising linkers |
|---|
| 1) |
| HHQK (SEQ ID NO: 1) |
| CGHHQKG, cyclo(CGHHQKG)(SEQ ID NO: 2) |
| CHHQKG, C-PEG2-HHQKG, cyclo(C-PEG2-HHQKG) (SEQ ID NO: 3) |
| CGHHQK, CGHHQK-PEG2, cyclo(CGHHQK-PEG2) (SEQ ID NO: 4) |
| QKLV (SEQ ID NO: 5) |
| CGQKLVG, cyclo(CGQKLVG)(SEQ ID NO: 6) |
| CQKLVG, C-PEG2-QKLVG, cyclo(C-PEG2-QKLVG) (SEQ ID NO: 7) |
| CGQKLV, CGQKLV-PEG2, cyclo(CGQKLV-PEG2) (SEQ ID NO: 8) |
| HDSG (SEQ ID NO: 9) |
| CGHDSGG, cyclo(CGHDSGG)(SEQ ID NO: 10) |
| CHDSGG, C-PEG2-HDSGG, cyclo(C-PEG2-HDSGG) (SEQ ID NO: 11) |
| CGHDSG, CGHDSG-PEG2, cyclo(CGHDSG-PEG2) (SEQ ID NO: 12) |
| 2) |
| HQKLVFFAED (SEQ ID NO: 13) |
| HHQKLVFFAEDVGSNK (SEQ ID NO: 14) |
| HQKLV (SEQ ID NO: 15) |
| HHQKLV (SEQ ID NO: 16) |
| HQKLVF (SEQ ID NO: 17) |
| HQKLVFF (SEQ ID NO: 18) |
| Human A-beta 1-42 |
| DAEFRHDSGYEVHHQKLVFFAEDVGSNKGAIIGLMVGGVVIA (SEQ ID NO: 19) |

Example 10

Mouse Novel Recognition Assay

The Novel Object Recognition (NOR) model utilizes the normal behavior of rodents to investigate novel objects for a significantly longer time than known objects. This test assesses recognition memory for items and its human equivalent is the visual pairwise-comparison (VPC). Recognition of objects is mediated by the perirhinal cortex in rodents, primates and humans. AD pathology develops first in the perirhinal and enthorinal cortex before the hippocampus. The VPC task detects memory deficit in mild cognitive impairment (MCI) and conversion from MCI to AD is predicted by this task.

The assay was performed by (SynAging SAS, Vandœuvre-lès-Nancy, France). Twelve C57BL6J mice per group (11-12 weeks old) were ICV-injected with vehicle (buffer used for Aβ oligomerization) or AβO (50 pmoles) in the presence of vehicle (PBS) or antibody (e.g. 301-17, 303-25 or 305-61) on day 0. The cognitive performance of all mice was determined by a Novel Object Recognition (NOR) test performed at days +7 and +8.

The study, done in blind to the operators, involved a total of 48 mice divided in four experimental groups with 12 mice per experimental group. All animals received a single (and unilateral) ICV injection of vehicle OR AβO in the absence or presence of antibody in a total volume of 5 μL. The experimental groups were defined as follow:

GROUP A (vehicle CTRL): ICV injection of vehicle (n=12)
GROUP B (AβO CTRL): ICV injection of AβO (n=12)
GROUP C (Antibody CTRL): ICV injection of AβO+ antibody (n=12)
GROUP D (Treatment): ICV injection of AβO+antibody (n=12)

Because a maximum of 24 mice can be ICV injected per day, the injections were performed in two independent runs. Six mice from all groups were included in each run.

Before ICV injection, 4 μL of antibody 1 (e.g. 112 pmoles) were incubated for 30 minutes at room temperature with 1 μL vehicle (i.e. buffer for Aβ oligomerization) or 1 μL ADO (50 pmoles) corresponding to an antibody/AβO molar ratio of 2.24 mouse monoclonal 301-17 antibody. Other ratios as noted were used in other experiments with other antibodies.

At day 0, mice received a single 5 μL ICV injection of vehicle or AβO in the presence of vehicle or antibody. The stereotactic coordinates were: from the Bregma (in mm): AP −0.22, L −1.0 and D 2.5. Under anesthesia (ip injection of a mixture of ketamine/xylasine at a dose of 110 and 15 mg/kg, respectively), 5 μL were injected into the right lateral ventricle. Injections are made using 10 μL Hamilton micro syringes fitted with a 26-gauge needle. The procedure is terminated by a subcutaneous injection of metacam (analgesia) at a dose of 5 mg/kg. Animals are then placed individually in their home cage and the cage is placed in a heated cabinet until the animal has fully recovered. Animals are carefully monitored to control recovery after anesthesia.

The NOR test was conducted in one trial with all 48 mice at days +7 and +8. One day before the cognitive test (i.e. at Day +7), mice are habituated during a 10 min trial during which they are placed in an empty open field. The day of the cognitive test (i.e. Day +8), animals are placed in the same open field and are allowed to explore freely two identical objects for a trial of five minutes (acquisition trial). Then the animals are returned to their home cage for an inter-trial time of five minutes. During the retention trial, animals are allowed to explore two different objects: the same familiar object and one novel object. During this time, the experimenter, blind to the treatment, records the time the mouse is actively exploring each object. All trials are video recorded (Smart v3.0 software, Bioseb). A discrimination index (DI) is then generated: (DI)=(time exploring novel object−time exploring familiar object)/total exploration time. If the total exploration time is <5 s, animals are excluded from the calculation of the discrimination index and statistical analysis.

Data analysis: Graphpad/Prism computer software is used for the statistical analyses. A non-parametric analysis of variance (Kruskal Wallis test) is carried out followed by non-parametric Mann-Whitney U tests in order to compare between groups. Values of $p<0.05$ are considered statistically significant. Data are presented as mean DI±SEM.

Example 11

The novel recognition test described in Example 10 was used to test an antibody raised using cyclo(CGHHQKG)

(301-17) (SEQ ID NO:2). As mentioned above, before ICV injection, 4 μL of antibody 1 (112 pmoles) were incubated for 30 minutes at room temperature with 1 μL vehicle (i.e. buffer for Aβ oligomerization) or 1 μL AβO (50 pmoles) corresponding to an antibody/AβO molar ratio of 2.24.

Figure 6A:
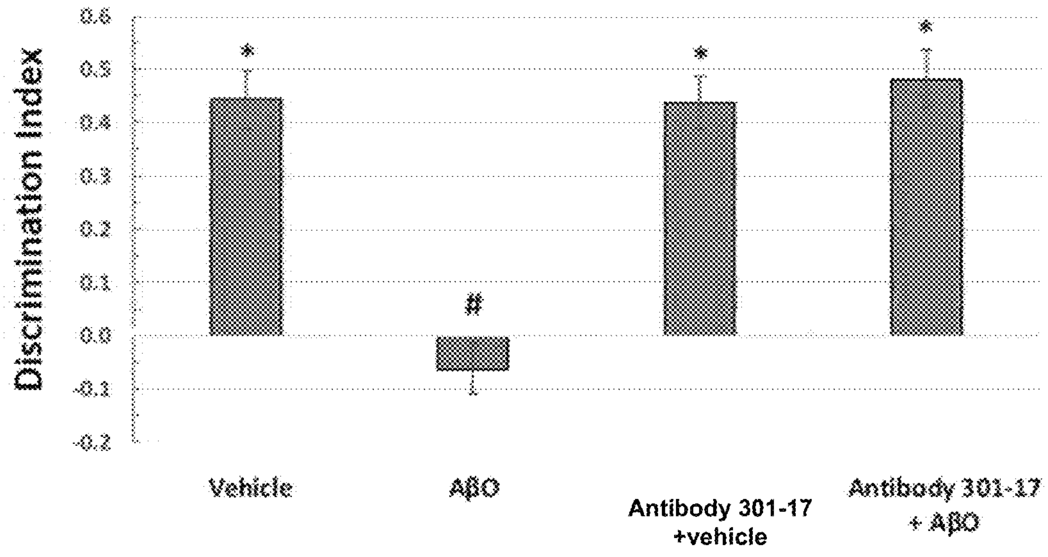
FIG. 6A: A plot showing that the loss of short term memory formation caused by A-beta oligomer is inhibited by an antibody that is specific and/or selective for a conformational epitope presented in SEQ ID NO: 2.

Results:

Mice from the vehicle control group (Group A) exhibited normal behavior with a mean discrimination index of 0.443±0.053 (FIG. 6A). These results are in agreement with previous observations of similar control groups at SynAging. As expected, a single ICV injection of AβO (Group B) resulted in a significant impairment ($p<0.0001$) of the cognitive performance when compared to vehicle control mice; with a mean discrimination index of −0.062±0.048. AβO-injected mice were not able to discriminate between novel and familiar objects (FIG. 6A).

Mice dosed with antibody in the presence of vehicle (Group C) were found to exhibit normal cognitive performances with a mean discrimination index of 0.439±0.049 (FIG. 6A). These mice were not significantly different from vehicle control mice ($p=0.9163$) and significantly different from AβO injected mice ($p<0.0001$).

When co-injected with AβO, the antibody fully prevented AβO-induced cognitive deficits in the NOR test. Indeed, mice from Group D exhibited a mean discrimination index of 0.481-0.055, not different from control mice ($p=0.6126$) but different from AβO-injected mice ($p=0.0002$) (FIG. 6A). Taken together, the data suggest that antibody 301-17 offered protection against AβO-induced cognitive deficits.

The NOR assay was repeated with the recombinant 301-17 comprising a mouse IgG1 backbone. The concentration of antibody used was however was less than the previously described experiment with the oligomer: antibody ratio being only 1.62. As shown in FIG. 6D, when co-injected with AβO, the lower ratio of antibody was still capable of fully preventing AβO-induced cognitive deficits in the NOR test.

Example 12

The novel object recognition test described in Example 10 was used to test a recombinant 305-61 antibody (mouse IgG1) (parent monoclonal raised using cyclo(CGQKLVG) (SEQ ID NO:6)). The following treatment schedule was used.

| GROUP | Treatment | ICV | N |
|---|---|---|---|
| A | Vehicle | Vehicle | 12 |
| B | Vehicle | AbO | 12 |
| C | Antibody (QKLV) | Vehicle | 12 |
| D | Antibody (QKLV) | AbO | 12 |

As described in Example 10, 24 animals were injected per day. In the present assay, before ICV injection, 4 μL of antibody 1 were incubated for 30 minutes at room temperature with 1 μL vehicle (i.e. buffer for Aβ oligomerization) or 1 μL ADO (50 pmoles) corresponding to an antibody/AβO molar ratio of 5:1.

Results

Figure 6B:
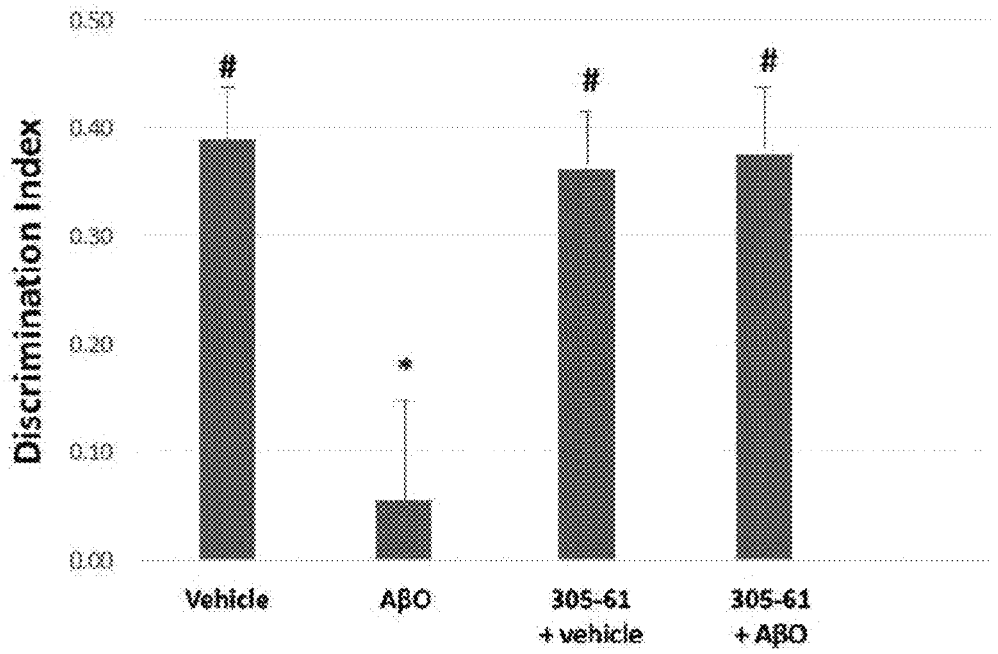
FIG. 6B: A plot showing that the loss of short term memory formation caused by A-beta oligomer is inhibited by an antibody that was raised using an immunogen comprising cyclo(CGQKLVG) (SEQ ID NO: 6).

Mice from the vehicle control group (Group A) exhibited normal behavior with a mean discrimination index of 0.39±0.05 (FIG. 6B). These results are in agreement with previous observations of similar control groups. As expected, a single ICV injection of AβO (Group B) resulted in a significant impairment (p+=0.0127) of the cognitive performance when compared to vehicle control mice; with a mean discrimination index of 0.05±0.09. AβO-injected mice were not able to discriminate between novel and familiar objects (FIG. 6B).

Mice dosed with antibody in the presence of vehicle (Group C) were found to exhibit normal cognitive performances with a mean discrimination index of 0.36±0.05 (FIG. 6B). These mice were not significantly different from vehicle control mice and were significantly different from AβO injected mice.

When co-injected with AβO, antibody 305-61 fully prevented AβO-induced cognitive deficits in the NOR test. Indeed, mice from Group D exhibited a mean discrimination index of 0.38±0.06, not different from control mice but different from AβO-injected mice ($p=0.0135$) (FIG. 6B). The data suggest this antibody offered protection against AβO-induced cognitive deficits.

Example 13

The novel object recognition test described in Example 10 was used to test an recombinant antibody (303-25, IgG1). The following treatment schedule was used.

| GROUP | Treatment | ICV | N |
|---|---|---|---|
| A | Vehicle | Vehicle | 12 |
| B | Vehicle | AbO | 12 |
| C | Antibody (HDSG) Ab1 | Vehicle | 12 |
| D | Antibody (HDSG) | AbO | 12 |
| E | Isotype control Ab2 | Vehicle | 12 |
| F | Isotype control | AbO | 12 |

An antibody:oligomer ratio of 5:1 was used. As described in Example 10, 24 animals were injected per day, ICV injection took place on day 0, the behavioural assay was conducted on day 7 or 8, and brains collected on day 10 for ELISA on hippocampal markers.

Results

Figure 6C:
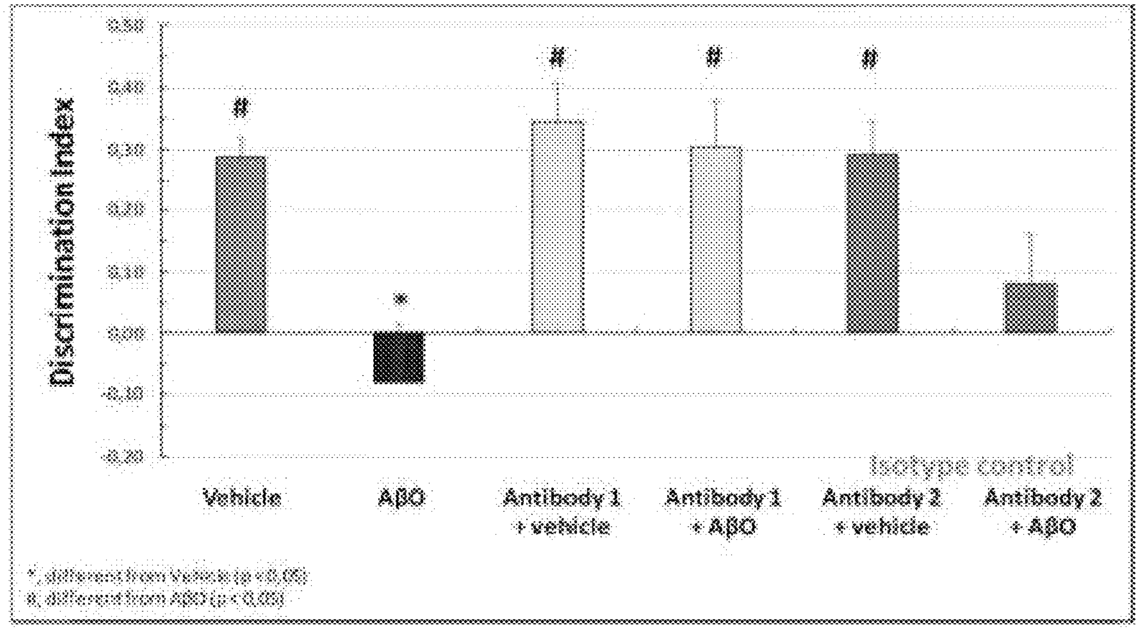
FIG. 6C: A plot showing that the loss of short term memory formation caused by A-beta oligomer is inhibited by recombinant antibody 303-25 antibody in a mouse IgG1 framework (HDSG epitope (SEQ ID NO: 9)) (antibody 1). Antibody 2 is mouse IgG1 isotype control.
Figure 6D:
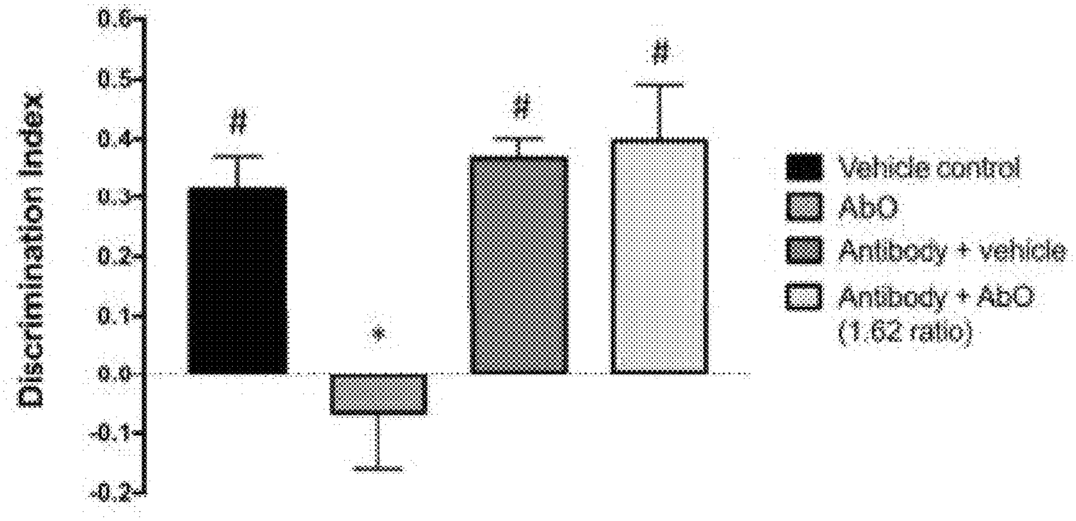
FIG. 6D: A plot showing that the loss of short term memory formation caused by A-beta oligomer is inhibited by a recombinant antibody 301-17 in a mouse IgG1 framework (HHQK epitope (SEQ ID NO: 1)) in a mouse IgG1 framework.

Mice from the vehicle control group (Group A) exhibited normal behavior with a mean discrimination index of 0.29±0.03 (FIG. 6C). These results are in agreement with previous observations of similar control groups at SynAging. As expected, a single icv injection of AβO (Group B) resulted in a significant impairment ($p=0.0150$) of the cognitive performance when compared to vehicle control mice; with a mean discrimination index of −0.08±0.1, AβO-injected mice were not able to discriminate between novel and familiar objects (FIG. 6C).

Mice dosed with the recombinant 303-25 antibody in the presence of vehicle (Group C) were found to exhibit normal cognitive performances with a mean discrimination index of 0.35±0.06 (FIG. 6C). These mice were not different from vehicle control mice ($p=0.4871$) and significantly different from AβO injected mice ($p=0.0047$).

Similarly, mice dosed with antibody 2 (isotype control) in the presence of vehicle (Group E) were found to exhibit normal cognitive performances with a mean discrimination index of 0.29±0.05 (FIG. 6C). These mice were not different from vehicle control mice ($p=0.9578$) and significantly different from AβO injected mice ($p=0.0121$).

When co-injected with AβO, test antibody prevented AβO-induced cognitive deficits in the NOR test. Indeed, mice from Group D exhibited a mean discrimination index of 0.30±0.08, not different from control mice ($p=0.6715$) but different from AβO-injected mice ($p=0.0120$) (FIG. 6C).

When co-injected with AβO, antibody 2 (isotype control) failed to prevent AβO-induced cognitive deficits in the NOR test. Indeed, mice from Group F exhibited a mean discrimination index of 0.080±0.079, not different from AβO-injected mice (p=0.1962), and lower but not statistically different from control mice (p=0.1176) (FIG. 6C).

Example 14

Brains were collected from the same mice that underwent the behavioral testing in Examples 11-13. The hippocampus (relevant structure for memory formation) was dissected and homogenized in RIPA buffer containing an anti-protease cocktail. The tissue was lysed by 3 freeze thaw cycles carried out in liquid nitrogen and a water bath at 37 C and the supernatants were recovered after centrifuging.

The lysate was analyzed for levels of TNF-alpha (increases with inflammation) and levels of the synaptic markers PSD-95 and SNAP-25 (which go down when there is synaptic damage) using commercial ELISA assays. Data are represented as mean±SEM. Data are expressed as pg protein per pg total protein. Statistical significance between groups are evaluated and considered statistically different to another group when p<0.05 (*: different from vehicle control mice, and #: different from AβO-injected mice).

303-25

Figure 7A:
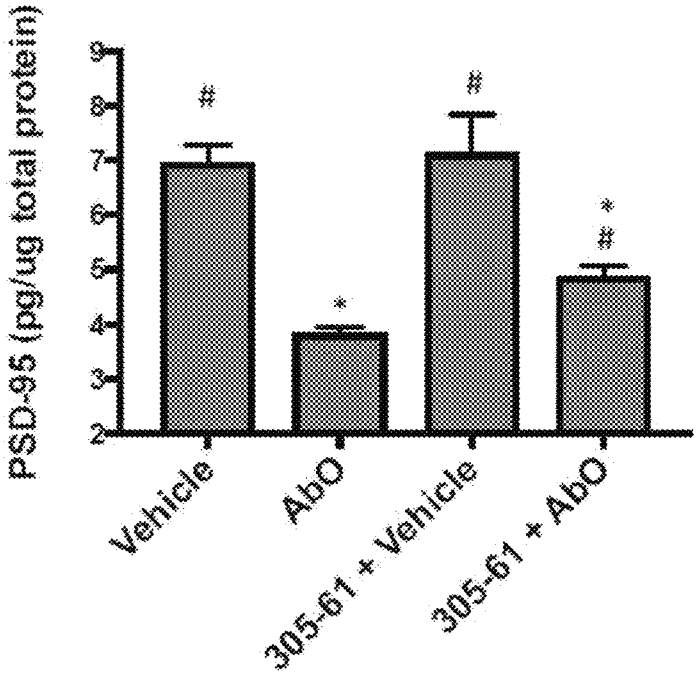
FIG. 7A-FIG. 7C: A series of plots showing hippocampal PSD-95 levels (A), SNAP25 levels (B) and TNF-alpha levels (C) in an vivo assay using antibody 305-61 (QKLV epitope SEQ ID NO: 5).
Figure 7B:
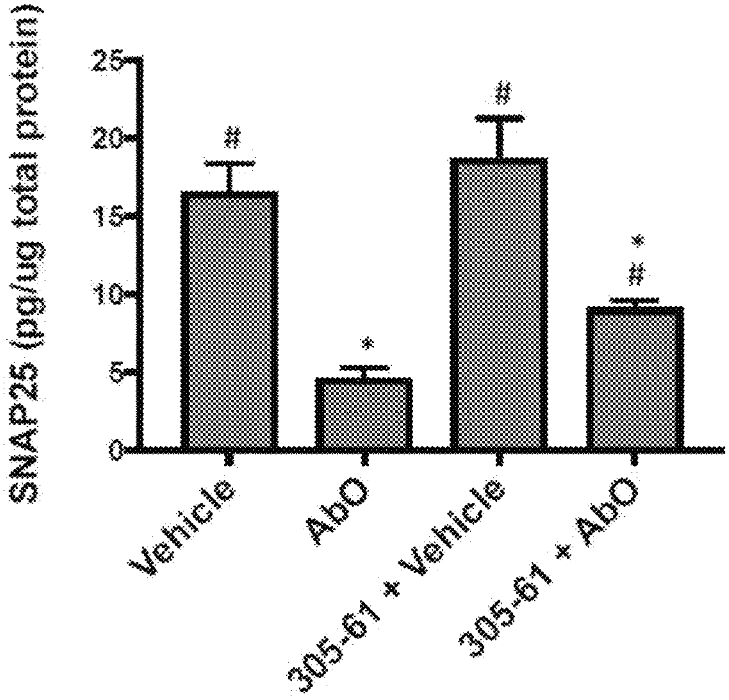
Figure 7C:
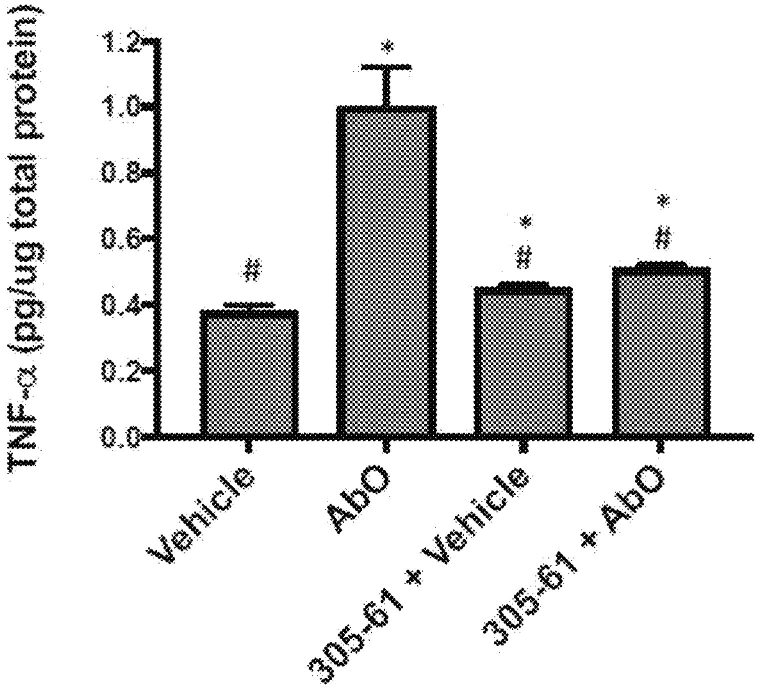
Figure 7D:
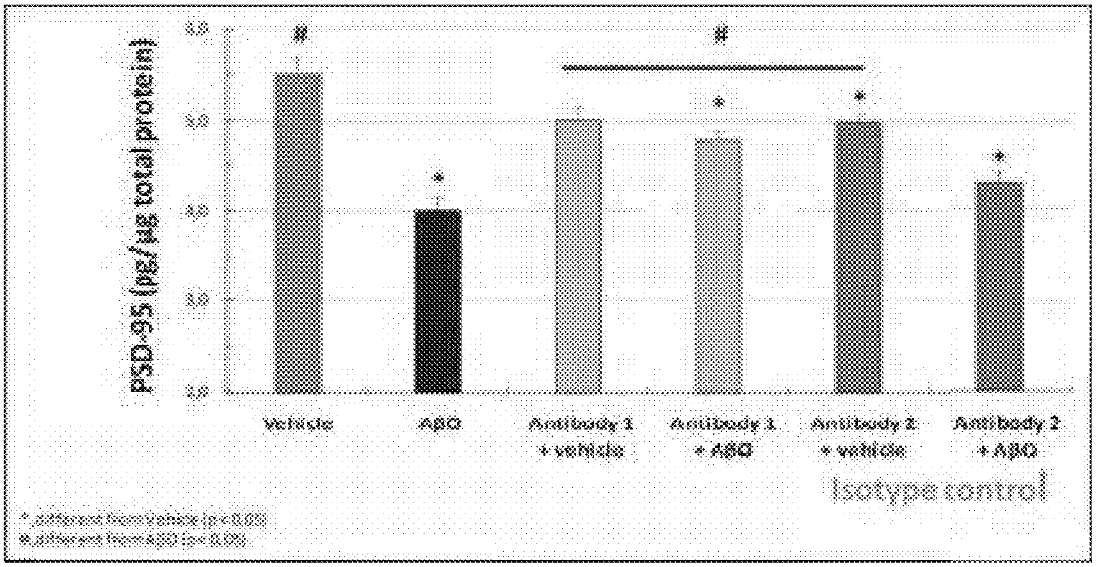
FIG. 7D-FIG. 7F: A series of plots showing hippocampal PSD-95 levels (D), SNAP25 levels (E) and TNF-alpha levels (F) in an vivo assay using recombinant antibody 303-25 antibody in a mouse IgG1 framework (HDSG epitope (SEQ ID NO: 9)). Antibody 2 is a mouse IgG1 isotype control.

As expected, mice ICV injected with AβO oligomers exhibited a decreased level of hippocampal PSD-95 (4.01±0.14 μg/pg total protein) statistically different from control mice (p<0.0001) (FIG. 7D).

Mice dosed with antibody 301-25 (antibody 1) or isotype control (antibody 2) in the presence of vehicle exhibited a normal level, not different from control mice, of hippocampal PSD-95 of 5.02±0.14 and 4.98±0.08 μg/pg total protein for antibody 1 and 2, respectively (FIG. 7D).

When co-injected with AβO, antibody 1 significantly improved PSD-95 level. Mice from Group D exhibited a level of hippocampal PSD-95 of 4.79±0.09 μg/pg total protein, different from control mice (p=0.0016) but also different from AβO-injected mice (p=0.0003) (FIG. 7D).

When co-injected with AβO, antibody 2 failed to improve hippocampal PSD-95 level. Mice from Group F exhibited a PSD-95 concentration of 4.34±0.11 μg/pg total protein, significantly lower than control mice (p<0.0001) and not different from AβO-injected mice (p=0.1189) (FIG. 7D).

Figure 7E:
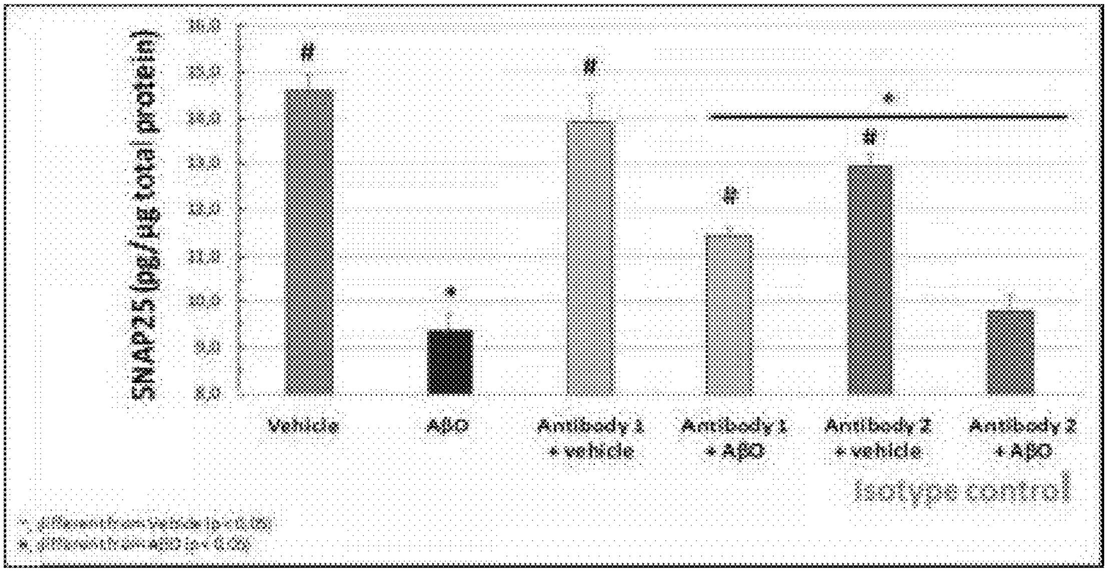

As expected, mice ICV injected with AβO oligomers exhibited a decreased level of hippocampal SNAP25 (9.36±0.34 μg/pg total protein) different from control mice (p<0.0001) (FIG. 7E).

Mice dosed with antibody 1 or antibody 2 in the presence of vehicle exhibited a normal level of hippocampal SNAP25 of 13.93±0.57 and 12.94±0.26 μg/pg total protein for antibody 1 and antibody 2, respectively (FIG. 7E). These values were not different from control mice (p=0.8399) for antibody 1 but statistically different from control mice (p=0.0015) for antibody 2.

Figure 7F:
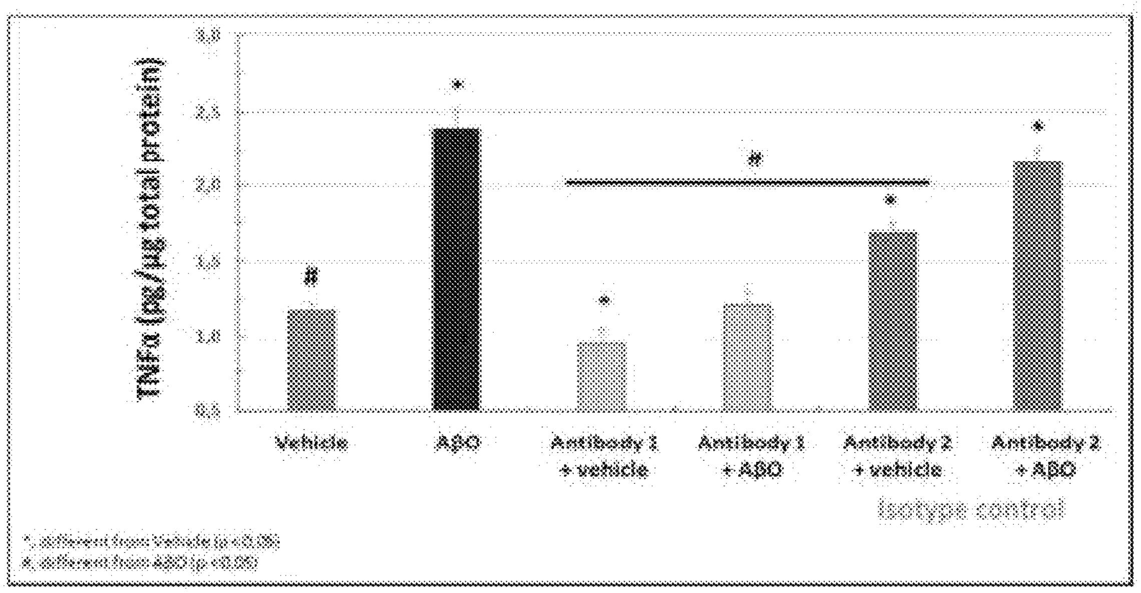

As expected, mice ICV injected with AβO oligomers exhibited an increased level of hippocampal TNFα (2.39±0.14 μg/pg total protein) different from control mice (p<0.0001) (FIG. 7F).

Mice dosed with antibody 1 in the presence of vehicle exhibited a normal level of hippocampal TNFα of 0.95±0.1 μg/pg total protein (FIG. 7F). In contrast and for unknown reason, mice dosed with antibody 2 in the presence of vehicle exhibited an increased level of hippocampal TNFα of 1.69±0.07 μg/pg total protein, as compared to control mice (p<0.0001).

The presence antibody 1 resulted in a decreased level of TNFα in mice co-injected with AβO (FIG. 7F). Mice from group D exhibited a level of hippocampal TNFα of 1.20±0.10 μg/pg total protein, not different from control mice (p=0.908) and different from AβO-injected mice (p<0.0001). When co-injected with AβO, antibody 2 failed to inhibit the AβO-induced increase of TNFα with a level of hippocampal TNFα of 2.16±0.10 μg/pg total protein (p<0.0001 as compared to control and p=0.2481 as compared to AβO-injected mice).

305-61

Similar results were seen with 305-61. The 305-61 antibody showed complete protection in the behavioral assay and also showed statistically significant improvement in both AbO induced SNAP25 (FIG. 7B) and PSD-95 level changes (FIG. 7A). The antibody alone had no effect. The antibody also significantly decreased levels of TNF-alpha induced by AbO, as shown in FIG. 7C.

301-17

Figure 7G:
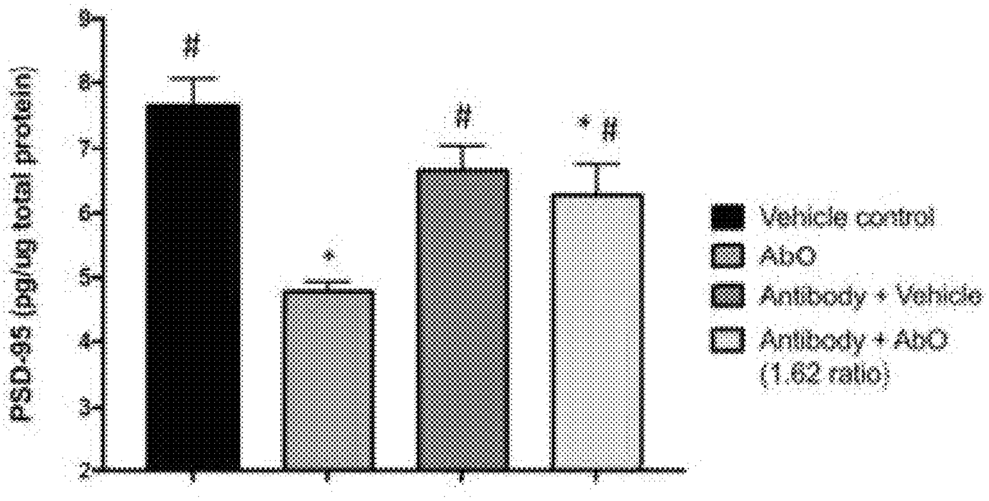
FIG. 7G, FIG. 7H: A series of plots showing hippocampal PSD-95 levels (G) and SNAP25 levels (H) in an vivo assay using recombinant antibody 301-17 (HHQK epitope (SEQ ID NO: 1)) in a mouse IgG1 framework at low concentration.
Figure 7H:
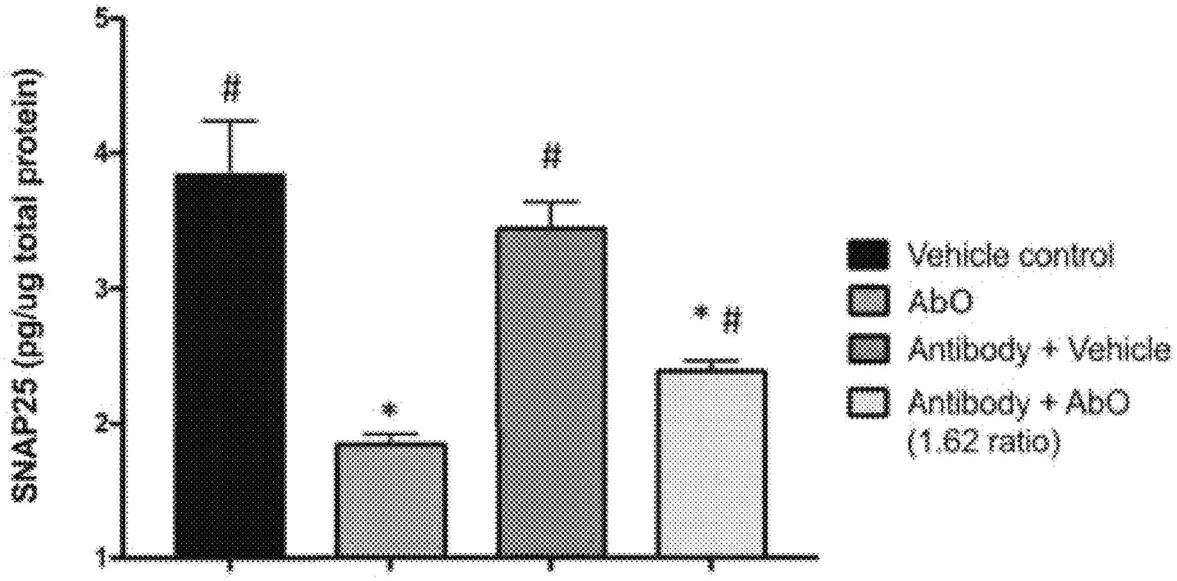

Both NOR experiments using 301-17 antibodies (e.g. monoclonal and IgG1 recombinant) showed complete protection in the behavioral assay. The brain of the animals treated with or without recombinant 301-17 were tested PSD-95, SNAP25 and TNF-alpha levels. The antibody also significantly improved both SNAP25 (FIG. 7H) and PSD-95 levels (FIG. 7G). There was a trend for reduced TNF-alpha levels.

Example 15

Recombinant Antibodies (HHQK)

Recombinant IgG1 and IgG2a 301-17 constructs were made by grafting the variable region of hybridoma-derived 301-17 onto a murine IgG1 or IgG2a backbone (WuXi, Biologics).

The 301-17 IgG1 and IgG2a antibodies were tested and compared to the parent hybridoma-purified IgG3 antibody for binding characteristics as described below.

301-17 IgG2a ProteOn Biosensor (BioRad) Binding to AbO: Recombinant 301-17 IgG2a and hybridoma-purified 301-17 IgG3 were captured with anti-mouse IgG or amine coupling on Proteon GLM Sensor chips and tested for AbO binding (SynAging AbO). AbO 3 fold-dilutions were used: 1 uM, 0.33 uM, 0.11 uM, 37 nM, 12.3 nM. Assay buffer was PBS-E+Tween 20+2 mg/ml BSA.

Results:

Approximate kinetic values were:

Hybridoma: KD=26.9 nM

IgG2a-301-17 antibody: KD=16.2-19.5 nM

No binding was detected with control mouse IgG.

Recombinant 301-17 IgG1 had a similar KD to the IgG2a recombinant.

301-17 IgG2a ProteOn Biosensor (BioRad) Binding to cyclic peptide epitope: Recombinant 301-17 IgG2a was amine-coupled to Proteon GLH biosensor chip and tested for binding to cyclopeptide of SEQ ID NO: 2 coupled to BSA. Cyclo-BSA 3-fold dilutions were used from 9 nM to 111 μM. Assay buffer was PBS-E+0.05% Tween+10 mg/ml BSA. Antibody 301-17 IgG2a was found to bind cyclic peptide (SEQ ID NO: 2) conjugated to BSA with an approximate KD of 17 μM (average of 3 tests). No or negligible binding was detected for other commercial A-beta antibodies tested (pan-Abeta 6E10, Biolegend) and rabbit anti-A-beta antibodies (D54D2, Cell Signaling; ab201060, (abcam; NBP1-78007, Novus).

301-17 IgG1 MAAS-2 binding to AbO: Recombinant 301-17 IgG1 and hybridoma-purified 301-17 IgG3 were immobilized on MAAS-2 sensor chips and tested for binding to AbO (SynAging) at 1 uM. Under the conditions tested, the recombinant IgG1 301-17 antibody gave a greater signal than the hybridoma-purified antibody in 2 tests (40-55 BRU vs 15-25 BRU, respectively). Little or no binding was detected with control mouse IgG.

301-17IgG1 MAAS-2 binding to cyclic peptide epitope: Recombinant 301-17 IgG1 was immobilized on MAAS-2 sensor chip and tested for binding to cyclopeptide of SEQ ID NO: 2 coupled to BSA at pH 6.5, 7.5 or 8.0. Equivalently high levels of binding were observed for 301-17 IgG1 under all 3 pH conditions (~400 BRUs). Little or no binding was detected under any of the pH conditions for control mouse IgG or the pan-Abeta 6E10 antibody (Biolegend)

Example 16

Humanized Antibodies (HHQK)

Humanized IgG4 antibody constructs were prepared for 301-17 and sequenced (Abzena Cambridge UK).

Briefly RNA was extracted from the hybridoma 301-17 cell pellet using an RNeasy Mini Kit (Qiagen, Hilden, Germany). V-regions were amplified by RT-PCR using degenerate primer pools for murine antibody signal sequences together with constant region primers for each of IgG and Igκ. Heavy chain V region mRNA was amplified using a set of six degenerate primer pools (A to F) specific for VH signal sequences together with IgG-specific constant region primers. The light chain V region mRNA was amplified using a set of eight signal sequence-specific degenerate primer pools, seven for the kappa cluster (Igκ-A to Igκ-G) and one for the lambda cluster (IgA), together with κ or λ constant region primers. The PCR products obtained were purified, cloned into a 'TA' cloning vector (pGEM-T Easy, Promega, Madison, USA), transformed into *E. coli* and individual colonies sequenced.

Chimeric constructs (V0H0 and V0k0) were prepared using the variable regions from the hybridoma which were cloned into a human IgG4 framework. The chimeric constructs were then humanized to create 6 humanized heavy chains (VH1-6) and 6 light chains (Vk1-6). VH1-6 and Vk4-6 constructs were mixed to create different humanized antibodies e.g. VH2Vk4.

The fully humanized antibodies were prepared using Composite Human Antibody™ technology. The designed variable region genes were cloned into vectors encoding a human IgG4 (S241P) heavy chain constant domain and a human kappa light chain constant domain. Chimeric and humanized antibodies were transiently expressed in CHO cells and Protein A purified and tested. All 301-17 humanized antibodies selectively bound SEQ ID NO: 2 BSA with binding affinities within 2-fold of the reference chimeric antibody. Binding was determined using single cycle Biacore analysis. Antibodies were analysed in two separate experiments.

Humanized antibody sequences are provided in Table 13 and 14 (301-17). The CDR sequences of each antibody sequences are bolded and underlined. The CDRs of 301-11 or any other antibody described herein can be used to replace the CDRs in the humanized constructs as shown for example in Table 12.

TABLE 12

Variable domain of humanized antibodies

| Chimeric/ Humanized Antibody 301-11 | cDNA Sequence | Polypeptide sequence |
|---|---|---|
| VH0*<br>SEQ ID NO:<br>125, 126<br>Chimeric | CAGGTCCAACTGCAGCAGCCTGGGGCTGAGCTTGTGAAGCCTGGG<br>GCTTCAGTGAAGATGTCCTGCAAGGCTTCT**GGATTCACTTTCAGT**<br>**GACTATTAC**ATAAACTGGGTGAAGCAGAGGCCTGGACAAGGCCTT<br>GAGTGGATTGGAGAT**ATTAGTGATGGTGGTAGTTACACC**TACAAT<br>GCTAAGTTCAAGAGCAAGGCCACACTGACTCTGGACACATCCTCC<br>AGCACAGCCTACATGCAGCTCAGCAGCCTGACATCTGAGGACTCT<br>GCGGTCTATTACTGT**GCAAGAGATTACTACGGTAGTAGTAGCTAC**<br>**ACCTCGGGCTTTGCTTAC**TGGGGCGCAGGCACCACGGTCACCGTC<br>TCCTCA | QVQLQQPGAELVKPGA<br>SVKMSCKAS**GFTFSDY**<br>**Y**INWVKQRPGQGLEWI<br>GD**ISDGGSYT**YNAKFK<br>SKATLTLDTSSSTAYM<br>QLSSLTSEDSAVYYC**A**<br>**RDYYGSSSYTSGFAY**W<br>GAGTTVTVSS |
| VH1<br>SEQ ID NO:<br>127, 128 | CAGGTCCAACTGGTGCAGTCTGGGGCTGAGCTTAAGAAGCCTGGG<br>GCTTCAGTGAAGATGTCCTGCAAGGCTTCT**GGATTCACTTTCAGT**<br>**GACTATTAC**ATAAACTGGGTGAAGCAGAGGCCTGGACAAGGCCTT<br>GAGTGGATTGGAGAT**ATTAGTGATGGTGGTAGTTACACC**TACAAT<br>GCTAAGTTCAAGAGCAGAGCCACACTGACTCTGGACACATCCATA<br>AGCACAGCCTACATGCAGCTCAGCAGCCTGACATCTGAGGACTCT<br>GCGGTCTATTACTGT**GCAAGAGATTACTACGGTAGTAGTAGCTAC**<br>**ACCTCGGGCTTTGCTTAC**TGGGGCCAAGGCACCACGGTCACCGTC<br>TCCTCA | QVQLVQSGAELKKPGA<br>SVKMSCKAS**GFTFSDY**<br>**Y**INWVKQRPGQGLEWI<br>GD**ISDGGSYT**YNAKFK<br>SRATLTLDTSISTAYM<br>QLSSLTSEDSAVYYC**A**<br>**RDYYGSSSYTSGFAY**W<br>GQGTTVTVSS |
| VH2<br>SEQ ID NO:<br>129, 130 | CAGGTCCAACTGGTGCAGTCTGGGGCTGAGGTGAAGAAGCCTGGG<br>GCTTCAGTGAAGATGTCCTGCAAGGCTTCT**GGATTCACTTTCAGT**<br>**GACTATTAC**ATAAACTGGGTGAAGCAGAGGCCTGGACAAGGCCTT<br>GAGTGGATTGGAGAT**ATTAGTGATGGTGGTAGTTACACC**TACAAT<br>GCTAAGTTCAAGAGCAGAGCCACACTGACTCTGGACACATCCATA<br>AGCACAGCCTACATGGAGCTCAGCAGCCTGAGATCTGAGGACACG<br>GCGGTCTATTACTGT**GCAAGAGATTACTACGGTAGTAGTAGCTAC**<br>**ACCTCGGGCTTTGCTTAC**TGGGGCCAAGGCACCACGGTCACCGTC<br>TCCTCA | QVQLVQSGAEVKKPGA<br>SVKMSCKAS**GFTFSDY**<br>**Y**INWVKQRPGQGLEWI<br>GD**ISDGGSYT**YNAKFK<br>SRATLTLDTSISTAYM<br>ELSSLRSEDTAVYYC**A**<br>**RDYYGSSSYTSGFAY**W<br>GQGTTVTVSS |

TABLE 12-continued

Variable domain of humanized antibodies

| Chimeric/ Humanized Antibody 301-11 | cDNA Sequence | Polypeptide sequence |
|---|---|---|
| VH3 | CAGGTCCAACTGGTGCAGTCTGGGGCTGAGGTGAAGAAGCCTGGG | QVQLVQSGAEVKKPGA |
| SEQ ID NO: | GCTTCAGTGAAGGTGTCCTGCAAGGCTTCT**GGATTCACTTTCAGT** | SVKVSCKAS**GFTFSDY** |
| 131, 132 | **GACTATTAC**ATAAACTGGGTGCGACAGAGGCCTGGACAAGGCCTT | **Y**INWVRQRPGQGLEWI |
| | GAGTGGATTGGAGAT**ATTAGTGATGGTGGTAGTTACACC**TACAAT | GD**ISDGGSYT**YNAKFK |
| | GCTAAGTTCAAGAGCAGAGCCACACTGACTCTGGACACATCCATA | SRATLTLDTSISTAYM |
| | AGCACAGCCTACATGGAGCTCAGCAGCCTGAGATCTGAGGACACG | ELSSLRSEDTAVYYC**A** |
| | GCGGTCTATTACTGT**GCAAGAGATTACTACGGTAGTAGTAGCTAC** | **RDYYGSSSYTSGFAY**W |
| | **ACCTCGGGCTTTGCTTAC**TGGGGCCAAGGCACCACGGTCACCGTC | GQGTTVTVSS |
| | TCCTCA | |
| VH4 | CAGGTCCAACTGGTGCAGTCTGGGGCTGAGGTGAAGAAGCCTGGG | QVQLVQSGAEVKKPGA |
| SEQ ID NO: | GCTTCAGTGAAGGTGTCCTGCAAGGCTTCT**GGATTCACTTTCAGT** | SVKVSCKAS**GFTFSDY** |
| 133, 134 | **GACTATTAC**ATAAACTGGGTGCGACAGAGGCCTGGACAAGGCCTT | **Y**INWVRQRPGQGLEWI |
| | GAGTGGATTGGAGAT**ATTAGTGATGGTGGTAGTTACACC**TACAAT | GD**ISDGGSYT**YNAKFK |
| | GCTAAGTTCAAGAGCAGAGTCACACTGACTCTGGACACATCCATA | SRVTLTLDTSISTAYM |
| | AGCACAGCCTACATGGAGCTCAGCAGCCTGAGATCTGAGGACACG | ELSSLRSEDTAVYYC**A** |
| | GCGGTCTATTACTGT**GCAAGAGATTACTACGGTAGTAGTAGCTAC** | **RDYYGSSSYTSGFAY**W |
| | **ACCTCGGGCTTTGCTTAC**TGGGGCCAAGGCACCACGGTCACCGTC | GQGTTVTVSS |
| | TCCTCA | |
| VH5 | CAGGTCCAACTGGTGCAGTCTGGGGCTGAGGTGAAGAAGCCTGGG | QVQLVQSGAEVKKPGA |
| SEQ ID NO: | GCTTCAGTGAAGGTGTCCTGCAAGGCTTCT**GGATTCACTTTCAGT** | SVKVSCKAS**GFTFSDY** |
| 135, 136 | **GACTATTAC**ATAAACTGGGTGCGACAGAGGCCTGGACAAGGCCTT | **Y**INWVRQRPGQGLEWM |
| | GAGTGGATGGGAGAT**ATTAGTGATGGTGGTAGTTACACC**TACAAT | GD**ISDGGSYT**YNAKFK |
| | GCTAAGTTCAAGAGCAGAGTCACACTGACTAGGGACACATCCATA | SRVTLTRDTSISTAYM |
| | AGCACAGCCTACATGGAGCTCAGCAGCCTGAGATCTGAGGACACG | ELSSLRSEDTAVYYC**A** |
| | GCGGTCTATTACTGT**GCAAGAGATTACTACGGTAGTAGTAGCTAC** | **RDYYGSSSYTSGFAY**W |
| | **ACCTCGGGCTTTGCTTAC**TGGGGCCAAGGCACCACGGTCACCGTC | GQGTTVTVSS |
| | TCCTCA | |
| VH6 | CAGGTCCAACTGGTGCAGTCTGGGGCTGAGGTGAAGAAGCCTGGG | QVQLVQSGAEVKKPGA |
| SEQ ID NO: | GCTTCAGTGAAGGTGTCCTGCAAGGCTTCT**GGATTCACTTTCAGT** | SVKVSCKAS**GFTFSDY** |
| 137, 138 | **GACTATTAC**ATAAACTGGGTGCGACAGAGGCCTGGACAAGGCCTT | **Y**INWVRQRPGQGLEWM |
| | GAGTGGATGGGAGAT**ATTAGTGATGGTGGTAGTTACACC**TACAAT | GD**ISDGGSYT**YNAKFQ |
| | GCTAAGTTCCAGGGCAGAGTCACAATGACTAGGGACACATCCATA | GRVTMTRDTSISTAYM |
| | AGCACAGCCTACATGGAGCTCAGCAGCCTGAGATCTGAGGACACG | ELSSLRSEDTAVYYC**A** |
| | GCGGTCTATTACTGT**GCAAGAGATTACTACGGTAGTAGTAGCTAC** | **RDYYGSSSYTSGFAY**W |
| | **ACCTCGGGCTTTGCTTAC**TGGGGCCAAGGCACCACGGTCACCGTC | GQGTTVTVSS |
| | TCCTCA | |
| VK0* | GATGTTTTGATGACCCAAACTCCACTCTCCCTGCCTGTCAGTCTT | DVLMTQTPLSLPVSLG |
| SEQ ID NO: | GGAGATCAAGCCTCCATCTCTTGCAGATCTAGT**CAGAGTCTGCTC** | DQASISCRSS**QSLLNS** |
| 139, 140 | **AACAGTAGAACCCGAAAGAACTAC**TTAGAATGGTACCTGCAGAAA | **RTRKNY**LEWYLQKPGQ |
| chimeric | CCAGGCCAGTCTCCAAAGCTCCTGATCTAC**TGGGCATCC**AACCGA | SPKLLIY**WAS**NRFSGV |
| | TTTTCTGGGGTCCCAGACAGGTTCAGTGGCAGTGGATCAGGGACA | PDRFSGSGSGTDFTLK |
| | GATTTCACACTCAAGATCAGCAGAGTGGAGGCTGAGGATCTGGGA | ISRVEAEDLGVYYC**KQ** |
| | GTTTATTACTGC**AAGCAATCTTATAATCTGTACACG**TTTGGCAGC | **SYNLYT**FGSGTKLEIK |
| | GGGACCAAGCTGGAGATCAAA | |
| VK1 | GATGTTTTGATGACCCAATCTCCACTCTCCCTGCCTGTCACCCTT | DVLMTQSPLSLPVTLG |
| SEQ ID NO: | GGACAGCCGGCCTCCATCTCTTGCAGATCTAGT**CAGAGTCTGCTC** | QPASISCRSS**QSLLNS** |
| 141, 142 | **AACAGTAGAACCCGAAAGAACTAC**TTAGAATGGTTTCAGCAGAAA | **RTRKNY**LEWFQQKPGQ |
| | CCAGGCCAGTCTCCAAGGCGCCTGATCTAC**TGGGCATCC**AACCGA | SPRRLIY**WAS**NRFSGV |
| | TTTTCTGGGGTCCCAGACAGGTTCAGTGGCAGTGGATCAGGGACA | PDRFSGSGSGTDFTLK |
| | GATTTCACACTCAAGATCAGCAGAGTGGAGGCTGAGGATGTTGGA | ISRVEAEDVGVYYC**KQ** |
| | GTTTATTACTGC**AAGCAATCTTATAATCTGTACACG**TTTGGCCAA | **SYNLYT**FGQGTKLEIK |
| | GGGACCAAGCTGGAGATCAAA | |
| VK2 | GATGTTGTGATGACCCAATCTCCACTCTCCCTGCCTGTCACCCTT | DVVMTQSPLSLPVTLG |
| SEQ ID NO: | GGACAGCCGGCCTCCATCTCTTGCAGATCTAGT**CAGAGTCTGCTC** | QPASISCRSS**QSLLNS** |
| 143, 144 | **AACAGTAGAACCCGAAAGAACTAC**TTAGAATGGTTTCAGCAGAAA | **RTRKNY**LEWFQQKPGQ |
| | CCAGGCCAGTCTCCAAGGCGCCTGATCTAC**TGGGCATCC**AACCGA | SPRRLIY**WAS**NRFSGV |
| | TTTTCTGGGGTCCCAGACAGGTTCAGTGGCAGTGGATCAGGGACA | PDRFSGSGSGTDFTLK |
| | GATTTCACACTCAAGATCAGCAGAGTGGAGGCTGAGGATGTTGGA | ISRVEAEDVGVYYC**KQ** |
| | GTTTATTACTGC**AAGCAATCTTATAATCTGTACACG**TTTGGCCAA | **SYNLYT**FGQGTKLEIK |
| | GGGACCAAGCTGGAGATCAAA | |
| VK3 | GATGTTGTGATGACCCAATCTCCACTCTCCCTGCCTGTCACCCTT | DVVMTQSPLSLPVTLG |
| SEQ ID NO. | GGACAGCCGGCCTCCATCTCTTGCAGATCTAGT**CAGAGTCTGCTC** | QPASISCRSS**QSLLNS** |
| 145, 146 | **AACAGTAGAACCCGAAAGAACTAC**TTAGAATGGTTTCAGCAGAGG | **RTRKNY**LEWFQQRPGQ |
| | CCAGGCCAGTCTCCAAGGCGCCTGATCTAC**TGGGCATCC**AACCGA | SPRRLIY**WAS**NRFSGV |
| | TTTTCTGGGGTCCCAGACAGGTTCAGTGGCAGTGGATCAGGGACA | PDRFSGSGSGTDFTLK |

TABLE 12-continued

Variable domain of humanized antibodies

| Chimeric/ Humanized Antibody 301-11 | cDNA Sequence | Polypeptide sequence |
|---|---|---|
| | GATTTCACACTCAAGATCAGCAGAGTGGAGGCTGAGGATGTTGGA | ISRVEAEDVGVYYC**KQ** |
| | GTTTATTACTGC**AAGCAATCTTATAATCTGTACACG**TTTGGCCAA | **SYNLYT**FGQGTKLEIK |
| | GGGACCAAGCTGGAGATCAAA | |
| VK4 | GATGTTCTGATGACCCAATCTCCACTCTCCCTGCCTGTCACCCTT | DVLMTQSPLSLPVTLG |
| SEQ ID NO. | GGACAGCCGGCCTCCATCTCTTGCAGATCTAGT**CAGAGTCTGCTC** | QPASISCRSS**QSLLNS** |
| 147, 148 | **AACAGTAGAACCCGAAAGAACTAC**TTAGAATGGTACCTGCAGAGG | **RTRKNY**LEWYLQRPGQ |
| | CCAGGCCAGTCTCCAAAGCTGCTGATCTAC**TGGGCATCC**AACCGA | SPKLLIY**WAS**NRFSGV |
| | TTTTCTGGGGTCCCAGACAGGTTCAGTGGCAGTGGATCAGGGACA | PDRFSGSGSGTDFTLK |
| | GATTTCACACTCAAGATCAGCAGAGTGGAGGCTGAGGATGTTGGA | ISRVEAEDVGVYYC**KQ** |
| | GTTTATTACTGC**AAGCAATCTTATAATCTGTACACG**TTTGGCCAA | **SYNLYT**FGQGTKLEIK |
| | GGGACCAAGCTGGAGATCAAA | |
| VK5 | GATGTTCTGATGACCCAATCTCCACTCTCCCTGCCTGTCACCCTT | DVLMTQSPLSLPVTLG |
| SEQ ID NO: | GGACAGCCGGCCTCCATCTCTTGCAGATCTAGT**CAGAGTCTGCTC** | QPASISCRSS**QSLLNS** |
| 149, 150 | **AACAGTAGAACCCGAAAGAACTAC**TTAGAATGGTACCAGCAGAGG | **RTRKNY**LEWYQQRPGQ |
| | CCAGGCCAGTCTCCAAGGCTGCTGATCTAC**TGGGCATCC**AACCGA | SPRLLIY**WAS**NRFSGV |
| | TTTTCTGGGGTCCCAGACAGGTTCAGTGGCAGTGGATCAGGGACA | PDRFSGSGSGTDFTLK |
| | GATTTCACACTCAAGATCAGCAGAGTGGAGGCTGAGGATGTTGGA | ISRVEAEDVGVYYC**KQ** |
| | GTTTATTACTGC**AAGCAATCTTATAATCTGTACACG**TTTGGCCAA | **SYNLYT**FGQGTKLEIK |
| | GGGACCAAGCTGGAGATCAAA | |
| VK6 | GATGTTGTGATGACCCAATCTCCACTCTCCCTGCCTGTCACCCTT | DVVMTQSPLSLPVTLG |
| SEQ ID NO: | GGACAGCCGGCCTCCATCTCTTGCAGATCTAGT**CAGAGTCTGCTC** | QPASISCRSS**QSLLNS** |
| 151, 152 | **AACAGTAGAACCCGAAAGAACTAC**TTAGAATGGTACCAGCAGAGG | **RTRKNY**LEWYQQRPGQ |
| | CCAGGCCAGTCTCCAAGGCTGCTGATCTAC**TGGGCATCC**AACCGA | SPRLLIY**WAS**NRFSGV |
| | TTTTCTGGGGTCCCAGACAGGTTCAGTGGCAGTGGATCAGGGACA | PDRFSGSGSGTDFTLK |
| | GATTTCACACTCAAGATCAGCAGAGTGGAGGCTGAGGATGTTGGA | ISRVEAEDVGVYYC**KQ** |
| | GTTTATTACTGC**AAGCAATCTTATAATCTGTACACG**TTTGGCCAA | **SYNLYT**FGQGTKLEIK |
| | GGGACCAAGCTGGAGATCAAA | |

*VH0 and VK0 denotes chimeric antibodies comprised of the human constant domain and mouse variable domain sequences and are provided for comparison.

TABLE 13

Variable domain of humanized antibodies

| Chimeric/ Humanized Antibody | cDNA Sequence | Polypeptide Sequence |
|---|---|---|
| 301-17 | CAGGTCCAACTGCAGCAGCCTGGGGCTGAGCTTGTGAAGCCTGGG | QVQLQQPGAELVKPGA |
| VH0* | GCTTCAGTGAAGATGTCCTGCAAGGCTTCT**GGCTACAGCTTCACC** | SVKMSCKAS**GYSFTSY** |
| SEQ ID NO: | **AGCTACTGG**ATAAACTGGGTGAAGCAGAGGCCTGGACAAGGCCTT | **W**INWVKQRPGQGLEWI |
| 153, 154 | GAGTGGATTGGAGAT**GTGCATCCTGGTAGAGGCGTGTCCACA**TAC | GD**VHPGRGVST**YNAKF |
| (chimeric) | AATGCTAAGTTCAAGAGCAAGGCCACACTGACTCTGGACACATCC | KSKATLTLDTSSSTAY |
| | TCCAGCACAGCCTACATGCAGCTCAGCAGCCTGACATCTGAGGAC | MQLSSLTSEDSAVYYC |
| | TCTGCGGTCTATTACTGT**AGCAGATCCCATGGTAACACCTACTGG** | **SRSHGNTYWFFDV**WGA |
| | **TTTTTTGACGTC**TGGGGCGCAGGCACCACGGTCACCGTCTCCTCA | GTTVTVSS |
| VH1 | CAGGTCCAACTGGTGCAGTCTGGGGCTGAGCTTAAGAAGCCTGGG | QVQLVQSGAELKKPGA |
| SEQ ID NO: | GCTTCAGTGAAGATGTCCTGCAAGGCTTCT**GGCTACAGCTTCACC** | SVKMSCKAS**GYSFTSY** |
| 155, 156 | **AGCTACTGG**ATAAACTGGGTGAAGCAGAGGCCTGGACAAGGCCTT | **W**INWVKQRPGQGLEWI |
| | GAGTGGATTGGAGAT**GTGCATCCTGGTAGAGGCGTGTCCACA**TAC | GD**VHPGRGVST**YNAKF |
| | AATGCTAAGTTCAAGAGCAGAGCCACACTGACTCTGGACACATCC | KSRATLTLDTSISTAY |
| | ATAAGCACAGCCTACATGCAGCTCAGCAGCCTGACATCTGAGGAC | MQLSSLTSEDSAVYYC |
| | TCTGCGGTCTATTACTGT**AGCAGATCCCATGGTAACACCTACTGG** | **SRSHGNTYWFFDV**WGQ |
| | **TTTTTTGACGTC**TGGGGCCAAGGCACCACGGTCACCGTCTCCTCA | GTTVTVSS |
| VH2 | CAGGTCCAACTGGTGCAGTCTGGGGCTGAGGTGAAGAAGCCTGGG | QVQLVQSGAEVKKPGA |
| SEQ ID NO: | GCTTCAGTGAAGATGTCCTGCAAGGCTTCT**GGCTACAGCTTCACC** | SVKMSCKAS**GYSFTSY** |
| 157, 158 | **AGCTACTGG**ATAAACTGGGTGAAGCAGAGGCCTGGACAAGGCCTT | **W**INWVKQRPGQGLEWI |
| | GAGTGGATTGGAGAT**GTGCATCCTGGTAGAGGCGTGTCCACA**TAC | GD**VHPGRGVST**YNAKF |
| | AATGCTAAGTTCAAGAGCAGAGCCACACTGACTCTGGACACATCC | KSRATLTLDTSISTAY |
| | ATAAGCACAGCCTACATGGAGCTCAGCAGCCTGAGATCTGAGGAC | MELSSLRSEDTAVYYC |
| | ACGGCGGTCTATTACTGT**AGCAGATCCCATGGTAACACCTACTGG** | **SRSHGNTYWFFDV**WGQ |
| | **TTTTTTGACGTC**TGGGGCCAAGGCACCACGGTCACCGTCTCCTCA | GTTVTVSS |

TABLE 13-continued

Variable domain of humanized antibodies

| Chimeric/<br>Humanized<br>Antibody | cDNA Sequence | Polypeptide<br>Sequence |
|---|---|---|
| VH3<br>SEQ ID NO:<br>159, 160 | CAGGTCCAACTGGTGCAGTCTGGGGCTGAGGTGAAGAAGCCTGGG<br>GCTTCAGTGAAGGTGTCCTGCAAGGCTTCT**GGCTACAGCTTCACC**<br>**AGCTACTGG**ATAAACTGGGTGCGACAGAGGCCTGGACAAGGCCTT<br>GAGTGGATTGGAGAT**GTGCATCCTGGTAGAGGCGTGTCCACA**TAC<br>AATGCTAAGTTCAAGAGCAGAGCCACACTGACTCTGGACACATCC<br>ATAAGCACAGCCTACATGGAGCTCAGCAGCCTGAGATCTGAGGAC<br>ACGGCGGTCTATTACTGT**AGCAGATCCCATGGTAACACCTACTGG**<br>**TTTTTTGACGTC**TGGGGCCAAGGCACCACGGTCACCGTCTCCTCA | QVQLVQSGAEVKKPGA<br>SVKVSCKAS**GYSFTSY**<br>**W**INWVRQRPGQGLEWI<br>GD**VHPGRGVST**YNAKF<br>KSRATLTLDTSISTAY<br>MELSSLRSEDTAVYYC<br>**SRSHGNTYWFFDV**WGQ<br>GTTVTVSS |
| VH4<br>SEQ ID NO:<br>161, 162 | CAGGTCCAACTGGTGCAGTCTGGGGCTGAGGTGAAGAAGCCTGGG<br>GCTTCAGTGAAGGTGTCCTGCAAGGCTTCT**GGCTACAGCTTCACC**<br>**AGCTACTGG**ATAAACTGGGTGCGACAGAGGCCTGGACAAGGCCTT<br>GAGTGGATTGGAGAT**GTGCATCCTGGTAGAGGCGTGTCCACA**TAC<br>AATGCTAAGTTCAAGAGCAGAGTCACACTGACTCTGGACACATCC<br>ATAAGCACAGCCTACATGGAGCTCAGCAGCCTGAGATCTGAGGAC<br>ACGGCGGTCTATTACTGT**AGCAGATCCCATGGTAACACCTACTGG**<br>**TTTTTTGACGTC**TGGGGCCAAGGCACCACGGTCACCGTCTCCTCA | QVQLVQSGAEVKKPGA<br>SVKVSCKAS**GYSFTSY**<br>**W**INWVRQRPGQGLEWI<br>GD**VHPGRGVST**YNAKF<br>KSRVTLTLDTSISTAY<br>MELSSLRSEDTAVYYC<br>**SRSHGNTYWFFDV**WGQ<br>GTTVTVSS |
| VHS<br>SEQ ID NO:<br>163, 164 | CAGGTCCAACTGGTGCAGTCTGGGGCTGAGGTGAAGAAGCCTGGG<br>GCTTCAGTGAAGGTGTCCTGCAAGGCTTCT**GGCTACAGCTTCACC**<br>**AGCTACTGG**ATAAACTGGGTGCGACAGAGGCCTGGACAAGGCCTT<br>GAGTGGATGGGAGAT**GTGCATCCTGGTAGAGGCGTGTCCACA**TAC<br>AATGCTAAGTTCAAGAGCAGAGTCACACTGACTAGGGACACATCC<br>ATAAGCACAGCCTACATGGAGCTCAGCAGCCTGAGATCTGAGGAC<br>ACGGCGGTCTATTACTGT**AGCAGATCCCATGGTAACACCTACTGG**<br>**TTTTTTGACGTC**TGGGGCCAAGGCACCACGGTCACCGTCTCCTCA | QVQLVQSGAEVKKPGA<br>SVKVSCKAS**GYSFTSY**<br>**W**INWVRQRPGQGLEWM<br>GD**VHPGRGVST**YNAKF<br>KSRVTLTRDTSISTAY<br>MELSSLRSEDTAVYYC<br>**SRSHGNTYWFFDV**WGQ<br>GTTVTVSS |
| VH6<br>SEQ ID NO:<br>165, 166 | CAGGTCCAACTGGTGCAGTCTGGGGCTGAGGTGAAGAAGCCTGGG<br>GCTTCAGTGAAGGTGTCCTGCAAGGCTTCT**GGCTACAGCTTCACC**<br>**AGCTACTGG**ATAAACTGGGTGCGACAGAGGCCTGGACAAGGCCTT<br>GAGTGGATGGGAGAT**GTGCATCCTGGTAGAGGCGTGTCCACA**TAC<br>AATGCTAAGTTCCAGGGCAGAGTCACAATGACTAGGGACACATCC<br>ATAAGCACAGCCTACATGGAGCTCAGCAGCCTGAGATCTGAGGAC<br>ACGGCGGTCTATTACTGT**AGCAGATCCCATGGTAACACCTACTGG**<br>**TTTTTTGACGTC**TGGGGCCAAGGCACCACGGTCACCGTCTCCTCA | QVQLVQSGAEVKKPGA<br>SVKVSCKAS**GYSFTSY**<br>**W**INWVRQRPGQGLEWM<br>GD**VHPGRGVST**YNAKF<br>QGRVTMTRDTSISTAY<br>MELSSLRSEDTAVYYC<br>**SRSHGNTYWFFDV**WGQ<br>GTTVTVSS |
| VK0*<br>SEQ ID NO:<br>167, 168<br>(Chimeric) | GATGTTTTGATGACCCAAACTCCACTCTCCCTGCCTGTCAGTCTT<br>GGAGATCAAGCCTCCATCTCTTGCAGATCTAGT**CAGAGCATTGTA**<br>**CATAGTAATGGAAACACCTAT**TTAGAATGGTACCTGCAGAAACCA<br>GGCCAGTCTCCAAAGCTCCTGATCTAC**AAAGTTTCC**AACCGATTT<br>TCTGGGGTCCCAGACAGGTTCAGTGGCAGTGGATCAGGGACAGAT<br>TTCACACTCAAGATCAGCAGAGTGGAGGCTGAGGATCTGGGAGTT<br>TATTACTGC**TTTCAAGGTTCACATGTTCCTTTCACT**TTTGGCAGC<br>GGGACCAAGCTGGAGATCAAA | DVLMTQTPLSLPVSLG<br>DQASISCRSS**QSIVHS**<br>**NGNTY**LEWYLQKPGQS<br>PKLLIY**KVS**NRFSGVP<br>DRFSGSGSGTDFTLKI<br>SRVEAEDLGVYYC**FQG**<br>**SHVPFT**FGSGTKLEIK |
| VK1<br>SEQ ID NO:<br>169, 170 | GATGTTTTGATGACCCAATCTCCACTCTCCCTGCCTGTCACCCTT<br>GGACAGCCGGCCTCCATCTCTTGCAGATCTAGT**CAGAGCATTGTA**<br>**CATAGTAATGGAAACACCTAT**TTAGAATGGTTTCAGCAGAAACCA<br>GGCCAGTCTCCAAGGCGCCTGATCTAC**AAAGTTTCC**AACCGATTT<br>TCTGGGGTCCCAGACAGGTTCAGTGGCAGTGGATCAGGGACAGAT<br>TTCACACTCAAGATCAGCAGAGTGGAGGCTGAGGATGTTGGAGTT<br>TATTACTGC**TTTCAAGGTTCACATGTTCCTTTCACT**TTTGGCCAA<br>GGGACCAAGCTGGAGATCAAA | DVLMTQSPLSLPVTLG<br>QPASISCRSS**QSIVHS**<br>**NGNTY**LEWFQQKPGQS<br>PRRLIY**KVS**NRFSGVP<br>DRFSGSGSGTDFTLKI<br>SRVEAEDVGVYYC**FQG**<br>**SHVPFT**FGQGTKLEIK |
| VK2<br>SEQ ID NO:<br>171-172 | GATGTTGTGATGACCCAATCTCCACTCTCCCTGCCTGTCACCCTT<br>GGACAGCCGGCCTCCATCTCTTGCAGATCTAGT**CAGAGCATTGTA**<br>**CATAGTAATGGAAACACCTAT**TTAGAATGGTTTCAGCAGAAACCA<br>GGCCAGTCTCCAAGGCGCCTGATCTAC**AAAGTTTCC**AACCGATTT<br>TCTGGGGTCCCAGACAGGTTCAGTGGCAGTGGATCAGGGACAGAT<br>TTCACACTCAAGATCAGCAGAGTGGAGGCTGAGGATGTTGGAGTT<br>TATTACTGC**TTTCAAGGTTCACATGTTCCTTTCACT**TTTGGCCAA<br>GGGACCAAGCTGGAGATCAAA | DVVMTQSPLSLPVTLG<br>QPASISCRSS**QSIVHS**<br>**NGNTY**LEWFQQKPGQS<br>PRRLIY**KVS**NRFSGVP<br>DRFSGSGSGTDFTLKI<br>SRVEAEDVGVYYC**FQG**<br>**SHVPFT**FGQGTKLEIK |
| VK3<br>SEQ ID NO:<br>173-174 | GATGTTGTGATGACCCAATCTCCACTCTCCCTGCCTGTCACCCTT<br>GGACAGCCGGCCTCCATCTCTTGCAGATCTAGT**CAGAGCATTGTA**<br>**CATAGTAATGGAAACACCTAT**TTAGAATGGTTTCAGCAGAGGCCA<br>GGCCAGTCTCCAAGGCGCCTGATCTAC**AAAGTTTCC**AACCGATTT<br>TCTGGGGTCCCAGACAGGTTCAGTGGCAGTGGATCAGGGACAGAT<br>TTCACACTCAAGATCAGCAGAGTGGAGGCTGAGGATGTTGGAGTT<br>TATTACTGC**TTTCAAGGTTCACATGTTCCTTTCACT**TTTGGCCAA<br>GGGACCAAGCTGGAGATCAAA | DVVMTQSPLSLPVTLG<br>QPASISCRSS**QSIVHS**<br>**NGNTY**LEWFQQRPGQS<br>PRRLIY**KVS**NRFSGVP<br>DRFSGSGSGTDFTLKI<br>SRVEAEDVGVYYC**FQG**<br>**SHVPFT**FGQGTKLEIK |

TABLE 13-continued

Variable domain of humanized antibodies

| Chimeric/<br>Humanized<br>Antibody | cDNA Sequence | Polypeptide<br>Sequence |
|---|---|---|
| VK4<br>SEQ ID NO:<br>175-176 | GATGTTCTGATGACCCAATCTCCACTCTCCCTGCCTGTCACCCTT<br>GGACAGCCGGCCTCCATCTCTTGCAGATCTAGT**CAGAGCATTGTA**<br>**CATAGTAATGGAAACACCTAT**TTAGAATGGTACCTGCAGAGGCCA<br>GGCCAGTCTCCAAAGCTGCTGATCTAC**AAAGTTTCC**AACCGATTT<br>TCTGGGGTCCCAGACAGGTTCAGTGGCAGTGGATCAGGGACAGAT<br>TTCACACTCAAGATCAGCAGAGTGGAGGCTGAGGATGTTGGAGTT<br>TATTACTGC**TTTCAAGGTTCACATGTTCCTTTCACT**TTTGGCCAA<br>GGGACCAAGCTGGAGATCAAA | DVLMTQSPLSLPVTLG<br>QPASISCRSS**QSIVHS**<br>**NGNTY**LEWYLQRPGQS<br>PKLLIY**KVS**NRFSGVP<br>DRFSGSGSGTDFTLKI<br>SRVEAEDVGVYYC**FQG**<br>**SHVPFT**FGQGTKLEIK |
| VK5<br>SEQ ID NO:<br>177-178 | GATGTTCTGATGACCCAATCTCCACTCTCCCTGCCTGTCACCCTT<br>GGACAGCCGGCCTCCATCTCTTGCAGATCTAGT**CAGAGCATTGTA**<br>**CATAGTAATGGAAACACCTAT**TTAGAATGGTACCAGCAGAGGCCA<br>GGCCAGTCTCCAAGGCTGCTGATCTAC**AAAGTTTCC**AACCGATTT<br>TCTGGGGTCCCAGACAGGTTCAGTGGCAGTGGATCAGGGACAGAT<br>TTCACACTCAAGATCAGCAGAGTGGAGGCTGAGGATGTTGGAGTT<br>TATTACTGC**TTTCAAGGTTCACATGTTCCTTTCACT**TTTGGCCAA<br>GGGACCAAGCTGGAGATCAAA | DVLMTQSPLSLPVTLG<br>QPASISCRSS**QSIVHS**<br>**NGNTY**LEWYQQRPGQS<br>PRLLIY**KVS**NRFSGVP<br>DRFSGSGSGTDFTLKI<br>SRVEAEDVGVYYC**FQG**<br>**SHVPFT**FGQGTKLEIK |
| VK6<br>SEQ ID NO:<br>179-180 | GATGTTGTGATGACCCAATCTCCACTCTCCCTGCCTGTCACCCTT<br>GGACAGCCGGCCTCCATCTCTTGCAGATCTAGT**CAGAGCATTGTA**<br>**CATAGTAATGGAAACACCTAT**TTAGAATGGTACCAGCAGAGGCCA<br>GGCCAGTCTCCAAGGCTGCTGATCTAC**AAAGTTTCC**AACCGATTT<br>TCTGGGGTCCCAGACAGGTTCAGTGGCAGTGGATCAGGGACAGAT<br>TTCACACTCAAGATCAGCAGAGTGGAGGCTGAGGATGTTGGAGTT<br>TATTACTGC**TTTCAAGGTTCACATGTTCCTTTCACT**TTTGGCCAA<br>GGGACCAAGCTGGAGATCAAA | DVVMTQSPLSLPVTLG<br>QPASISCRSS**QSIVHS**<br>**NGNTY**LEWYQQRPGQS<br>PRLLIY**KVS**NRFSGVP<br>DRFSGSGSGTDFTLKI<br>SRVEAEDVGVYYC**FQG**<br>**SHVPFT**FGQGTKLEIK |

*VH0 and VK0 denotes chimeric antibodies comprised of the human constant domain and mouse variable domain sequences and are provided for comparison.

TABLE 14

Humanized antibody IgG4 sequence

| Constant<br>regions | cDNA<br>Sequence | Polypeptide<br>sequence |
|---|---|---|
| IgG4 heavy<br>chain<br>SEQ ID NO:<br>181-182 | GCTTCCACCAAGGGCCCATCCGTCTTCCCCCTGGCGCCCTGCTCC<br>AGGAGCACCTCCGAGAGCACAGCCGCCCTGGGCTGCCTGGTCAAG<br>GACTACTTCCCCGAACCGGTGACGGTGTCGTGGAACTCAGGCGCC<br>CTGACCAGCGGCGTGCACACCTTCCCGGCTGTCCTACAGTCCTCA<br>GGACTCTACTCCCTCAGCAGCGTGGTGACCGTGCCCTCCAGCAGC<br>TTGGGCACGAAGACCTACACCTGCAATGTAGATCACAAGCCCAGC<br>AACACCAAGGTGGACAAGAGAGTTGAGTCCAAATATGGTCCCCCA<br>TGCCCACCATGCCCAGCACCTGAGTTCCTGGGGGGACCATCAGTC<br>TTCCTGTTCCCCCCAAAACCCAAGGACACTCTCATGATCTCCCGG<br>ACCCCTGAGGTCACGTGCGTGGTGGTGGACGTGAGCCAGGAAGAC<br>CCCGAGGTCCAGTTCAACTGGTACGTGGATGGCGTGGAGGTGCAT<br>AATGCCAAGACAAAGCCGCGGGAGGAGCAGTTCAACAGCACGTAC<br>CGTGTGGTCAGCGTCCTCACCGTCCTGCACCAGGACTGGCTGAAC<br>GGCAAGGAGTACAAGTGCAAGGTCTCCAACAAAGGCCTCCCGTCC<br>TCCATCGAGAAAACCATCTCCAAAGCCAAAGGGCAGCCCCGAGAG<br>CCACAGGTGTACACCCTGCCCCCATCCCAGGAGGAGATGACCAAG<br>AACCAGGTCAGCCTGACCTGCCTGGTCAAAGGCTTCTACCCCAGC<br>GACATCGCCGTGGAGTGGGAGAGCAATGGGCAGCCGGAGAACAAC<br>TACAAGACCACGCCTCCCGTGCTGGACTCCGACGGCTCCTTCTTC<br>CTCTACAGCAGGCTAACCGTGGACAAGAGCAGGTGGCAGGAGGGG<br>AATGTCTTCTCATGCTCCGTGATGCATGAGGCTCTGCACAACCAC<br>TACACACAGAAGAGCCTCTCCCTGTCTCTGGGTAAATGA | ASTKGPSVFPLAPCSR<br>STSESTAALGCLVKDY<br>FPEPVTVSWNSGALTS<br>GVHTFPAVLQSSGLYS<br>LSSVVTVPSSSLGTKT<br>YTCNVDHKPSNTKVDK<br>RVESKYGPPCPPCPAP<br>EFLGGPSVFLFPPKPK<br>DTLMISRTPEVTCVVV<br>DVSQEDPEVQFNWYVD<br>GVEVHNAKTKPREEQF<br>NSTYRVVSVLTVLHQD<br>WLNGKEYKCKVSNKGL<br>PSSIEKTISKAKGQPR<br>EPQVYTLPPSQEEMTK<br>NQVSLTCLVKGFYPSD<br>IAVEWESNGQPENNYK<br>TTPPVLDSDGSFFLYS<br>RLTVDKSRWQEGNVFS<br>CSVMHEALHNHYTQKS<br>LSLSLGK |
| Kappa<br>SEQ ID NO:<br>183-184 | CGAACTGTGGCTGCACCATCTGTCTTCATCTTCCCGCCATCTGAT<br>GAGCAGTTGAAATCTGGAACTGCCTCTGTTGTGTGCCTGCTGAAT<br>AACTTCTATCCCAGAGAGGCCAAAGTACAGTGGAAGGTGGATAAC<br>GCCCTCCAATCGGGTAACTCCCAGGAGAGTGTCACAGAGCAGGAC<br>AGCAAGGACAGCACCTACAGCCTCAGCAGCACCCTGACGCTGAGC<br>AAAGCAGACTACGAGAAACACAAAGTCTACGCCTGCGAAGTCACC<br>CATCAGGGCCTGAGCTCGCCCGTCACAAAGAGCTTCAACAGGGGA<br>GAGTGTTAG | RTVAAPSVFIFPPSDE<br>QLKSGTASVVCLLNNF<br>YPREAKVQWKVDNALQ<br>SGNSQESVTEQDSKDS<br>TYSLSSTLTLSKADYE<br>KHKVYACEVTHQGLSS<br>PVTKSFNRGEC |

Example 17

Figure 8:
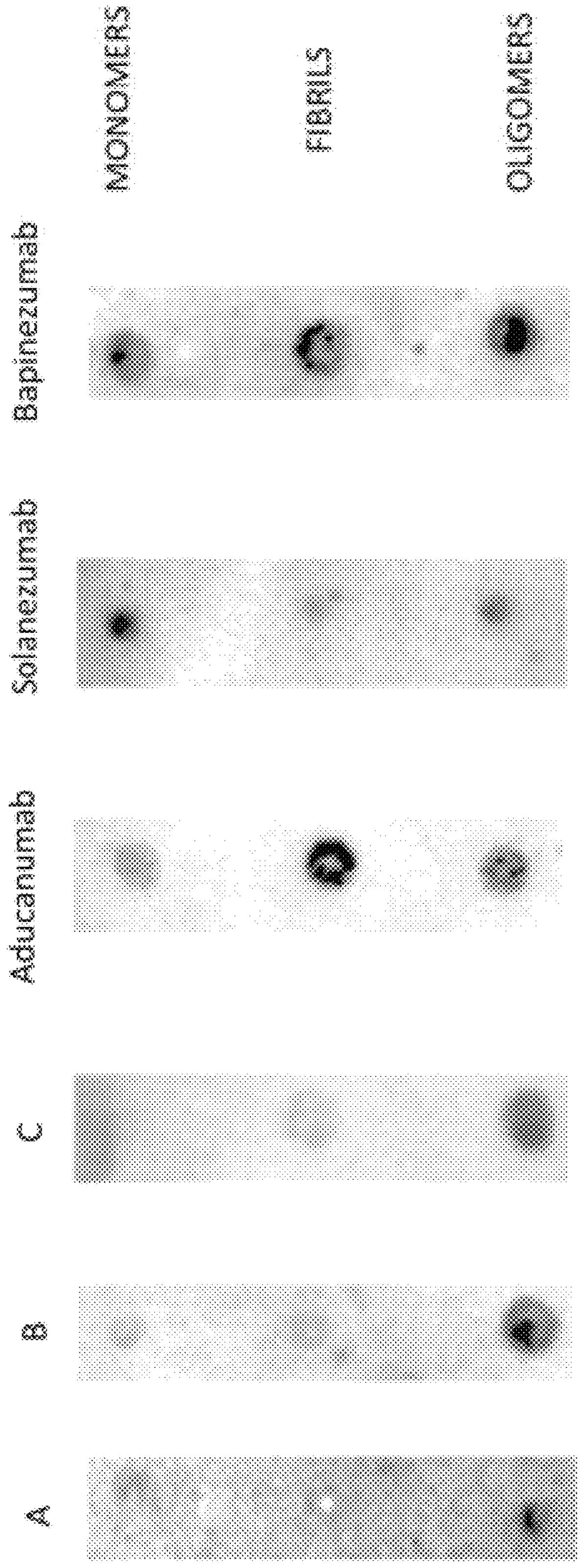
FIG. 8 is a dot blot image showing antibody binding to monomeric, oligomeric and fibrillary A-beta.

A dot blot assay was used to detect antibody binding of antibodies to monomeric, oligomeric and fibrillary A-beta. 10 ng of monomeric and fibril and 100 ng oligomeric A-beta was spotted on a PVDF membrane. The membrane was blotted with antibodies 301-17, 303-25 and 305-62 as well as prior art antibodies aducanumab, solanezumab and bapinezumab (Creative Biolabs). Antibodies 301-17 (FIG. 8 panel C), 303-25 (FIG. 8 panel A) and 305-62 (FIG. 8 panel B) bound oligomeric but not monomeric or fibrillar A-beta. Aducanumab exhibited preferential binding for fibrils, solanezumab exhibited preferential binding for monomers and bapinezumab showed significant binding to monomers, fibrils and oligomers.

Example 18

CDRs can also be identified using the Kabat numbering scheme. For example the CDRs for the humanized 301-17 constructs using the Kabat numbering system are:

TABLE 15

| Chain | CDR | Sequence | SEQ ID NO. |
|---|---|---|---|
| Heavy | CDR-H1 | SYWIN | 195 |
| | CDR-H2* | DVHPGRGVSTYNAKFKS* | 196 |
| | CDR-H3 | SHGNTYWFFDV | 197 |
| Light | CDR-L1 | RSSQSIVHSNGNTYLE | 198 |
| | CDR-L2 | KVSNRFS | 199 |
| | CDR-L3 | FQGSHVPFT | 200 |

*For VH6, CDR-H2sequence is DVHPGRGVSTYNAKFQG (SEQ ID NO. 201)

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

REFERENCES

[8] J. X. Lu, W. Qiang, W. M. Yau, C. D. Schwieters, S. C. Meredith, R. Tycko, MOLECULAR STRUCTURE OF BETA-AMYLOID FIBRILS IN ALZHEIMER'S DISEASE BRAIN TISSUE. CELL Vol. 154 p. 1257 (2013)

[9] Y. Xiao, B. MA, D. McElheny, S. Parthasarathy, F. Long, M. Hoshi, R. Nussinov, Y. Ishii, A BETA (1-42) FIBRIL STRUCTURE ILLUMINATES SELF-RECOGNITION AND REPLICATION OF AMYLOID IN ALZHEIMER'S DISEASE. NAT. STRUCT. MOL. BIOL. Vol. 22 p. 499 (2015).

[10] A. Petkova, W. Yau, R. Tycko EXPERIMENTAL CONSTRAINTS ON QUATERNARY STRUCTURE IN ALZHEIMER'S BETA-AMYLOID FIBRILS BIOCHEMISTRY V. 45 498 2006.

[11] Giulian D, Haverkamp L J, Yu J, Karshin W, Tom D, Li J, Kazanskaia A, Kirkpatrick J, Roher A E. The HHQK domain of β-amyloid provides a structural basis for the immunopathology of Alzheimer's disease, *J. Biol. Chem.* 1998, 273(45), 29719-26.

[12] Winkler K, Scharnagl H, Tisljar U, HoschOtzky H, Friedrich I, Hoffmann MM, Hattinger M, Wieland H, März W. Competition of Aβ amyloid peptide and apolipoprotein E for receptor-mediated endocytosis. J. Lipid Res. 1999, 40(3), 447-55.

[16] SCIENTIFIC REPORTS|5:9649|DOI: 10.1038/srep09649

The invention claimed is:

1. A composition comprising a combination of two or more different immunogens, wherein the two or more immunogens are selected from:

i) an immunogen comprising a cyclic compound consisting of the sequence of cyclo(CGHHQKG) (SEQ ID NO: 2);

ii) an immunogen comprising a cyclic compound consisting of the sequence of cyclo(CGQKLVG) (SEQ ID NO: 6); and iii) an immunogen comprising a cyclic compound consisting of the sequence of cyclo(CGHDSGG) (SEQ ID NO: 10).

2. The composition of claim 1, wherein a detectable tag, a carrier or an immunogenicity enhancing agent is coupled to a cysteine residue of the cyclic compound, wherein the immunogenicity agent is Keyhole Limpet Hemocyanin.

3. The composition of claim 2, wherein the carrier is bovine serum albumin.

4. The composition of claim 1, wherein the composition is a pharmaceutical composition.

5. The composition of claim 4, wherein the pharmaceutical composition is in the form of a pharmaceutically acceptable salt.

6. The composition of claim 1, wherein the composition comprises an adjuvant.

7. The composition of claim 6, wherein the adjuvant comprises alum.

8. The composition of claim 6, wherein the adjuvant comprises polyphosphazene.

9. The pharmaceutical composition of claim 4, wherein the pharmaceutical composition comprises a pharmaceutically acceptable carrier.

* * * * *

SEQUENCE LISTING

```
<160> NUMBER OF SEQ ID NOS: 205

<210> SEQ ID NO 1
<211> LENGTH: 4
<212> TYPE: PRT
<213> ORGANISM: Homo Sapiens

<400> SEQUENCE: 1

His His Gln Lys
1


<210> SEQ ID NO 2
<211> LENGTH: 7
<212> TYPE: PRT
<213> ORGANISM: Homo Sapiens

<400> SEQUENCE: 2

Cys Gly His His Gln Lys Gly
1               5
```

<210> SEQ ID NO 3
<211> LENGTH: 6
<212> TYPE: PRT
<213> ORGANISM: Homo Sapiens

<400> SEQUENCE: 3

Cys His His Gln Lys Gly
1 5

<210> SEQ ID NO 4
<211> LENGTH: 6
<212> TYPE: PRT
<213> ORGANISM: Homo Sapiens

<400> SEQUENCE: 4

Cys Gly His His Gln Lys
1 5

<210> SEQ ID NO 5
<211> LENGTH: 4
<212> TYPE: PRT
<213> ORGANISM: Homo Sapiens

<400> SEQUENCE: 5

Gln Lys Leu Val
1

<210> SEQ ID NO 6
<211> LENGTH: 7
<212> TYPE: PRT
<213> ORGANISM: Homo Sapiens

<400> SEQUENCE: 6

Cys Gly Gln Lys Leu Val Gly
1 5

<210> SEQ ID NO 7
<211> LENGTH: 6
<212> TYPE: PRT
<213> ORGANISM: Homo Sapiens

<400> SEQUENCE: 7

Cys Gln Lys Leu Val Gly
1 5

<210> SEQ ID NO 8
<211> LENGTH: 6
<212> TYPE: PRT
<213> ORGANISM: Homo Sapiens

<400> SEQUENCE: 8

Cys Gly Gln Lys Leu Val
1 5

<210> SEQ ID NO 9
<211> LENGTH: 4
<212> TYPE: PRT
<213> ORGANISM: Homo Sapiens

<400> SEQUENCE: 9

His Asp Ser Gly
1

<210> SEQ ID NO 10

<211> LENGTH: 7
<212> TYPE: PRT
<213> ORGANISM: Homo Sapiens

<400> SEQUENCE: 10

Cys Gly His Asp Ser Gly Gly
1               5

<210> SEQ ID NO 11
<211> LENGTH: 6
<212> TYPE: PRT
<213> ORGANISM: Homo Sapiens

<400> SEQUENCE: 11

Cys His Asp Ser Gly Gly
1               5

<210> SEQ ID NO 12
<211> LENGTH: 6
<212> TYPE: PRT
<213> ORGANISM: Homo Sapiens

<400> SEQUENCE: 12

Cys Gly His Asp Ser Gly
1               5

<210> SEQ ID NO 13
<211> LENGTH: 10
<212> TYPE: PRT
<213> ORGANISM: Homo Sapiens

<400> SEQUENCE: 13

His Gln Lys Leu Val Phe Phe Ala Glu Asp
1               5                   10

<210> SEQ ID NO 14
<211> LENGTH: 16
<212> TYPE: PRT
<213> ORGANISM: Homo Sapiens

<400> SEQUENCE: 14

His His Gln Lys Leu Val Phe Phe Ala Glu Asp Val Gly Ser Asn Lys
1               5                   10                  15

<210> SEQ ID NO 15
<211> LENGTH: 5
<212> TYPE: PRT
<213> ORGANISM: Homo Sapiens

<400> SEQUENCE: 15

His Gln Lys Leu Val
1               5

<210> SEQ ID NO 16
<211> LENGTH: 6
<212> TYPE: PRT
<213> ORGANISM: Homo Sapiens

<400> SEQUENCE: 16

His His Gln Lys Leu Val
1               5

<210> SEQ ID NO 17
<211> LENGTH: 6
<212> TYPE: PRT

<213> ORGANISM: Homo Sapiens

<400> SEQUENCE: 17

His Gln Lys Leu Val Phe
1 5

<210> SEQ ID NO 18
<211> LENGTH: 7
<212> TYPE: PRT
<213> ORGANISM: Homo Sapiens

<400> SEQUENCE: 18

His Gln Lys Leu Val Phe Phe
1 5

<210> SEQ ID NO 19
<211> LENGTH: 42
<212> TYPE: PRT
<213> ORGANISM: Homo Sapiens

<400> SEQUENCE: 19

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly Val Val Ile Ala
35 40

<210> SEQ ID NO 20
<211> LENGTH: 8
<212> TYPE: PRT
<213> ORGANISM: Mus Musculus

<400> SEQUENCE: 20

Gly Tyr Ser Phe Thr Ser Tyr Trp
1 5

<210> SEQ ID NO 21
<211> LENGTH: 9
<212> TYPE: PRT
<213> ORGANISM: Mus Musculus

<400> SEQUENCE: 21

Val His Pro Gly Arg Gly Val Ser Thr
1 5

<210> SEQ ID NO 22
<211> LENGTH: 13
<212> TYPE: PRT
<213> ORGANISM: Mus Musculus

<400> SEQUENCE: 22

Ser Arg Ser His Gly Asn Thr Tyr Trp Phe Phe Asp Val
1 5 10

<210> SEQ ID NO 23
<211> LENGTH: 11
<212> TYPE: PRT
<213> ORGANISM: Mus Musculus

<400> SEQUENCE: 23

Gln Ser Ile Val His Ser Asn Gly Asn Thr Tyr
1 5 10

<210> SEQ ID NO 24
<211> LENGTH: 3
<212> TYPE: PRT
<213> ORGANISM: Mus Musculus

<400> SEQUENCE: 24

Lys Val Ser
1

<210> SEQ ID NO 25
<211> LENGTH: 9
<212> TYPE: PRT
<213> ORGANISM: Mus Musculus

<400> SEQUENCE: 25

Phe Gln Gly Ser His Val Pro Phe Thr
1               5

<210> SEQ ID NO 26
<211> LENGTH: 8
<212> TYPE: PRT
<213> ORGANISM: Mus Musculus

<400> SEQUENCE: 26

Gly Phe Thr Phe Ser Asp Tyr Tyr
1               5

<210> SEQ ID NO 27
<211> LENGTH: 8
<212> TYPE: PRT
<213> ORGANISM: Mus Musculus

<400> SEQUENCE: 27

Ile Ser Asp Gly Gly Ser Tyr Thr
1               5

<210> SEQ ID NO 28
<211> LENGTH: 16
<212> TYPE: PRT
<213> ORGANISM: Mus Musculus

<400> SEQUENCE: 28

Ala Arg Asp Tyr Tyr Gly Ser Ser Ser Tyr Thr Ser Gly Phe Ala Tyr
1               5                   10                  15

<210> SEQ ID NO 29
<211> LENGTH: 12
<212> TYPE: PRT
<213> ORGANISM: Mus Musculus

<400> SEQUENCE: 29

Gln Ser Leu Leu Asn Ser Arg Thr Arg Lys Asn Tyr
1               5                   10

<210> SEQ ID NO 30
<211> LENGTH: 3
<212> TYPE: PRT
<213> ORGANISM: Mus Musculus

<400> SEQUENCE: 30

Trp Ala Ser
1

<210> SEQ ID NO 31

-continued

<211> LENGTH: 8
<212> TYPE: PRT
<213> ORGANISM: Mus Musculus

<400> SEQUENCE: 31

Lys Gln Ser Tyr Asn Leu Tyr Thr
1 5

<210> SEQ ID NO 32
<211> LENGTH: 8
<212> TYPE: PRT
<213> ORGANISM: Mus Musculus

<400> SEQUENCE: 32

Gly Phe Thr Phe Ser Asp Tyr Tyr
1 5

<210> SEQ ID NO 33
<211> LENGTH: 8
<212> TYPE: PRT
<213> ORGANISM: Mus Musculus

<400> SEQUENCE: 33

Ile Ser Asp Gly Gly Ser Tyr Thr
1 5

<210> SEQ ID NO 34
<211> LENGTH: 16
<212> TYPE: PRT
<213> ORGANISM: Mus Musculus

<400> SEQUENCE: 34

Ala Arg Asp Tyr Tyr Gly Ser Asn Ser Tyr Thr Ser Gly Phe Ala Tyr
1 5 10 15

<210> SEQ ID NO 35
<211> LENGTH: 12
<212> TYPE: PRT
<213> ORGANISM: Mus Musculus

<400> SEQUENCE: 35

Gln Ser Leu Leu Asn Ser Arg Thr Arg Lys Asn Tyr
1 5 10

<210> SEQ ID NO 36
<211> LENGTH: 3
<212> TYPE: PRT
<213> ORGANISM: Mus Musculus

<400> SEQUENCE: 36

Trp Ala Ser
1

<210> SEQ ID NO 37
<211> LENGTH: 8
<212> TYPE: PRT
<213> ORGANISM: Mus Musculus

<400> SEQUENCE: 37

Lys Gln Ser Tyr Asn Leu Tyr Thr
1 5

<210> SEQ ID NO 38
<211> LENGTH: 11
<212> TYPE: PRT

<213> ORGANISM: Mus Musculus

<400> SEQUENCE: 38

Gln Ser Ile Val His Ser Asn Gly Asn Thr Tyr
1 5 10

<210> SEQ ID NO 39
<211> LENGTH: 3
<212> TYPE: PRT
<213> ORGANISM: Mus Musculus

<400> SEQUENCE: 39

Lys Val Ser
1

<210> SEQ ID NO 40
<211> LENGTH: 9
<212> TYPE: PRT
<213> ORGANISM: Mus Musculus

<400> SEQUENCE: 40

Phe Gln Gly Ser His Val Pro Leu Thr
1 5

<210> SEQ ID NO 41
<211> LENGTH: 8
<212> TYPE: PRT
<213> ORGANISM: Mus Musculus

<400> SEQUENCE: 41

Gly Tyr Thr Phe Thr Asp Tyr Glu
1 5

<210> SEQ ID NO 42
<211> LENGTH: 8
<212> TYPE: PRT
<213> ORGANISM: Mus Musculus

<400> SEQUENCE: 42

Ile Asp Pro Glu Thr Gly Asp Thr
1 5

<210> SEQ ID NO 43
<211> LENGTH: 13
<212> TYPE: PRT
<213> ORGANISM: Mus Musculus

<400> SEQUENCE: 43

Thr Ser Pro Ile Tyr Tyr Asp Tyr Asp Trp Phe Ala Tyr
1 5 10

<210> SEQ ID NO 44
<211> LENGTH: 12
<212> TYPE: PRT
<213> ORGANISM: Mus Musculus

<400> SEQUENCE: 44

Gln Ser Leu Leu Asn Asn Arg Thr Arg Lys Asn Tyr
1 5 10

<210> SEQ ID NO 45
<211> LENGTH: 3
<212> TYPE: PRT
<213> ORGANISM: Mus Musculus

<400> SEQUENCE: 45

Trp Ala Ser
1

<210> SEQ ID NO 46
<211> LENGTH: 8
<212> TYPE: PRT
<213> ORGANISM: Mus Musculus

<400> SEQUENCE: 46

Lys Gln Ser Tyr Asn Leu Arg Thr
1               5

<210> SEQ ID NO 47
<211> LENGTH: 10
<212> TYPE: PRT
<213> ORGANISM: Mus Musculus

<400> SEQUENCE: 47

Gly Phe Ser Leu Ser Thr Ser Gly Met Gly
1               5                   10

<210> SEQ ID NO 48
<211> LENGTH: 7
<212> TYPE: PRT
<213> ORGANISM: Mus Musculus

<400> SEQUENCE: 48

Ile Trp Trp Asp Asp Asp Lys
1               5

<210> SEQ ID NO 49
<211> LENGTH: 14
<212> TYPE: PRT
<213> ORGANISM: Mus Musculus

<400> SEQUENCE: 49

Ala Arg Ser Ile Thr Thr Val Val Ala Thr Pro Phe Asp Tyr
1               5                   10

<210> SEQ ID NO 50
<211> LENGTH: 6
<212> TYPE: PRT
<213> ORGANISM: Mus Musculus

<400> SEQUENCE: 50

Gln Asn Val Arg Ser Ala
1               5

<210> SEQ ID NO 51
<211> LENGTH: 3
<212> TYPE: PRT
<213> ORGANISM: Mus Musculus

<400> SEQUENCE: 51

Leu Ala Ser
1

<210> SEQ ID NO 52
<211> LENGTH: 9
<212> TYPE: PRT
<213> ORGANISM: Mus Musculus

<400> SEQUENCE: 52

Leu Gln His Trp Asn Ser Pro Phe Thr
1               5

<210> SEQ ID NO 53
<211> LENGTH: 8
<212> TYPE: PRT
<213> ORGANISM: Mus Musculus

<400> SEQUENCE: 53

Gly Tyr Thr Phe Thr Ser Tyr Trp
1               5

<210> SEQ ID NO 54
<211> LENGTH: 8
<212> TYPE: PRT
<213> ORGANISM: Mus Musculus

<400> SEQUENCE: 54

Ile Asp Pro Ser Asp Ser Gln Thr
1               5

<210> SEQ ID NO 55
<211> LENGTH: 5
<212> TYPE: PRT
<213> ORGANISM: Mus Musculus

<400> SEQUENCE: 55

Ser Arg Gly Gly Tyr
1               5

<210> SEQ ID NO 56
<211> LENGTH: 6
<212> TYPE: PRT
<213> ORGANISM: Mus Musculus

<400> SEQUENCE: 56

Gln Asp Ile Asn Asn Tyr
1               5

<210> SEQ ID NO 57
<211> LENGTH: 3
<212> TYPE: PRT
<213> ORGANISM: Mus Musculus

<400> SEQUENCE: 57

Tyr Thr Ser
1

<210> SEQ ID NO 58
<211> LENGTH: 8
<212> TYPE: PRT
<213> ORGANISM: Mus Musculus

<400> SEQUENCE: 58

Leu Gln Tyr Asp Asn Leu Trp Thr
1               5

<210> SEQ ID NO 59
<211> LENGTH: 8
<212> TYPE: PRT
<213> ORGANISM: Mus Musculus

<400> SEQUENCE: 59

Gly Tyr Thr Phe Thr Ser Tyr Trp
1               5

<210> SEQ ID NO 60
<211> LENGTH: 8
<212> TYPE: PRT
<213> ORGANISM: Mus Musculus

<400> SEQUENCE: 60

Ile Asp Pro Ser Asp Ser Glu Thr
1 5

<210> SEQ ID NO 61
<211> LENGTH: 5
<212> TYPE: PRT
<213> ORGANISM: Mus Musculus

<400> SEQUENCE: 61

Thr Arg Gly Thr Tyr
1 5

<210> SEQ ID NO 62
<211> LENGTH: 10
<212> TYPE: PRT
<213> ORGANISM: Mus Musculus

<400> SEQUENCE: 62

Gln Ser Val Ser Thr Ser Ser Tyr Ser Tyr
1 5 10

<210> SEQ ID NO 63
<211> LENGTH: 3
<212> TYPE: PRT
<213> ORGANISM: Mus Musculus

<400> SEQUENCE: 63

Tyr Ala Ser
1

<210> SEQ ID NO 64
<211> LENGTH: 9
<212> TYPE: PRT
<213> ORGANISM: Mus Musculus

<400> SEQUENCE: 64

Gln His Ser Leu Glu Ile Pro Trp Thr
1 5

<210> SEQ ID NO 65
<211> LENGTH: 7
<212> TYPE: PRT
<213> ORGANISM: Mus Musculus

<400> SEQUENCE: 65

Ser Ser Val Ser Ser Ala Tyr
1 5

<210> SEQ ID NO 66
<211> LENGTH: 3
<212> TYPE: PRT
<213> ORGANISM: Mus Musculus

<400> SEQUENCE: 66

Ser Thr Ser
1

<210> SEQ ID NO 67
<211> LENGTH: 9
<212> TYPE: PRT
<213> ORGANISM: Mus Musculus

<400> SEQUENCE: 67

His Gln Tyr His Arg Ser Pro Phe Thr
1 5

<210> SEQ ID NO 68
<211> LENGTH: 11
<212> TYPE: PRT
<213> ORGANISM: Mus Musculus

<400> SEQUENCE: 68

Ser Gln Asp Ile Asn Lys Tyr Ile Ala Trp Tyr
1 5 10

<210> SEQ ID NO 69
<211> LENGTH: 3
<212> TYPE: PRT
<213> ORGANISM: Mus Musculus

<400> SEQUENCE: 69

Asn Thr Ser
1

<210> SEQ ID NO 70
<211> LENGTH: 8
<212> TYPE: PRT
<213> ORGANISM: Mus Musculus

<400> SEQUENCE: 70

Leu Gln His Asp Asn Leu Trp Thr
1 5

<210> SEQ ID NO 71
<211> LENGTH: 8
<212> TYPE: PRT
<213> ORGANISM: Mus Musculus

<400> SEQUENCE: 71

Gly Tyr Thr Phe Thr Ser Tyr Trp
1 5

<210> SEQ ID NO 72
<211> LENGTH: 8
<212> TYPE: PRT
<213> ORGANISM: Mus Musculus

<400> SEQUENCE: 72

Ile Asp Pro Ser Asp Ser Glu Thr
1 5

<210> SEQ ID NO 73
<211> LENGTH: 5
<212> TYPE: PRT
<213> ORGANISM: Mus Musculus

<400> SEQUENCE: 73

Thr Arg Gly Thr Tyr
1 5

<210> SEQ ID NO 74
<211> LENGTH: 10

<212> TYPE: PRT
<213> ORGANISM: Mus Musculus

<400> SEQUENCE: 74

Gln Ser Val Ser Thr Ser Ser Tyr Ser Tyr
1               5                   10

<210> SEQ ID NO 75
<211> LENGTH: 3
<212> TYPE: PRT
<213> ORGANISM: Mus Musculus

<400> SEQUENCE: 75

Tyr Ala Ser
1

<210> SEQ ID NO 76
<211> LENGTH: 9
<212> TYPE: PRT
<213> ORGANISM: Mus Musculus

<400> SEQUENCE: 76

Gln His Ser Leu Glu Ile Pro Trp Thr
1               5

<210> SEQ ID NO 77
<211> LENGTH: 7
<212> TYPE: PRT
<213> ORGANISM: Mus Musculus

<400> SEQUENCE: 77

Ser Ser Val Ser Ser Ala Tyr
1               5

<210> SEQ ID NO 78
<211> LENGTH: 3
<212> TYPE: PRT
<213> ORGANISM: Mus Musculus

<400> SEQUENCE: 78

Ser Thr Ser
1

<210> SEQ ID NO 79
<211> LENGTH: 9
<212> TYPE: PRT
<213> ORGANISM: Mus Musculus

<400> SEQUENCE: 79

His Gln Tyr His Arg Ser Pro Phe Thr
1               5

<210> SEQ ID NO 80
<211> LENGTH: 11
<212> TYPE: PRT
<213> ORGANISM: Mus Musculus

<400> SEQUENCE: 80

Ser Gln Asp Ile Asn Lys Tyr Ile Ala Trp Tyr
1               5                   10

<210> SEQ ID NO 81
<211> LENGTH: 3
<212> TYPE: PRT
<213> ORGANISM: Mus Musculus

<400> SEQUENCE: 81

Asn Thr Ser
1

<210> SEQ ID NO 82
<211> LENGTH: 8
<212> TYPE: PRT
<213> ORGANISM: Mus Musculus

<400> SEQUENCE: 82

Leu Gln His Asp Asn Leu Trp Thr
1               5

<210> SEQ ID NO 83
<211> LENGTH: 438
<212> TYPE: DNA
<213> ORGANISM: Mus Musculus

<400> SEQUENCE: 83
atgggatgga gctgtatcat cctctttttg gtagcaacag ctacaggtgt ccactcccag     60
gtccaactgc agcagcctgg ggctgagctt gtgaagcctg gggcttcagt gaaaatgtcc    120
tgcaaggctt ctggctacag cttcaccagc tactggataa actgggtgaa gcagaggcct    180
ggacaaggcc ttgagtggat tggagatgtt catcctggta gaggtgtttc tacctacaat    240
gcgaagttca agagcaaggc cacactgact ctagacacgt cctccagcac agcctacatg    300
cagctcagca gcctgacatc tgaggactct gcggtctatt attgttcaag atcccacggt    360
aatacctact ggttcttcga tgtctggggc gcagggacca cggtcaccgt ctcctcagct    420
acaacaacag ccccatct                                                  438

<210> SEQ ID NO 84
<211> LENGTH: 146
<212> TYPE: PRT
<213> ORGANISM: Mus Musculus

<400> SEQUENCE: 84

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Ser Phe
        35                  40                  45

Thr Ser Tyr Trp Ile Asn Trp Val Lys Gln Arg Pro Gly Gln Gly Leu
    50                  55                  60

Glu Trp Ile Gly Asp Val His Pro Gly Arg Gly Val Ser Thr Tyr Asn
65                  70                  75                  80

Ala Lys Phe Lys Ser Lys Ala Thr Leu Thr Leu Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ser Arg Ser His Gly Asn Thr Tyr Trp Phe Phe Asp Val
        115                 120                 125

Trp Gly Ala Gly Thr Thr Val Thr Val Ser Ser Ala Thr Thr Thr Ala
    130                 135                 140

Pro Ser
145

<210> SEQ ID NO 85
<211> LENGTH: 405
<212> TYPE: DNA
<213> ORGANISM: Mus Musculus

<400> SEQUENCE: 85
atgaagttgc ctgttaggct gttggtgctg atgttctgga ttcctgcttc cagcagtgat 60
gttttgatga cccaaactcc actctccctg cctgtcagtc ttggagatca agcctccatc 120
tcttgcagat ctagtcagag cattgtacat agtaatggaa acacctattt agaatggtac 180
ctgcagaaac caggccagtc tccaaagctc ctgatctaca aagtttccaa ccgattttct 240
ggggtcccag acaggttcag tggcagtgga tcagggacag atttcacact caagatcagc 300
agagtggagg ctgaggatct gggagtttat tactgctttc aaggttcaca tgttccattc 360
acgttcggct cggggacaaa gttggaaata aaacgggctg atgct 405

<210> SEQ ID NO 86
<211> LENGTH: 135
<212> TYPE: PRT
<213> ORGANISM: Mus Musculus

<400> SEQUENCE: 86

Met Lys Leu Pro Val Arg Leu Leu Val Leu Met Phe Trp Ile Pro Ala
1 5 10 15

Ser Ser Ser Asp Val Leu Met Thr Gln Thr Pro Leu Ser Leu Pro Val
20 25 30

Ser Leu Gly Asp Gln Ala Ser Ile Ser Cys Arg Ser Ser Gln Ser Ile
35 40 45

Val His Ser Asn Gly Asn Thr Tyr Leu Glu Trp Tyr Leu Gln Lys Pro
50 55 60

Gly Gln Ser Pro Lys Leu Leu Ile Tyr Lys Val Ser Asn Arg Phe Ser
65 70 75 80

Gly Val Pro Asp Arg Phe Ser Gly Ser Gly Ser Gly Thr Asp Phe Thr
85 90 95

Leu Lys Ile Ser Arg Val Glu Ala Glu Asp Leu Gly Val Tyr Tyr Cys
100 105 110

Phe Gln Gly Ser His Val Pro Phe Thr Phe Gly Ser Gly Thr Lys Leu
115 120 125

Glu Ile Lys Arg Ala Asp Ala
130 135

<210> SEQ ID NO 87
<211> LENGTH: 426
<212> TYPE: DNA
<213> ORGANISM: Mus Musculus

<400> SEQUENCE: 87
atgaactttg ggctcagctt gattttcctt gtccttgttt taaaaggtgt ccagtgtgaa 60
gtgcagctgg tggagtctgg gggaggctta gtgaagcctg gagggtccct gaaactctcc 120
tgtgcagcct ctggattcac tttcagtgac tattacatgt attgggttcg ccagactccg 180
gaaaagaggc tggagtgggt cgcaaccatt agtgatggtg gtagttacac ctcctatcca 240
gacagtgtga agggacgatt caccatctcc agagacaatg ccaagaacaa cctgtacctg 300
caaatgagca gtctgaggtc tgaggacaca gccatgtatt actgtgcaag agattactac 360
ggtagtagta gctacacctc gggctttgct tactggggcc aagggactct ggtcactgtc 420

```
tctgca                                                                426

<210> SEQ ID NO 88
<211> LENGTH: 142
<212> TYPE: PRT
<213> ORGANISM: Mus Musculus

<400> SEQUENCE: 88

Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Asp Gly Gly Ser Tyr Thr Ser Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Arg Ser Glu Asp Thr Ala Met
            100                 105                 110

Tyr Tyr Cys Ala Arg Asp Tyr Tyr Gly Ser Ser Ser Tyr Thr Ser Gly
        115                 120                 125

Phe Ala Tyr Trp Gly Gln Gly Thr Leu Val Thr Val Ser Ala
    130                 135                 140

<210> SEQ ID NO 89
<211> LENGTH: 396
<212> TYPE: DNA
<213> ORGANISM: Mus Musculus

<400> SEQUENCE: 89

atggattcac aggcccaggt tcttatattg ctgctgctat gggtatctgg tacctgtggg     60

gacattgtga tgtcacagtc tccatcctcc ctggctgtgt caacaggaga gaaggtcact    120

atgagctgca aatccagtca gagtctgctc aacagtagaa cccgaaagaa ctacttggct    180

tggtaccagc agaaaccagg gcagtctcct aaactgctga tctactgggc atccactagg    240

gaatctgggg tccctgatcg cttcacaggc agtggatctg ggacagattt cactctcacc    300

atcagcagtg tgcaggctga agacctggca gtttattact gcaagcaatc ttataatctg    360

tacacgttcg gaggggggac caagctggaa ataaaa                              396

<210> SEQ ID NO 90
<211> LENGTH: 132
<212> TYPE: PRT
<213> ORGANISM: Mus Musculus

<400> SEQUENCE: 90

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Thr Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60
```

```
Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
        115                 120                 125

Leu Glu Ile Lys
    130


<210> SEQ ID NO 91
<211> LENGTH: 426
<212> TYPE: DNA
<213> ORGANISM: Mus Musculus

<400> SEQUENCE: 91

atgaacttcg ggctcagctt gattttcctt gtccttgttt taaaaggtgt ccagtgtgaa      60

gtgcagctgg tggagtctgg gggaggctta gtgaagcctg gagggtccct gaaactctcc     120

tgtgcagcct ctggattcac tttcagtgac tattacatgt attgggttcg ccagactccg     180

gaaaagaggc tggagtgggt cgcaaccatt agtgatggtg gtagttacac ctcctatcca     240

gacagtgtga aggggcgatt caccatctcc agagacagtg ccaagaacaa cctgtacctg     300

caaatgagca gtctgaagtc tgaggacaca gccatgtatt actgtgcaag agattactac     360

ggtagtaata gttacacctc gggctttgct tactggggcc aagggactct ggtcactgtc     420

tctgca                                                                426


<210> SEQ ID NO 92
<211> LENGTH: 142
<212> TYPE: PRT
<213> ORGANISM: Mus Musculus

<400> SEQUENCE: 92

Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Asp Gly Gly Ser Tyr Thr Ser Tyr Pro
65                  70                  75                  80

Asp Ser Val Lys Gly Arg Phe Thr Ile Ser Arg Asp Ser Ala Lys Asn
                85                  90                  95

Asn Leu Tyr Leu Gln Met Ser Ser Leu Lys Ser Glu Asp Thr Ala Met
            100                 105                 110

Tyr Tyr Cys Ala Arg Asp Tyr Tyr Gly Ser Asn Ser Tyr Thr Ser Gly
        115                 120                 125

Phe Ala Tyr Trp Gly Gln Gly Thr Leu Val Thr Val Ser Ala
    130                 135                 140


<210> SEQ ID NO 93
<211> LENGTH: 396
<212> TYPE: DNA
<213> ORGANISM: Mus Musculus
```

<400> SEQUENCE: 93
atggattcac aggcccaggt tcttatattg ctgctgctat gggtatctgg tacctgtggg 60
gacattgtga tgtcacagtc tccatcctcc ctggctgtgt cagcaggaga gaaggtcact 120
atgagctgca aatccagtca gagtctgctc aatagtagaa cccgaaagaa ctacttggct 180
tggtaccagc agaaaccagg gcagtctcct aaactgctga tctactgggc atccactagg 240
gaatctgggg tccctgatcg cttcacaggc agtggatctg ggacagattt cactctcacc 300
atcagcagtg tgcaggctga agacctggca gtttattact gcaagcaatc ttataatctg 360
tacacgttcg gaggggggac caagctggaa ataaaa 396

<210> SEQ ID NO 94
<211> LENGTH: 132
<212> TYPE: PRT
<213> ORGANISM: Mus Musculus

<400> SEQUENCE: 94

Met Asp Ser Gln Ala Gln Val Leu Ile Leu Leu Leu Leu Trp Val Ser
1 5 10 15

Gly Thr Cys Gly Asp Ile Val Met Ser Gln Ser Pro Ser Ser Leu Ala
20 25 30

Val Ser Ala Gly Glu Lys Val Thr Met Ser Cys Lys Ser Ser Gln Ser
35 40 45

Leu Leu Asn Ser Arg Thr Arg Lys Asn Tyr Leu Ala Trp Tyr Gln Gln
50 55 60

Lys Pro Gly Gln Ser Pro Lys Leu Leu Ile Tyr Trp Ala Ser Thr Arg
65 70 75 80

Glu Ser Gly Val Pro Asp Arg Phe Thr Gly Ser Gly Ser Gly Thr Asp
85 90 95

Phe Thr Leu Thr Ile Ser Ser Val Gln Ala Glu Asp Leu Ala Val Tyr
100 105 110

Tyr Cys Lys Gln Ser Tyr Asn Leu Tyr Thr Phe Gly Gly Gly Thr Lys
115 120 125

Leu Glu Ile Lys
130

<210> SEQ ID NO 95
<211> LENGTH: 393
<212> TYPE: DNA
<213> ORGANISM: Mus Musculus

<400> SEQUENCE: 95
atgaagttgc ctgttaggct gttggtgctg atgttctgga ttcctgcttc cagcagtgat 60
gttttgatga cccaaactcc actctccctg cctgtcagtc ttggagatca agcctccatc 120
tcttgcagat ctagtcagag cattgtacat agtaatggaa acacctattt agaatggtac 180
ctgcagaaac caggccagtc tccaaagctc ctgatctaca aagtttccaa ccgattttct 240
ggggtcccag acaggttcag tggcagtgga tcagggacag atttcacact caagatcagc 300
agagtggagg ctgaggatct gggagtttat ttctgctttc aaggttcaca tgttcctctc 360
acgttcggtg ctgggaccaa gctggagctg aaa 393

<210> SEQ ID NO 96
<211> LENGTH: 131
<212> TYPE: PRT
<213> ORGANISM: Mus Musculus

<400> SEQUENCE: 96

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Phe Gln Gly Ser His Val Pro Leu Thr Phe Gly Ala Gly Thr Lys Leu
        115                 120                 125

Glu Leu Lys
    130

<210> SEQ ID NO 97
<211> LENGTH: 438
<212> TYPE: DNA
<213> ORGANISM: Mus Musculus

<400> SEQUENCE: 97
atggaatgga gctgggtctt tctcttcctc ctgtcagtaa ttgcaggtgt ccaatcccag 60
gttcaactgc agcagtctgg ggctgagctg gtgaggcctg gggcttcagt gacgctgtcc 120
tgcaaggctt cgggctacac atttactgac tatgaaatgc actgggtgaa gcagacacct 180
gtgcatggcc tggaatggat tggagctatt gatcctgaaa ctggtgatac tgcctacaat 240
caggagttca agggcaaggc cacactgact gcagacaaat cctccagcac agcctacatg 300
gagctccgca gcctgacatc tgaggactct gccgtctatt actgtacaag ccccatctac 360
tatgattacg actggtttgc ttactggggc cacgggactc tggtcactgt ctctgcagct 420
acaacaacag ccccatct 438

<210> SEQ ID NO 98
<211> LENGTH: 146
<212> TYPE: PRT
<213> ORGANISM: Mus Musculus

<400> SEQUENCE: 98

Met Glu Trp Ser Trp Val Phe Leu Phe Leu Leu Ser Val Ile Ala Gly
1               5                   10                  15

Val Gln Ser Gln Val Gln Leu Gln Gln Ser Gly Ala Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Asp Thr Ala Tyr Asn
65                  70                  75                  80

Gln Glu Phe Lys Gly Lys Ala Thr Leu Thr Ala Asp Lys Ser Ser Ser
                85                  90                  95

-continued

```
Thr Ala Tyr Met Glu Leu Arg Ser Leu Thr Ser Glu Asp Ser Ala Val
            100                 105                 110

Tyr Tyr Cys Thr Ser Pro Ile Tyr Tyr Asp Tyr Asp Trp Phe Ala Tyr
        115                 120                 125

Trp Gly His Gly Thr Leu Val Thr Val Ser Ala Ala Thr Thr Thr Ala
    130                 135                 140

Pro Ser
145
```

```
<210> SEQ ID NO 99
<211> LENGTH: 408
<212> TYPE: DNA
<213> ORGANISM: Mus Musculus

<400> SEQUENCE: 99

atggattcac aggcccaggt tcttatattg ctgctgctat gggtatctgg tacctgtggg      60

gacattgtga tgtcacagtc tccatcctcc ctggctgtgt cagcaggaga gaaggtcact     120

atgagctgca aatccagtca gagtctgctc aacaatagaa cccgaaagaa ctacttggct     180

tggtaccagc agaaaccagg gcagtctcct aaactgctga tctactgggc atccactagg     240

gaatctgggg tccctgatcg cttcacaggc agtggatctg ggacagattt cactctcacc     300

atcagcagtg tgcaggctga agacctggca gtttattact gcaagcaatc ttataatctt     360

cggacgttcg gtggaggcac caagctggaa atcaaacggg ctgatgct                  408
```

```
<210> SEQ ID NO 100
<211> LENGTH: 136
<212> TYPE: PRT
<213> ORGANISM: Mus Musculus

<400> SEQUENCE: 100

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Asn Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Lys Arg Ala Asp Ala
    130                 135
```

```
<210> SEQ ID NO 101
<211> LENGTH: 436
<212> TYPE: DNA
<213> ORGANISM: Mus Musculus

<400> SEQUENCE: 101

atggacaggc ttacttcttc attcctgctg ctgattgtcc ctgcatatgt cttgtcccaa      60
```

```
gttactctaa aagagtctgg ccctgggata ttgaagccct cacagaccct cagtctgact    120

tgttctttct ctgggttttc actgagcact tctggtatgg gtgtaggctg gattcgtcag    180

ccttcaggga agggtctgga gtggctggca cacatttggt gggatgatga taagtactat    240

aacccatccc tgaagagcca gctcacaatc tccaaggata cctccagaaa ccaggtattc    300

ctcaagatca ccagtgtgga cactgcagat actgccactt actactgtgc tcgaagtatt    360

actacggtag tagctacgcc ctttgactac tggggccaag gcaccactct cacagtctcc    420

tcagccaaaa cgacac                                                    436
```

<210> SEQ ID NO 102
<211> LENGTH: 145
<212> TYPE: PRT
<213> ORGANISM: Mus Musculus

<400> SEQUENCE: 102

```
Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Ser Ile Thr Thr Val Val Ala Thr Pro Phe
        115                 120                 125

Asp Tyr Trp Gly Gln Gly Thr Thr Leu Thr Val Ser Ser Ala Lys Thr
    130                 135                 140

Thr
145
```

<210> SEQ ID NO 103
<211> LENGTH: 405
<212> TYPE: DNA
<213> ORGANISM: Mus Musculus

<400> SEQUENCE: 103

```
atgggcatca agatggagtt tcagacccag gtctttgtat tcgtgttgct ctggttgtct     60

ggtgttgatg gagacattgt gatgacccag tctcaaaaat tcatgtccac atcagtagga    120

gacagggtca gcatcacctg caaggccagt cagaatgttc gttctgctgt agcctggtat    180

caacagaaac cagggcagtc tcctaaagca ctgatttacc tggcatccaa ccggcacact    240

ggagtccctg atcgcttcac aggcagtgga tctgggacag atttcactct caccattagc    300

aatgtgcatt ctgaagacct gacagattat ttctgtctgc aacattggaa ttctccgttc    360

acgttcggag gggggaccaa gctggaaata aaacgggctg atgct                    405
```

<210> SEQ ID NO 104
<211> LENGTH: 135
<212> TYPE: PRT

<213> ORGANISM: Mus Musculus

<400> SEQUENCE: 104

```
Met Gly Ile Lys Met Glu Phe Gln Thr Gln Val Phe Val Phe Val Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Ile Thr Cys Lys
        35                  40                  45

Ala Ser Gln Asn Val Arg Ser Ala Val Ala Trp Tyr Gln Gln Lys Pro
    50                  55                  60

Gly Gln Ser Pro Lys Ala Leu Ile Tyr Leu Ala Ser Asn Arg His Thr
65                  70                  75                  80

Gly Val Pro Asp Arg Phe Thr Gly Ser Gly Ser Gly Thr Asp Phe Thr
                85                  90                  95

Leu Thr Ile Ser Asn Val His Ser Glu Asp Leu Thr Asp Tyr Phe Cys
            100                 105                 110

Leu Gln His Trp Asn Ser Pro Phe Thr Phe Gly Gly Gly Thr Lys Leu
        115                 120                 125

Glu Ile Lys Arg Ala Asp Ala
    130                 135
```

<210> SEQ ID NO 105
<211> LENGTH: 393
<212> TYPE: DNA
<213> ORGANISM: Mus Musculus

<400> SEQUENCE: 105

```
atgggatgga gctgtatcat cctcttcttg gtagcaacag ctacaggtgt ccactcccag      60

gtccaactgc agcagcctgg ggctgagctg gtgaggcctg gggcttcagt gaagctgtcc     120

tgcaaggctt ctggctacac cttcaccagc tactggatga actgggtgaa gcagaggcct     180

ggacaaggcc ttgaatggat tggtatgatt gatccttcag acagtcaaac tcactacaat     240

caaatgttca aggacaaggc cacattgact gtagacaaat cctccagcac agcctacctg     300

cagctcagca gcctgacatc tgaggactct gcggtctatt actgttcaag agggggctac     360

tggggccaag gcaccactct cacagtctcc tca                                  393
```

<210> SEQ ID NO 106
<211> LENGTH: 131
<212> TYPE: PRT
<213> ORGANISM: Mus Musculus

<400> SEQUENCE: 106

```
Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Met Asn Trp Val Lys Gln Arg Pro Gly Gln Gly Leu
    50                  55                  60

Glu Trp Ile Gly Met Ile Asp Pro Ser Asp Ser Gln Thr His Tyr Asn
65                  70                  75                  80

Gln Met Phe Lys Asp Lys Ala Thr Leu Thr Val Asp Lys Ser Ser Ser
                85                  90                  95
```

```
Thr Ala Tyr Leu Gln Leu Ser Ser Leu Thr Ser Glu Asp Ser Ala Val
            100                 105                 110

Tyr Tyr Cys Ser Arg Gly Gly Tyr Trp Gly Gln Gly Thr Thr Leu Thr
        115                 120                 125

Val Ser Ser
    130


<210> SEQ ID NO 107
<211> LENGTH: 378
<212> TYPE: DNA
<213> ORGANISM: Mus Musculus

<400> SEQUENCE: 107

atgagaccgt ctattcagtt cctggggctc ttgttgttct ggcttcatgg tgctcagtgt      60

gacatccaga tgacacagtc tccatcctca ctgtctgcat ctctgggagg caaagtcacc     120

atcacttgca aggcaagcca agacattaac aactatatag cttggtacca acacaagcct     180

ggaaaaggtc ctaggcagct catatattac acatctacat tgcagccagg catcccatca     240

aggttcagtg gaagtgggtc tgggagagat tattccttca ccatcagcga cctggagcct     300

gaagatattg caacttatta ttgtctacag tatgataatc tgtggacgtt cggtggaggc     360

accaagctgg aaatcaaa                                                   378


<210> SEQ ID NO 108
<211> LENGTH: 126
<212> TYPE: PRT
<213> ORGANISM: Mus Musculus

<400> SEQUENCE: 108

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Asn Tyr Ile Ala Trp Tyr Gln His Lys Pro Gly Lys Gly Pro
    50                  55                  60

Arg Gln Leu Ile Tyr Tyr Thr Ser Thr Leu Gln Pro Gly Ile Pro Ser
65                  70                  75                  80

Arg Phe Ser Gly Ser Gly Ser Gly Arg Asp Tyr Ser Phe Thr Ile Ser
                85                  90                  95

Asp Leu Glu Pro Glu Asp Ile Ala Thr Tyr Tyr Cys Leu Gln Tyr Asp
            100                 105                 110

Asn Leu Trp Thr Phe Gly Gly Gly Thr Lys Leu Glu Ile Lys
        115                 120                 125


<210> SEQ ID NO 109
<211> LENGTH: 393
<212> TYPE: DNA
<213> ORGANISM: Mus Musculus

<400> SEQUENCE: 109

atgggatgga gctgtatcat cctctttttg gtagcaacag ctacaggtgt ccactcccag      60

gtccaactgc agcagcctgg ggctgagctg gtgaggcctg ggtcttcagt gaagctgtcc     120

tgcaaggctt ctggctacac cttcaccagc tactggatga actgggtgaa gcagaggcct     180

ggacaaggcc ttgaatggat tggtatgatt gatccttcag acagtgaaac tcactacaat     240
```

caaatgttca aggacaaggc cacattgact gtagacaaat cctccagcac agcctacatg 300
cagctcagca gcctgacatc tgaggactct gcggtctatt actgtacaag agggacttac 360
tggggccaag ggactcaggt cactgtctct gca 393

<210> SEQ ID NO 110
<211> LENGTH: 131
<212> TYPE: PRT
<213> ORGANISM: Mus Musculus

<400> SEQUENCE: 110

Met Gly Trp Ser Cys Ile Ile Leu Phe Leu Val Ala Thr Ala Thr Gly
1 5 10 15

Val His Ser Gln Val Gln Leu Gln Gln Pro Gly Ala Glu Leu Val Arg
20 25 30

Pro Gly Ser Ser Val Lys Leu Ser Cys Lys Ala Ser Gly Tyr Thr Phe
35 40 45

Thr Ser Tyr Trp Met Asn Trp Val Lys Gln Arg Pro Gly Gln Gly Leu
50 55 60

Glu Trp Ile Gly Met Ile Asp Pro Ser Asp Ser Glu Thr His Tyr Asn
65 70 75 80

Gln Met Phe Lys Asp Lys Ala Thr Leu Thr Val Asp Lys Ser Ser Ser
85 90 95

Thr Ala Tyr Met Gln Leu Ser Ser Leu Thr Ser Glu Asp Ser Ala Val
100 105 110

Tyr Tyr Cys Thr Arg Gly Thr Tyr Trp Gly Gln Gly Thr Gln Val Thr
115 120 125

Val Ser Ala
130

<210> SEQ ID NO 111
<211> LENGTH: 393
<212> TYPE: DNA
<213> ORGANISM: Mus Musculus

<400> SEQUENCE: 111
atggagacag acacactcct gctatgggtg ctgctgctct gggttccagg ttccactggt 60
gacattgtgc tgacacagtc tcctgcttcc ttagctgtat ctctggggca gagggccacc 120
atctcatgca gggccagcca aagtgtcagt acatctagct atagttatat gcactggtac 180
caacagaaac caggacagcc acccaaactc ctcatcaagt atgcatccaa cctagaatct 240
ggggtccctg ccaggttcag tggcagtggg tctgggacag acttcaccct caacatccat 300
cctgtggagg aggaggatac tgcaacatat tactgtcagc acagtttgga gattccgtgg 360
acgttcggtg gaggcaccaa gctggaaatc aaa 393

<210> SEQ ID NO 112
<211> LENGTH: 131
<212> TYPE: PRT
<213> ORGANISM: Mus Musculus

<400> SEQUENCE: 112

Met Glu Thr Asp Thr Leu Leu Leu Trp Val Leu Leu Leu Trp Val Pro
1 5 10 15

Gly Ser Thr Gly Asp Ile Val Leu Thr Gln Ser Pro Ala Ser Leu Ala
20 25 30

Val Ser Leu Gly Gln Arg Ala Thr Ile Ser Cys Arg Ala Ser Gln Ser
35 40 45

```
Val Ser Thr Ser Ser Tyr Ser Tyr Met His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Thr Ala Thr Tyr Tyr Cys
            100                 105                 110

Gln His Ser Leu Glu Ile Pro Trp Thr Phe Gly Gly Gly Thr Lys Leu
        115                 120                 125

Glu Ile Lys
    130


<210> SEQ ID NO 113
<211> LENGTH: 390
<212> TYPE: DNA
<213> ORGANISM: Mus Musculus

<400> SEQUENCE: 113

atggattttc aggtgcagat tttcagcttc atgctaatca gtgcctcagt cataatgtcc      60

agaggacaaa ttgttctcac ccagtctcca gcaatcatgt ctgcatctct aggggaacgg     120

gtcaccatga cctgcactgc cagctcaagt gttagttccg cttacttgca ctggtaccag     180

cagaagccag gatcctcccc caaactctgg atttatagca catccaacct ggcttctgga     240

gtcccaactc gcttcagtgg cagtggatct gggacctctt actctctcac aatcagcagc     300

atggaggctg aagatgctgc cacttattac tgccaccagt atcatcgttc cccgttcacg     360

ttcggtgctg ggaccaagct ggagctgaaa                                      390


<210> SEQ ID NO 114
<211> LENGTH: 130
<212> TYPE: PRT
<213> ORGANISM: Mus Musculus

<400> SEQUENCE: 114

Met Asp Phe Gln Val Gln Ile Phe Ser Phe Met Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Ala Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Thr Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Phe Thr Phe Gly Ala Gly Thr Lys Leu Glu
        115                 120                 125

Leu Lys
    130


<210> SEQ ID NO 115
<211> LENGTH: 378
```

<212> TYPE: DNA
<213> ORGANISM: Mus Musculus

<400> SEQUENCE: 115
atgagaccgt ctattcagtt cctggggctc ttgttgttct ggcttcatgg tgctcagtgt 60
gacatccaga tgacacagtc tccatactca ctgtctgcat ctctgggagg caaagtcacc 120
atcacttgca aggcaagcca agacattaac aagtatatag cttggtacca acacaagcct 180
ggaaaaggtc ctaggctgct catacataac acatctacat tacagccagg catcccatca 240
aggttcagtg gaagtgggtc tgggagagat tattccttca gcatcagcaa cctggagcct 300
gaagatattg caacttatta ttgtctacag catgataatc tgtggacgtt cggtggaggc 360
accaagctgg aaatcaaa 378

<210> SEQ ID NO 116
<211> LENGTH: 126
<212> TYPE: PRT
<213> ORGANISM: Mus Musculus

<400> SEQUENCE: 116

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Tyr Ser Leu Ser
            20                  25                  30

Ala Ser Leu Gly Gly Lys Val Thr Ile Thr Cys Lys Ala Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Asn Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln His Asp
            100                 105                 110

Asn Leu Trp Thr Phe Gly Gly Gly Thr Lys Leu Glu Ile Lys
        115                 120                 125

<210> SEQ ID NO 117
<211> LENGTH: 393
<212> TYPE: DNA
<213> ORGANISM: Mus Musculus

<400> SEQUENCE: 117
atgggatgga gctgtatcat cctctttttg gtagcaacag ctacaggtgt ccactcccag 60
gtccaactgc agcagcctgg ggctgagctg gtgaggcctg ggtcttcagt gaagctgtcc 120
tgcaaggctt ctggctacac cttcaccagc tactggatga actgggtgaa gcagaggcct 180
ggacaaggcc ttgaatggat tggtatgatt gatccttcag acagtgaaac tcactacaat 240
caaatgttca aggacaaggc cacattgact gtagacaaat cctccagcac agcctacatg 300
cagctcagca gcctgacatc tgaggactct gcggtctatt actgtacaag agggacttac 360
tggggccaag ggactcaggt cactgtctct gca 393

<210> SEQ ID NO 118
<211> LENGTH: 131
<212> TYPE: PRT
<213> ORGANISM: Mus Musculus

<400> SEQUENCE: 118

Met Gly Trp Ser Cys Ile Ile Leu Phe Leu Val Ala Thr Ala Thr Gly
1 5 10 15

Val His Ser Gln Val Gln Leu Gln Gln Pro Gly Ala Glu Leu Val Arg
20 25 30

Pro Gly Ser Ser Val Lys Leu Ser Cys Lys Ala Ser Gly Tyr Thr Phe
35 40 45

Thr Ser Tyr Trp Met Asn Trp Val Lys Gln Arg Pro Gly Gln Gly Leu
50 55 60

Glu Trp Ile Gly Met Ile Asp Pro Ser Asp Ser Glu Thr His Tyr Asn
65 70 75 80

Gln Met Phe Lys Asp Lys Ala Thr Leu Thr Val Asp Lys Ser Ser Ser
85 90 95

Thr Ala Tyr Met Gln Leu Ser Ser Leu Thr Ser Glu Asp Ser Ala Val
100 105 110

Tyr Tyr Cys Thr Arg Gly Thr Tyr Trp Gly Gln Gly Thr Gln Val Thr
115 120 125

Val Ser Ala
130

<210> SEQ ID NO 119
<211> LENGTH: 393
<212> TYPE: DNA
<213> ORGANISM: Mus Musculus

<400> SEQUENCE: 119
atggagacag acacactcct gctatgggtg ctgctgctct gggttccagg ttccactggt 60
gacattgtgc tgacacagtc tcctgcttcc ttagctgtat ctctggggca gagggccacc 120
atctcatgca gggccagcca aagtgtcagt acatctagct atagttatat gcactggtac 180
caacagaaac caggacagcc acccaaactc ctcatcaagt atgcatccaa cctagaatct 240
ggggtccctg ccaggttcag tggcagtggg tctgggacag acttcaccct caacatccat 300
cctgtggagg aggaggatac tgcaacatat tactgtcagc acagtttgga gattccgtgg 360
acgttcggtg gaggcaccaa gctggaaatc aaa 393

<210> SEQ ID NO 120
<211> LENGTH: 131
<212> TYPE: PRT
<213> ORGANISM: Mus Musculus

<400> SEQUENCE: 120

Met Glu Thr Asp Thr Leu Leu Leu Trp Val Leu Leu Leu Trp Val Pro
1 5 10 15

Gly Ser Thr Gly Asp Ile Val Leu Thr Gln Ser Pro Ala Ser Leu Ala
20 25 30

Val Ser Leu Gly Gln Arg Ala Thr Ile Ser Cys Arg Ala Ser Gln Ser
35 40 45

Val Ser Thr Ser Ser Tyr Ser Tyr Met His Trp Tyr Gln Gln Lys Pro
50 55 60

Gly Gln Pro Pro Lys Leu Leu Ile Lys Tyr Ala Ser Asn Leu Glu Ser
65 70 75 80

Gly Val Pro Ala Arg Phe Ser Gly Ser Gly Ser Gly Thr Asp Phe Thr
85 90 95

Leu Asn Ile His Pro Val Glu Glu Glu Asp Thr Ala Thr Tyr Tyr Cys
100 105 110

Gln His Ser Leu Glu Ile Pro Trp Thr Phe Gly Gly Gly Thr Lys Leu
115 120 125

Glu Ile Lys
130

<210> SEQ ID NO 121
<211> LENGTH: 390
<212> TYPE: DNA
<213> ORGANISM: Mus Musculus

<400> SEQUENCE: 121 atggatttc aggtgcagat tttcagcttc atgctaatca gtgcctcagt cataatgtcc 60
agaggacaaa ttgttctcac ccagtctcca gcaatcatgt ctgcatctct aggggaacgg 120
gtcaccatga cctgcactgc cagctcaagt gttagttccg cttacttgca ctggtaccag 180
cagaagccag gatcctcccc caaactctgg atttatagca catccaacct ggcttctgga 240
gtcccaactc gcttcagtgg cagtggatct gggacctctt actctctcac aatcagcagc 300
atggaggctg aagatgctgc cacttattac tgccaccagt atcatcgttc cccgttcacg 360
ttcggtgctg ggaccaagct ggagctgaaa 390

<210> SEQ ID NO 122
<211> LENGTH: 130
<212> TYPE: PRT
<213> ORGANISM: Mus Musculus

<400> SEQUENCE: 122

Met Asp Phe Gln Val Gln Ile Phe Ser Phe Met Leu Ile Ser Ala Ser
1 5 10 15

Val Ile Met Ser Arg Gly Gln Ile Val Leu Thr Gln Ser Pro Ala Ile
20 25 30

Met Ser Ala Ser Leu Gly Glu Arg Val Thr Met Thr Cys Thr Ala Ser
35 40 45

Ser Ser Val Ser Ser Ala Tyr Leu His Trp Tyr Gln Gln Lys Pro Gly
50 55 60

Ser Ser Pro Lys Leu Trp Ile Tyr Ser Thr Ser Asn Leu Ala Ser Gly
65 70 75 80

Val Pro Thr Arg Phe Ser Gly Ser Gly Ser Gly Thr Ser Tyr Ser Leu
85 90 95

Thr Ile Ser Ser Met Glu Ala Glu Asp Ala Ala Thr Tyr Tyr Cys His
100 105 110

Gln Tyr His Arg Ser Pro Phe Thr Phe Gly Ala Gly Thr Lys Leu Glu
115 120 125

Leu Lys
130

<210> SEQ ID NO 123
<211> LENGTH: 378
<212> TYPE: DNA
<213> ORGANISM: Mus Musculus

<400> SEQUENCE: 123
atgagaccgt ctattcagtt cctggggctc ttgttgttct ggcttcatgg tgctcagtgt 60
gacatccaga tgacacagtc tccatactca ctgtctgcat ctctgggagg caaagtcacc 120
atcacttgca aggcaagcca agacattaac aagtatatag cttggtacca acacaagcct 180
ggaaaaggtc ctaggctgct catacataac acatctacat tacagccagg catcccatca 240
aggttcagtg gaagtgggtc tgggagagat tattccttca gcatcagcaa cctggagcct 300
gaagatattg caacttatta ttgtctacag catgataatc tgtggacgtt cggtggaggc 360
accaagctgg aaatcaaa 378

<210> SEQ ID NO 124
<211> LENGTH: 126
<212> TYPE: PRT
<213> ORGANISM: Mus Musculus

<400> SEQUENCE: 124

Met Arg Pro Ser Ile Gln Phe Leu Gly Leu Leu Leu Phe Trp Leu His
1 5 10 15

Gly Ala Gln Cys Asp Ile Gln Met Thr Gln Ser Pro Tyr Ser Leu Ser
20 25 30

Ala Ser Leu Gly Gly Lys Val Thr Ile Thr Cys Lys Ala Ser Gln Asp
35 40 45

Ile Asn Lys Tyr Ile Ala Trp Tyr Gln His Lys Pro Gly Lys Gly Pro
50 55 60

Arg Leu Leu Ile His Asn Thr Ser Thr Leu Gln Pro Gly Ile Pro Ser
65 70 75 80

Arg Phe Ser Gly Ser Gly Ser Gly Arg Asp Tyr Ser Phe Ser Ile Ser
85 90 95

Asn Leu Glu Pro Glu Asp Ile Ala Thr Tyr Tyr Cys Leu Gln His Asp
100 105 110

Asn Leu Trp Thr Phe Gly Gly Gly Thr Lys Leu Glu Ile Lys
115 120 125

<210> SEQ ID NO 125
<211> LENGTH: 366
<212> TYPE: DNA
<213> ORGANISM: Artificial Sequence
<220> FEATURE:
<223> OTHER INFORMATION: Synthetic Construct

<400> SEQUENCE: 125
caggtccaac tgcagcagcc tggggctgag cttgtgaagc ctggggcttc agtgaagatg 60
tcctgcaagg cttctggatt cactttcagt gactattaca taaactgggt gaagcagagg 120
cctggacaag gccttgagtg gattggagat attagtgatg gtggtagtta cacctacaat 180
gctaagttca agagcaaggc cacactgact ctggacacat cctccagcac agcctacatg 240
cagctcagca gcctgacatc tgaggactct gcggtctatt actgtgcaag agattactac 300
ggtagtagta gctacacctc gggctttgct tactggggcg caggcaccac ggtcaccgtc 360
tcctca 366

<210> SEQ ID NO 126
<211> LENGTH: 122
<212> TYPE: PRT
<213> ORGANISM: Artificial Sequence
<220> FEATURE:
<223> OTHER INFORMATION: Synthetic Construct

<400> SEQUENCE: 126

Gln Val Gln Leu Gln Gln Pro Gly Ala Glu Leu Val Lys Pro Gly Ala
1 5 10 15

Ser Val Lys Met Ser Cys Lys Ala Ser Gly Phe Thr Phe Ser Asp Tyr
20 25 30

```
Tyr Ile Asn Trp Val Lys Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
    50                  55                  60

Ser Lys Ala Thr Leu Thr Leu Asp Thr Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Asp Tyr Tyr Gly Ser Ser Ser Tyr Thr Ser Gly Phe Ala Tyr Trp
            100                 105                 110

Gly Ala Gly Thr Thr Val Thr Val Ser Ser
        115                 120


<210> SEQ ID NO 127
<211> LENGTH: 366
<212> TYPE: DNA
<213> ORGANISM: Artificial Sequence
<220> FEATURE:
<223> OTHER INFORMATION: Synthetic Construct

<400> SEQUENCE: 127

caggtccaac tggtgcagtc tggggctgag cttaagaagc ctggggcttc agtgaagatg      60

tcctgcaagg cttctggatt cactttcagt gactattaca taaactgggt gaagcagagg     120

cctggacaag gccttgagtg gattggagat attagtgatg gtggtagtta cacctacaat     180

gctaagttca agagcagagc cacactgact ctggacacat ccataagcac agcctacatg     240

cagctcagca gcctgacatc tgaggactct gcggtctatt actgtgcaag agattactac     300

ggtagtagta gctacacctc gggctttgct tactggggcc aaggcaccac ggtcaccgtc     360

tcctca                                                                366


<210> SEQ ID NO 128
<211> LENGTH: 122
<212> TYPE: PRT
<213> ORGANISM: Artificial Sequence
<220> FEATURE:
<223> OTHER INFORMATION: Synthetic Construct

<400> SEQUENCE: 128

Gln Val Gln Leu Val Gln Ser Gly Ala Glu Leu Lys Lys Pro Gly Ala
1               5                   10                  15

Ser Val Lys Met Ser Cys Lys Ala Ser Gly Phe Thr Phe Ser Asp Tyr
            20                  25                  30

Tyr Ile Asn Trp Val Lys Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
    50                  55                  60

Ser Arg Ala Thr Leu Thr Leu Asp Thr Ser Ile Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Asp Tyr Tyr Gly Ser Ser Ser Tyr Thr Ser Gly Phe Ala Tyr Trp
            100                 105                 110

Gly Gln Gly Thr Thr Val Thr Val Ser Ser
        115                 120


<210> SEQ ID NO 129
<211> LENGTH: 366
```

<212> TYPE: DNA
<213> ORGANISM: Artificial Sequence
<220> FEATURE:
<223> OTHER INFORMATION: Synthetic Construct

<400> SEQUENCE: 129
caggtccaac tggtgcagtc tggggctgag gtgaagaagc ctggggcttc agtgaagatg 60
tcctgcaagg cttctggatt cactttcagt gactattaca taaactgggt gaagcagagg 120
cctggacaag gccttgagtg gattggagat attagtgatg gtggtagtta cacctacaat 180
gctaagttca agagcagagc cacactgact ctggacacat ccataagcac agcctacatg 240
gagctcagca gcctgagatc tgaggacacg gcggtctatt actgtgcaag agattactac 300
ggtagtagta gctacacctc gggctttgct tactggggcc aaggcaccac ggtcaccgtc 360
tcctca 366

<210> SEQ ID NO 130
<211> LENGTH: 122
<212> TYPE: PRT
<213> ORGANISM: Artificial Sequence
<220> FEATURE:
<223> OTHER INFORMATION: Synthetic Construct

<400> SEQUENCE: 130

Gln Val Gln Leu Val Gln Ser Gly Ala Glu Val Lys Lys Pro Gly Ala
1 5 10 15

Ser Val Lys Met Ser Cys Lys Ala Ser Gly Phe Thr Phe Ser Asp Tyr
20 25 30

Tyr Ile Asn Trp Val Lys Gln Arg Pro Gly Gln Gly Leu Glu Trp Ile
35 40 45

Gly Asp Ile Ser Asp Gly Gly Ser Tyr Thr Tyr Asn Ala Lys Phe Lys
50 55 60

Ser Arg Ala Thr Leu Thr Leu Asp Thr Ser Ile Ser Thr Ala Tyr Met
65 70 75 80

Glu Leu Ser Ser Leu Arg Ser Glu Asp Thr Ala Val Tyr Tyr Cys Ala
85 90 95

Arg Asp Tyr Tyr Gly Ser Ser Ser Tyr Thr Ser Gly Phe Ala Tyr Trp
100 105 110

Gly Gln Gly Thr Thr Val Thr Val Ser Ser
115 120

<210> SEQ ID NO 131
<211> LENGTH: 366
<212> TYPE: DNA
<213> ORGANISM: Artificial Sequence
<220> FEATURE:
<223> OTHER INFORMATION: Synthetic Construct

<400> SEQUENCE: 131
caggtccaac tggtgcagtc tggggctgag gtgaagaagc ctggggcttc agtgaaggtg 60
tcctgcaagg cttctggatt cactttcagt gactattaca taaactgggt gcgacagagg 120
cctggacaag gccttgagtg gattggagat attagtgatg gtggtagtta cacctacaat 180
gctaagttca agagcagagc cacactgact ctggacacat ccataagcac agcctacatg 240
gagctcagca gcctgagatc tgaggacacg gcggtctatt actgtgcaag agattactac 300
ggtagtagta gctacacctc gggctttgct tactggggcc aaggcaccac ggtcaccgtc 360
tcctca 366

<210> SEQ ID NO 132
<211> LENGTH: 122
<212> TYPE: PRT
<213> ORGANISM: Artificial Sequence
<220> FEATURE:
<223> OTHER INFORMATION: Synthetic Construct

<400> SEQUENCE: 132

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Tyr Ile Asn Trp Val Arg Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
    50                  55                  60

Ser Arg Ala Thr Leu Thr Leu Asp Thr Ser Ile Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Tyr Tyr Gly Ser Ser Ser Tyr Thr Ser Gly Phe Ala Tyr Trp
            100                 105                 110

Gly Gln Gly Thr Thr Val Thr Val Ser Ser
        115                 120
```

<210> SEQ ID NO 133
<211> LENGTH: 366
<212> TYPE: DNA
<213> ORGANISM: Artificial Sequence
<220> FEATURE:
<223> OTHER INFORMATION: Synthetic Construct

<400> SEQUENCE: 133

```
caggtccaac tggtgcagtc tggggctgag gtgaagaagc ctggggcttc agtgaaggtg     60

tcctgcaagg cttctggatt cactttcagt gactattaca taaactgggt gcgacagagg    120

cctggacaag gccttgagtg gattggagat attagtgatg gtggtagtta cacctacaat    180

gctaagttca agagcagagt cacactgact ctggacacat ccataagcac agcctacatg    240

gagctcagca gcctgagatc tgaggacacg gcggtctatt actgtgcaag agattactac    300

ggtagtagta gctacacctc gggctttgct tactggggcc aaggcaccac ggtcaccgtc    360

tcctca                                                               366
```

<210> SEQ ID NO 134
<211> LENGTH: 122
<212> TYPE: PRT
<213> ORGANISM: Artificial Sequence
<220> FEATURE:
<223> OTHER INFORMATION: Synthetic Construct

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Tyr Ile Asn Trp Val Arg Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
    50                  55                  60
```

```
Ser Arg Val Thr Leu Thr Leu Asp Thr Ser Ile Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Tyr Tyr Gly Ser Ser Ser Tyr Thr Ser Gly Phe Ala Tyr Trp
            100                 105                 110

Gly Gln Gly Thr Thr Val Thr Val Ser Ser
        115                 120


<210> SEQ ID NO 135
<211> LENGTH: 366
<212> TYPE: DNA
<213> ORGANISM: Artificial Sequence
<220> FEATURE:
<223> OTHER INFORMATION: Synthetic Construct

<400> SEQUENCE: 135

caggtccaac tggtgcagtc tggggctgag gtgaagaagc ctggggcttc agtgaaggtg      60

tcctgcaagg cttctggatt cactttcagt gactattaca taaactgggt gcgacagagg     120

cctggacaag gccttgagtg gatgggagat attagtgatg gtggtagtta cacctacaat     180

gctaagttca agagcagagt cacactgact agggacacat ccataagcac agcctacatg     240

gagctcagca gcctgagatc tgaggacacg gcggtctatt actgtgcaag agattactac     300

ggtagtagta gctacacctc gggctttgct tactggggcc aaggcaccac ggtcaccgtc     360

tcctca                                                                366


<210> SEQ ID NO 136
<211> LENGTH: 122
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Tyr Ile Asn Trp Val Arg Gln Arg Pro Gly Gln Gly Leu Glu Trp Met
        35                  40                  45

Gly Asp Ile Ser Asp Gly Gly Ser Tyr Thr Tyr Asn Ala Lys Phe Lys
    50                  55                  60

Ser Arg Val Thr Leu Thr Arg Asp Thr Ser Ile Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Tyr Tyr Gly Ser Ser Ser Tyr Thr Ser Gly Phe Ala Tyr Trp
            100                 105                 110

Gly Gln Gly Thr Thr Val Thr Val Ser Ser
        115                 120


<210> SEQ ID NO 137
<211> LENGTH: 366
<212> TYPE: DNA
<213> ORGANISM: Artificial Sequence
<220> FEATURE:
<223> OTHER INFORMATION: Synthetic Construct
```

<400> SEQUENCE: 137
caggtccaac tggtgcagtc tggggctgag gtgaagaagc ctggggcttc agtgaaggtg 60
tcctgcaagg cttctggatt cactttcagt gactattaca taaactgggt gcgacagagg 120
cctggacaag gccttgagtg gatgggagat attagtgatg gtggtagtta cacctacaat 180
gctaagttcc agggcagagt cacaatgact agggacacat ccataagcac agcctacatg 240
gagctcagca gcctgagatc tgaggacacg gcggtctatt actgtgcaag agattactac 300
ggtagtagta gctacacctc gggctttgct tactggggcc aaggcaccac ggtcaccgtc 360
tcctca 366

<210> SEQ ID NO 138
<211> LENGTH: 122
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Phe Ser Asp Tyr
20 25 30

Tyr Ile Asn Trp Val Arg Gln Arg Pro Gly Gln Gly Leu Glu Trp Met
35 40 45

Gly Asp Ile Ser Asp Gly Gly Ser Tyr Thr Tyr Asn Ala Lys Phe Gln
50 55 60

Gly Arg Val Thr Met Thr Arg Asp Thr Ser Ile Ser Thr Ala Tyr Met
65 70 75 80

Glu Leu Ser Ser Leu Arg Ser Glu Asp Thr Ala Val Tyr Tyr Cys Ala
85 90 95

Arg Asp Tyr Tyr Gly Ser Ser Ser Tyr Thr Ser Gly Phe Ala Tyr Trp
100 105 110

Gly Gln Gly Thr Thr Val Thr Val Ser Ser
115 120

<210> SEQ ID NO 139
<211> LENGTH: 336
<212> TYPE: DNA
<213> ORGANISM: Artificial Sequence
<220> FEATURE:
<223> OTHER INFORMATION: Synthetic Construct

<400> SEQUENCE: 139
gatgttttga tgacccaaac tccactctcc ctgcctgtca gtcttggaga tcaagcctcc 60
atctcttgca gatctagtca gagtctgctc aacagtagaa cccgaaagaa ctacttagaa 120
tggtacctgc agaaaccagg ccagtctcca aagctcctga tctactgggc atccaaccga 180
ttttctgggg tcccagacag gttcagtggc agtggatcag ggacagattt cacactcaag 240
atcagcagag tggaggctga ggatctggga gtttattact gcaagcaatc ttataatctg 300
tacacgtttg gcagcgggac caagctggag atcaaa 336

<210> SEQ ID NO 140
<211> LENGTH: 112
<212> TYPE: PRT
<213> ORGANISM: Artificial Sequence
<220> FEATURE:
<223> OTHER INFORMATION: Synthetic Construct

<400> SEQUENCE: 140

Asp Val Leu Met Thr Gln Thr Pro Leu Ser Leu Pro Val Ser Leu Gly
1 5 10 15

Asp Gln Ala Ser Ile Ser Cys Arg Ser Ser Gln Ser Leu Leu Asn Ser
20 25 30

Arg Thr Arg Lys Asn Tyr Leu Glu Trp Tyr Leu Gln Lys Pro Gly Gln
35 40 45

Ser Pro Lys Leu Leu Ile Tyr Trp Ala Ser Asn Arg Phe Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Leu Gly Val Tyr Tyr Cys Lys Gln
85 90 95

Ser Tyr Asn Leu Tyr Thr Phe Gly Ser Gly Thr Lys Leu Glu Ile Lys
100 105 110

<210> SEQ ID NO 141
<211> LENGTH: 336
<212> TYPE: DNA
<213> ORGANISM: Artificial Sequence
<220> FEATURE:
<223> OTHER INFORMATION: Synthetic Construct

<400> SEQUENCE: 141
gatgttttga tgacccaatc tccactctcc ctgcctgtca cccttggaca gccggcctcc 60
atctcttgca gatctagtca gagtctgctc aacagtagaa cccgaaagaa ctacttagaa 120
tggtttcagc agaaaccagg ccagtctcca aggcgcctga tctactgggc atccaaccga 180
ttttctgggg tcccagacag gttcagtggc agtggatcag ggacagattt cacactcaag 240
atcagcagag tggaggctga ggatgttgga gtttattact gcaagcaatc ttataatctg 300
tacacgtttg gccaagggac caagctggag atcaaa 336

<210> SEQ ID NO 142
<211> LENGTH: 112
<212> TYPE: PRT
<213> ORGANISM: Artificial Sequence
<220> FEATURE:
<223> OTHER INFORMATION: Synthetic Construct

<400> SEQUENCE: 142

Asp Val Leu Met Thr Gln Ser Pro Leu Ser Leu Pro Val Thr Leu Gly
1 5 10 15

Gln Pro Ala Ser Ile Ser Cys Arg Ser Ser Gln Ser Leu Leu Asn Ser
20 25 30

Arg Thr Arg Lys Asn Tyr Leu Glu Trp Phe Gln Gln Lys Pro Gly Gln
35 40 45

Ser Pro Arg Arg Leu Ile Tyr Trp Ala Ser Asn Arg Phe Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Lys Gln
85 90 95

Ser Tyr Asn Leu Tyr Thr Phe Gly Gln Gly Thr Lys Leu Glu Ile Lys
100 105 110

<210> SEQ ID NO 143

```
<211> LENGTH: 336
<212> TYPE: DNA
<213> ORGANISM: Artificial Sequence
<220> FEATURE:
<223> OTHER INFORMATION: Synthetic Construct

<400> SEQUENCE: 143

gatgttgtga tgacccaatc tccactctcc ctgcctgtca cccttggaca gccggcctcc      60

atctcttgca gatctagtca gagtctgctc aacagtagaa cccgaaagaa ctacttagaa     120

tggtttcagc agaaaccagg ccagtctcca aggcgcctga tctactgggc atccaaccga     180

ttttctgggg tcccagacag gttcagtggc agtggatcag ggacagattt cacactcaag     240

atcagcagag tggaggctga ggatgttgga gtttattact gcaagcaatc ttataatctg     300

tacacgtttg gccaagggac caagctggag atcaaa                               336


<210> SEQ ID NO 144
<211> LENGTH: 112
<212> TYPE: PRT
<213> ORGANISM: Artificial Sequence
<220> FEATURE:
<223> OTHER INFORMATION: Synthetic Construct

<400> SEQUENCE: 144

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asn Ser
            20                  25                  30

Arg Thr Arg Lys Asn Tyr Leu Glu Trp Phe Gln Gln Lys Pro Gly Gln
        35                  40                  45

Ser Pro Arg Arg Leu Ile Tyr Trp Ala Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Tyr Asn Leu Tyr Thr Phe Gly Gln Gly Thr Lys Leu Glu Ile Lys
            100                 105                 110


<210> SEQ ID NO 145
<211> LENGTH: 336
<212> TYPE: DNA
<213> ORGANISM: Artificial Sequence
<220> FEATURE:
<223> OTHER INFORMATION: Synthetic Construct

<400> SEQUENCE: 145

gatgttgtga tgacccaatc tccactctcc ctgcctgtca cccttggaca gccggcctcc      60

atctcttgca gatctagtca gagtctgctc aacagtagaa cccgaaagaa ctacttagaa     120

tggtttcagc agaggccagg ccagtctcca aggcgcctga tctactgggc atccaaccga     180

ttttctgggg tcccagacag gttcagtggc agtggatcag ggacagattt cacactcaag     240

atcagcagag tggaggctga ggatgttgga gtttattact gcaagcaatc ttataatctg     300

tacacgtttg gccaagggac caagctggag atcaaa                               336


<210> SEQ ID NO 146
<211> LENGTH: 112
<212> TYPE: PRT
<213> ORGANISM: Artificial Sequence
<220> FEATURE:
```

<223> OTHER INFORMATION: Synthetic Construct

<400> SEQUENCE: 146

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asn Ser
            20                  25                  30

Arg Thr Arg Lys Asn Tyr Leu Glu Trp Phe Gln Gln Arg Pro Gly Gln
        35                  40                  45

Ser Pro Arg Arg Leu Ile Tyr Trp Ala Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Tyr Asn Leu Tyr Thr Phe Gly Gln Gly Thr Lys Leu Glu Ile Lys
            100                 105                 110
```

<210> SEQ ID NO 147
<211> LENGTH: 336
<212> TYPE: DNA
<213> ORGANISM: Artificial Sequence
<220> FEATURE:
<223> OTHER INFORMATION: Synthetic Construct

<400> SEQUENCE: 147

```
gatgttctga tgacccaatc tccactctcc ctgcctgtca cccttggaca gccggcctcc      60

atctcttgca gatctagtca gagtctgctc aacagtagaa cccgaaagaa ctacttagaa     120

tggtacctgc agaggccagg ccagtctcca aagctgctga tctactgggc atccaaccga     180

ttttctgggg tcccagacag gttcagtggc agtggatcag ggacagattt cacactcaag     240

atcagcagag tggaggctga ggatgttgga gtttattact gcaagcaatc ttataatctg     300

tacacgtttg gccaagggac caagctggag atcaaa                               336
```

<210> SEQ ID NO 148
<211> LENGTH: 112
<212> TYPE: PRT
<213> ORGANISM: Artificial Sequence
<220> FEATURE:
<223> OTHER INFORMATION: Synthetic Construct

<400> SEQUENCE: 148

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asn Ser
            20                  25                  30

Arg Thr Arg Lys Asn Tyr Leu Glu Trp Tyr Leu Gln Arg Pro Gly Gln
        35                  40                  45

Ser Pro Lys Leu Leu Ile Tyr Trp Ala Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Tyr Asn Leu Tyr Thr Phe Gly Gln Gly Thr Lys Leu Glu Ile Lys
            100                 105                 110
```

<210> SEQ ID NO 149
<211> LENGTH: 336
<212> TYPE: DNA
<213> ORGANISM: Artificial Sequence
<220> FEATURE:
<223> OTHER INFORMATION: Synthetic Construct

<400> SEQUENCE: 149
gatgttctga tgacccaatc tccactctcc ctgcctgtca cccttggaca gccggcctcc 60
atctcttgca gatctagtca gagtctgctc aacagtagaa cccgaaagaa ctacttagaa 120
tggtaccagc agaggccagg ccagtctcca aggctgctga tctactgggc atccaaccga 180
ttttctgggg tcccagacag gttcagtggc agtggatcag ggacagattt cacactcaag 240
atcagcagag tggaggctga ggatgttgga gtttattact gcaagcaatc ttataatctg 300
tacacgtttg gccaagggac caagctggag atcaaa 336

<210> SEQ ID NO 150
<211> LENGTH: 112
<212> TYPE: PRT
<213> ORGANISM: Artificial Sequence
<220> FEATURE:
<223> OTHER INFORMATION: Synthetic Construct

<400> SEQUENCE: 150

Asp Val Leu Met Thr Gln Ser Pro Leu Ser Leu Pro Val Thr Leu Gly
1 5 10 15

Gln Pro Ala Ser Ile Ser Cys Arg Ser Ser Gln Ser Leu Leu Asn Ser
20 25 30

Arg Thr Arg Lys Asn Tyr Leu Glu Trp Tyr Gln Gln Arg Pro Gly Gln
35 40 45

Ser Pro Arg Leu Leu Ile Tyr Trp Ala Ser Asn Arg Phe Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Lys Gln
85 90 95

Ser Tyr Asn Leu Tyr Thr Phe Gly Gln Gly Thr Lys Leu Glu Ile Lys
100 105 110

<210> SEQ ID NO 151
<211> LENGTH: 336
<212> TYPE: DNA
<213> ORGANISM: Artificial Sequence
<220> FEATURE:
<223> OTHER INFORMATION: Synthetic Construct

<400> SEQUENCE: 151
gatgttgtga tgacccaatc tccactctcc ctgcctgtca cccttggaca gccggcctcc 60
atctcttgca gatctagtca gagtctgctc aacagtagaa cccgaaagaa ctacttagaa 120
tggtaccagc agaggccagg ccagtctcca aggctgctga tctactgggc atccaaccga 180
ttttctgggg tcccagacag gttcagtggc agtggatcag ggacagattt cacactcaag 240
atcagcagag tggaggctga ggatgttgga gtttattact gcaagcaatc ttataatctg 300
tacacgtttg gccaagggac caagctggag atcaaa 336

<210> SEQ ID NO 152
<211> LENGTH: 112
<212> TYPE: PRT
<213> ORGANISM: Artificial Sequence
<220> FEATURE:
<223> OTHER INFORMATION: Synthetic Construct

<400> SEQUENCE: 152

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu Asn Ser
20 25 30

Arg Thr Arg Lys Asn Tyr Leu Glu Trp Tyr Gln Gln Arg Pro Gly Gln
35 40 45

Ser Pro Arg Leu Leu Ile Tyr Trp Ala Ser Asn Arg Phe Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Lys Gln
85 90 95

Ser Tyr Asn Leu Tyr Thr Phe Gly Gln Gly Thr Lys Leu Glu Ile Lys
100 105 110

<210> SEQ ID NO 153
<211> LENGTH: 360
<212> TYPE: DNA
<213> ORGANISM: Artificial Sequence
<220> FEATURE:
<223> OTHER INFORMATION: Synthetic Construct

<400> SEQUENCE: 153
caggtccaac tgcagcagcc tggggctgag cttgtgaagc ctggggcttc agtgaagatg 60
tcctgcaagg cttctggcta cagcttcacc agctactgga taaactgggt gaagcagagg 120
cctggacaag gccttgagtg gattggagat gtgcatcctg gtagaggcgt gtccacatac 180
aatgctaagt tcaagagcaa ggccacactg actctggaca catcctccag cacagcctac 240
atgcagctca gcagcctgac atctgaggac tctgcggtct attactgtag cagatcccat 300
ggtaacacct actggttttt tgacgtctgg ggcgcaggca ccacggtcac cgtctcctca 360

<210> SEQ ID NO 154
<211> LENGTH: 120
<212> TYPE: PRT
<213> ORGANISM: Artificial Sequence
<220> FEATURE:
<223> OTHER INFORMATION: Synthetic Construct

<400> SEQUENCE: 154

Gln Val Gln Leu Gln Gln Pro Gly Ala Glu Leu Val Lys Pro Gly Ala
1 5 10 15

Ser Val Lys Met Ser Cys Lys Ala Ser Gly Tyr Ser Phe Thr Ser Tyr
20 25 30

Trp Ile Asn Trp Val Lys Gln Arg Pro Gly Gln Gly Leu Glu Trp Ile
35 40 45

Gly Asp Val His Pro Gly Arg Gly Val Ser Thr Tyr Asn Ala Lys Phe
50 55 60

Lys Ser Lys Ala Thr Leu Thr Leu Asp Thr Ser Ser Ser Thr Ala Tyr
65 70 75 80

Met Gln Leu Ser Ser Leu Thr Ser Glu Asp Ser Ala Val Tyr Tyr Cys
85 90 95

Ser Arg Ser His Gly Asn Thr Tyr Trp Phe Phe Asp Val Trp Gly Ala
100 105 110

Gly Thr Thr Val Thr Val Ser Ser
        115                 120

<210> SEQ ID NO 155
<211> LENGTH: 360
<212> TYPE: DNA
<213> ORGANISM: Artificial Sequence
<220> FEATURE:
<223> OTHER INFORMATION: Synthetic Construct

<400> SEQUENCE: 155
caggtccaac tggtgcagtc tggggctgag cttaagaagc ctggggcttc agtgaagatg 60
tcctgcaagg cttctggcta cagcttcacc agctactgga taaactgggt gaagcagagg 120
cctggacaag gccttgagtg gattggagat gtgcatcctg gtagaggcgt gtccacatac 180
aatgctaagt tcaagagcag agccacactg actctggaca catccataag cacagcctac 240
atgcagctca gcagcctgac atctgaggac tctgcggtct attactgtag cagatcccat 300
ggtaacacct actggttttt tgacgtctgg ggccaaggca ccacggtcac cgtctcctca 360

<210> SEQ ID NO 156
<211> LENGTH: 120
<212> TYPE: PRT
<213> ORGANISM: Artificial Sequence
<220> FEATURE:
<223> OTHER INFORMATION: Synthetic Construct

<400> SEQUENCE: 156

Gln Val Gln Leu Val Gln Ser Gly Ala Glu Leu Lys Lys Pro Gly Ala
1               5                   10                  15

Ser Val Lys Met Ser Cys Lys Ala Ser Gly Tyr Ser Phe Thr Ser Tyr
            20                  25                  30

Trp Ile Asn Trp Val Lys Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60

Lys Ser Arg Ala Thr Leu Thr Leu Asp Thr Ser Ile Ser Thr Ala Tyr
65                  70                  75                  80

Met Gln Leu Ser Ser Leu Thr Ser Glu Asp Ser Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120

<210> SEQ ID NO 157
<211> LENGTH: 360
<212> TYPE: DNA
<213> ORGANISM: Artificial Sequence
<220> FEATURE:
<223> OTHER INFORMATION: Synthetic Construct

<400> SEQUENCE: 157
caggtccaac tggtgcagtc tggggctgag gtgaagaagc ctggggcttc agtgaagatg 60
tcctgcaagg cttctggcta cagcttcacc agctactgga taaactgggt gaagcagagg 120
cctggacaag gccttgagtg gattggagat gtgcatcctg gtagaggcgt gtccacatac 180
aatgctaagt tcaagagcag agccacactg actctggaca catccataag cacagcctac 240
atggagctca gcagcctgag atctgaggac acggcggtct attactgtag cagatcccat 300

-continued

```
ggtaacacct actggttttt tgacgtctgg ggccaaggca ccacggtcac cgtctcctca    360


<210> SEQ ID NO 158
<211> LENGTH: 120
<212> TYPE: PRT
<213> ORGANISM: Artificial Sequence
<220> FEATURE:
<223> OTHER INFORMATION: Synthetic Construct

<400> SEQUENCE: 158

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ser Phe Thr Ser Tyr
            20                  25                  30

Trp Ile Asn Trp Val Lys Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60

Lys Ser Arg Ala Thr Leu Thr Leu Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120


<210> SEQ ID NO 159
<211> LENGTH: 360
<212> TYPE: DNA
<213> ORGANISM: Artificial Sequence
<220> FEATURE:
<223> OTHER INFORMATION: Synthetic Construct

<400> SEQUENCE: 159

caggtccaac tggtgcagtc tggggctgag gtgaagaagc ctggggcttc agtgaaggtg     60

tcctgcaagg cttctggcta cagcttcacc agctactgga taaactgggt gcgacagagg    120

cctggacaag gccttgagtg gattggagat gtgcatcctg gtagaggcgt gtccacatac    180

aatgctaagt tcaagagcag agccacactg actctggaca catccataag cacagcctac    240

atggagctca gcagcctgag atctgaggac acggcggtct attactgtag cagatcccat    300

ggtaacacct actggttttt tgacgtctgg ggccaaggca ccacggtcac cgtctcctca    360


<210> SEQ ID NO 160
<211> LENGTH: 120
<212> TYPE: PRT
<213> ORGANISM: Artificial Sequence
<220> FEATURE:
<223> OTHER INFORMATION: Synthetic Construct

<400> SEQUENCE: 160

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Ile Asn Trp Val Arg Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60
```

```
Lys Ser Arg Ala Thr Leu Thr Leu Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120


<210> SEQ ID NO 161
<211> LENGTH: 360
<212> TYPE: DNA
<213> ORGANISM: Artificial Sequence
<220> FEATURE:
<223> OTHER INFORMATION: Synthetic Construct

<400> SEQUENCE: 161

caggtccaac tggtgcagtc tggggctgag gtgaagaagc ctggggcttc agtgaaggtg      60

tcctgcaagg cttctggcta cagcttcacc agctactgga taaactgggt gcgacagagg     120

cctggacaag gccttgagtg gattggagat gtgcatcctg gtagaggcgt gtccacatac     180

aatgctaagt tcaagagcag agtcacactg actctggaca catccataag cacagcctac     240

atggagctca gcagcctgag atctgaggac acggcggtct attactgtag cagatcccat     300

ggtaacacct actggttttt tgacgtctgg ggccaaggca ccacggtcac cgtctcctca     360


<210> SEQ ID NO 162
<211> LENGTH: 120
<212> TYPE: PRT
<213> ORGANISM: Artificial Sequence
<220> FEATURE:
<223> OTHER INFORMATION: Synthetic Construct

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Ile Asn Trp Val Arg Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60

Lys Ser Arg Val Thr Leu Thr Leu Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120


<210> SEQ ID NO 163
<211> LENGTH: 360
<212> TYPE: DNA
<213> ORGANISM: Artificial Sequence
<220> FEATURE:
<223> OTHER INFORMATION: Synthetic Construct

<400> SEQUENCE: 163
```

-continued

```
caggtccaac tggtgcagtc tggggctgag gtgaagaagc ctggggcttc agtgaaggtg     60

tcctgcaagg cttctggcta cagcttcacc agctactgga taaactgggt gcgacagagg    120

cctggacaag gccttgagtg gatgggagat gtgcatcctg gtagaggcgt gtccacatac    180

aatgctaagt tcaagagcag agtcacactg actagggaca catccataag cacagcctac    240

atggagctca gcagcctgag atctgaggac acggcggtct attactgtag cagatcccat    300

ggtaacacct actggttttt tgacgtctgg ggccaaggca ccacggtcac cgtctcctca    360


<210> SEQ ID NO 164
<211> LENGTH: 120
<212> TYPE: PRT
<213> ORGANISM: Artificial Sequence
<220> FEATURE:
<223> OTHER INFORMATION: Synthetic Construct

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Ile Asn Trp Val Arg Gln Arg Pro Gly Gln Gly Leu Glu Trp Met
        35                  40                  45

Gly Asp Val His Pro Gly Arg Gly Val Ser Thr Tyr Asn Ala Lys Phe
    50                  55                  60

Lys Ser Arg Val Thr Leu Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120


<210> SEQ ID NO 165
<211> LENGTH: 360
<212> TYPE: DNA
<213> ORGANISM: Artificial Sequence
<220> FEATURE:
<223> OTHER INFORMATION: Synthetic Construct

<400> SEQUENCE: 165

caggtccaac tggtgcagtc tggggctgag gtgaagaagc ctggggcttc agtgaaggtg     60

tcctgcaagg cttctggcta cagcttcacc agctactgga taaactgggt gcgacagagg    120

cctggacaag gccttgagtg gatgggagat gtgcatcctg gtagaggcgt gtccacatac    180

aatgctaagt tccagggcag agtcacaatg actagggaca catccataag cacagcctac    240

atggagctca gcagcctgag atctgaggac acggcggtct attactgtag cagatcccat    300

ggtaacacct actggttttt tgacgtctgg ggccaaggca ccacggtcac cgtctcctca    360


<210> SEQ ID NO 166
<211> LENGTH: 120
<212> TYPE: PRT
<213> ORGANISM: Artificial Sequence
<220> FEATURE:
<223> OTHER INFORMATION: Synthetic Construct

<400> SEQUENCE: 166

Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Ser Phe Thr Ser Tyr
            20                  25                  30

Trp Ile Asn Trp Val Arg Gln Arg Pro Gly Gln Gly Leu Glu Trp Met
        35                  40                  45

Gly Asp Val His Pro Gly Arg Gly Val Ser Thr Tyr Asn Ala Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120
```

<210> SEQ ID NO 167
<211> LENGTH: 336
<212> TYPE: DNA
<213> ORGANISM: Artificial Sequence
<220> FEATURE:
<223> OTHER INFORMATION: Synthetic Construct

<400> SEQUENCE: 167

```
gatgttttga tgacccaaac tccactctcc ctgcctgtca gtcttggaga tcaagcctcc      60

atctcttgca gatctagtca gagcattgta catagtaatg gaaacaccta tttagaatgg     120

tacctgcaga aaccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tctgggagtt tattactgct ttcaaggttc acatgttcct     300

ttcacttttg gcagcgggac caagctggag atcaaa                               336
```

<210> SEQ ID NO 168
<211> LENGTH: 112
<212> TYPE: PRT
<213> ORGANISM: Artificial Sequence
<220> FEATURE:
<223> OTHER INFORMATION: Synthetic Construct

<400> SEQUENCE: 168

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 169
<211> LENGTH: 336

<212> TYPE: DNA
<213> ORGANISM: Artificial Sequence
<220> FEATURE:
<223> OTHER INFORMATION: Synthetic Construct

<400> SEQUENCE: 169
gatgttttga tgacccaatc tccactctcc ctgcctgtca cccttggaca gccggcctcc 60
atctcttgca gatctagtca gagcattgta catagtaatg gaaacaccta tttagaatgg 120
tttcagcaga aaccaggcca gtctccaagg cgcctgatct acaaagtttc caaccgattt 180
tctggggtcc cagacaggtt cagtggcagt ggatcaggga cagatttcac actcaagatc 240
agcagagtgg aggctgagga tgttggagtt tattactgct ttcaaggttc acatgttcct 300
ttcacttttg gccaagggac caagctggag atcaaa 336

<210> SEQ ID NO 170
<211> LENGTH: 112
<212> TYPE: PRT
<213> ORGANISM: Artificial Sequence
<220> FEATURE:
<223> OTHER INFORMATION: Synthetic Construct

<400> SEQUENCE: 170

Asp Val Leu Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Gly Asn Thr Tyr Leu Glu Trp Phe Gln Gln Lys Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Phe Thr Phe Gly Gln Gly Thr Lys Leu Glu Ile Lys
100 105 110

<210> SEQ ID NO 171
<211> LENGTH: 336
<212> TYPE: DNA
<213> ORGANISM: Artificial Sequence
<220> FEATURE:
<223> OTHER INFORMATION: Synthetic Construct

<400> SEQUENCE: 171
gatgttgtga tgacccaatc tccactctcc ctgcctgtca cccttggaca gccggcctcc 60
atctcttgca gatctagtca gagcattgta catagtaatg gaaacaccta tttagaatgg 120
tttcagcaga aaccaggcca gtctccaagg cgcctgatct acaaagtttc caaccgattt 180
tctggggtcc cagacaggtt cagtggcagt ggatcaggga cagatttcac actcaagatc 240
agcagagtgg aggctgagga tgttggagtt tattactgct ttcaaggttc acatgttcct 300
ttcacttttg gccaagggac caagctggag atcaaa 336

<210> SEQ ID NO 172
<211> LENGTH: 112
<212> TYPE: PRT
<213> ORGANISM: Artificial Sequence
<220> FEATURE:
<223> OTHER INFORMATION: Synthetic Construct

<400> SEQUENCE: 172

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Gly Asn Thr Tyr Leu Glu Trp Phe Gln Gln Lys Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Phe Thr Phe Gly Gln Gly Thr Lys Leu Glu Ile Lys
100 105 110

<210> SEQ ID NO 173
<211> LENGTH: 336
<212> TYPE: DNA
<213> ORGANISM: Artificial Sequence
<220> FEATURE:
<223> OTHER INFORMATION: Synthetic Construct

<400> SEQUENCE: 173
gatgttgtga tgacccaatc tccactctcc ctgcctgtca cccttggaca gccggcctcc 60
atctcttgca gatctagtca gagcattgta catagtaatg gaaacaccta tttagaatgg 120
tttcagcaga ggccaggcca gtctccaagg cgcctgatct acaaagtttc caaccgattt 180
tctggggtcc cagacaggtt cagtggcagt ggatcaggga cagatttcac actcaagatc 240
agcagagtgg aggctgagga tgttggagtt tattactgct ttcaaggttc acatgttcct 300
ttcacttttg gccaagggac caagctggag atcaaa 336

<210> SEQ ID NO 174
<211> LENGTH: 112
<212> TYPE: PRT
<213> ORGANISM: Artificial Sequence
<220> FEATURE:
<223> OTHER INFORMATION: Synthetic Construct

<400> SEQUENCE: 174

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Gly Asn Thr Tyr Leu Glu Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Phe Thr Phe Gly Gln Gly Thr Lys Leu Glu Ile Lys
100 105 110

<210> SEQ ID NO 175

<211> LENGTH: 336
<212> TYPE: DNA
<213> ORGANISM: Artificial Sequence
<220> FEATURE:
<223> OTHER INFORMATION: Synthetic Construct

<400> SEQUENCE: 175
gatgttctga tgacccaatc tccactctcc ctgcctgtca cccttggaca gccggcctcc 60
atctcttgca gatctagtca gagcattgta catagtaatg gaaacaccta tttagaatgg 120
tacctgcaga ggccaggcca gtctccaaag ctgctgatct acaaagtttc caaccgattt 180
tctggggtcc cagacaggtt cagtggcagt ggatcaggga cagatttcac actcaagatc 240
agcagagtgg aggctgagga tgttggagtt tattactgct ttcaaggttc acatgttcct 300
ttcacttttg gccaagggac caagctggag atcaaa 336

<210> SEQ ID NO 176
<211> LENGTH: 112
<212> TYPE: PRT
<213> ORGANISM: Artificial Sequence
<220> FEATURE:
<223> OTHER INFORMATION: Synthetic Construct

<400> SEQUENCE: 176

Asp Val Leu Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Gly Asn Thr Tyr Leu Glu Trp Tyr Leu Gln Arg Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Phe Thr Phe Gly Gln Gly Thr Lys Leu Glu Ile Lys
100 105 110

<210> SEQ ID NO 177
<211> LENGTH: 336
<212> TYPE: DNA
<213> ORGANISM: Artificial Sequence
<220> FEATURE:
<223> OTHER INFORMATION: Synthetic Construct

<400> SEQUENCE: 177
gatgttctga tgacccaatc tccactctcc ctgcctgtca cccttggaca gccggcctcc 60
atctcttgca gatctagtca gagcattgta catagtaatg gaaacaccta tttagaatgg 120
taccagcaga ggccaggcca gtctccaagg ctgctgatct acaaagtttc caaccgattt 180
tctggggtcc cagacaggtt cagtggcagt ggatcaggga cagatttcac actcaagatc 240
agcagagtgg aggctgagga tgttggagtt tattactgct ttcaaggttc acatgttcct 300
ttcacttttg gccaagggac caagctggag atcaaa 336

<210> SEQ ID NO 178
<211> LENGTH: 112
<212> TYPE: PRT
<213> ORGANISM: Artificial Sequence
<220> FEATURE:

<223> OTHER INFORMATION: Synthetic Construct

<400> SEQUENCE: 178

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110
```

<210> SEQ ID NO 179
<211> LENGTH: 336
<212> TYPE: DNA
<213> ORGANISM: Artificial Sequence
<220> FEATURE:
<223> OTHER INFORMATION: Synthetic Construct

<400> SEQUENCE: 179

```
gatgttgtga tgacccaatc tccactctcc ctgcctgtca cccttggaca gccggcctcc     60

atctcttgca gatctagtca gagcattgta catagtaatg gaaacaccta tttagaatgg    120

taccagcaga ggccaggcca gtctccaagg ctgctgatct acaaagtttc caaccgattt    180

tctggggtcc cagacaggtt cagtggcagt ggatcaggga cagatttcac actcaagatc    240

agcagagtgg aggctgagga tgttggagtt tattactgct ttcaaggttc acatgttcct    300

ttcacttttg gccaagggac caagctggag atcaaa                              336
```

<210> SEQ ID NO 180
<211> LENGTH: 112
<212> TYPE: PRT
<213> ORGANISM: Artificial Sequence
<220> FEATURE:
<223> OTHER INFORMATION: Synthetic Construct

<400> SEQUENCE: 180

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110
```

<210> SEQ ID NO 181
<211> LENGTH: 984
<212> TYPE: DNA
<213> ORGANISM: Homo Sapiens

<400> SEQUENCE: 181

```
gcttccacca agggcccatc cgtcttcccc ctggcgccct gctccaggag cacctccgag     60

agcacagccg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca atgtagatca caagcccagc aacaccaagg tggacaagag agttgagtcc    300

aaatatggtc ccccatgccc accatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaggcta accgtggaca agagcaggtg gcaggagggg    900

aatgtcttct catgctccgt gatgcatgag gctctgcaca accactacac acagaagagc    960

ctctccctgt ctctgggtaa atga                                           984
```

<210> SEQ ID NO 182
<211> LENGTH: 327
<212> TYPE: PRT
<213> ORGANISM: Homo Sapiens

<400> SEQUENCE: 182

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 183
<211> LENGTH: 324
<212> TYPE: DNA
<213> ORGANISM: Homo Sapiens

<400> SEQUENCE: 183

cgaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagctcgcc cgtcacaaag     300

agcttcaaca ggggagagtg ttag                                            324


<210> SEQ ID NO 184
<211> LENGTH: 107
<212> TYPE: PRT
<213> ORGANISM: Homo Sapiens

<400> SEQUENCE: 184

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

-continued

Pro Val Thr Lys Ser Phe Asn Arg Gly Glu Cys
            100                 105

<210> SEQ ID NO 185
<211> LENGTH: 8
<212> TYPE: PRT
<213> ORGANISM: Mus Musculus

<400> SEQUENCE: 185

Gly Phe Asn Ile Lys Asp Thr Tyr
1               5

<210> SEQ ID NO 186
<211> LENGTH: 8
<212> TYPE: PRT
<213> ORGANISM: Mus Musculus

<400> SEQUENCE: 186

Ile Ala Pro Ala Ser Gly Asn Thr
1               5

<210> SEQ ID NO 187
<211> LENGTH: 5
<212> TYPE: PRT
<213> ORGANISM: Mus Musculus

<400> SEQUENCE: 187

Ala Arg His Val Tyr
1               5

<210> SEQ ID NO 188
<211> LENGTH: 6
<212> TYPE: PRT
<213> ORGANISM: Mus Musculus

<400> SEQUENCE: 188

Gln Ser Val Ser Asn Asp
1               5

<210> SEQ ID NO 189
<211> LENGTH: 3
<212> TYPE: PRT
<213> ORGANISM: Mus Musculus

<400> SEQUENCE: 189

Tyr Ala Ser
1

<210> SEQ ID NO 190
<211> LENGTH: 9
<212> TYPE: PRT
<213> ORGANISM: Mus Musculus

<400> SEQUENCE: 190

Gln Gln Asp Tyr Ile Ser Pro Tyr Thr
1               5

<210> SEQ ID NO 191
<211> LENGTH: 393
<212> TYPE: DNA
<213> ORGANISM: Mus Musculus

<400> SEQUENCE: 191
atgaaattca gctgggtcat cttcttcctg atggcagtgg ttacaggggt caattcagag     60
gttcagctgc agcagtctgg ggcagagctt gtgaagccag gggcctcagt caagttgtcc 120
tgcacagttt ctggcttcaa cattaaagac acctatgtgc actgggtgaa gcagaggcct 180
gaacagggcc tggagtggat tggaaggatt gctcctgcga gtggtaatac taaatatgcc 240
ccgaatttcc aggacaaggc cactataaca gcggacacat cctccaacac agcctacctg 300
cagctcaaca gcctgacatc tgaggacact gccgtctatt actgtgcgcg tcacgtctac 360
tggggccaag ggactctggt cactgtctct gca 393

<210> SEQ ID NO 192
<211> LENGTH: 131
<212> TYPE: PRT
<213> ORGANISM: Mus Musculus

<400> SEQUENCE: 192

Met Lys Phe Ser Trp Val Ile Phe Phe Leu Met Ala Val Val Thr Gly
1 5 10 15

Val Asn Ser Glu Val Gln Leu Gln Gln Ser Gly Ala Glu Leu Val Lys
20 25 30

Pro Gly Ala Ser Val Lys Leu Ser Cys Thr Val Ser Gly Phe Asn Ile
35 40 45

Lys Asp Thr Tyr Val His Trp Val Lys Gln Arg Pro Glu Gln Gly Leu
50 55 60

Glu Trp Ile Gly Arg Ile Ala Pro Ala Ser Gly Asn Thr Lys Tyr Ala
65 70 75 80

Pro Asn Phe Gln Asp Lys Ala Thr Ile Thr Ala Asp Thr Ser Ser Asn
85 90 95

Thr Ala Tyr Leu Gln Leu Asn Ser Leu Thr Ser Glu Asp Thr Ala Val
100 105 110

Tyr Tyr Cys Ala Arg His Val Tyr Trp Gly Gln Gly Thr Leu Val Thr
115 120 125

Val Ser Ala
130

<210> SEQ ID NO 193
<211> LENGTH: 381
<212> TYPE: DNA
<213> ORGANISM: Mus Musculus

<400> SEQUENCE: 193
atgaagtcac agacccaggt cttcgtattt ctactgctct gtgtgtctgg tgctcatggg 60
agtattgtga tgacccagac tcccaaattc ctgcttgtat cagcaggaga cagggttacc 120
ataacctgca aggccagtca gagtgtgagt aatgatgtag tttggtacca acagaagcca 180
gggcagtctc ctaaactgct gatatactat gcatccaatc gctacactgg agtccctgat 240
cgctttactg gcagtggata tgggacggat ttcactttca ccatcagcac tgtgcaggct 300
gaagacctgg cagtttattt ctgtcagcag gattatatct ctccgtacac gttcggaggg 360
gggaccaagc tggaaataaa a 381

<210> SEQ ID NO 194
<211> LENGTH: 127
<212> TYPE: PRT
<213> ORGANISM: Mus Musculus

<400> SEQUENCE: 194

Met Lys Ser Gln Thr Gln Val Phe Val Phe Leu Leu Leu Cys Val Ser
1 5 10 15

-continued

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Val Trp Tyr Gln Gln Lys Pro Gly Gln Ser Pro
    50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ile Ser Pro Tyr Thr Phe Gly Gly Gly Thr Lys Leu Glu Ile Lys
        115                 120                 125

<210> SEQ ID NO 195
<211> LENGTH: 5
<212> TYPE: PRT
<213> ORGANISM: Artificial Sequence
<220> FEATURE:
<223> OTHER INFORMATION: Synthetic Construct

<400> SEQUENCE: 195

Ser Tyr Trp Ile Asn
1               5

<210> SEQ ID NO 196
<211> LENGTH: 17
<212> TYPE: PRT
<213> ORGANISM: Artificial Sequence
<220> FEATURE:
<223> OTHER INFORMATION: Synthetic Construct

<400> SEQUENCE: 196

Asp Val His Pro Gly Arg Gly Val Ser Thr Tyr Asn Ala Lys Phe Lys
1               5                   10                  15

Ser

<210> SEQ ID NO 197
<211> LENGTH: 11
<212> TYPE: PRT
<213> ORGANISM: Artificial Sequence
<220> FEATURE:
<223> OTHER INFORMATION: Synthetic Construct

<400> SEQUENCE: 197

Ser His Gly Asn Thr Tyr Trp Phe Phe Asp Val
1               5                   10

<210> SEQ ID NO 198
<211> LENGTH: 16
<212> TYPE: PRT
<213> ORGANISM: Artificial Sequence
<220> FEATURE:
<223> OTHER INFORMATION: Synthetic Construct

<400> SEQUENCE: 198

Arg Ser Ser Gln Ser Ile Val His Ser Asn Gly Asn Thr Tyr Leu Glu
1               5                   10                  15

<210> SEQ ID NO 199
<211> LENGTH: 7

<212> TYPE: PRT
<213> ORGANISM: Artificial Sequence
<220> FEATURE:
<223> OTHER INFORMATION: Synthetic Construct

<400> SEQUENCE: 199

Lys Val Ser Asn Arg Phe Ser
1 5

<210> SEQ ID NO 200
<211> LENGTH: 9
<212> TYPE: PRT
<213> ORGANISM: Artificial Sequence
<220> FEATURE:
<223> OTHER INFORMATION: Synthetic Construct

<400> SEQUENCE: 200

Phe Gln Gly Ser His Val Pro Phe Thr
1 5

<210> SEQ ID NO 201
<211> LENGTH: 17
<212> TYPE: PRT
<213> ORGANISM: Artificial Sequence
<220> FEATURE:
<223> OTHER INFORMATION: Synthetic Construct

<400> SEQUENCE: 201

Asp Val His Pro Gly Arg Gly Val Ser Thr Tyr Asn Ala Lys Phe Gln
1 5 10 15

Gly

<210> SEQ ID NO 202
<211> LENGTH: 4
<212> TYPE: PRT
<213> ORGANISM: Homo Sapiens

<400> SEQUENCE: 202

His Gln Lys Leu
1

<210> SEQ ID NO 203
<211> LENGTH: 9
<212> TYPE: PRT
<213> ORGANISM: Homo sapiens

<400> SEQUENCE: 203

Ala Glu Phe Arg His Asp Ser Gly Tyr
1 5

<210> SEQ ID NO 204
<211> LENGTH: 14
<212> TYPE: PRT
<213> ORGANISM: Homo sapiens

<400> SEQUENCE: 204

Val His His Gln Lys Leu Val Phe Phe Ala Glu Asp Val Gly
1 5 10

<210> SEQ ID NO 205
<211> LENGTH: 7

-continued

```
<212> TYPE: PRT
<213> ORGANISM: Homo sapiens

<400> SEQUENCE: 205

Glu Val His His Gln Lys Leu
1               5
```